(12) United States Patent
Wentz et al.

(10) Patent No.: US 12,076,051 B2
(45) Date of Patent: Sep. 3, 2024

(54) SYSTEMS AND METHODS FOR VERTEBRAL ADJUSTMENT

(71) Applicant: NuVasive Specialized Orthopedics, Inc., San Diego, CA (US)

(72) Inventors: Michael Wentz, Zionsville, PA (US); Joon Ki An, La Mirada, CA (US); Ronald Litke, Sandy Hook, CT (US); Glenn DiCostanzo, Woodbury, CT (US); Ernest Corrao, Bethel, CT (US); Robert L. Richards, Beverly Hills, MI (US); Sepehr Fariabi, Newport Coast, CA (US); Adam G. Beckett, Mission Viejo, CA (US); Luke A. Bilger, Hunnington Beach, CA (US); Daniel Dongelmans, San Clemente, CA (US); Scott Pool, Laguna Hills, CA (US); Shanbao Cheng, Irvine, CA (US); Matthew Dwight, Lake Forest, CA (US); Andy W. Choi, Irvine, CA (US); Martin Leugers, San Francisco, CA (US)

(73) Assignee: NUVASIVE SPECIALIZED ORTHOPEDICS, INC., San Diego, CA (US)

( * ) Notice: Subject to any disclaimer, the term of this patent is extended or adjusted under 35 U.S.C. 154(b) by 0 days.

(21) Appl. No.: 18/157,923

(22) Filed: Jan. 23, 2023

(65) Prior Publication Data
US 2023/0149048 A1    May 18, 2023

Related U.S. Application Data

(63) Continuation of application No. 16/270,976, filed on Feb. 8, 2019, now Pat. No. 11,612,416, which is a
(Continued)

(51) Int. Cl.
| A61B 17/70 | (2006.01) |
| A61B 17/00 | (2006.01) |
| A61B 17/68 | (2006.01) |

(52) U.S. Cl.
CPC ............. *A61B 17/7016* (2013.01); *A61B 2017/00212* (2013.01); *A61B 2017/00221* (2013.01); *A61B 2017/681* (2013.01)

(58) Field of Classification Search
CPC ............ A61B 17/7014; A61B 17/7016; A61B 17/7017; A61B 17/7025
See application file for complete search history.

(56) References Cited

U.S. PATENT DOCUMENTS

| 1,599,538 A | 9/1926 | Ludger |
| 3,111,945 A | 11/1963 | Von |
(Continued)

FOREIGN PATENT DOCUMENTS

| AU | 20068468 | 3/2001 |
| CN | 101040807 | 9/2007 |
(Continued)

OTHER PUBLICATIONS

US 9,161,784 B2, 10/2015, Buttermann (withdrawn)
(Continued)

*Primary Examiner* — Julianna N Harvey

(57) ABSTRACT

A system for non-invasively adjusting the curvature of a spine includes a housing having a first end and a second end, a first rod having a first end telescopically disposed within a cavity of the housing along a first longitudinal axis at the first end of the housing and having a first threaded portion extending thereon, and a second end configured to be coupled to a first portion of a spinal system of a subject, a second rod having a first end telescopically disposed within the cavity along a second longitudinal axis at the second end
(Continued)

of the housing and having a second threaded portion extending thereon, and a second end configured to be coupled to a second portion of the spinal system of the subject, a driving member rotatably disposed within the cavity and configured to be activated from a location external to the body of the subject.

12 Claims, 55 Drawing Sheets

Related U.S. Application Data continuation of application No. 15/048,928, filed on Feb. 19, 2016, now Pat. No. 10,238,427.

(60) Provisional application No. 62/118,411, filed on Feb. 19, 2015.

(56) References Cited

U.S. PATENT DOCUMENTS

| | | |
|---|---|---|
| 3,372,476 A | 3/1968 | Richard et al. |
| 3,377,576 A | 4/1968 | Edwin et al. |
| 3,527,220 A | 6/1968 | Summers |
| 3,397,928 A | 8/1968 | Galle |
| 3,512,901 A | 5/1970 | Law |
| 3,597,781 A | 8/1971 | Eibes et al. |
| 3,726,279 A | 4/1973 | Barefoot et al. |
| 3,749,098 A | 7/1973 | De Bennetot |
| 3,750,194 A | 8/1973 | Summers |
| 3,810,259 A | 5/1974 | Summers |
| 3,840,018 A | 10/1974 | Heifetz |
| 3,866,510 A | 2/1975 | Eibes et al. |
| 3,900,025 A | 8/1975 | Barnes, Jr. |
| 3,915,151 A | 10/1975 | Kraus |
| RE28,907 E | 7/1976 | Eibes et al. |
| 3,976,060 A | 8/1976 | Hildebrandt et al. |
| 4,010,758 A | 3/1977 | Rockland et al. |
| 4,056,743 A | 11/1977 | Clifford et al. |
| 4,068,821 A | 1/1978 | Morrison |
| 4,078,559 A | 3/1978 | Nissinen |
| 4,118,805 A | 10/1978 | Reimels |
| 4,204,541 A | 5/1980 | Kapitanov |
| 4,222,374 A | 9/1980 | Sampson et al. |
| 4,235,246 A | 11/1980 | Weiss |
| 4,256,094 A | 3/1981 | Kapp et al. |
| 4,286,584 A | 9/1981 | Sampson et al. |
| 4,300,223 A | 11/1981 | Maire |
| 4,357,946 A | 11/1982 | Dutcher et al. |
| 4,386,603 A | 6/1983 | Mayfield |
| 4,395,259 A | 7/1983 | Prestele et al. |
| 4,448,191 A | 5/1984 | Rodnyansky et al. |
| 4,484,570 A | 11/1984 | Sutter ............... A61B 17/8038 606/285 |
| 4,486,176 A | 12/1984 | Tardieu et al. |
| 4,501,266 A | 2/1985 | McDaniel |
| 4,522,501 A | 6/1985 | Shannon |
| 4,537,520 A | 8/1985 | Ochiai et al. |
| 4,550,279 A | 10/1985 | Klein |
| 4,561,798 A | 12/1985 | Elcrin et al. |
| 4,573,454 A | 3/1986 | Hoffman |
| 4,592,339 A | 6/1986 | Kuzmak et al. |
| 4,592,355 A | 6/1986 | Antebi |
| 4,595,007 A | 6/1986 | Mericle |
| 4,642,257 A | 2/1987 | Chase |
| 4,658,809 A | 4/1987 | Ulrich et al. |
| 4,696,288 A | 9/1987 | Kuzmak et al. |
| 4,700,091 A | 10/1987 | Wuthrich |
| 4,747,832 A | 5/1988 | Buffet |
| 4,760,837 A | 8/1988 | Petit |
| 4,854,304 A | 8/1989 | Zielke |
| 4,872,515 A | 10/1989 | Lundell |
| 4,904,861 A | 2/1990 | Epstein et al. |
| 4,931,055 A | 6/1990 | Bumpus et al. |
| 4,940,467 A | 7/1990 | Tronzo |
| 4,957,495 A | 9/1990 | Kluger |
| 4,973,331 A | 11/1990 | Pursley et al. |
| 4,978,323 A | 12/1990 | Freedman |
| 4,998,013 A | 3/1991 | Epstein et al. |
| 5,010,879 A | 4/1991 | Moriya et al. |
| 5,030,235 A | 7/1991 | Campbell, Jr. |
| 5,041,112 A | 8/1991 | Mingozzi et al. |
| 5,053,047 A | 10/1991 | Yoon |
| 5,064,004 A | 11/1991 | Lundell |
| 5,074,868 A | 12/1991 | Kuzmak |
| 5,074,882 A | 12/1991 | Grammont et al. |
| 5,092,889 A | 3/1992 | Campbell, Jr. |
| 5,133,716 A | 7/1992 | Plaza |
| 5,142,407 A | 8/1992 | Varaprasad et al. |
| 5,152,770 A | 10/1992 | Bengmark et al. |
| 5,156,605 A | 10/1992 | Pursley et al. |
| 5,176,618 A | 1/1993 | Freedman |
| 5,180,380 A | 1/1993 | Pursley et al. |
| 5,222,976 A | 6/1993 | Yoon |
| 5,226,429 A | 7/1993 | Kuzmak |
| 5,261,908 A | 11/1993 | Campbell, Jr. |
| 5,263,955 A | 11/1993 | Baumgart et al. |
| 5,290,289 A | 3/1994 | Sanders et al. |
| 5,306,275 A | 4/1994 | Bryan |
| 5,330,503 A | 7/1994 | Yoon |
| 5,334,202 A | 8/1994 | Carter |
| 5,336,223 A | 8/1994 | Rogers |
| 5,356,411 A | 10/1994 | Spievack |
| 5,356,424 A | 10/1994 | Buzerak et al. |
| 5,360,407 A | 11/1994 | Leonard et al. |
| 5,364,396 A | 11/1994 | Robinson et al. |
| 5,381,943 A | 1/1995 | Allen et al. |
| 5,399,168 A | 3/1995 | Wadsworth, Jr. et al. |
| 5,403,322 A | 4/1995 | Herzenberg et al. |
| 5,429,638 A | 7/1995 | Muschler et al. |
| 5,433,721 A | 7/1995 | Hooven et al. |
| 5,437,266 A | 8/1995 | McPherson et al. |
| 5,449,368 A | 9/1995 | Kuzmak |
| 5,466,261 A | 11/1995 | Richelsoph |
| 5,468,030 A | 11/1995 | Walling |
| 5,468,241 A | 11/1995 | Metz-Stavenhagen |
| 5,480,437 A | 1/1996 | Draenert |
| 5,498,262 A | 3/1996 | Bryan |
| 5,509,888 A | 4/1996 | Miller |
| 5,516,335 A | 5/1996 | Kummer et al. |
| 5,527,309 A | 6/1996 | Shelton |
| 5,536,269 A | 7/1996 | Spievack |
| 5,536,296 A | 7/1996 | Ten Eyck et al. |
| 5,549,610 A | 8/1996 | Russell et al. |
| 5,573,496 A | 11/1996 | McPherson et al. |
| 5,575,790 A | 11/1996 | Chen et al. |
| 5,582,616 A | 12/1996 | Bolduc et al. |
| 5,601,224 A | 2/1997 | Bishop et al. |
| 5,620,445 A | 4/1997 | Brosnahan et al. |
| 5,620,449 A | 4/1997 | Faccioli et al. |
| 5,626,579 A | 5/1997 | Muschler et al. |
| 5,626,613 A | 5/1997 | Schmieding |
| 5,628,888 A | 5/1997 | Bakhir et al. |
| 5,632,744 A | 5/1997 | Campbell, Jr. |
| 5,659,217 A | 8/1997 | Petersen |
| 5,662,683 A | 9/1997 | Kay |
| 5,672,175 A | 9/1997 | Martin |
| 5,672,177 A | 9/1997 | Seldin |
| 5,676,162 A | 10/1997 | Larson, Jr. et al. |
| 5,693,091 A | 12/1997 | Larson, Jr. et al. |
| 5,700,263 A | 12/1997 | Schendel |
| 5,702,430 A | 12/1997 | Larson, Jr. et al. |
| 5,704,893 A | 1/1998 | Timm |
| 5,704,938 A | 1/1998 | Staehlin et al. |
| 5,704,939 A | 1/1998 | Justin |
| 5,720,746 A | 2/1998 | Soubeiran |
| 5,722,429 A | 3/1998 | Larson, Jr. et al. |
| 5,722,930 A | 3/1998 | Larson, Jr. et al. |
| 5,743,910 A | 4/1998 | Bays et al. |
| 5,758,666 A | 6/1998 | Larson, Jr. et al. |
| 5,762,599 A | 6/1998 | Sohn |
| 5,766,208 A | 6/1998 | McEwan |
| 5,771,903 A | 6/1998 | Jakobsson |

(56) References Cited

U.S. PATENT DOCUMENTS

| | | |
|---|---|---|
| 5,800,434 A | 9/1998 | Campbell, Jr. |
| 5,810,815 A | 9/1998 | Morales |
| 5,824,008 A | 10/1998 | Bolduc et al. |
| 5,827,286 A | 10/1998 | Incavo et al. |
| 5,829,662 A | 11/1998 | Allen et al. |
| 5,830,221 A | 11/1998 | Stein et al. |
| 5,843,129 A | 12/1998 | Larson, Jr. et al. |
| 5,874,796 A | 2/1999 | Petersen |
| 5,879,375 A | 3/1999 | Larson, Jr. et al. |
| 5,902,304 A | 5/1999 | Walker et al. |
| 5,935,127 A | 8/1999 | Border |
| 5,938,669 A | 8/1999 | Klaiber et al. |
| 5,945,762 A | 8/1999 | Chen et al. |
| 5,954,915 A | 9/1999 | Voorhees et al. |
| 5,961,553 A | 10/1999 | Coty et al. |
| 5,964,763 A | 10/1999 | Incavo et al. |
| 5,976,138 A | 11/1999 | Baumgart et al. |
| 5,979,456 A | 11/1999 | Magovern |
| 5,985,110 A | 11/1999 | Bakhir et al. |
| 5,997,490 A | 12/1999 | McLeod et al. |
| 6,009,837 A | 1/2000 | McClasky |
| 6,022,349 A | 2/2000 | McLeod et al. |
| 6,033,412 A | 3/2000 | Losken et al. |
| 6,034,296 A | 3/2000 | Elvin et al. |
| 6,067,991 A | 5/2000 | Forsell |
| 6,074,341 A | 6/2000 | Anderson et al. |
| 6,074,882 A | 6/2000 | Eckardt |
| 6,092,531 A | 7/2000 | Chen et al. |
| 6,102,922 A | 8/2000 | Jakobsson et al. |
| 6,106,525 A | 8/2000 | Sachse |
| 6,126,660 A | 10/2000 | Dietz |
| 6,126,661 A | 10/2000 | Faccioli et al. |
| 6,138,681 A | 10/2000 | Chen et al. |
| 6,139,316 A | 10/2000 | Sachdeva et al. |
| 6,162,223 A | 12/2000 | Orsak et al. |
| 6,183,476 B1 | 2/2001 | Gerhardt et al. |
| 6,200,317 B1 | 3/2001 | Aalsma et al. |
| 6,210,347 B1 | 4/2001 | Forsell |
| 6,217,847 B1 | 4/2001 | Contag et al. |
| 6,221,074 B1 | 4/2001 | Cole et al. |
| 6,234,299 B1 | 5/2001 | Voorhees et al. |
| 6,234,956 B1 | 5/2001 | He et al. |
| 6,241,730 B1 | 6/2001 | Alby |
| 6,245,075 B1 | 6/2001 | Betz et al. |
| 6,283,156 B1 | 9/2001 | Motley |
| 6,296,643 B1 | 10/2001 | Hopf et al. |
| 6,296,656 B1 | 10/2001 | Bolduc et al. |
| 6,299,613 B1 | 10/2001 | Ogilvie et al. |
| 6,315,784 B1 | 11/2001 | Djurovic |
| 6,319,255 B1 | 11/2001 | Grundei et al. |
| 6,321,106 B1 | 11/2001 | Lemelson |
| 6,325,805 B1 | 12/2001 | Ogilvie et al. |
| 6,327,492 B1 | 12/2001 | Lemelson |
| 6,331,744 B1 | 12/2001 | Chen et al. |
| 6,336,929 B1 | 1/2002 | Justin |
| 6,343,568 B1 | 2/2002 | McClasky |
| 6,358,283 B1 | 3/2002 | Hogfors et al. |
| 6,375,682 B1 | 4/2002 | Fleischmann et al. |
| 6,386,083 B1 | 5/2002 | Hwang |
| 6,389,187 B1 | 5/2002 | Greenaway et al. |
| 6,400,980 B1 | 6/2002 | Lemelson |
| 6,402,753 B1 | 6/2002 | Cole et al. |
| 6,409,175 B1 | 6/2002 | Evans et al. |
| 6,416,516 B1 | 7/2002 | Stauch et al. |
| 6,417,750 B1 | 7/2002 | Sohn |
| 6,423,061 B1 | 7/2002 | Bryant |
| 6,432,040 B1 | 8/2002 | Meah |
| 6,450,173 B1 | 9/2002 | Forsell |
| 6,450,946 B1 | 9/2002 | Forsell |
| 6,453,907 B1 | 9/2002 | Forsell |
| 6,454,698 B1 | 9/2002 | Forsell |
| 6,454,699 B1 | 9/2002 | Forsell |
| 6,454,700 B1 | 9/2002 | Forsell |
| 6,454,701 B1 | 9/2002 | Forsell |
| 6,460,543 B1 | 10/2002 | Forsell |
| 6,461,292 B1 | 10/2002 | Forsell |
| 6,461,293 B1 | 10/2002 | Forsell |
| 6,463,935 B1 | 10/2002 | Forsell |
| 6,464,628 B1 | 10/2002 | Forsell |
| 6,470,892 B1 | 10/2002 | Forsell |
| 6,471,635 B1 | 10/2002 | Forsell |
| 6,475,136 B1 | 11/2002 | Forsell |
| 6,482,145 B1 | 11/2002 | Forsell |
| 6,494,879 B2 | 12/2002 | Lennox et al. |
| 6,499,907 B1 | 12/2002 | Baur |
| 6,500,110 B1 | 12/2002 | Davey et al. |
| 6,503,189 B1 | 1/2003 | Forsell |
| 6,508,820 B2 | 1/2003 | Bales |
| 6,510,345 B1 | 1/2003 | Van Bentem |
| 6,511,490 B2 | 1/2003 | Robert |
| 6,527,701 B1 | 3/2003 | Sayet et al. |
| 6,527,702 B2 | 3/2003 | Whalen et al. |
| 6,536,499 B2 | 3/2003 | Voorhees et al. |
| 6,537,196 B1 | 3/2003 | Creighton, IV et al. |
| 6,547,801 B1 | 4/2003 | Dargent et al. |
| 6,554,831 B1 | 4/2003 | Rivard et al. |
| 6,558,400 B2 | 5/2003 | Deem et al. |
| 6,562,051 B1 | 5/2003 | Bolduc et al. |
| 6,565,573 B1 | 5/2003 | Ferrante et al. |
| 6,565,576 B1 | 5/2003 | Stauch et al. |
| 6,573,706 B2 | 6/2003 | Mendes et al. |
| 6,582,313 B2 | 6/2003 | Perrow |
| 6,583,630 B2 | 6/2003 | Mendes et al. |
| 6,587,719 B1 | 7/2003 | Barrett et al. |
| 6,595,912 B2 | 7/2003 | Lau et al. |
| 6,602,184 B2 | 8/2003 | Lau et al. |
| 6,604,529 B2 | 8/2003 | Kim |
| 6,607,363 B1 | 8/2003 | Domroese |
| 6,609,025 B2 | 8/2003 | Barrett et al. |
| 6,612,978 B2 | 9/2003 | Lau et al. |
| 6,612,979 B2 | 9/2003 | Lau et al. |
| 6,616,669 B2 | 9/2003 | Ogilvie et al. |
| 6,621,956 B2 | 9/2003 | Greenaway et al. |
| 6,626,899 B2 | 9/2003 | Houser et al. |
| 6,626,917 B1 | 9/2003 | Craig |
| 6,627,206 B2 | 9/2003 | Lloyd |
| 6,649,143 B1 | 11/2003 | Contag et al. |
| 6,656,135 B2 | 12/2003 | Zogbi et al. |
| 6,656,194 B1 | 12/2003 | Gannoe et al. |
| 6,657,351 B2 | 12/2003 | Chen et al. |
| 6,667,725 B1 | 12/2003 | Simons et al. |
| 6,669,687 B1 | 12/2003 | Saadat |
| 6,673,079 B1 | 1/2004 | Kane |
| 6,676,674 B1 | 1/2004 | Dudai |
| 6,682,474 B2 | 1/2004 | Lau et al. |
| 6,689,046 B2 | 2/2004 | Sayet et al. |
| 6,702,732 B1 | 3/2004 | Lau et al. |
| 6,702,816 B2 | 3/2004 | Buhler |
| 6,706,042 B2 | 3/2004 | Taylor |
| 6,709,293 B2 | 3/2004 | Mori et al. |
| 6,709,385 B2 | 3/2004 | Forsell |
| 6,730,087 B1 | 5/2004 | Butsch |
| 6,749,556 B2 | 6/2004 | Banik |
| 6,752,754 B1 | 6/2004 | Feng et al. |
| 6,761,503 B2 | 7/2004 | Breese |
| 6,765,330 B2 | 7/2004 | Baur |
| 6,769,499 B2 | 8/2004 | Cargill et al. |
| 6,773,437 B2 | 8/2004 | Ogilvie et al. |
| 6,774,624 B2 | 8/2004 | Anderson et al. |
| 6,789,442 B2 | 9/2004 | Forch |
| 6,796,984 B2 | 9/2004 | Soubeiran |
| 6,802,844 B2 | 10/2004 | Ferree |
| 6,802,847 B1 | 10/2004 | Carson et al. |
| 6,809,434 B1 | 10/2004 | Duncan et al. |
| 6,835,183 B2 | 12/2004 | Lennox et al. |
| 6,835,207 B2 | 12/2004 | Zacouto et al. |
| 6,849,076 B2 | 2/2005 | Blunn et al. |
| 6,852,113 B2 | 2/2005 | Nathanson et al. |
| 6,864,647 B2 | 3/2005 | Duncan et al. |
| 6,884,248 B2 | 4/2005 | Bolduc et al. |
| 6,890,515 B2 | 5/2005 | Contag et al. |
| 6,908,605 B2 | 6/2005 | Contag et al. |
| 6,915,165 B2 | 7/2005 | Forsell |
| 6,916,462 B2 | 7/2005 | Contag et al. |

(56) References Cited

U.S. PATENT DOCUMENTS

| | | |
|---|---|---|
| 6,918,838 B2 | 7/2005 | Schwarzler et al. |
| 6,918,910 B2 | 7/2005 | Smith et al. |
| 6,921,360 B2 | 7/2005 | Banik |
| 6,921,400 B2 | 7/2005 | Sohngen |
| 6,923,951 B2 | 8/2005 | Contag et al. |
| 6,926,719 B2 | 8/2005 | Sohngen et al. |
| 6,939,533 B2 | 9/2005 | Contag et al. |
| 6,953,429 B2 | 10/2005 | Forsell |
| 6,961,553 B2 | 11/2005 | Zhao et al. |
| 6,971,143 B2 | 12/2005 | Domroese |
| 6,980,921 B2 | 12/2005 | Anderson et al. |
| 6,997,952 B2 | 2/2006 | Furukawa et al. |
| 7,001,327 B2 | 2/2006 | Whalen et al. |
| 7,001,346 B2 | 2/2006 | White |
| 7,008,425 B2 | 3/2006 | Phillips |
| 7,011,621 B2 | 3/2006 | Sayet et al. |
| 7,011,658 B2 | 3/2006 | Young |
| 7,011,682 B2 | 3/2006 | Lashinski et al. |
| 7,018,380 B2 | 3/2006 | Cole |
| 7,029,475 B2 | 4/2006 | Panjabi |
| 7,041,105 B2 | 5/2006 | Michelson |
| 7,060,075 B2 | 6/2006 | Govari et al. |
| 7,060,080 B2 | 6/2006 | Bachmann |
| 7,063,706 B2 | 6/2006 | Wittenstein |
| 7,077,802 B2 | 7/2006 | Lau et al. |
| 7,081,086 B2 | 7/2006 | Lau et al. |
| 7,083,629 B2 | 8/2006 | Weller et al. |
| 7,096,148 B2 | 8/2006 | Anderson et al. |
| 7,097,611 B2 | 8/2006 | Lau et al. |
| 7,105,029 B2 | 9/2006 | Doubler et al. |
| 7,105,968 B2 | 9/2006 | Nissen |
| 7,114,501 B2 | 10/2006 | Johnson et al. |
| 7,115,129 B2 | 10/2006 | Heggeness |
| 7,115,130 B2 | 10/2006 | Michelson |
| 7,124,493 B2 | 10/2006 | Lau et al. |
| 7,128,707 B2 | 10/2006 | Banik |
| 7,135,022 B2 | 11/2006 | Kosashvili et al. |
| 7,160,312 B2 | 1/2007 | Saadat |
| 7,163,538 B2 | 1/2007 | Altarac et al. |
| 7,172,607 B2 | 2/2007 | Hofle et al. |
| 7,175,589 B2 | 2/2007 | Deem et al. |
| 7,175,660 B2 | 2/2007 | Cartledge et al. |
| 7,186,262 B2 | 3/2007 | Saadat |
| 7,188,627 B2 | 3/2007 | Nelson et al. |
| 7,189,005 B2 | 3/2007 | Ward |
| 7,189,202 B2 | 3/2007 | Lau et al. |
| 7,189,251 B2 | 3/2007 | Kay |
| 7,191,007 B2 | 3/2007 | Desai et al. |
| 7,194,297 B2 | 3/2007 | Talpade et al. |
| 7,195,608 B2 | 3/2007 | Burnett |
| 7,198,774 B2 | 4/2007 | Contag et al. |
| 7,211,094 B2 | 5/2007 | Gannoe et al. |
| 7,216,648 B2 | 5/2007 | Nelson et al. |
| 7,217,284 B2 | 5/2007 | Houser et al. |
| 7,218,232 B2 | 5/2007 | DiSilvestro et al. |
| 7,232,449 B2 | 6/2007 | Sharkawy et al. |
| 7,234,468 B2 | 6/2007 | Johnson et al. |
| 7,234,544 B2 | 6/2007 | Kent |
| 7,238,152 B2 | 7/2007 | Lau et al. |
| 7,238,191 B2 | 7/2007 | Bachmann |
| 7,241,300 B2 | 7/2007 | Sharkawy et al. |
| 7,243,719 B2 | 7/2007 | Baron et al. |
| 7,255,682 B1 | 8/2007 | Bartol, Jr. et al. |
| 7,255,714 B2 | 8/2007 | Malek |
| 7,255,851 B2 | 8/2007 | Contag et al. |
| 7,276,022 B2 | 10/2007 | Lau et al. |
| 7,282,023 B2 | 10/2007 | Frering |
| 7,285,087 B2 | 10/2007 | Moaddeb et al. |
| 7,288,064 B2 | 10/2007 | Boustani et al. |
| 7,288,099 B2 | 10/2007 | Deem et al. |
| 7,288,101 B2 | 10/2007 | Deem et al. |
| 7,296,577 B2 | 11/2007 | Lashinski et al. |
| 7,297,150 B2 | 11/2007 | Cartledge et al. |
| 7,299,091 B2 | 11/2007 | Barrett et al. |
| 7,302,858 B2 | 12/2007 | Walsh et al. |
| 7,306,614 B2 | 12/2007 | Weller et al. |
| 7,311,690 B2 | 12/2007 | Burnett |
| 7,314,372 B2 | 1/2008 | Belfor et al. |
| 7,314,443 B2 | 1/2008 | Jordan et al. |
| 7,320,706 B2 | 1/2008 | Al-Najjar |
| 7,331,995 B2 | 2/2008 | Eisermann et al. |
| 7,333,013 B2 | 2/2008 | Berger |
| 7,338,433 B2 | 3/2008 | Coe |
| 7,340,306 B2 | 3/2008 | Barrett et al. |
| 7,351,198 B2 | 4/2008 | Byrum et al. |
| 7,351,240 B2 | 4/2008 | Hassler, Jr. et al. |
| 7,353,747 B2 | 4/2008 | Swayze et al. |
| 7,357,037 B2 | 4/2008 | Hnat et al. |
| 7,357,635 B2 | 4/2008 | Belfor et al. |
| 7,360,542 B2 | 4/2008 | Nelson et al. |
| 7,361,192 B2 | 4/2008 | Doty |
| 7,364,542 B2 | 4/2008 | Jambor et al. |
| 7,364,589 B2 | 4/2008 | Eisermann |
| 7,367,340 B2 | 5/2008 | Nelson et al. |
| 7,367,937 B2 | 5/2008 | Jambor et al. |
| 7,367,938 B2 | 5/2008 | Forsell |
| 7,371,244 B2 | 5/2008 | Chatlynne et al. |
| 7,374,557 B2 | 5/2008 | Conlon et al. |
| 7,390,007 B2 | 6/2008 | Helms et al. |
| 7,390,294 B2 | 6/2008 | Hassler, Jr. |
| 7,400,926 B2 | 7/2008 | Forsell |
| 7,402,134 B2 | 7/2008 | Moaddeb et al. |
| 7,402,176 B2 | 7/2008 | Malek |
| 7,410,461 B2 | 8/2008 | Lau et al. |
| 7,416,528 B2 | 8/2008 | Crawford et al. |
| 7,422,566 B2 | 9/2008 | Miethke |
| 7,429,259 B2 | 9/2008 | Cadeddu et al. |
| 7,431,692 B2 | 10/2008 | Zollinger et al. |
| 7,441,559 B2 | 10/2008 | Nelson et al. |
| 7,442,196 B2 | 10/2008 | Fisher et al. |
| 7,445,010 B2 | 11/2008 | Kugler et al. |
| 7,455,690 B2 | 11/2008 | Cartledge et al. |
| 7,458,981 B2 | 12/2008 | Fielding et al. |
| 7,468,060 B2 | 12/2008 | Utley et al. |
| 7,476,195 B2 | 1/2009 | Sayet et al. |
| 7,476,238 B2 | 1/2009 | Panjabi |
| 7,481,224 B2 | 1/2009 | Nelson et al. |
| 7,481,763 B2 | 1/2009 | Hassler, Jr. et al. |
| 7,481,841 B2 | 1/2009 | Hazebrouck et al. |
| 7,485,149 B1 | 2/2009 | White |
| 7,489,495 B2 | 2/2009 | Stevenson |
| 7,494,459 B2 | 2/2009 | Anstadt et al. |
| 7,500,484 B2 | 3/2009 | Nelson et al. |
| 7,503,922 B2 | 3/2009 | Deem et al. |
| 7,503,934 B2 | 3/2009 | Eisermann et al. |
| 7,507,252 B2 | 3/2009 | Lashinski et al. |
| 7,510,559 B2 | 3/2009 | Deem et al. |
| 7,530,981 B2 | 5/2009 | Kutsenko |
| 7,531,002 B2 | 5/2009 | Sutton et al. |
| 7,547,291 B2 | 6/2009 | Lennox et al. |
| 7,553,298 B2 | 6/2009 | Hunt et al. |
| 7,559,951 B2 | 7/2009 | DiSilvestro et al. |
| 7,561,916 B2 | 7/2009 | Hunt et al. |
| 7,562,660 B2 | 7/2009 | Saadat |
| 7,566,297 B2 | 7/2009 | Banik |
| 7,569,057 B2 | 8/2009 | Liu et al. |
| 7,578,821 B2 | 8/2009 | Fisher et al. |
| 7,584,788 B2 | 9/2009 | Baron et al. |
| 7,594,887 B2 | 9/2009 | Moaddeb et al. |
| 7,601,156 B2 | 10/2009 | Robinson |
| 7,601,162 B2 | 10/2009 | Hassler, Jr. et al. |
| 7,601,171 B2 | 10/2009 | Ainsworth et al. |
| 7,611,526 B2 | 11/2009 | Carl et al. |
| 7,615,001 B2 | 11/2009 | Jambor et al. |
| 7,615,068 B2 | 11/2009 | Timm et al. |
| 7,618,435 B2 | 11/2009 | Opolski |
| 7,621,886 B2 | 11/2009 | Burnett |
| 7,635,379 B2 | 12/2009 | Callahan et al. |
| 7,651,483 B2 | 1/2010 | Byrum et al. |
| 7,658,753 B2 | 2/2010 | Carl et al. |
| 7,666,132 B2 | 2/2010 | Forsell |
| 7,666,184 B2 | 2/2010 | Stauch |
| 7,666,210 B2 | 2/2010 | Franck et al. |
| 7,678,136 B2 | 3/2010 | Doubler et al. |

(56) References Cited

U.S. PATENT DOCUMENTS

| | | |
|---|---|---|
| 7,678,139 B2 | 3/2010 | Garamszegi et al. |
| 7,691,144 B2 | 4/2010 | Chang et al. |
| 7,695,512 B2 | 4/2010 | Lashinski et al. |
| 7,704,279 B2 | 4/2010 | Moskowitz et al. |
| 7,704,282 B2 | 4/2010 | Disilvestro et al. |
| 7,708,737 B2 | 5/2010 | Kraft et al. |
| 7,708,762 B2 | 5/2010 | McCarthy et al. |
| 7,708,765 B2 | 5/2010 | Carl et al. |
| 7,708,779 B2 | 5/2010 | Edie et al. |
| 7,713,287 B2 | 5/2010 | Timm et al. |
| 7,717,959 B2 | 5/2010 | William et al. |
| 7,727,141 B2 | 6/2010 | Hassler, Jr. et al. |
| 7,727,143 B2 | 6/2010 | Birk et al. |
| 7,749,224 B2 | 7/2010 | Cresina et al. |
| 7,753,913 B2 | 7/2010 | Szakelyhidi, Jr. et al. |
| 7,753,915 B1 | 7/2010 | Eksler et al. |
| 7,757,552 B2 | 7/2010 | Bogath et al. |
| 7,762,998 B2 | 7/2010 | Birk et al. |
| 7,763,053 B2 | 7/2010 | Gordon |
| 7,763,080 B2 | 7/2010 | Southworth |
| 7,766,815 B2 | 8/2010 | Ortiz |
| 7,775,099 B2 | 8/2010 | Bogath et al. |
| 7,775,215 B2 | 8/2010 | Hassler, Jr. et al. |
| 7,776,061 B2 | 8/2010 | Garner et al. |
| 7,776,068 B2 | 8/2010 | Ainsworth et al. |
| 7,776,075 B2 | 8/2010 | Bruneau et al. |
| 7,776,091 B2 | 8/2010 | Mastrorio et al. |
| 7,780,590 B2 | 8/2010 | Birk et al. |
| 7,787,958 B2 | 8/2010 | Stevenson |
| 7,789,912 B2 | 9/2010 | Manzi et al. |
| 7,793,583 B2 | 9/2010 | Radinger et al. |
| 7,794,447 B2 | 9/2010 | Dann et al. |
| 7,794,476 B2 | 9/2010 | Wisnewski |
| 7,798,954 B2 | 9/2010 | Birk et al. |
| 7,799,080 B2 | 9/2010 | Doty |
| 7,803,106 B2 | 9/2010 | Whalen et al. |
| 7,803,157 B2 | 9/2010 | Michelson |
| 7,811,275 B2 | 10/2010 | Birk et al. |
| 7,811,298 B2 | 10/2010 | Birk |
| 7,811,328 B2 | 10/2010 | Molz, IV et al. |
| 7,815,643 B2 | 10/2010 | Johnson et al. |
| 7,828,714 B2 | 11/2010 | Feng et al. |
| 7,828,813 B2 | 11/2010 | Mouton |
| 7,833,228 B1 | 11/2010 | Hershberger |
| 7,835,779 B2 | 11/2010 | Anderson et al. |
| 7,837,669 B2 | 11/2010 | Dann et al. |
| 7,837,691 B2 | 11/2010 | Cordes et al. |
| 7,842,036 B2 | 11/2010 | Phillips |
| 7,845,356 B2 | 12/2010 | Paraschac et al. |
| 7,846,188 B2 | 12/2010 | Moskowitz et al. |
| 7,850,660 B2 | 12/2010 | Uth et al. |
| 7,850,735 B2 | 12/2010 | Eisermann et al. |
| 7,854,769 B2 | 12/2010 | Hershberger |
| 7,862,546 B2 | 1/2011 | Conlon et al. |
| 7,862,574 B2 | 1/2011 | Deem et al. |
| 7,862,586 B2 | 1/2011 | Malek |
| 7,867,235 B2 | 1/2011 | Fell et al. |
| 7,871,368 B2 | 1/2011 | Zollinger et al. |
| 7,875,033 B2 | 1/2011 | Richter et al. |
| 7,887,566 B2 | 2/2011 | Hynes |
| 7,901,381 B2 | 3/2011 | Birk et al. |
| 7,901,419 B2 | 3/2011 | Bachmann et al. |
| 7,909,790 B2 | 3/2011 | Burnett |
| 7,909,838 B2 | 3/2011 | Deem et al. |
| 7,909,839 B2 | 3/2011 | Fields |
| 7,909,852 B2 | 3/2011 | Boomer et al. |
| 7,918,844 B2 | 4/2011 | Byrum et al. |
| 7,921,850 B2 | 4/2011 | Nelson et al. |
| 7,922,765 B2 | 4/2011 | Reiley |
| 7,927,354 B2 | 4/2011 | Edidin et al. |
| 7,927,357 B2 | 4/2011 | Sacher et al. |
| 7,931,679 B2 | 4/2011 | Heggeness |
| 7,932,825 B2 | 4/2011 | Berger |
| 7,938,836 B2 | 5/2011 | Ainsworth et al. |
| 7,938,841 B2 | 5/2011 | Sharkawy et al. |
| 7,942,903 B2 | 5/2011 | Moskowitz et al. |
| 7,942,908 B2 | 5/2011 | Sacher et al. |
| 7,947,011 B2 | 5/2011 | Birk et al. |
| 7,951,067 B2 | 5/2011 | Byrum et al. |
| 7,951,180 B2 | 5/2011 | Moskowitz et al. |
| 7,958,895 B2 | 6/2011 | Nelson et al. |
| 7,958,896 B2 | 6/2011 | Nelson et al. |
| 7,959,552 B2 | 6/2011 | Jordan et al. |
| 7,972,315 B2 | 7/2011 | Birk et al. |
| 7,972,346 B2 | 7/2011 | Bachmann et al. |
| 7,972,363 B2 | 7/2011 | Moskowitz et al. |
| 7,976,545 B2 | 7/2011 | Hershberger et al. |
| 7,983,763 B2 | 7/2011 | Stevenson et al. |
| 7,985,256 B2 | 7/2011 | Grotz et al. |
| 7,987,241 B2 | 7/2011 | Jacques, Jr. et al. |
| 7,988,707 B2 | 8/2011 | Panjabi |
| 7,988,709 B2 | 8/2011 | Clark et al. |
| 7,993,342 B2 | 8/2011 | Malandain et al. |
| 7,993,397 B2 | 8/2011 | Lashinski et al. |
| 7,998,174 B2 | 8/2011 | Malandain et al. |
| 7,998,208 B2 | 8/2011 | Kohm et al. |
| 8,002,801 B2 | 8/2011 | Carl et al. |
| 8,002,809 B2 | 8/2011 | Baynham |
| 8,007,458 B2 | 8/2011 | Lennox et al. |
| 8,007,474 B2 | 8/2011 | Uth et al. |
| 8,007,479 B2 | 8/2011 | Birk et al. |
| 8,011,308 B2 | 9/2011 | Picchio |
| 8,012,162 B2 | 9/2011 | Bachmann |
| 8,016,745 B2 | 9/2011 | Hassler, Jr. et al. |
| 8,016,837 B2 | 9/2011 | Giger et al. |
| 8,016,860 B2 | 9/2011 | Carl et al. |
| 8,026,729 B2 | 9/2011 | Kroh et al. |
| 8,029,477 B2 | 10/2011 | Byrum et al. |
| 8,029,567 B2 | 10/2011 | Edidin et al. |
| 8,034,080 B2 | 10/2011 | Malandain et al. |
| 8,037,871 B2 | 10/2011 | McClendon |
| 8,038,680 B2 | 10/2011 | Ainsworth et al. |
| 8,038,698 B2 | 10/2011 | Edidin et al. |
| 8,043,206 B2 | 10/2011 | Birk |
| 8,043,290 B2 | 10/2011 | Harrison et al. |
| 8,043,299 B2 | 10/2011 | Conway |
| 8,043,338 B2 | 10/2011 | Dant |
| 8,043,345 B2 | 10/2011 | Carl et al. |
| 8,048,169 B2 | 11/2011 | Burnett et al. |
| 8,057,473 B2 | 11/2011 | Orsak et al. |
| 8,057,513 B2 | 11/2011 | Kohm et al. |
| 8,066,650 B2 | 11/2011 | Lee et al. |
| 8,070,670 B2 | 12/2011 | Deem et al. |
| 8,070,671 B2 | 12/2011 | Deem et al. |
| 8,070,695 B2 | 12/2011 | Gupta et al. |
| 8,070,813 B2 | 12/2011 | Grotz et al. |
| 8,074,654 B2 | 12/2011 | Paraschac et al. |
| 8,075,577 B2 | 12/2011 | Deem et al. |
| 8,079,974 B2 | 12/2011 | Stergiopulos |
| 8,079,989 B2 | 12/2011 | Birk et al. |
| 8,080,022 B2 | 12/2011 | Deem et al. |
| 8,080,025 B2 | 12/2011 | Deem et al. |
| 8,088,166 B2 | 1/2012 | Makower et al. |
| 8,092,459 B2 | 1/2012 | Malandain |
| 8,092,499 B1 | 1/2012 | Roth |
| 8,095,317 B2 | 1/2012 | Ekseth et al. |
| 8,096,302 B2 | 1/2012 | Nelson et al. |
| 8,096,938 B2 | 1/2012 | Forsell |
| 8,096,995 B2 | 1/2012 | Kohm et al. |
| 8,097,018 B2 | 1/2012 | Malandain et al. |
| 8,097,038 B2 | 1/2012 | Malek |
| 8,100,819 B2 | 1/2012 | Banik |
| 8,100,943 B2 | 1/2012 | Malandain et al. |
| 8,100,967 B2 | 1/2012 | Makower et al. |
| 8,105,360 B1 | 1/2012 | Connor |
| 8,105,363 B2 | 1/2012 | Fielding et al. |
| 8,105,364 B2 | 1/2012 | McCarthy et al. |
| 8,109,974 B2 | 2/2012 | Boomer et al. |
| 8,114,158 B2 | 2/2012 | Carl et al. |
| 8,123,765 B2 | 2/2012 | Deem et al. |
| 8,123,805 B2 | 2/2012 | Makower et al. |
| 8,128,628 B2 | 3/2012 | Freid et al. |
| 8,133,280 B2 | 3/2012 | Voellmicke et al. |
| 8,137,349 B2 | 3/2012 | Soubeiran |

(56) References Cited

U.S. PATENT DOCUMENTS

| | | |
|---|---|---|
| 8,137,366 B2 | 3/2012 | Deem et al. |
| 8,137,367 B2 | 3/2012 | Deem et al. |
| 8,142,454 B2 | 3/2012 | Harrison et al. |
| 8,142,494 B2 | 3/2012 | Rahdert et al. |
| 8,147,517 B2 | 4/2012 | Trieu et al. |
| 8,147,549 B2 | 4/2012 | Metcalf, Jr. et al. |
| 8,157,841 B2 | 4/2012 | Malandain et al. |
| 8,162,897 B2 | 4/2012 | Byrum |
| 8,162,979 B2 | 4/2012 | Sachs et al. |
| 8,163,013 B2 | 4/2012 | Machold et al. |
| 8,177,789 B2 | 5/2012 | Magill et al. |
| 8,182,411 B2 | 5/2012 | Dlugos |
| 8,187,324 B2 | 5/2012 | Webler et al. |
| 8,197,544 B1 | 6/2012 | Manzi et al. |
| 8,202,305 B2 | 6/2012 | Reiley |
| 8,211,127 B2 | 7/2012 | Uth et al. |
| 8,211,149 B2 | 7/2012 | Justis |
| 8,211,151 B2 | 7/2012 | Schwab et al. |
| 8,211,179 B2 | 7/2012 | Molz, IV et al. |
| 8,216,275 B2 | 7/2012 | Fielding et al. |
| 8,221,420 B2 | 7/2012 | Keller |
| 8,226,690 B2 | 7/2012 | Altarac et al. |
| 8,236,002 B2 | 8/2012 | Fortin et al. |
| 8,241,292 B2 | 8/2012 | Collazo |
| 8,241,293 B2 | 8/2012 | Stone et al. |
| 8,241,331 B2 | 8/2012 | Arnin |
| 8,246,630 B2 | 8/2012 | Manzi et al. |
| 8,251,888 B2 | 8/2012 | Roslin et al. |
| 8,252,063 B2 | 8/2012 | Stauch |
| 8,257,370 B2 | 9/2012 | Moskowitz et al. |
| 8,257,442 B2 | 9/2012 | Edie et al. |
| 8,263,024 B2 | 9/2012 | Wan et al. |
| 8,267,969 B2 | 9/2012 | Altarac et al. |
| 8,273,112 B2 | 9/2012 | Garamszegi et al. |
| 8,278,941 B2 | 10/2012 | Kroh et al. |
| 8,282,671 B2 | 10/2012 | Connor |
| 8,287,540 B2 | 10/2012 | LeCronier et al. |
| 8,298,133 B2 | 10/2012 | Wiley et al. |
| 8,298,240 B2 | 10/2012 | Giger et al. |
| 8,308,779 B2 | 11/2012 | Reiley |
| 8,313,423 B2 | 11/2012 | Forsell |
| 8,316,856 B2 | 11/2012 | Nelson et al. |
| 8,317,761 B2 | 11/2012 | Birk et al. |
| 8,317,802 B1 | 11/2012 | Manzi et al. |
| 8,323,290 B2 | 12/2012 | Metzger et al. |
| 8,326,435 B2 | 12/2012 | Stevenson |
| 8,328,807 B2 | 12/2012 | Brigido |
| 8,328,854 B2 | 12/2012 | Baynham et al. |
| 8,333,204 B2 | 12/2012 | Saadat |
| 8,333,790 B2 | 12/2012 | Timm et al. |
| 8,353,913 B2 | 1/2013 | Moskowitz et al. |
| 8,357,169 B2 | 1/2013 | Henniges et al. |
| 8,357,182 B2 | 1/2013 | Seme |
| 8,357,183 B2 | 1/2013 | Seme et al. |
| 8,360,955 B2 | 1/2013 | Sayet et al. |
| 8,366,628 B2 | 2/2013 | Denker et al. |
| 8,372,078 B2 | 2/2013 | Collazo |
| 8,382,652 B2 | 2/2013 | Sayet et al. |
| 8,386,018 B2 | 2/2013 | Stauch et al. |
| 8,388,667 B2 | 3/2013 | Reiley et al. |
| 8,394,124 B2 | 3/2013 | Biyani |
| 8,394,143 B2 | 3/2013 | Grotz et al. |
| 8,403,958 B2 | 3/2013 | Schwab |
| 8,409,203 B2 | 4/2013 | Birk et al. |
| 8,409,281 B2 | 4/2013 | Makower et al. |
| 8,414,584 B2 | 4/2013 | Brigido |
| 8,414,648 B2 | 4/2013 | Reiley |
| 8,419,755 B2 | 4/2013 | Deem et al. |
| 8,419,801 B2 | 4/2013 | DiSilvestro et al. |
| 8,425,570 B2 | 4/2013 | Reiley |
| 8,425,608 B2 | 4/2013 | Dewey et al. |
| 8,433,519 B2 | 4/2013 | Ekseth et al. |
| 8,435,268 B2 | 5/2013 | Thompson et al. |
| 8,439,915 B2 | 5/2013 | Harrison et al. |
| 8,439,926 B2 | 5/2013 | Bojarski et al. |
| 8,444,693 B2 | 5/2013 | Reiley |
| 8,449,553 B2 | 5/2013 | Kam et al. |
| 8,449,580 B2 | 5/2013 | Voellmicke et al. |
| 8,454,695 B2 | 6/2013 | Grotz et al. |
| 8,469,908 B2 | 6/2013 | Asfora |
| 8,469,978 B2 | 6/2013 | Fobi et al. |
| 8,470,003 B2 | 6/2013 | Voellmicke et al. |
| 8,470,004 B2 | 6/2013 | Reiley |
| 8,475,354 B2 | 7/2013 | Phillips et al. |
| 8,475,356 B2 | 7/2013 | Feng et al. |
| 8,475,499 B2 | 7/2013 | Cournoyer et al. |
| 8,480,554 B2 | 7/2013 | Phillips et al. |
| 8,480,668 B2 | 7/2013 | Fernandez et al. |
| 8,480,741 B2 | 7/2013 | Grotz et al. |
| 8,486,070 B2 | 7/2013 | Morgan et al. |
| 8,486,076 B2 | 7/2013 | Chavarria et al. |
| 8,486,110 B2 | 7/2013 | Fielding et al. |
| 8,486,113 B2 | 7/2013 | Malek |
| 8,486,147 B2 | 7/2013 | de Villiers et al. |
| 8,491,589 B2 | 7/2013 | Fisher et al. |
| 8,494,805 B2 | 7/2013 | Roche et al. |
| 8,496,662 B2 | 7/2013 | Novak et al. |
| 8,500,810 B2 | 8/2013 | Mastrorio et al. |
| 8,506,517 B2 | 8/2013 | Stergiopulos |
| 8,506,569 B2 | 8/2013 | Keefer et al. |
| 8,517,973 B2 | 8/2013 | Burnett |
| 8,518,062 B2 | 8/2013 | Cole et al. |
| 8,518,086 B2 | 8/2013 | Seme et al. |
| 8,522,790 B2 | 9/2013 | Nelson et al. |
| 8,523,865 B2 | 9/2013 | Reglos et al. |
| 8,523,866 B2 | 9/2013 | Sidebotham et al. |
| 8,523,883 B2 | 9/2013 | Saadat |
| 8,529,474 B2 | 9/2013 | Gupta et al. |
| 8,529,606 B2 | 9/2013 | Alamin et al. |
| 8,529,607 B2 | 9/2013 | Alamin et al. |
| 8,529,630 B2 | 9/2013 | Bojarski et al. |
| 8,545,384 B2 | 10/2013 | Forsell |
| 8,545,508 B2 | 10/2013 | Collazo |
| 8,545,814 B2 | 10/2013 | Contag et al. |
| 8,551,092 B2 | 10/2013 | Morgan et al. |
| 8,551,142 B2 | 10/2013 | Altarac et al. |
| 8,551,422 B2 | 10/2013 | Wan et al. |
| 8,556,901 B2 | 10/2013 | Anthony et al. |
| 8,556,911 B2 | 10/2013 | Mehta et al. |
| 8,556,975 B2 | 10/2013 | Ciupik et al. |
| 8,562,653 B2 | 10/2013 | Alamin et al. |
| 8,568,416 B2 | 10/2013 | Schmitz et al. |
| 8,568,457 B2 | 10/2013 | Hunziker |
| 8,574,267 B2 | 11/2013 | Linares |
| 8,579,919 B2 | 11/2013 | Bolduc et al. |
| 8,579,979 B2 | 11/2013 | Edie et al. |
| 8,585,595 B2 | 11/2013 | Heilman |
| 8,585,702 B2 | 11/2013 | Orsak et al. |
| 8,585,738 B2 | 11/2013 | Linares |
| 8,585,740 B1 | 11/2013 | Ross ............... A61B 17/66 606/259 |
| 8,591,549 B2 | 11/2013 | Lange |
| 8,597,362 B2 | 12/2013 | Shenoy et al. |
| 8,613,749 B2 | 12/2013 | Deem et al. |
| 8,613,758 B2 | 12/2013 | Linares |
| 8,617,212 B2 | 12/2013 | Linares |
| 8,617,220 B2 | 12/2013 | Skaggs |
| 8,617,243 B2 | 12/2013 | Eisermann et al. |
| 8,622,936 B2 | 1/2014 | Schenberger et al. |
| 8,623,036 B2 | 1/2014 | Harrison et al. |
| 8,623,042 B2 | 1/2014 | Roslin et al. |
| 8,623,056 B2 | 1/2014 | Linares |
| 8,632,544 B2 | 1/2014 | Haaja et al. |
| 8,632,547 B2 | 1/2014 | Maxson et al. |
| 8,632,548 B2 | 1/2014 | Soubeiran |
| 8,632,563 B2 | 1/2014 | Nagase et al. |
| 8,632,594 B2 | 1/2014 | Williams et al. |
| 8,636,770 B2 | 1/2014 | Hestad et al. |
| 8,636,771 B2 | 1/2014 | Butler et al. |
| 8,636,802 B2 | 1/2014 | Serhan et al. |
| 8,641,719 B2 | 2/2014 | Gephart et al. |
| 8,641,723 B2 | 2/2014 | Connor |
| 8,652,175 B2 | 2/2014 | Timm et al. |
| 8,657,765 B2 | 2/2014 | Asfora |

(56) References Cited

U.S. PATENT DOCUMENTS

| | | |
|---|---|---|
| 8,657,856 B2 | 2/2014 | Gephart et al. |
| 8,657,885 B2 | 2/2014 | Burnett et al. |
| 8,663,139 B2 | 3/2014 | Asfora |
| 8,663,140 B2 | 3/2014 | Asfora |
| 8,663,285 B2 | 3/2014 | Dall et al. |
| 8,663,287 B2 | 3/2014 | Butler et al. |
| 8,663,338 B2 | 3/2014 | Burnett et al. |
| 8,668,719 B2 | 3/2014 | Alamin et al. |
| 8,673,001 B2 | 3/2014 | Cartledge et al. |
| 8,679,161 B2 | 3/2014 | Malandain et al. |
| 8,690,858 B2 | 4/2014 | Machold et al. |
| 8,707,959 B2 | 4/2014 | Paraschac et al. |
| 8,709,090 B2 | 4/2014 | Makower et al. |
| 8,715,243 B2 | 5/2014 | Uth et al. |
| 8,715,290 B2 | 5/2014 | Fisher et al. |
| 8,721,570 B2 | 5/2014 | Gupta et al. |
| 8,721,643 B2 | 5/2014 | Morgan et al. |
| 8,728,125 B2 | 5/2014 | Bruneau et al. |
| 8,734,318 B2 | 5/2014 | Forsell |
| 8,734,516 B2 | 5/2014 | Moskowitz et al. |
| 8,734,519 B2 | 5/2014 | de Villiers et al. |
| 8,747,444 B2 | 6/2014 | Moskowitz et al. |
| 8,752,552 B2 | 6/2014 | Nelson et al. |
| 8,758,303 B2 | 6/2014 | Uth et al. |
| 8,758,347 B2 | 6/2014 | Weiner et al. |
| 8,758,355 B2 | 6/2014 | Fisher et al. |
| 8,758,372 B2 | 6/2014 | Cartledge et al. |
| 8,762,308 B2 | 6/2014 | Najarian et al. |
| 8,764,713 B2 | 7/2014 | Uth et al. |
| 8,771,272 B2 | 7/2014 | LeCronier et al. |
| 8,777,947 B2 | 7/2014 | Zahrly et al. |
| 8,777,995 B2 | 7/2014 | McClintock et al. |
| 8,781,744 B2 | 7/2014 | Ekseth et al. |
| 8,784,482 B2 | 7/2014 | Rahdert et al. |
| 8,790,343 B2 | 7/2014 | McClellan et al. |
| 8,790,380 B2 | 7/2014 | Buttermann |
| 8,790,409 B2 | 7/2014 | Van den Heuvel et al. |
| 8,794,243 B2 | 8/2014 | Deem et al. |
| 8,795,339 B2 | 8/2014 | Boomer et al. |
| 8,801,795 B2 | 8/2014 | Makower et al. |
| 8,808,206 B2 | 8/2014 | Asfora |
| 8,813,727 B2 | 8/2014 | Mcclendon |
| 8,814,869 B2 | 8/2014 | Freid et al. |
| 8,828,058 B2 | 9/2014 | Elsebaie et al. |
| 8,828,087 B2 | 9/2014 | Stone et al. |
| 8,840,623 B2 | 9/2014 | Reiley |
| 8,840,651 B2 | 9/2014 | Reiley |
| 8,845,692 B2 | 9/2014 | Wisnewski |
| 8,845,724 B2 | 9/2014 | Shenoy et al. |
| 8,864,717 B2 | 10/2014 | Conlon et al. |
| 8,864,823 B2 | 10/2014 | Cartledge et al. |
| 8,870,881 B2 | 10/2014 | Rezach et al. |
| 8,870,918 B2 | 10/2014 | Boomer et al. |
| 8,870,959 B2 | 10/2014 | Arnin |
| 8,882,699 B2 | 11/2014 | Burnett |
| 8,882,830 B2 | 11/2014 | Cartledge et al. |
| 8,888,672 B2 | 11/2014 | Phillips et al. |
| 8,888,673 B2 | 11/2014 | Phillips et al. |
| 8,894,663 B2 | 11/2014 | Giger et al. |
| 8,915,915 B2 | 12/2014 | Harrison et al. |
| 8,915,917 B2 | 12/2014 | Doherty et al. |
| 8,920,422 B2 | 12/2014 | Homeier et al. |
| 8,932,247 B2 | 1/2015 | Stergiopulos |
| 8,945,188 B2 | 2/2015 | Rezach et al. |
| 8,945,210 B2 | 2/2015 | Cartledge et al. |
| 8,956,407 B2 | 2/2015 | Macoviak et al. |
| 8,961,386 B2 | 2/2015 | Phillips et al. |
| 8,961,521 B2 | 2/2015 | Keefer et al. |
| 8,961,567 B2 | 2/2015 | Hunziker |
| 8,968,402 B2 | 3/2015 | Myers et al. |
| 8,968,406 B2 | 3/2015 | Arnin |
| 8,986,348 B2 | 3/2015 | Reiley |
| 8,992,527 B2 | 3/2015 | Guichet |
| 9,005,251 B2 | 4/2015 | Heggeness |
| 9,005,293 B2 | 4/2015 | Moskowitz et al. |
| 9,005,298 B2 | 4/2015 | Makower et al. |
| 9,011,491 B2 | 4/2015 | Carl et al. |
| 9,015,057 B2 | 4/2015 | Phillips et al. |
| 9,022,917 B2 | 5/2015 | Kasic et al. |
| 9,028,550 B2 | 5/2015 | Shulock et al. |
| 9,033,957 B2 | 5/2015 | Cadeddu et al. |
| 9,033,988 B2 | 5/2015 | Gephart et al. |
| 9,034,016 B2 | 5/2015 | Panjabi |
| 9,044,218 B2 | 6/2015 | Young |
| 9,060,810 B2 | 6/2015 | Kercher et al. |
| 9,060,844 B2 | 6/2015 | Kagan et al. |
| 9,072,530 B2 | 7/2015 | Mehta et al. |
| 9,072,606 B2 | 7/2015 | Lucas et al. |
| 9,078,703 B2 | 7/2015 | Arnin |
| 9,084,632 B2 | 7/2015 | Orsak et al. |
| 9,089,348 B2 | 7/2015 | Chavarria et al. |
| 9,095,436 B2 | 8/2015 | Boyden et al. |
| 9,095,437 B2 | 8/2015 | Boyden et al. |
| 9,101,422 B2 | 8/2015 | Freid et al. |
| 9,101,427 B2 | 8/2015 | Globerman et al. |
| 9,107,706 B2 | 8/2015 | Alamin et al. |
| 9,113,967 B2 | 8/2015 | Soubeiran |
| 9,114,016 B2 | 8/2015 | Shenoy et al. |
| 9,125,746 B2 | 9/2015 | Clifford et al. |
| 9,138,266 B2 | 9/2015 | Stauch |
| 9,144,482 B2 | 9/2015 | Sayet |
| 9,155,565 B2 | 10/2015 | Boomer et al. |
| 9,161,856 B2 | 10/2015 | Nelson et al. |
| 9,168,071 B2 | 10/2015 | Seme et al. |
| 9,168,076 B2 | 10/2015 | Patty et al. |
| 9,173,681 B2 | 11/2015 | Seme |
| 9,173,715 B2 | 11/2015 | Baumgartner |
| 9,186,158 B2 | 11/2015 | Anthony et al. |
| 9,186,185 B2 | 11/2015 | Hestad et al. |
| 9,198,771 B2 | 12/2015 | Ciupik |
| 9,204,899 B2 | 12/2015 | Buttermann |
| 9,204,908 B2 | 12/2015 | Buttermann |
| 9,220,536 B2 | 12/2015 | Skaggs |
| 9,226,783 B2 | 1/2016 | Brigido |
| 9,242,070 B2 | 1/2016 | Tieu |
| 9,259,243 B2 | 2/2016 | Giger et al. |
| 9,272,159 B2 | 3/2016 | Phillips et al. |
| 9,278,004 B2 | 3/2016 | Shenoy et al. |
| 9,278,046 B2 | 3/2016 | Asfora |
| 9,282,997 B2 | 3/2016 | Hunziker |
| 9,301,792 B2 | 4/2016 | Henniges et al. |
| 9,301,854 B2 | 4/2016 | Moskowitz et al. |
| 9,308,089 B2 | 4/2016 | Vicatos et al. |
| 9,308,387 B2 | 4/2016 | Phillips et al. |
| 9,320,618 B2 | 4/2016 | Schmitz et al. |
| 9,326,728 B2 | 5/2016 | Demir et al. |
| 9,333,009 B2 | 5/2016 | Kroll et al. |
| 9,339,197 B2 | 5/2016 | Griswold et al. |
| 9,339,300 B2 | 5/2016 | Kantelhardt |
| 9,339,307 B2 | 5/2016 | McClintock et al. |
| 9,339,312 B2 | 5/2016 | Doherty et al. |
| 9,358,044 B2 | 6/2016 | Seme et al. |
| 9,364,267 B2 | 6/2016 | Northcutt et al. |
| 9,370,388 B2 | 6/2016 | Globerman et al. |
| 9,393,123 B2 | 7/2016 | Lucas et al. |
| 9,408,644 B2 | 8/2016 | Zahrly et al. |
| 9,421,347 B2 | 8/2016 | Burnett |
| 9,427,267 B2 | 8/2016 | Homeier et al. |
| 9,439,744 B2 | 9/2016 | Forsell |
| 9,439,797 B2 | 9/2016 | Baym et al. |
| 9,445,848 B2 | 9/2016 | Anderson et al. |
| 9,451,997 B2 | 9/2016 | Carl et al. |
| 9,456,953 B2 | 10/2016 | Asfora |
| 9,474,612 B2 | 10/2016 | Haaja et al. |
| 9,492,199 B2 | 11/2016 | Orsak et al. |
| 9,492,276 B2 | 11/2016 | Lee et al. |
| 9,498,258 B2 | 11/2016 | Boomer et al. |
| 9,498,366 B2 | 11/2016 | Burnett et al. |
| 9,510,834 B2 | 12/2016 | Burnett et al. |
| 9,532,804 B2 | 1/2017 | Clifford et al. |
| 9,561,062 B2 | 2/2017 | Hayes et al. |
| 9,561,063 B2 | 2/2017 | Reiley |
| 9,572,588 B2 | 2/2017 | Fisher et al. |
| 9,572,746 B2 | 2/2017 | Asfora |

(56) References Cited

U.S. PATENT DOCUMENTS

| | | |
|---|---|---|
| 9,572,910 B2 | 2/2017 | Messersmith et al. |
| 9,579,110 B2 | 2/2017 | Bojarski et al. |
| 9,579,203 B2 | 2/2017 | Soubeiran |
| 9,603,605 B2 | 3/2017 | Collazo |
| 9,603,713 B2 | 3/2017 | Moskowitz et al. |
| 9,610,161 B2 | 4/2017 | Macoviak et al. |
| 9,622,875 B2 | 4/2017 | Moskowitz et al. |
| 9,642,735 B2 | 5/2017 | Burnett |
| 9,655,651 B2 | 5/2017 | Panjabi |
| 9,668,868 B2 | 6/2017 | Shenoy et al. |
| 9,687,243 B2 | 6/2017 | Burnett et al. |
| 9,687,414 B2 | 6/2017 | Asfora |
| 9,693,867 B2 | 7/2017 | Lucas et al. |
| 9,700,419 B2 | 7/2017 | Clifford et al. |
| 9,700,450 B2 | 7/2017 | Burnett |
| 9,717,537 B2 | 8/2017 | Gordon |
| 9,724,135 B2 | 8/2017 | Koch et al. |
| 9,724,265 B2 | 8/2017 | Asfora |
| 9,730,738 B2 | 8/2017 | Gephart et al. |
| 9,743,969 B2 | 8/2017 | Reiley |
| 9,782,206 B2 | 10/2017 | Mueckter et al. |
| 9,795,410 B2 | 10/2017 | Shenoy et al. |
| 9,814,600 B2 | 11/2017 | Shulock et al. |
| 9,820,789 B2 | 11/2017 | Reiley |
| 9,826,987 B2 | 11/2017 | Keefer et al. |
| 9,833,291 B2 | 12/2017 | Baumgartner |
| 9,848,894 B2 | 12/2017 | Burley et al. |
| 9,848,993 B2 | 12/2017 | Moskowitz et al. |
| 9,861,376 B2 | 1/2018 | Chavarria et al. |
| 9,861,390 B2 | 1/2018 | Hunziker |
| 9,861,404 B2 | 1/2018 | Reiley |
| 9,867,719 B2 | 1/2018 | Moskowitz et al. |
| 2001/0011543 A1 | 8/2001 | Forsell |
| 2002/0019580 A1 | 2/2002 | Lau et al. |
| 2002/0050112 A1 | 5/2002 | Koch et al. |
| 2002/0072758 A1 | 6/2002 | Reo et al. |
| 2002/0164905 A1 | 11/2002 | Bryant |
| 2003/0019498 A1 | 1/2003 | Forsell |
| 2003/0040671 A1 | 2/2003 | Somogyi et al. |
| 2003/0066536 A1 | 4/2003 | Forsell |
| 2003/0114731 A1 | 6/2003 | Cadeddu et al. |
| 2003/0187447 A1 | 10/2003 | Ferrante et al. |
| 2003/0208212 A1 | 11/2003 | Cigaina |
| 2003/0220643 A1 | 11/2003 | Ferree |
| 2003/0220644 A1 | 11/2003 | Thelen et al. |
| 2004/0006342 A1 | 1/2004 | Altarac et al. |
| 2004/0011137 A1 | 1/2004 | Hnat et al. |
| 2004/0011365 A1 | 1/2004 | Govari et al. |
| 2004/0019353 A1 | 1/2004 | Freid et al. |
| 2004/0023623 A1 | 2/2004 | Stauch et al. |
| 2004/0055610 A1 | 3/2004 | Forsell |
| 2004/0064030 A1 | 4/2004 | Forsell |
| 2004/0068205 A1 | 4/2004 | Zogbi et al. |
| 2004/0092939 A1 | 5/2004 | Freid et al. |
| 2004/0098121 A1 | 5/2004 | Opolski |
| 2004/0116773 A1 | 6/2004 | Furness et al. |
| 2004/0133219 A1 | 7/2004 | Forsell |
| 2004/0138725 A1 | 7/2004 | Forsell |
| 2004/0147928 A1 | 7/2004 | Landry ............... A61B 90/92 606/264 |
| 2004/0153106 A1 | 8/2004 | Dudai |
| 2004/0158254 A1 | 8/2004 | Eisermann |
| 2004/0172040 A1 | 9/2004 | Heggeness |
| 2004/0173222 A1 | 9/2004 | Kim |
| 2004/0193266 A1 | 9/2004 | Meyer |
| 2004/0220567 A1 | 11/2004 | Eisermann et al. |
| 2004/0220668 A1 | 11/2004 | Eisermann et al. |
| 2004/0230307 A1 | 11/2004 | Eisermann |
| 2004/0250820 A1 | 12/2004 | Forsell |
| 2004/0260287 A1 | 12/2004 | Ferree |
| 2004/0260319 A1 | 12/2004 | Egle |
| 2005/0002984 A1 | 1/2005 | Byrum et al. |
| 2005/0043802 A1 | 2/2005 | Eisermann et al. |
| 2005/0055025 A1 | 3/2005 | Zacouto et al. |
| 2005/0070937 A1 | 3/2005 | Jambor et al. |
| 2005/0080427 A1 | 4/2005 | Govari et al. |
| 2005/0080439 A1 | 4/2005 | Carson et al. |
| 2005/0090823 A1 | 4/2005 | Bartimus |
| 2005/0096750 A1 | 5/2005 | Kagan et al. |
| 2005/0131352 A1 | 6/2005 | Conlon et al. |
| 2005/0159754 A1 | 7/2005 | Odrich |
| 2005/0159755 A1 | 7/2005 | Odrich |
| 2005/0165440 A1 | 7/2005 | Cancel et al. |
| 2005/0171543 A1 | 8/2005 | Timm et al. |
| 2005/0177164 A1 | 8/2005 | Walters et al. |
| 2005/0182400 A1 | 8/2005 | White |
| 2005/0182401 A1 | 8/2005 | Timm et al. |
| 2005/0182412 A1 | 8/2005 | Johnson et al. |
| 2005/0192629 A1 | 9/2005 | Saadat et al. |
| 2005/0222489 A1 | 10/2005 | Rahdert et al. |
| 2005/0234289 A1 | 10/2005 | Anstadt et al. |
| 2005/0234448 A1 | 10/2005 | McCarthy |
| 2005/0234462 A1 | 10/2005 | Hershberger |
| 2005/0246034 A1 | 11/2005 | Soubeiran |
| 2005/0251109 A1 | 11/2005 | Soubeiran |
| 2005/0261779 A1 | 11/2005 | Meyer |
| 2005/0272976 A1 | 12/2005 | Tanaka et al. |
| 2005/0288672 A1 | 12/2005 | Ferree |
| 2006/0020278 A1 | 1/2006 | Burnett et al. |
| 2006/0036251 A1 | 2/2006 | Reiley |
| 2006/0036259 A1 | 2/2006 | Carl et al. |
| 2006/0036323 A1 | 2/2006 | Carl et al. |
| 2006/0036324 A1 | 2/2006 | Sachs et al. |
| 2006/0079897 A1 | 4/2006 | Harrison et al. |
| 2006/0116757 A1 | 6/2006 | Lashinski et al. |
| 2006/0124140 A1 | 6/2006 | Forsell |
| 2006/0136062 A1 | 6/2006 | DiNello et al. |
| 2006/0142634 A1 | 6/2006 | Anstadt et al. |
| 2006/0142767 A1 | 6/2006 | Green et al. |
| 2006/0155279 A1 | 7/2006 | Ogilvie |
| 2006/0155347 A1 | 7/2006 | Forsell |
| 2006/0184240 A1 | 8/2006 | Jimenez et al. |
| 2006/0184248 A1 | 8/2006 | Edidin et al. |
| 2006/0195102 A1 | 8/2006 | Malandain |
| 2006/0204156 A1 | 9/2006 | Takehara et al. |
| 2006/0211909 A1 | 9/2006 | Anstadt et al. |
| 2006/0235299 A1 | 10/2006 | Martinelli |
| 2006/0235424 A1 | 10/2006 | Vitale et al. |
| 2006/0241746 A1 | 10/2006 | Shaoulian et al. |
| 2006/0249914 A1 | 11/2006 | Dulin |
| 2006/0252983 A1 | 11/2006 | Lembo et al. |
| 2006/0271107 A1 | 11/2006 | Harrison et al. |
| 2006/0276812 A1 | 12/2006 | Hill et al. |
| 2006/0282073 A1 | 12/2006 | Simanovsky |
| 2006/0289014 A1 | 12/2006 | Purdy et al. |
| 2006/0293671 A1 | 12/2006 | Heggeness |
| 2006/0293683 A1 | 12/2006 | Stauch |
| 2007/0010814 A1 | 1/2007 | Stauch |
| 2007/0015955 A1 | 1/2007 | Tsonton |
| 2007/0021644 A1 | 1/2007 | Woolson et al. |
| 2007/0031131 A1 | 2/2007 | Griffitts |
| 2007/0043376 A1 | 2/2007 | Leatherbury et al. |
| 2007/0050030 A1 | 3/2007 | Kim |
| 2007/0055237 A1 | 3/2007 | Edidin et al. |
| 2007/0055368 A1 | 3/2007 | Rhee et al. |
| 2007/0118215 A1 | 5/2007 | Moaddeb |
| 2007/0135913 A1 | 6/2007 | Moaddeb et al. |
| 2007/0162032 A1 | 7/2007 | Johnson et al. |
| 2007/0173837 A1 | 7/2007 | Chan et al. |
| 2007/0173869 A1 | 7/2007 | Gannoe et al. |
| 2007/0179493 A1 | 8/2007 | Kim |
| 2007/0213751 A1 | 9/2007 | Scirica et al. |
| 2007/0239159 A1 | 10/2007 | Altarac et al. |
| 2007/0250084 A1 | 10/2007 | Sharkawy et al. |
| 2007/0255088 A1 | 11/2007 | Jacobson et al. |
| 2007/0256693 A1 | 11/2007 | Paraschac et al. |
| 2007/0260270 A1 | 11/2007 | Assell et al. |
| 2007/0264605 A1 | 11/2007 | Belfor et al. |
| 2007/0270631 A1 | 11/2007 | Nelson et al. |
| 2007/0276369 A1 | 11/2007 | Allard et al. |
| 2007/0276372 A1 | 11/2007 | Malandain et al. |
| 2007/0276373 A1 | 11/2007 | Malandain |
| 2007/0276493 A1 | 11/2007 | Malandain et al. |
| 2007/0288024 A1 | 12/2007 | Gollogly |

(56) References Cited

U.S. PATENT DOCUMENTS

| | | |
|---|---|---|
| 2007/0288183 A1 | 12/2007 | Bulkes et al. |
| 2008/0015577 A1 | 1/2008 | Loeb |
| 2008/0021454 A1 | 1/2008 | Chao et al. |
| 2008/0021455 A1 | 1/2008 | Chao et al. |
| 2008/0021456 A1 | 1/2008 | Gupta et al. |
| 2008/0033431 A1 | 2/2008 | Jung et al. |
| 2008/0051784 A1 | 2/2008 | Gollogly |
| 2008/0051895 A1 | 2/2008 | Malandain et al. |
| 2008/0058936 A1 | 3/2008 | Malandain et al. |
| 2008/0058937 A1 | 3/2008 | Malandain et al. |
| 2008/0065077 A1 | 3/2008 | Ferree |
| 2008/0065215 A1 | 3/2008 | Reiley |
| 2008/0066764 A1 | 3/2008 | Paraschac et al. |
| 2008/0071275 A1 | 3/2008 | Ferree |
| 2008/0071276 A1 | 3/2008 | Ferree |
| 2008/0082118 A1 | 4/2008 | Edidin et al. |
| 2008/0082167 A1 | 4/2008 | Edidin et al. |
| 2008/0083413 A1 | 4/2008 | Forsell |
| 2008/0086128 A1 | 4/2008 | Lewis |
| 2008/0091059 A1 | 4/2008 | Machold et al. |
| 2008/0097523 A1 | 4/2008 | Bolduc et al. |
| 2008/0108995 A1 | 5/2008 | Conway et al. |
| 2008/0140188 A1 | 6/2008 | Rahdert et al. |
| 2008/0147139 A1 | 6/2008 | Barrett et al. |
| 2008/0147192 A1 | 6/2008 | Edidin et al. |
| 2008/0161933 A1 | 7/2008 | Grotz et al. |
| 2008/0167685 A1 | 7/2008 | Allard et al. |
| 2008/0172063 A1 | 7/2008 | Taylor |
| 2008/0177319 A1 | 7/2008 | Schwab |
| 2008/0177326 A1 | 7/2008 | Thompson |
| 2008/0195156 A1 | 8/2008 | Ainsworth et al. |
| 2008/0226563 A1 | 9/2008 | Contag et al. |
| 2008/0228186 A1 | 9/2008 | Gall et al. |
| 2008/0255615 A1 | 10/2008 | Vittur et al. |
| 2008/0272928 A1 | 11/2008 | Shuster |
| 2008/0275552 A1 | 11/2008 | Makower et al. |
| 2008/0275555 A1 | 11/2008 | Makower et al. |
| 2008/0275557 A1 | 11/2008 | Makower et al. |
| 2008/0275567 A1 | 11/2008 | Makower et al. |
| 2008/0293995 A1 | 11/2008 | Moaddeb et al. |
| 2009/0076597 A1 | 3/2009 | Dahlgren et al. |
| 2009/0082815 A1 | 3/2009 | Zylber et al. |
| 2009/0088803 A1 | 4/2009 | Justis et al. |
| 2009/0093820 A1 | 4/2009 | Trieu et al. |
| 2009/0093890 A1 | 4/2009 | Gelbart |
| 2009/0112207 A1 | 4/2009 | Walker ............... A61B 17/8004 600/12 |
| 2009/0118699 A1 | 5/2009 | Utley et al. |
| 2009/0171356 A1 | 7/2009 | Klett |
| 2009/0177203 A1 | 7/2009 | Reiley |
| 2009/0182356 A1 | 7/2009 | Coe |
| 2009/0192514 A1 | 7/2009 | Feinberg et al. |
| 2009/0198144 A1 | 8/2009 | Phillips et al. |
| 2009/0204055 A1 | 8/2009 | Lennox et al. |
| 2009/0216113 A1 | 8/2009 | Meier et al. |
| 2009/0216262 A1 | 8/2009 | Burnett et al. |
| 2009/0240173 A1 | 9/2009 | Hsia et al. |
| 2009/0259236 A2 | 10/2009 | Burnett et al. |
| 2009/0270871 A1 | 10/2009 | Liu et al. |
| 2009/0275984 A1 | 11/2009 | Kim et al. |
| 2009/0281575 A1 | 11/2009 | Carls ............... A61B 17/7014 606/151 |
| 2009/0318919 A1 | 12/2009 | Robinson |
| 2010/0004654 A1 | 1/2010 | Schmitz et al. |
| 2010/0030281 A1 | 2/2010 | Gollogly |
| 2010/0057127 A1 | 3/2010 | McGuire et al. |
| 2010/0081868 A1 | 4/2010 | Moaddeb et al. |
| 2010/0100185 A1 | 4/2010 | Trieu et al. |
| 2010/0106192 A1 | 4/2010 | Barry |
| 2010/0106193 A1 | 4/2010 | Barry |
| 2010/0114103 A1 | 5/2010 | Harrison et al. |
| 2010/0121457 A1 | 5/2010 | Clifford et al. |
| 2010/0130941 A1 | 5/2010 | Conlon et al. |
| 2010/0137872 A1 | 6/2010 | Kam et al. |
| 2010/0145449 A1 | 6/2010 | Makower et al. |
| 2010/0145462 A1 | 6/2010 | Ainsworth et al. |
| 2010/0168751 A1 | 7/2010 | Anderson et al. |
| 2010/0179601 A1 | 7/2010 | Jung et al. |
| 2010/0198261 A1 | 8/2010 | Trieu et al. |
| 2010/0228167 A1 | 9/2010 | Ilovich et al. |
| 2010/0241168 A1 | 9/2010 | Franck et al. |
| 2010/0249782 A1 | 9/2010 | Durham |
| 2010/0249839 A1 | 9/2010 | Alamin et al. |
| 2010/0249847 A1 | 9/2010 | Jung et al. |
| 2010/0256626 A1 | 10/2010 | Muller et al. |
| 2010/0274290 A1 | 10/2010 | Jung et al. |
| 2010/0286730 A1 | 11/2010 | Gordon |
| 2010/0286791 A1 | 11/2010 | Goldsmith |
| 2010/0318129 A1 | 12/2010 | Seme et al. |
| 2010/0324684 A1 | 12/2010 | Eisermann et al. |
| 2010/0331883 A1 | 12/2010 | Schmitz et al. |
| 2011/0004076 A1 | 1/2011 | Janna et al. |
| 2011/0057756 A1 | 3/2011 | Marinescu et al. |
| 2011/0060422 A1 | 3/2011 | Makower et al. |
| 2011/0098748 A1 | 4/2011 | Jangra |
| 2011/0130702 A1 | 6/2011 | Stergiopulos |
| 2011/0184505 A1 | 7/2011 | Sharkawy et al. |
| 2011/0196371 A1 | 8/2011 | Forsell |
| 2011/0196435 A1 | 8/2011 | Forsell |
| 2011/0202138 A1 | 8/2011 | Shenoy et al. |
| 2011/0257655 A1 | 10/2011 | Copf, Jr. |
| 2011/0275879 A1 | 11/2011 | Nelson et al. |
| 2011/0284014 A1 | 11/2011 | Cadeddu et al. |
| 2012/0019341 A1 | 1/2012 | Gabay et al. |
| 2012/0019342 A1 | 1/2012 | Gabay et al. |
| 2012/0053633 A1 | 3/2012 | Stauch |
| 2012/0088953 A1 | 4/2012 | King |
| 2012/0089186 A1 | 4/2012 | Carl et al. |
| 2012/0089191 A1 | 4/2012 | Altarac et al. |
| 2012/0109126 A1* | 5/2012 | Steele ............... A61B 17/8875 606/53 |
| 2012/0109207 A1 | 5/2012 | Trieu |
| 2012/0116522 A1 | 5/2012 | Makower et al. |
| 2012/0116535 A1 | 5/2012 | Ratron et al. |
| 2012/0130426 A1 | 5/2012 | Thompson |
| 2012/0136449 A1 | 5/2012 | Makower et al. |
| 2012/0172883 A1 | 7/2012 | Sayago |
| 2012/0179273 A1 | 7/2012 | Clifford et al. |
| 2012/0185040 A1 | 7/2012 | Rahdert et al. |
| 2012/0221101 A1 | 8/2012 | Moaddeb et al. |
| 2012/0271353 A1 | 10/2012 | Barry |
| 2012/0277747 A1 | 11/2012 | Keller |
| 2012/0296234 A1 | 11/2012 | Wilhelm et al. |
| 2012/0312307 A1 | 12/2012 | Paraschac et al. |
| 2013/0013066 A1 | 1/2013 | Landry et al. |
| 2013/0018468 A1 | 1/2013 | Moskowitz et al. |
| 2013/0018469 A1 | 1/2013 | Moskowitz et al. |
| 2013/0023991 A1 | 1/2013 | Moskowitz et al. |
| 2013/0079830 A1 | 3/2013 | Garamszegi et al. |
| 2013/0138017 A1 | 5/2013 | Jundt et al. |
| 2013/0138154 A1 | 5/2013 | Reiley |
| 2013/0150889 A1 | 6/2013 | Fening et al. |
| 2013/0178903 A1 | 7/2013 | Abdou |
| 2013/0197639 A1 | 8/2013 | Clifford et al. |
| 2013/0204266 A1 | 8/2013 | Heilman |
| 2013/0204376 A1 | 8/2013 | DiSilvestro et al. |
| 2013/0238094 A1 | 9/2013 | Voellmicke et al. |
| 2013/0253587 A1 | 9/2013 | Carls et al. |
| 2013/0261623 A1 | 10/2013 | Voellmicke et al. |
| 2013/0261672 A1 | 10/2013 | Horvath |
| 2013/0296863 A1 | 11/2013 | Globerman et al. |
| 2013/0325006 A1 | 12/2013 | Michelinie et al. |
| 2013/0325071 A1 | 12/2013 | Niemiec et al. |
| 2013/0331889 A1 | 12/2013 | Alamin et al. |
| 2013/0345802 A1 | 12/2013 | Cartledge et al. |
| 2014/0018913 A1 | 1/2014 | Cartledge et al. |
| 2014/0031826 A1 | 1/2014 | Bojarski et al. |
| 2014/0031929 A1 | 1/2014 | Cartledge et al. |
| 2014/0039558 A1 | 2/2014 | Alamin et al. |
| 2014/0051914 A1 | 2/2014 | Fobi et al. |
| 2014/0052134 A1 | 2/2014 | Orisek |
| 2014/0058392 A1 | 2/2014 | Mueckter et al. |
| 2014/0058450 A1 | 2/2014 | Arlet |
| 2014/0067075 A1 | 3/2014 | Makower et al. |

(56) References Cited

U.S. PATENT DOCUMENTS

| | | |
|---|---|---|
| 2014/0080203 A1 | 3/2014 | Wan et al. |
| 2014/0107704 A1 | 4/2014 | Serhan et al. |
| 2014/0135838 A1 | 5/2014 | Alamin et al. |
| 2014/0142698 A1 | 5/2014 | Landry et al. |
| 2014/0163664 A1 | 6/2014 | Goldsmith |
| 2014/0172097 A1 | 6/2014 | Clifford et al. |
| 2014/0194932 A1 | 7/2014 | Bruneau et al. |
| 2014/0222138 A1 | 8/2014 | Machold et al. |
| 2014/0296918 A1 | 10/2014 | Fening et al. |
| 2014/0303539 A1 | 10/2014 | Baym et al. |
| 2014/0303540 A1 | 10/2014 | Baym et al. |
| 2014/0336756 A1 | 11/2014 | Lee et al. |
| 2014/0358150 A1 | 12/2014 | Kaufman et al. |
| 2015/0013687 A1 | 1/2015 | Paraschac et al. |
| 2015/0057490 A1 | 2/2015 | Forsell |
| 2015/0073565 A1 | 3/2015 | Nelson et al. |
| 2015/0105782 A1 | 4/2015 | D'Lima et al. |
| 2015/0105824 A1 | 4/2015 | Moskowitz et al. |
| 2015/0132174 A1 | 5/2015 | Marinescu et al. |
| 2015/0134007 A1 | 5/2015 | Alamin et al. |
| 2015/0142110 A1 | 5/2015 | Myers et al. |
| 2015/0150561 A1 | 6/2015 | Burnett et al. |
| 2015/0272600 A1 | 10/2015 | Mehta et al. |
| 2015/0313649 A1 | 11/2015 | Alamin et al. |
| 2016/0022316 A1 | 1/2016 | Agarwal |
| 2017/0172624 A1* | 6/2017 | Brunner ............ A61B 17/7225 |
| 2019/0239927 A1 | 8/2019 | Wentz et al. |

FOREIGN PATENT DOCUMENTS

| | | |
|---|---|---|
| DE | 1541262 | 6/1969 |
| DE | 8515687 | 12/1985 |
| DE | 68515687.6 | 12/1985 |
| DE | 19626230 | 1/1998 |
| DE | 19751733 | 12/1998 |
| DE | 19745654 | 4/1999 |
| DE | 102005045070 | 4/2007 |
| DE | 102007053362 | 5/2009 |
| EP | 0663184 | 7/1995 |
| EP | 1547549 | 6/2005 |
| EP | 1745765 | 1/2007 |
| EP | 1905388 | 4/2008 |
| FR | 2802406 | 6/2001 |
| FR | 2823663 | 10/2002 |
| FR | 2827756 | 1/2003 |
| FR | 2892617 | 5/2007 |
| FR | 2900563 | 11/2007 |
| FR | 2901991 | 12/2007 |
| FR | 2916622 | 12/2008 |
| FR | 2961386 | 12/2011 |
| GB | 1174814 | 12/1969 |
| HU | 223454 | 4/2002 |
| JP | 05-104022 | 4/1993 |
| JP | 09-056736 | 3/1997 |
| JP | 2001-507608 | 6/2001 |
| JP | 2003-172372 | 6/2003 |
| JP | 2003-530195 | 10/2003 |
| JP | 2007-050339 | 3/2007 |
| WO | WO8604498 | 8/1986 |
| WO | WO8707134 | 12/1987 |
| WO | WO8906940 | 8/1989 |
| WO | WO9601597 | 1/1996 |
| WO | WO9808454 | 3/1998 |
| WO | WO9830163 | 7/1998 |
| WO | WO1998044858 | 10/1998 |
| WO | WO9850309 | 11/1998 |
| WO | WO9903348 | 1/1999 |
| WO | WO9923744 | 5/1999 |
| WO | WO9951160 | 10/1999 |
| WO | WO1999051160 | 10/1999 |
| WO | WO9963907 | 12/1999 |
| WO | WO0000108 | 1/2000 |
| WO | WO0072768 | 12/2000 |
| WO | WO0105463 | 1/2001 |
| WO | WO0112108 | 2/2001 |
| WO | WO0124742 | 4/2001 |
| WO | WO2001024697 | 4/2001 |
| WO | WO0141671 | 6/2001 |
| WO | WO0145485 | 6/2001 |
| WO | WO0145487 | 6/2001 |
| WO | WO0145597 | 6/2001 |
| WO | WO0158390 | 8/2001 |
| WO | WO0167973 | 9/2001 |
| WO | WO0178614 | 10/2001 |
| WO | WO0236975 | 5/2002 |
| WO | WO03059215 | 7/2003 |
| WO | WO2004014245 | 2/2004 |
| WO | WO2004019796 | 3/2004 |
| WO | WO2004021870 | 3/2004 |
| WO | WO2004043280 | 5/2004 |
| WO | WO2005023090 | 3/2005 |
| WO | WO2005072195 | 8/2005 |
| WO | WO2005072664 | 8/2005 |
| WO | WO2005105001 | 11/2005 |
| WO | WO2006019520 | 2/2006 |
| WO | WO2006019521 | 2/2006 |
| WO | WO2006089085 | 8/2006 |
| WO | WO2006090380 | 8/2006 |
| WO | WO2006103071 | 10/2006 |
| WO | WO2006103074 | 10/2006 |
| WO | WO2006105084 | 10/2006 |
| WO | WO2007013059 | 2/2007 |
| WO | WO2007015239 | 2/2007 |
| WO | WO2007025191 | 3/2007 |
| WO | WO2007048012 | 4/2007 |
| WO | WO2007081304 | 7/2007 |
| WO | WO2007118179 | 10/2007 |
| WO | WO2007140180 | 12/2007 |
| WO | WO2007149555 | 12/2007 |
| WO | WO20071144489 | 12/2007 |
| WO | WO2008003952 | 1/2008 |
| WO | WO2008013623 | 1/2008 |
| WO | WO2008015679 | 2/2008 |
| WO | WO2008040880 | 4/2008 |
| WO | WO2008140756 | 11/2008 |
| WO | WO2010017649 | 2/2010 |
| WO | WO2010050891 | 5/2010 |
| WO | WO2010056650 | 5/2010 |
| WO | WO2011018778 | 2/2011 |
| WO | WO2011116158 | 9/2011 |
| WO | WO2013119528 | 8/2013 |
| WO | WO2013181329 | 12/2013 |
| WO | WO2014040013 | 3/2014 |
| WO | WO2011041398 | 4/2015 |
| WO | WO-2015132382 A1 * | 9/2015 ............ A61B 17/60 |

OTHER PUBLICATIONS

Abe, Jun, Kensei Nagata, Mamoru Ariyoshi, and Akio Inoue. "Experimental external fixation combined with percutaneous discectomy in the management of scoliosis." Spine 24, No. 7 (1999): 646-653.

Amer, A. R. A. L., and Ashraf A. Khanfour. "Evaluation of treatment of late-onset tibia vara using gradual angulationtranslation high tibial osteotomy." Acta orthopaedica Belgica 76, No. 3 (2010): 360.

Baumgart, Rainer, Stefan Hinterwimmer, Michael Krammer, Oliver Muensterer, and Wolf Mutschler. "The bioexpandable prosthesis: a new perspective after resection of malignant bone tumors in children." Journal of pediatric hematology/oncology 27, No. 8 (2005): 452-455.

Baumgart, R., P. Thaller, S. Hinterwimmer, M. Krammer, T. Hierl, and W. Mutschler. "A fully implantable, programmable distraction nail (Fitbone)—new perspectives for corrective and reconstructive limb surgery." In Practice of Intramedullary Locked Nails, pp. 189-198. Springer Berlin Heidelberg, 2006.

Bodó, László, László Hangody, Balázs Borsitzky, György Béres, Gabriella Arató, Péter Nagy, and Gábor K. Ráthonyi. "Development of a tension-adjustable implant for anterior cruciate ligament reconstruction." Eklem Hast Cerrahisi 19, No. 1 (2008): 27-32.

Boudjemline, Younes, Emmanuelle Pineau, Caroline Bonnet, Alix Mollet, Sylvia Abadir, Damien Bonnet, Daniel Sidi, and Gabriella Agnoletti. "Off-label use of an adjustable gastric banding system for

(56) References Cited

OTHER PUBLICATIONS pulmonary artery banding." The Journal of thoracic and cardiovascular surgery 131, No. 5 (2006): 1130-1135.
Brochure-VEPTR II Technique Guide Apr. 2008.
Brochure-VEPTR Patient Guide dated Feb. 2005.
Brown, S. "Single Port Surgery and the Dundee Endocone." SAGES Annual Scientific Sessions, Poster Abstracts (2007): 323-324.
Buchowski, Jacob M., Rishi Bhatnagar, David L. Skaggs, and Paul D. Sponseller. "Temporary internal distraction as an aid to correction of severe scoliosis." The Journal of Bone & Joint Surgery 88, No. 9 (2006): 2035-2041.
Burghardt, R. D., J. E. Herzenberg, S. C. Specht, and D. Paley. "Mechanical failure of the Intramedullary Skeletal Kinetic Distractor in limb lengthening." Journal of Bone & Joint Surgery, British vol. 93, No. 5 (2011): 639-643.
Burke, John Gerard. "Design of a minimally invasive non fusion device for the surgical management of scoliosis in the skeletally immature." Studies in health technology and informatics 123 (2005): 378-384.
Carter, D. R., and W. E. Caler. "A cumulative damage model for bone fracture." Journal of Orthopaedic Research 3, No. 1 (1985): 84-90.
Chapman, Andrew E., George Kiroff, Philip Game, Bruce Foster, Paul O'Brien, John Ham, and Guy J. Maddern. "Laparoscopic adjustable gastric banding in the treatment of obesity: a systematic literature review." Surgery 135, No. 3 (2004): 326-351.
Cole, J. Dean, Daniel Justin, Tagus Kasparis, Derk DeVlught, and Carl Knobloch. "The intramedullary skeletal distractor (ISKD): first clinical results of a new intramedullary nail for lengthening of the femur and tibia." Injury 32 (2001):129-139.
Cole, J., D. Paley, and M. Dahl. "Operative Technique. ISKD. Intramedullary Skeletal Kinetic Distractor. Tibial Surgical Technique." IS-0508 (A)-OPT-US © Orthofix Inc 28 (2005).
Dailey, Hannah L., Charles J. Daly, John G. Galbraith, Michael Cronin, and James A. Harty. "A novel intramedullary nail for micromotion stimulation of tibial fractures." Clinical Biomechanics 27, No. 2 (2012): 182-188.
Daniels, A. U., Patrick Gemperline, Allen R. Grahn, and Harold K. Dunn. "A new method for continuous intraoperative measurement of Harrington rod loading patterns." Annals of biomedical engineering 12, No. 3 (1984): 233-246.
De Giorgi, G., G. Stella, S. Becchetti, G. Martucci, and D. Miscioscia. "Cotrel-Dubousset instrumentation for the treatment of severe scoliosis." European Spine Journal 8, No. 1 (1999): 8-15.
Dorsey, W. O., Bruce S. Miller, Jared P. Tadje, and Cari R. Bryant. "The stability of three commercially available implants used in medial opening wedge high tibial osteotomy." The journal of knee surgery 19, No. 2 (2006): 95-98.
Edeland, H. G., G. Eriksson, and E. Dahlberg. "Instrumentation for distraction by limited surgery in scoliosis treatment." Journal of biomedical engineering 3, No. 2 (1981): 143-146.
Ember, T., and H. Noordeen. "Distraction forces required during growth rod lengthening." Journal of Bone & Joint Surgery, British vol. 88, No. Supp II (2006): 229-229.
Fabry, Hans, Robrecht Van Hee, Leo Hendrickx, and Eric Totté. "A technique for prevention of port adjustable silicone gastric banding." Obesity surgery 12, No. 2 (2002): 285-288.
Fried, M., W. Lechner, and K. Kormanova. "In vivo measurements of different gastric band pressures towards the gastric wall at the stoma region." In Obesity Surgery, vol. 14, No. 7, pp. 914-914. 3100 Bayview Ave, Unit 4, Toronto, Ontario M2N 5L3, Canada: F D-Communications Inc, 2004.
Gao, Xiaochong, Derek Gordon, Dongping Zhang, Richard Browne, Cynthia Helms, Joseph Gillum, Samuel Weber et al. "CHD7 gene polymorphisms are associated with susceptibility to idiopathic scoliosis." The American Journal of Human Genetics 80, No. 5 (2007): 957-965.
Gebhart, M., M. Neel, A. Soubeiran, and J. Dubousset. "Early clinical experience with a custom made growing endoprosthesis in children with malignant bone tumors of the lower extremity actioned by an external permanent magnet: the Phenix M system." In International Society of Limb Salvage 14th International Symposium on Limb Salvage.2007.
Gillespie, R., and J. Obrien. "Harrington instrumentation without fusion." In Journal of Bone and Joint Surgerybritish Volume, vol. 63, No. 3, pp. 461-461. 22 Buckingham Street, London, England WC2N 6ET: British Editorial Soc Bone Joint Surgery, 1981.
Goodship, Allen E., James L. Cunningham, and John Kenwright. "Strain rate and timing of stimulation in mechanical modulation of fracture healing." Clinical orthopaedics and related research 355 (1998): S105-S115.
Grass, P. Jose, A. Valentin Soto, and H. Paula Araya. "Intermittent distracting rod for correction of high neurologic risk congenital scoliosis." Spine 22, No. 16 (1997): 1922-1927.
Gray's Anatomy, http://education.yahoo.com/reference/gray/subjects/subject/128, published Jul. 1, 2007.
Grimer, R., S. Carter, R. Tillman, A. Abudu, and L. Jeys. "Non-Invasive Extendable Endoprostheses for Children-Expensive but Worth It!." Journal of Bone & Joint Surgery, British vol. 93, No. Supp I (2011): 5-5.
Grünert, R. D. "[The development of a totally implantable electronic sphincter]." Langenbecks Archiv fur Chirurgie 325 (1968): 1170-1174.
Guichet, Jean-Marc, Barbara Deromedis, Leo T. Donnan, Giovanni Peretti, Pierre Lascombes, and Flavio Bado. "Gradual femoral lengthening with the Albizzia intramedullary nail." The Journal of Bone & Joint Surgery 85, No. 5 (2003): 838- 848.
Gupta, A., J. Meswania, R. Pollock, S. R. Cannon, T. W. R. Briggs, S. Taylor, and G. Blunn. "Non-invasive distal femoral expandable endoprosthesis for limb-salvage surgery in paediatric tumours." Journal of Bone & Joint Surgery, British vol. 88, No. 5 (2006): 649-654.
Hankemeier S, Gösling T, Pape HC, et al. Limb lengthening with the Intramedullary Skeletal Kinetic Distractor (ISKD) Oper Orthop Traumatol. 2005;17:79-101.
Harrington PR (1962) Treatment of scoliosis. Correction and internal fixation by spine instrumentation. J Bone Joint Surg Am 44-A:591-610.
Hazem Elsebaie, M. D. "Single Growing Rods." Changing the Foundations: Does it affect the Results., J Child Orthop. (2007) 1:258.
Hennig, Alex C.; Incavo, Stephen J.; Beynnon, Bruce D.; Abate, Joseph A.; Urse, John S.; Kelly, Stephen / The safety and efficacy of a new adjustable plate used for proximal tibial opening wedge osteotomy in the treatment of unicompartmental knee osteoarthrosis. In: The journal of knee surgery, vol. 20, No. 1, Jan. 1, 2007, p. 6-14.
Hofmeister, M., C. Hierholzer, and V. Bühren. "Callus Distraction with the Albizzia Nail." In Practice of Intramedullary Locked Nails, pp. 211-215. Springer Berlin Heidelberg, 2006.
Horbach, T., D. Herzog, and I. Knerr. "First experiences with the routine use of the Rapid Port (TM) system with the Lap- Band (R)." In Obesity Surgery, vol. 16, No. 4, pp. 418-418. 3100 Bayview Ave, Unit 4, Toronto, Ontario M2N 5L3, Canada: F D-Communications Inc, 2006.
Hyodo, Akira, Helmuth Kotschi, Helen Kambic, and George Muschler. "Bone transport using intramedullary fixation and a single flexible traction cable." Clinical orthopaedics and related research 325 (1996): 256-268.
Ahlbom, A., U. Bergqvist, J. H. Bernhardt, J. P. Cesarini, M. Grandolfo, M. Hietanen, A. F. Mckinlay et al. "Guidelines for limiting exposure to time-varying electric, magnetic, and electromagnetic fields (up to 300 GHz). International Commission on Non-Ionizing Radiation Protection." Health Phys 74, No. 4 (1998): 494-522.
International Commission on Non-Ionizing Radiation Protection. "Guidelines on limits of exposure to static magnetic fields." Health Physics 96, No. 4 (2009): 504-514.
INVIS®/Lamello Catalog, 2006, Article No. 68906A001 GB.
Kasliwal, Manish K., Justin S. Smith, Adam Kanter, Ching-Jen Chen, Praveen V. Mummaneni, Robert A. Hart, and Christopher I. Shaffrey. "Management of high-grade spondylolisthesis." Neurosurgery Clinics of North America 24, No. 2 (2013): 275-291.

(56) References Cited

OTHER PUBLICATIONS

Kenawey, Mohamed, Christian Krettek, Emmanouil Liodakis, Ulrich Wiebking, and Stefan Hankemeier. "Leg lengthening using intramedullay skeletal kinetic distractor: results of 57 consecutive applications." Injury 42, No. 2 (2011): 150-155.

Kent, Matthew E., Arvind Arora, P. Julian Owen, and Vikas Khanduja. "Assessment and correction of femoral malrotation following intramedullary nailing of the femur." Acta Orthop Belg 76, No. 5 (2010): 580-4.

Klemme, William R., Francis Denis, Robert B. Winter, John W. Lonstein, and Steven E. Koop. "Spinal instrumentation without fusion for progressive scoliosis in young children." Journal of Pediatric Orthopaedics 17, No. 6 (1997): 734-742.

Korenkov, M., S. Sauerland, N. Yücel, L. Köhler, P. Goh, J. Schierholz, and H. Troidl. "Port function after laparoscopic adjustable gastric banding for morbid obesity." Surgical Endoscopy And Other Interventional Techniquesinc 17, No. 7 (2003): 1068-1071.

Krieg, Andreas H., Bernhard M. Speth, and Bruce K. Foster. "Leg lengthening with a motorized nail in adolescents." Clinical orthopaedics and related research 466, No. 1 (2008): 189-197.

Kucukkaya, Metin, Raffi Armagan, and Unal Kuzgun. "The new intramedullary cable bone transport technique." Journal of orthopaedic trauma 23, No. 7 (2009): 531-536.

Lechner, W. L., W. Kirchmayr, and G. Schwab. "In vivo band manometry: a new method in band adjustment." In Obesity Surgery, vol. 15, No. 7, pp. 935-935. 3100 Bayview Ave, Unit 4, Toronto, Ontario M2N 5L3, Canada: F Dcommunicationsinc, 2005.

Lechner, W., M. Gadenstatter, R. Ciovica, W. Kirchmayer, and G. Schwab. "Intra-band manometry for band adjustments: The basics." In Obesity Surgery, vol. 16, No. 4, pp. 417-418. 3100 Bayview Ave, Unit 4, Toronto, Ontario M2N 5L3, Canada: F D-Communications Inc, 2006.

Li, G., S. Berven, N. A. Athanasou, and A. H. R. W. Simpson. "Bone transport over an intramedullary nail: A case report with histologic examination of the regenerated segment." Injury 30, No. 8 (1999): 525-534.

Lonner, Baron S. "Emerging minimally invasive technologies for the management of scoliosis." Orthopedic Clinics of North America 38, No. 3 (2007): 431-440.

Teli, Marco MD. "Measurement of Forces Generated During Distraction of Growing Rods, J." Marco Teli. Journal of Child Orthop 1 (2007): 257-258.

Matthews, Michael Wayne, Harry Conrad Eggleston, Steven D. Pekarek, and Greg Eugene Hilmas. "Magnetically adjustable intraocular lens." Journal of Cataract & Refractive Surgery 29, No. 11 (2003): 2211-2216.

Micromotion "Micro Drive Engineering·General catalogue" pp. 14·24; Jun. 2009.

Mineiro, Jorge, and Stuart L. Weinstein. "Subcutaneous rodding for progressive spinal curvatures: early results." Journal of Pediatric Orthopaedics 22, No. 3 (2002): 290-295.

Moe, John H., Khalil Kharrat, Robert B. Winter, and John L. Cummine. "Harrington instrumentation without fusion plus external orthotic support for the treatment of difficult curvature problems in young children." Clinical orthopaedics and related research 185 (1984): 35-45.

Montague, R. G., C. M. Bingham, and K. Atallah. "Magnetic gear dynamics for servo control." In Melecon 2010-2010 15th IEEE Mediterranean Electrotechnical Conference, pp. 1192-1197. IEEE, 2010.

Montague, Ryan, Chris Bingham, and Kais Atallah. "Servo control of magnetic gears." Mechatronics, IEEE/ASME Transactions on 17, No. 2 (2012): 269-278.

Nachemson, Alf, and Gösta Elfström. "Intravital wireless telemetry of axial forces in Harrington distraction rods in patients with idiopathic scoliosis." The Journal of Bone & Joint Surgery 53, No. 3 (1971): 445-465.

Nachlas, I. William, and Jesse N. Borden. "The cure of experimental scoliosis by directed growth control." The Journal of Bone & Joint Surgery 33, No. 1 (1951): 24-34.

Newton, P. "Fusionless Scoliosis Correction by Anterolateral Tethering . . . Can it Work?." In 39th Annual Scoliosis Research Society Meeting. 2004.

Observations by a third party under Article 115 EPC issued by the European Patent Office dated Feb. 15, 2010 in European Patent Application No. 08805612.2, Applicant: Soubeiran, Arnaud (7 pages).

Oh, Chang-Wug, Hae-Ryong Song, Jae-Young Roh, Jong-Keon Oh, Woo-Kie Min, Hee-Soo Kyung, Joon-Woo Kim, Poong-Taek Kim, and Joo-Chul Ihn. "Bone transport over an intramedullary nail for reconstruction of long bone defects in tibia." Archives of orthopaedic and trauma surgery 128, No. 8 (2008): 801-808.

Ozcivici, Engin, Yen Kim Luu, Ben Adler, Yi-Xian Qin, Janet Rubin, Stefan Judex, and Clinton T. Rubin. "Mechanical signals as anabolic agents in bone." Nature Reviews Rheumatology 6, No. 1 (2010): 50-59.

Patient Guide, VEPTR Vertical Expandable Prosthetic Titanium Rib, Synthes Spine (2005) (23pages).

Piorkowski, James R., Scott J. Ellner, Arun A. Mavanur, and Carlos A. Barba. "Preventing port site inversion in laparoscopic adjustable gastric banding." Surgery for Obesity and Related Diseases 3, No. 2 (2007): 159-161.

Prontes, Isabel, http://wwwehow.com/about_4795793_longest-bone-body.html, published Jun. 12, 2012.

Rathjen, Karl, Megan Wood, Anna McClung, and Zachary Vest. "Clinical and radiographic results after implant removal in idiopathic scoliosis." Spine 32, No. 20 (2007): 2184-2188.

Ren, Christine J., and George A. Fielding. "Laparoscopic adjustable gastric banding: surgical technique." Journal of Laparoendoscopic & Advanced Surgical Techniques 13, No. 4 (2003): 257-263.

Reyes-Sánchez, Alejandro, Luis Miguel Rosales, and Víctor Miramontes. "External fixation for dynamic correction of severe scoliosis." The Spine Journal 5, No. 4 (2005): 418-426.

Rinsky, Lawrence A., James G. Gamble, and Eugene E. Bleck. "Segmental Instrumentation Without Fusion in Children With Progressive Scoliosis." Journal of Pediatric Orthopedics 5, No. 6 (1985): 687-690.

Rode, V., F. Gay, A. J. Baraza, and J. Dargent. "A simple way to adjust bands under radiologic control." In Obesity Surgery, vol. 16, No. 4, pp. 418-418. 3100 Bayview Ave, Unit 4, Toronto, Ontario M2N 5L3, Canada: F Dcommunications Inc, 2006.

Schmerling, M. A., M. A. Wilkov, A. E. Sanders, and J. E. Woosley. "Using the shape recovery of nitinol in the Harrington rod treatment of scoliosis." Journal of biomedical materials research 10, No. 6 (1976): 879-892.

Scott, D. J., S. J. Tang, R. Fernandez, R. Bergs, and J. A. Cadeddu. "Transgastric, transcolonic, and transvaginal cholecystectomy using magnetically anchored instruments." In SAGES Meeting, p. P511. 2007.

Sharke, Paul. "The machinery of life." Mechanical Engineering 126, No. 2 (2004): 30.

Shiha, Anis, Mohamed Alam El-Deen, Abdel Rahman Khalifa, and Mohamed Kenawey. "Ilizarov gradual correction of genu varum deformity in adults." Acta Orthop Belg 75 (2009): 784-91.

Simpson, A. H. W. R., H. Shalaby, and G. Keenan. "Femoral lengthening with the intramedullary skeletal kinetic distractor." Journal of Bone & Joint Surgery, British vol. 91, No. 7 (2009): 955-961.

Smith, John T. "The use of growth-sparing instrumentation in pediatric spinal deformity." Orthopedic Clinics of North America 38, No. 4 (2007): 547-552.

Soubeiran, A., M. Gebhart, L. Miladi, J. Griffet, M. Neel, and J. Dubousset. "The Phenix M System. A Mechanical Fully Implanted Lengthening Device Externally Controllable Through the Skin with a Palm Size Permanent Magnet; Applications to Pediatric Orthopaedics." In 6th European Research Conference in Pediatric Orthopaedics. 2006.

Sun, Zongyang, Katherine L. Rafferty, Mark A. Egbert, and Susan W. Herring. "Masticatory mechanics of a mandibular distraction osteogenesis site: interfragmentary micromovement." Bone 41, No. 2 (2007): 188-196.

Takaso, Masashi, Hideshige Moriya, Hiroshi Kitahara, Shohei Minami, Kazuhisa Takahashi, Keijiro Isobe, Masatsune Yamagata, Yoshinori

(56) References Cited

OTHER PUBLICATIONS

Otsuka, Yoshinori Nakata, and Masatoshi Inoue. "New remote-controlled growing-rod spinal instrumentation possibly applicable for scoliosis in young children." Journal of orthopaedic science 3, No. 6 (1998): 336-340.

Tello, Carlos A. "Harrington instrumentation without arthrodesis and consecutive distraction program for young children with severe spinal deformities. Experience and technical details." The Orthopedic clinics of North America 25, No. 2 (1994): 333-351.

Thaller, Peter Helmut, Julian Fürmetz, Florian Wolf, Thorsten Eilers, and Wolf Mutschler. "Limb lengthening with fully implantable magnetically actuated mechanical nails (PHENIX®)—Preliminary results." Injury 45 (2014): S60-S65.

Thompson, George H., Lawrence G. Lenke, Behrooz A. Akbarnia, Richard E. McCarthy, and Robert M. Campbell. "Early onset scoliosis: future directions." The Journal of Bone & Joint Surgery 89, No. suppl 1 (2007): 163-166.

Thonse, Raghuram, John E. Herzenberg, Shawn C. Standard, and Dror Paley. "Limb lengthening with a fully implantable, telescopic, intramedullary nail." Operative Techniques in Orthopedics 15, No. 4 (2005): 355-362.

Trias, A., P. Bourassa, and M. Massoud. "Dynamic loads experienced in correction of idiopathic scoliosis using two types of Harrington rods." Spine 4, No. 3 (1978): 228-235.

VEPTR II. Vertical Expandable Prosthetic Titanium Rib II, Technique Guide, Systhes Spine (2008) (40 pages).

Verkerke, G. J., Koops H. Schraffordt, R. P. Veth, H. J. Grootenboer, L. J. De Boer, J. Oldhoff, and A. Postma. "Development and test of an extendable endoprosthesis for bone reconstruction in the leg." The International journal of artificial organs 17, No. 3 (1994): 155-162.

Verkerke, G. J., H. Schraffordt Koops, R. P. H. Veth, J. Oldhoff, H. K. L. Nielsen, H. H. Van den Kroonenberg, H. J. Grootenboer, and F. M. Van Krieken. "Design of a lengthening element for a modular femur endoprosthetic system." Proceedings of the Institution of Mechanical Engineers, Part H: Journal of Engineering in Medicine 203, No. 2 (1989): 97-102.

Verkerke, G. J., H. Schraffordt Koops, R. P. H. Veth, H. H. van den Kroonenberg, H. J. Grootenboer, H. K. L. Nielsen, J. Oldhoff, and A. Postma. "An extendable modular endoprosthetic system for bone tumour management in the leg." Journal of biomedical engineering 12, No. 2 (1990): 91-96.

Weiner, Rudolph A., Michael Korenkov, Esther Matzig, Sylvia Weiner, and Woiteck K. Karcz. "Initial clinical experience with telemetrically adjustable gastric banding." Surgical technology international 15 (2005): 63-69.

Wenger, H. L. "Spine Jack Operation in the Correction of Scoliotic Deformity: A Direct Intrathoracic Attack to Straighten the Laterally Bent Spine: Preliminary Report." Archives of Surgery 83, No. 6 (1961): 901-910.

White III, Augustus A., and Manohar M. Panjabi. "The clinical biomechanics of scoliosis." Clinical orthopaedics and related research 118 (1976): 100-112.

Yonnet, Jean-Paul. "Passive magnetic bearings with permanent magnets." Magnetics, IEEE Transactions on 14, No. 5 (1978): 803-805.

Yonnet, Jean-Paul. "A new type of permanent magnet coupling." Magnetics, IEEE Transactions on 17, No. 6 (1981): 2991-2993.

Zheng, Pan, Yousef Haik, Mohammad Kilani, and Ching-Jen Chen. "Force and torque characteristics for magnetically driven blood pump." Journal of Magnetism and Magnetic Materials 241, No. 2 (2002): 292-302.

Angrisani et al., "Lap-Band® Rapid Port™ System: Preliminary results in 21 patients", Obesity Surgery, 2005, p. 936, 15, No. 7.

Stokes et al., "Reducing radiation exposure in early-onset scoliosis surgery patients: Novel use of ultrasonography to measure lengthening in magnetically-controlled growing rods. Prospective validation study and assessment of clinical algorithm", 20th International Meeting on Advanced Spine Techniques, Jul. 11, 2013. Vancouver, Canada. Scoliosis Research Society.

\* cited by examiner

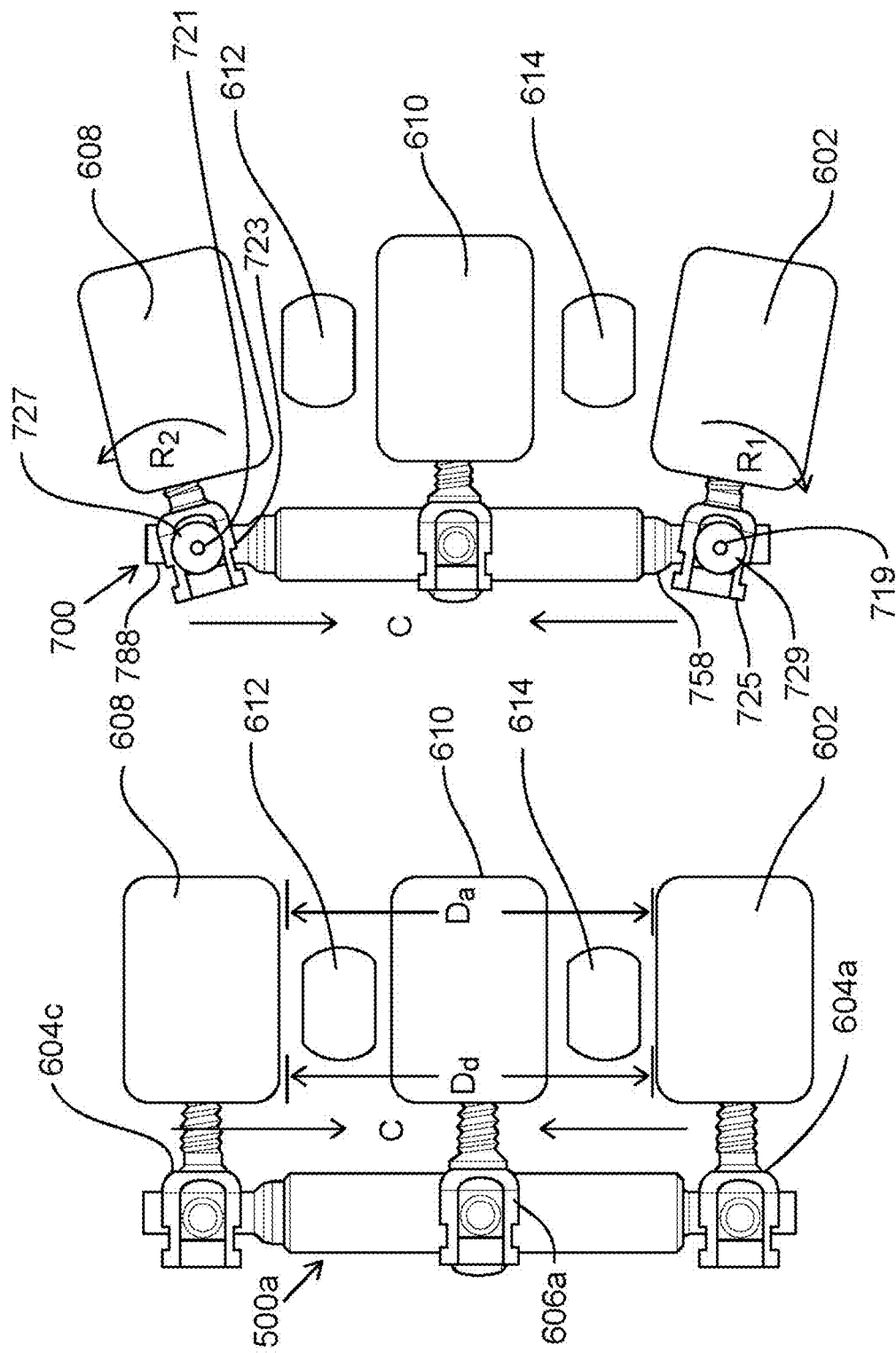

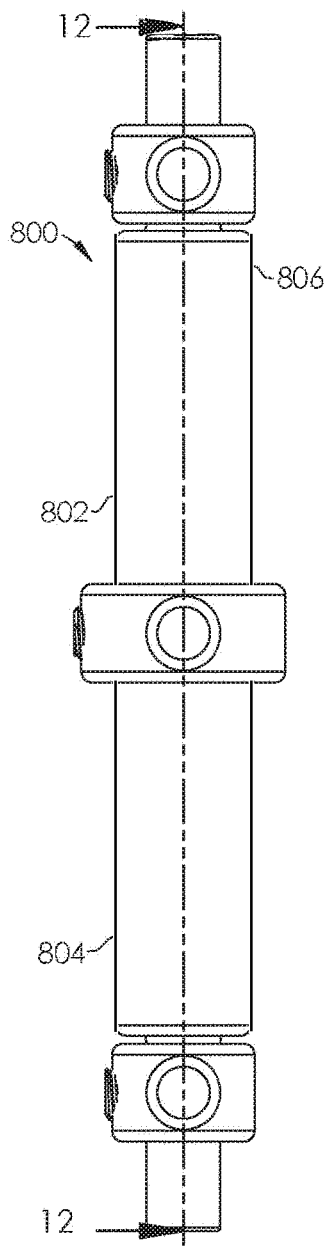
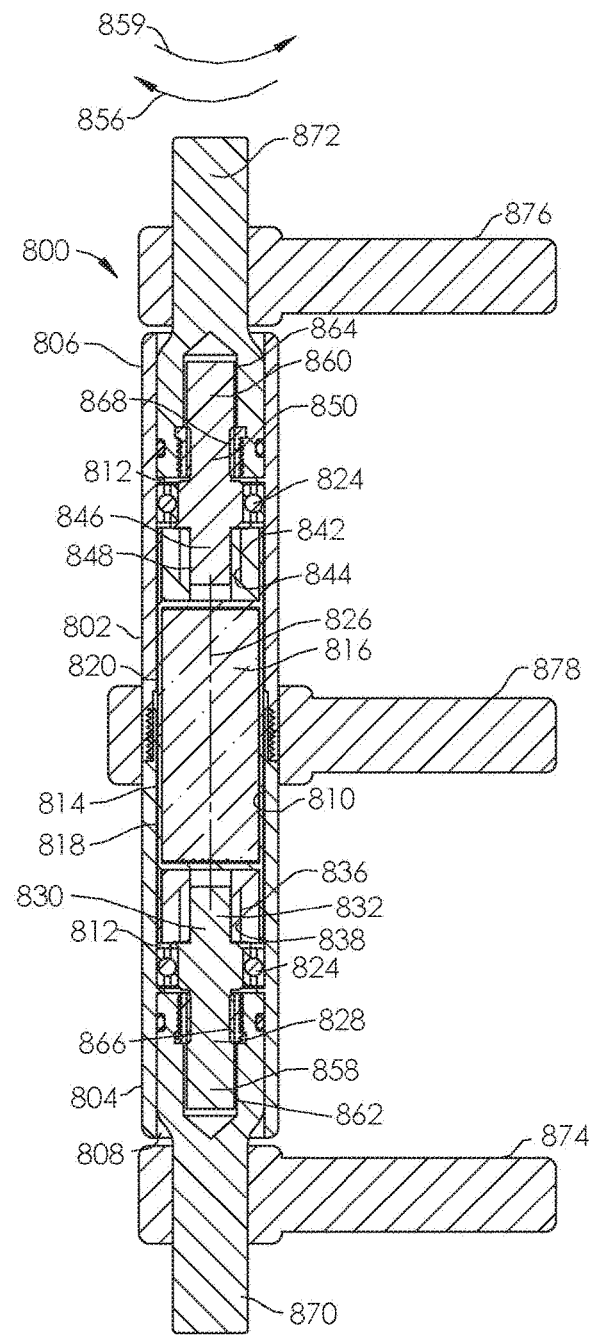
FIG. 11
FIG. 12

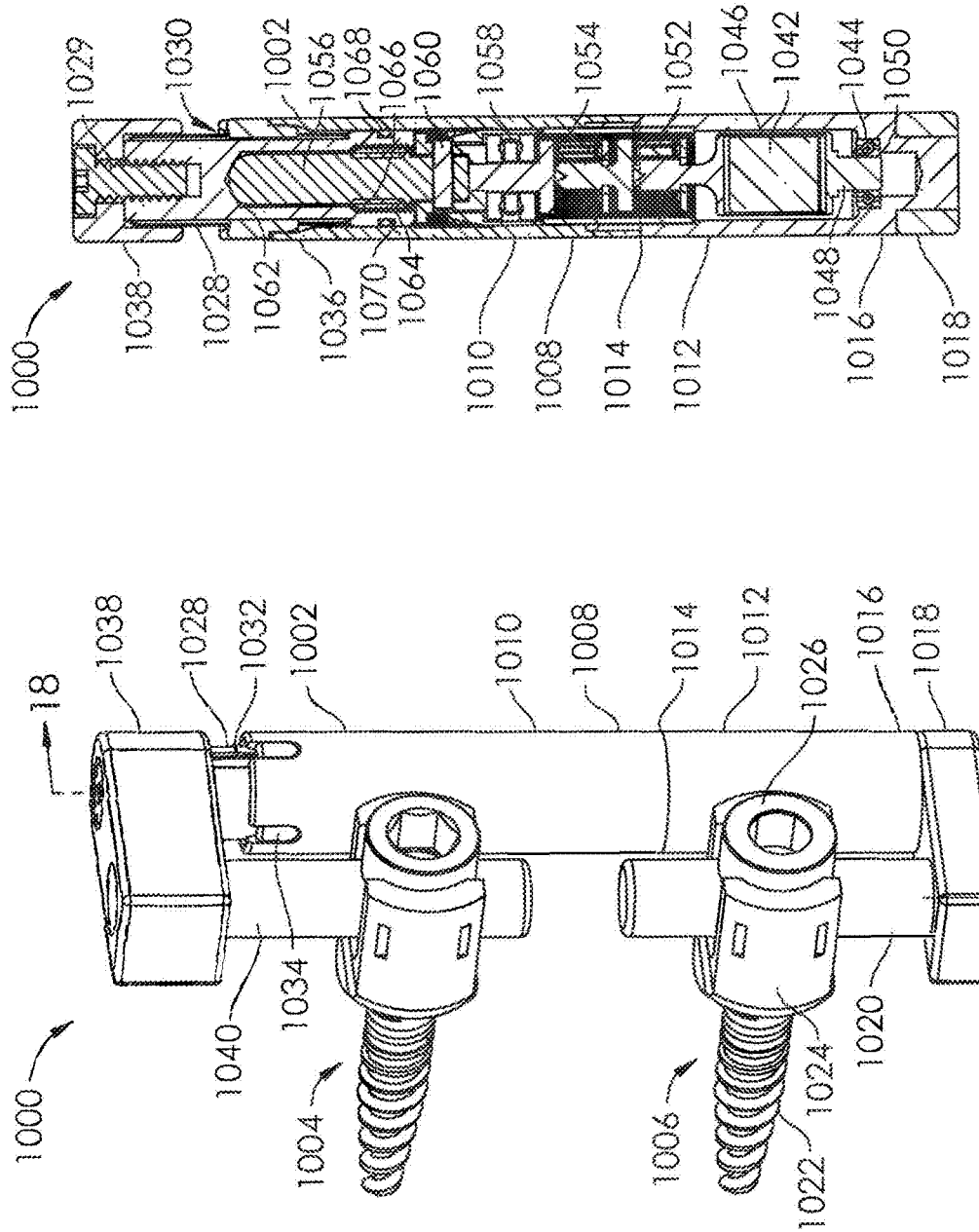

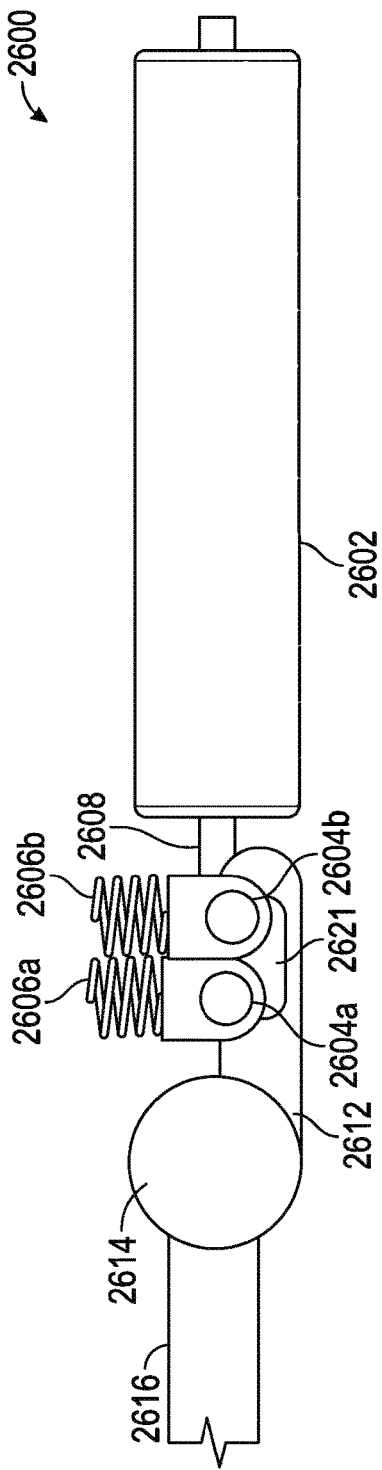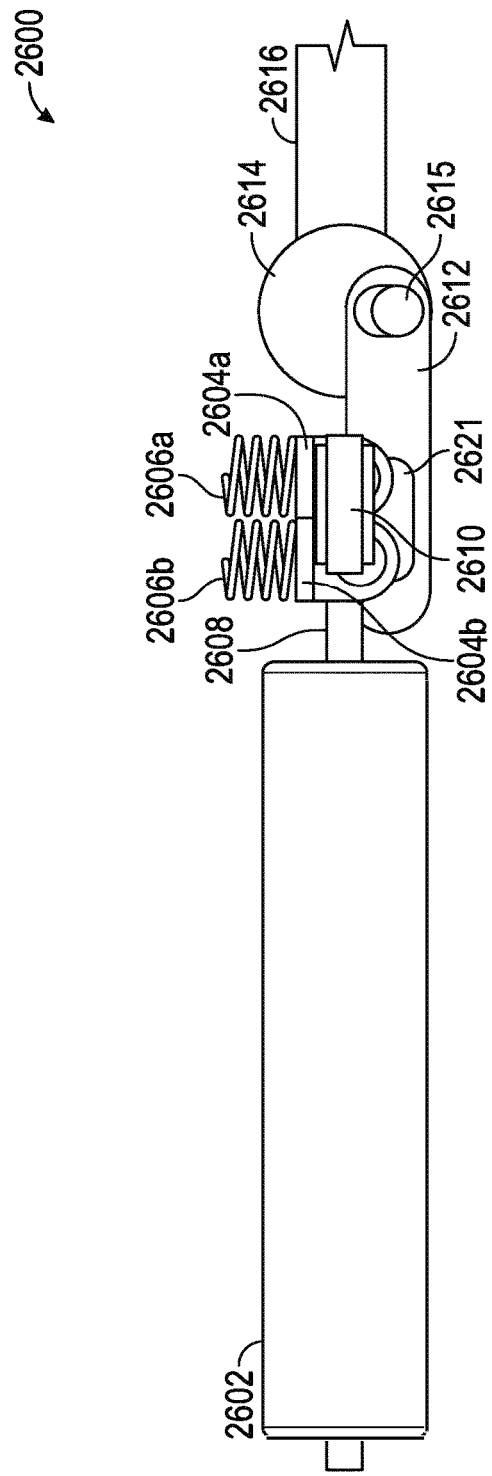
FIG. 26B
FIG. 26C

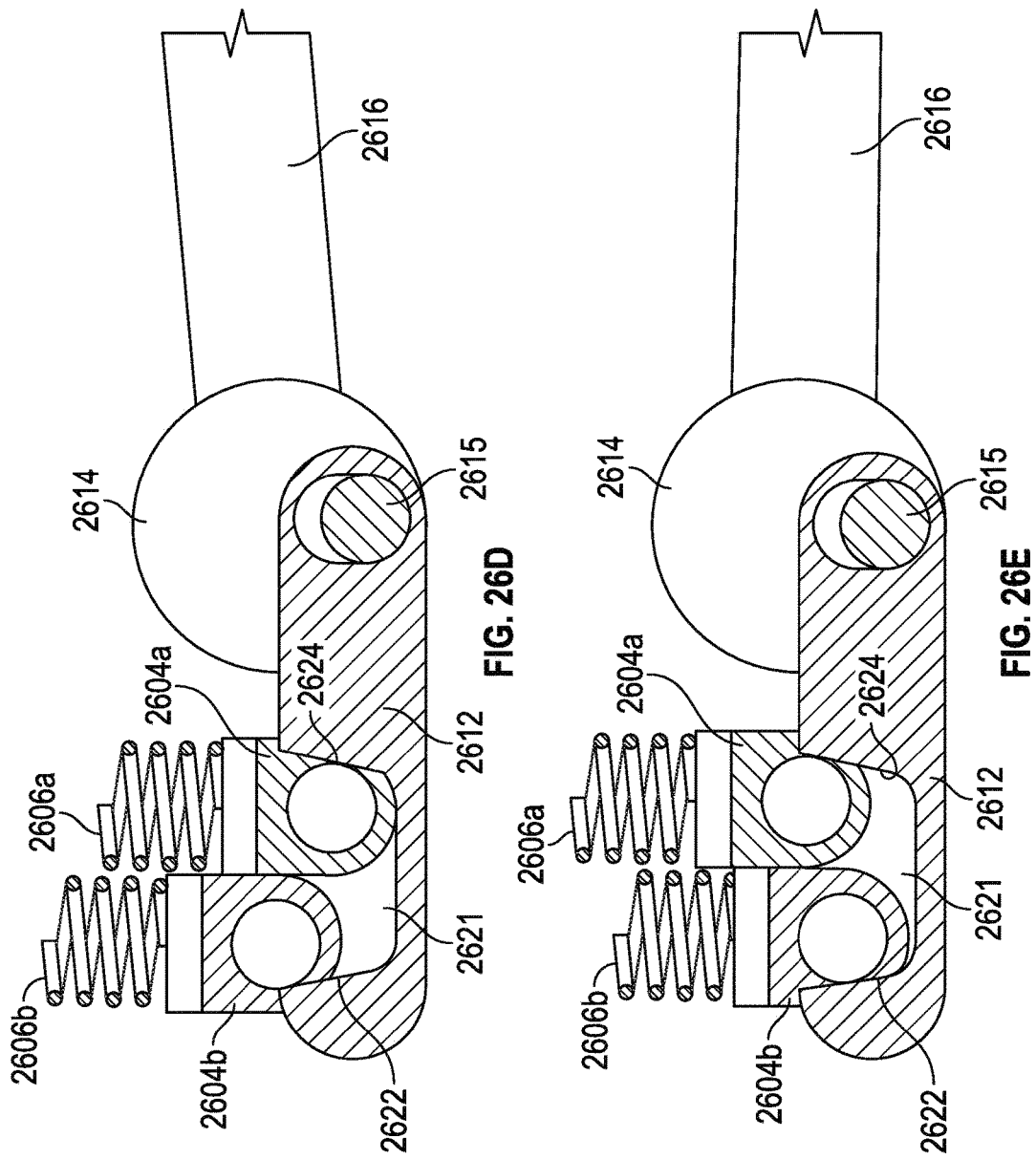

SYSTEMS AND METHODS FOR VERTEBRAL ADJUSTMENT

CROSS REFERENCES TO RELATED APPLICATIONS

The present application is a continuation of U.S. patent application Ser. No. 16/270,976, filed Feb. 8, 2019, which is a continuation of U.S. patent application Ser. No. 15/048,928 (now U.S. Pat. No. 10,238,427), filed Feb. 19, 2016, which claims the benefit of priority of U.S. Provisional Application No. 62/118,411, filed Feb. 19, 2015, the entire contents of which are hereby incorporated by reference into this disclosure as if set forth fully herein.

FIELD

The present disclosure relates to systems and methods for distraction within the human body. In particular, the present invention relates to distraction devices for the adjustment of sagittal curvature in a spine.

BACKGROUND

Degenerative disc disease affects 65 million Americans. Up to 85% of the population over the age of 50 will suffer from back pain each year. Degenerative disc disease is part of the natural process of aging. As people age, their intervertebral discs lose their flexibility, elasticity, and shock absorbing characteristics. The ligaments that surround the disc, known as the annulus fibrosis, become brittle and are more easily torn. At the same time, the soft gel-like center of the disc, known as the nucleus pulposus, starts to dry out and shrink. The combination of damage to the intervertebral discs, the development of bone spurs, and a gradual thickening of the ligaments that support the spine can all contribute to degenerative arthritis of the lumbar spine.

When degenerative disc disease becomes painful or symptomatic, it can cause several different symptoms, including back pain, leg pain, and weakness that are due to compression of the nerve roots. These symptoms are caused by the fact that worn out discs are a source of pain because they do not function as well as they once did, and as they shrink, the space available for the nerve roots also shrinks. As the discs between the intervertebral bodies start to wear out, the entire lumbar spine becomes less flexible. As a result, people complain of back pain and stiffness, especially towards the end of each day.

Depending on its severity and condition, there are many ways to treat degenerative disc disease patients with fusion being the most common surgical option. The estimated number of thoracolumbar fixation procedures in 2009 was 250,000. Surgery for degenerative disc disease often involves removing the damaged disc(s). In some cases, the bone is then permanently joined or fused to protect the spinal cord. There are many different techniques and approaches to a fusion procedure. Some of the most common are Anterior Lumbar Interbody Fusion (ALIF), Posterior Lumbar Interbody Fusion (PLIF), Transforaminal Lumbar Interbody Fusion (TLIF), Direct Lateral Interbody Fusion (DLIF), eXtreme Lateral Interbody Fusion (XLIF) (lateral), etc. Almost all these techniques now involve some sort of interbody fusion device supplemented with posterior fixation (i.e., 360 fusion).

Another spinal malady that commonly affects patients is stenosis of the spine. Stenosis is related to degeneration of the spine and typically presents itself in later life. Spinal stenosis can occur in a variety of ways in the spine. Most cases of stenosis occur in the lumbar region (i.e., lower back) of the spine although stenosis is also common in the cervical region of the spine. Central stenosis is a choking of the central canal that compresses the nerve tissue within the spinal canal. Lateral stenosis occurs due to trapping or compression of nerves after they have left the spinal canal. This can be caused by bony spur protrusions, or bulging or herniated discs.

Non-invasively adjustable devices of the type presented may also be used in patients having scoliosis, spondylolisthesis, Scheuermann's kyphosis, limb length deformity, limb angle deformity, limb rotational deformity, macrognathia, high tibial osteotomy, or other orthopedic deformities.

SUMMARY

The present disclosure provides various systems for non-invasively adjusting the curvature of a spine. One or more embodiments of those systems include a housing having a first end and a second end and a cavity between the first end and the second end, a first rod having a first end telescopically disposed within the cavity of the housing along a first longitudinal axis at the first end of the housing and having a first threaded portion extending thereon, and a second end configured to be coupled to a first portion of a spinal system of a subject, a second rod having a first end telescopically disposed within the cavity of the housing along a second longitudinal axis at the second end of the housing and having a second threaded portion extending thereon, and a second end configured to be coupled to a second portion of the spinal system of the subject, a driving member rotatably disposed within the cavity of the housing and configured to be activated from a location external to the body of the subject, a first interface rotationally coupling a first threaded driver to the driving member, the first threaded driver threadingly engaging the first threaded portion of the first rod, a second interface rotationally coupling a second threaded driver to the driving member, the second threaded driver threadingly engaging the second threaded portion of the second rod, and wherein rotation of the driving member in a first direction causes the first threaded driver to move the first end of the first rod into the cavity of the housing along the first longitudinal axis and causes the second threaded driver to move the first end of the second rod into the cavity of the housing along the second longitudinal axis.

The present disclosure further provides for a method for adjusting the curvature of a spine includes providing a non-invasively adjustable system including a housing having a first end and a second end and a cavity extending between the first end and the second end, a first rod having a first end telescopically disposed within the cavity of the housing along a first longitudinal axis at the first end of the housing and having a first threaded portion extending thereon, and a second end configured to be coupled to a first portion of a spinal system of a subject, a second rod having a first end telescopically disposed within the cavity of the housing along a second longitudinal axis at the second end of the housing and having a second threaded portion extending thereon, and a second end configured to be coupled to a second portion of the spinal system of the subject, a driving member rotatably disposed within the cavity of the housing and configured to be activated from a location external to the body of the subject, a first interface rotationally coupling a first threaded driver to the driving member, the first threaded driver threadingly engaging the first threaded portion of the first rod, and a second interface rotationally coupling a second threaded driver to the driving member, the second threaded driver threadingly engaging the second threaded portion of the second rod, wherein rotation of the driving member in a first direction causes the first threaded driver to move the first end of the first rod into the cavity of the housing along the first longitudinal axis and causes the second threaded driver to move the first end of the second rod into the cavity of the housing along the second longitudinal axis; creating an opening in the skin of a patient as part of a lumbar fusion surgery; coupling the second end of the first rod to a dorsal portion of a first vertebra of the patient; coupling the second end of the second rod to a dorsal portion of a second vertebra of the patient; and closing or causing to close the opening in the skin of the patient.

The present disclosure still further provides for s system for adjusting the curvature of a spine includes a housing having a first end and a second end and a cavity between the first end and the second end, a first rod having a first end telescopically disposed within the cavity of the housing along a first longitudinal axis at the first end of the housing and having a first threaded portion extending thereon, and a second end configured to be coupled to a first portion of a spinal system of a subject, a second rod having a first end telescopically disposed within the cavity of the housing along a second longitudinal axis at the second end of the housing and having a second threaded portion extending thereon, and a second end configured to be coupled to a second portion of the spinal system of the subject, a driving member rotatably disposed within the cavity of the housing and configured to be activated from a location external to the body of the subject, a first interface rotationally coupling a first threaded driver to the driving member, the first threaded driver threadingly engaging the first threaded portion of the first rod, a second interface rotationally coupling a second threaded driver to the driving member, the second threaded driver threadingly engaging the second threaded portion of the second rod, and wherein rotation of the driving member in a first direction causes the first threaded driver to move the first end of the first rod into the cavity of the housing along the first longitudinal axis and rotation of the driving member in a second direction, opposite the first direction, causes the second threaded driver to move the first end of the second rod into the cavity of the housing along the second longitudinal axis.

The present disclosure even further provides for a method for adjusting the curvature of a spine includes providing a non-invasively adjustable system including a housing having a first end and a second end and a cavity extending between the first end and the second end, a first rod having a first end telescopically disposed within the cavity of the housing along a first longitudinal axis at the first end of the housing and having a first threaded portion extending thereon, and a second end configured to be coupled to a first portion of a spinal system of a subject, a second rod having a first end telescopically disposed within the cavity of the housing along a second longitudinal axis at the second end of the housing and having a second threaded portion extending thereon, and a second end configured to be coupled to a second portion of the spinal system of the subject, a driving member rotatably disposed within the cavity of the housing and configured to be activated from a location external to the body of the subject, a first interface rotationally coupling a first threaded driver to the driving member, the first threaded driver threadingly engaging the first threaded portion of the first rod, and a second interface rotationally coupling a second threaded driver to the driving member, the second threaded driver threadingly engaging the second threaded portion of the second rod, wherein rotation of the driving member in a first direction causes the first threaded driver to move the first end of the first rod into the cavity of the housing along the first longitudinal axis and rotation of the driving member in a second direction, opposite the first direction, causes the second threaded driver to move the first end of the second rod into the cavity of the housing along the second longitudinal axis; creating an opening in the skin of a patient as part of a lumbar fusion surgery; coupling the second end of the first rod to a dorsal portion of a first vertebra of the patient; coupling the second end of the second rod to a dorsal portion of a second vertebra of the patient; and closing or causing to close the opening in the skin of the patient.

The present disclosure additionally provides for a system for adjusting the curvature of a spine including a housing having a first end and a second end and a cavity extending therein, a first rod having a first end telescopically disposed within the cavity of the housing along a longitudinal axis at the first end of the housing and having a first threaded portion extending thereon, and a second end configured to be coupled to a first vertebra of a spinal system of a subject, a driving member rotatably disposed within the cavity of the housing and configured to be activated from a location external to the body of the subject, a second rod extending in a direction generally parallel to the longitudinal axis, the second rod having a first end coupled to the housing and a second end configured to be coupled to a second vertebra of the spinal system of the subject, the second vertebra immediately adjacent the first vertebra, and wherein the direction from the first end to the second end of the first rod is generally parallel to the direction from the first end to the second end of the second rod.

BRIEF DESCRIPTION OF THE DRAWINGS

FIG. 8 shows another embodiment of a spinal adjustment implant.

FIG. 9 shows an embodiment of a spinal adjustment implant having a pivotable interface.

FIG. 11 is a side view of the spinal adjustment implant of FIG. 10.

FIG. 12 is a cross-sectional view of the spinal adjustment implant of FIG. 11, taken along line 12-12.

FIG. 17 shows another embodiment of a spinal adjustment implant.

FIGS. 18-19 are sectional views of the implant of FIG. 17, taken along line 18-18.

FIGS. 26A-26H illustrate a motor or magnet is able to intermittently lock o unlock a mechanism, as it is adjusted. In some embodiments, the unlocking may temporarily allow for change in angulation, which is then locked again, after the change occurs.

DETAILED DESCRIPTION

Figure 1:
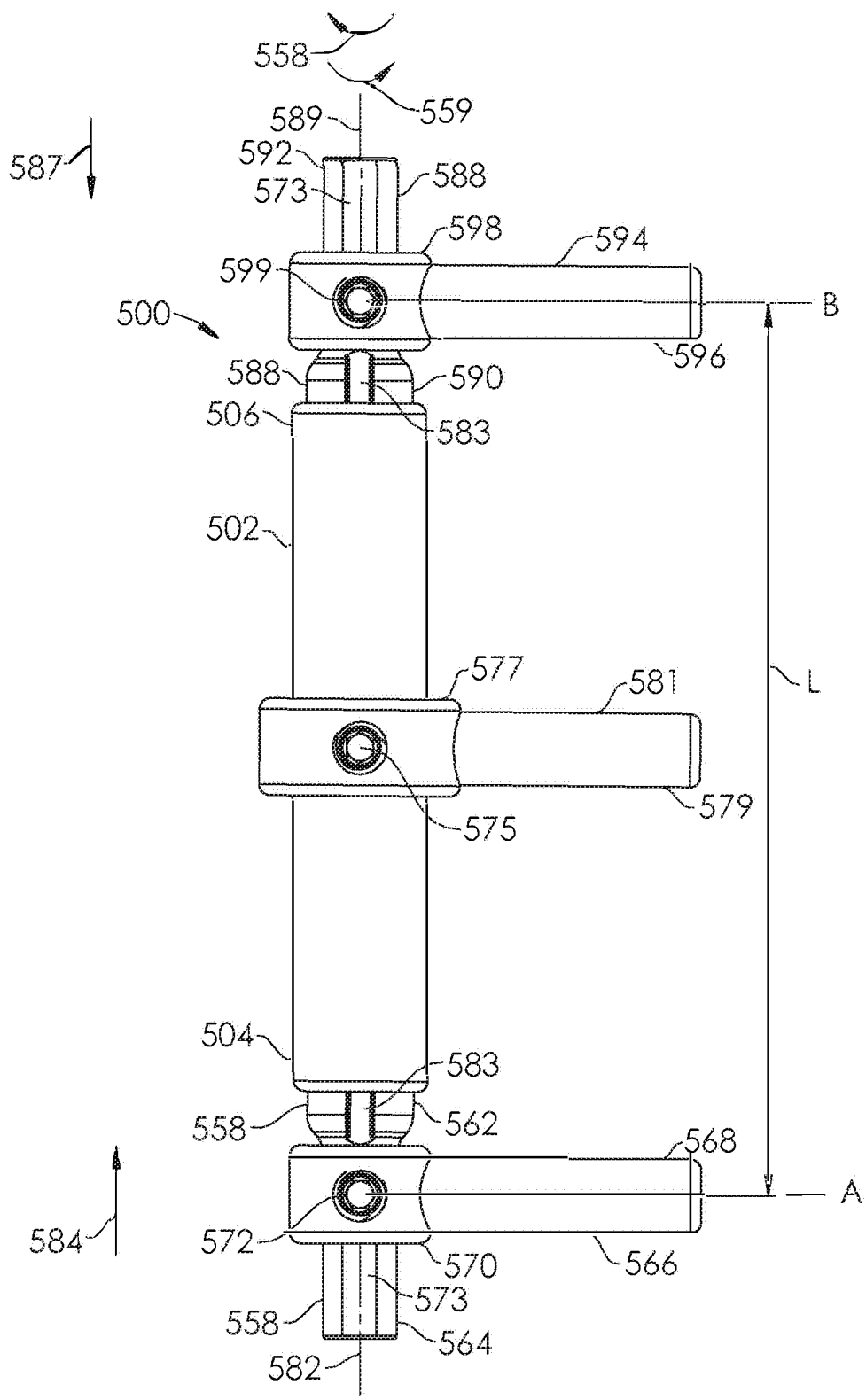
FIG. 1 shows an embodiment of a spinal adjustment implant.
Figure 2:
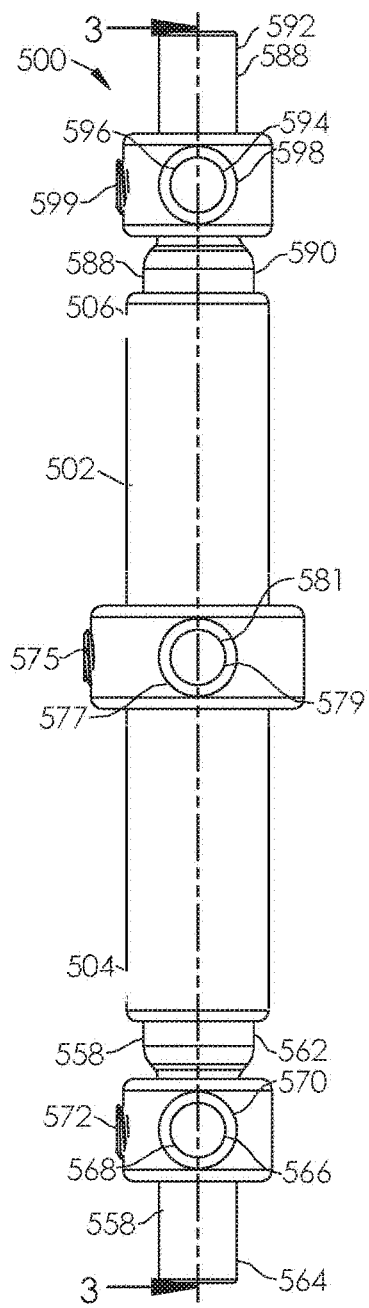
FIG. 2 is a side view of the spinal adjustment implant of FIG. 1.

One or more embodiments of the present invention provide for implantable and adjustable devices that provide fixation and non-invasive adjustment of the sagittal curvature of the spine. Sagittal imbalance can be a negative aftereffect of some spinal fusion surgeries. Patient satisfaction with surgery has been correlated with proper restoration of sagittal balance—patients having a sagittal imbalance have been known to express dissatisfaction with their surgery. Spinal fusion surgeries generally involve at least: adding a bone graft material, e.g., an interbody graft, to at least a portion of the spine (e.g., one of more segments or vertebrae of the spine); precipitating a physiologic response to initiate bone ingrowth (e.g., causing osteogenesis into or from or through the bone graft material); and causing a solid bony fusion to form thereby stopping motion or fusing the portion of the spine being treated. If compression of the interbody graft is not maintained during/after fusion surgery, instability and/or non-union may result. Furthermore, if lumbar lordosis is not maintained during/after fusion surgery, sagittal balance may be compromised, leading to potential muscle fatigue and pain, among other potential consequences. In some cases, the sagittal balance may be sufficiently compromised to merit/require revision surgery. Proximal junctional kyphosis (insufficient lumbar lordosis) is a common reason for repeat surgeries. There is a high incidence of insufficient or lower-than-desired lordosis after lumbar fusion surgery. In fact, it has been estimated that about 12% of spines having adjacent segment pathology (sometimes called "flat back syndrome" or "lumbar flat back syndrome") require repeat, revisionary surgery. Some embodiments of the present invention may be used to non-invasively maintain or change the magnitude of compression between two vertebrae. For example, following a fusion surgery (post-operatively) and/or non-invasively changing the magnitude of lordosis. This may be done to maintain a desired degree of lordosis or to regain a desired degree of lordosis after it has been lost. It may also be done to achieve the desired degree of lordosis when post-surgical studies (e.g., medical imaging) demonstrate that the desired degree of lordosis was not achieved during surgery (e.g., fusion surgery). Some embodiments of the systems and devices disclosed herein can be used to increase the success of fusion, reduce pseudo-arthrosis (e.g., non-union), and/or increase or preserve sagittal balance. "Fine tuning" the magnitude of compression and/or degree of lordosis may allow for reduced symptoms in portions of the spine, such as those adjacent to the fusion.

FIGS. 1-3C illustrate a spinal adjustment implant 500 for implantation along or attachment/coupling to the spinal system of a subject (e.g., one or more vertebrae). In some cases, the subject may be a patient having degenerative disc disease that necessitates fusion of some or all of the lumbar vertebrae through fusion surgery. The spinal adjustment implant 500 can be used in place of traditional rods, which are used to maintain posterior decompression and stabilize during fusion surgery. Some embodiments of the spinal adjustment implant 500 are compatible with interbody spacers placed between the vertebrae being treated.

The spinal adjustment implant 500 includes a housing 502 having a first end 504 and a second end 506. The housing 502 that has a cavity 508 generally defining an inner wall 510 and extending between the first end 504 of the housing 502 and the second end 506 of the housing 502. The cavity 508 may have a variable inner diameter along its length (e.g., the inner diameter of the cavity 508 changes along its length) or may have a generally constant inner diameter. Variable inner diameter cavities 508 may include one or more ledges, steps, abutments, ramps, chamfered or sloped surfaces, and/or radiused or rounded surfaces, which may be used and/or helpful to hold inner components of the spinal adjustment implant 500, as will be discussed in further detail, below. In some embodiments, the inner wall 510 of the housing 502 has circumferential grooves and/or abutments 512 that axially maintain certain elements of the assembly (e.g., internal elements). In some embodiments, the abutments 512 include one or more retaining rings or snap rings.

Figure 3A:
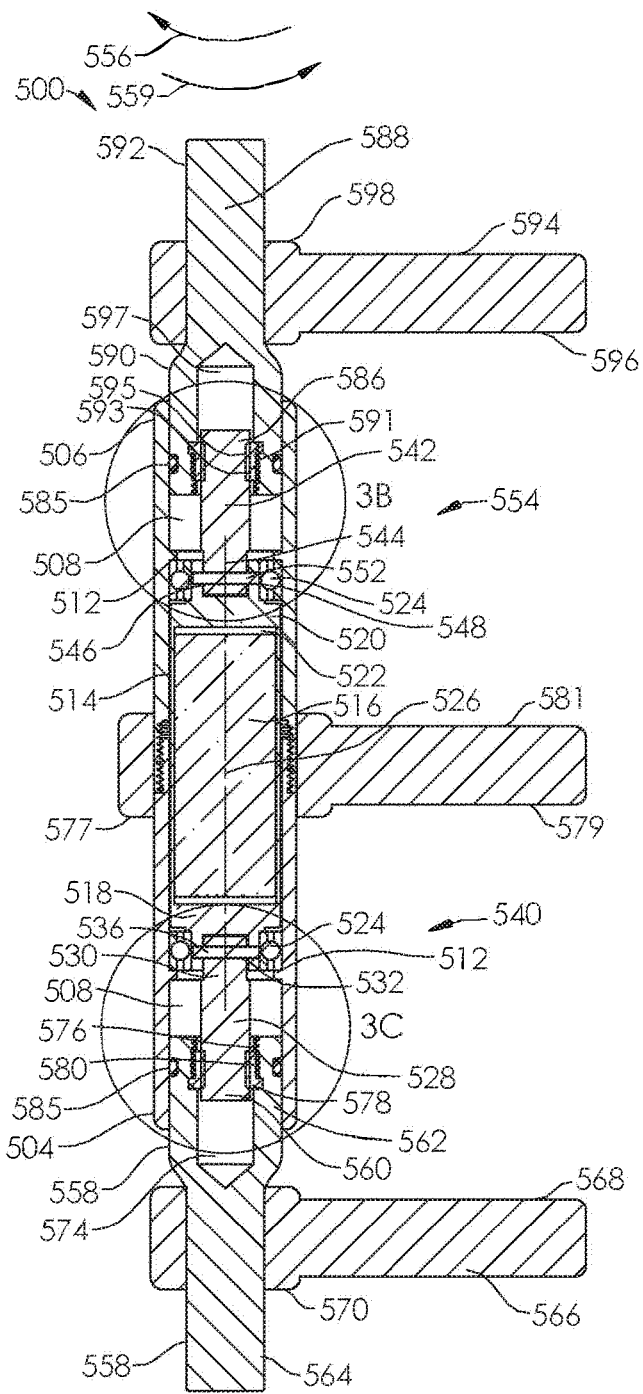
FIG. 3A is a cross-sectional view of the spinal adjustment implant of FIG. 2, taken along line 3-3.

A driving member 514 may be disposed, placed, or located within the cavity 508 (e.g., rotatably disposed). In some embodiments, the driving member 514 includes a non-invasively rotatable element, such as described with respect to FIGS. 20-23. As illustrated in FIG. 3A, the driving member 514 may include a cylindrical, radially-poled permanent magnet 516 secured within a first magnet housing 518 and a second magnet housing 520. The radially-poled permanent magnet may be a cylindrical or partially cylindrical rare earth magnet and may have two poles, four poles, or more. The permanent magnet may be constructed from rare earth magnet materials, such as Neodymium-Iron-Boron (Nd—Fe—B), which have exceptionally high coercive strengths. The individual magnets may be enclosed within a stainless steel casing or various layers of nickel, gold or copper plating to protect the magnet material from the environment inside the body (or vice versa). In certain embodiments, other magnetic materials may be used, including, but not necessarily limited to, $SmCo_5$ (Samarium Cobalt) or AlNiCo (Aluminum Nickel Cobalt). In other embodiments, Iron Platinum (Fe—Pt) magnets may be used. Iron platinum magnets achieve a high level of magnetism without the risk of corrosion, and may possibly preclude the need to encapsulate. In yet other embodiments, the permanent magnet may be replaced by magnetically responsive materials such as Vanadium Permendur (also known as Hiperco).

The first and second magnet housings 518, 520 may, together, provide an internal cavity to hold the cylindrical, radially-poled, permanent magnet 516. In some embodiments, the internal cavity created by the housings 518, 520 is longer than the length of the cylindrical, radially-poled, permanent magnet 516, thus leaving at least some longitudinal space 522. In other embodiments, the internal cavity is substantially the same side as the cylindrical, radially-poled, permanent magnet 516. The first and second magnet housings 518, 520 may be welded or bonded to each other, as well as to the cylindrical, radially-poled, permanent magnet 516. These two design features (i.e., 1. an internal cavity that is longer than the magnet, and 2. a first and second housing that are fixed to each other and/or the magnet) may together serve to limit or eliminate compressive and/or tensile stresses on the cylindrical, radially-poled permanent magnet 516. The first and second magnet housings 518, 520 may be made from robust materials (e.g., titanium alloys) in order to provide strength at a comparatively small wall thickness. Of course, as will be readily understood, any of a number of other materials may be used.

In the embodiment of FIGS. 1-3A, the driving member 514 (e.g., drive system, actuator, motor, driver) is positioned longitudinally between two abutments 512 by two radial bearings 524, which facilitate free rotation of the driving member 514 about a driving member axis 526. In some embodiments, the abutments 512 incorporate a cornered surface, such as, for example, ledges, steps, corners, etc. In other embodiments, the abutments 512 incorporate a flat or curved surface, including, for example, ramps, chamfered or sloped surfaces, and/or radiused or rounded surfaces. In some embodiments, one or more of the radial bearings 524 are replaced by thrust bearings and/or angular bushings. In some embodiments, the bearings comprise stainless steel. In some embodiments, the bearings comprise 400 series stainless steel. In some embodiments, the bearings comprise electro-polished 316 stainless steel, PEEK, or a combination of these. Forming the bearings out of PEEK and/or plating the bearings may increase efficiency by as much as about 50% or up to about 80% or more. Depending on the locations of the abutments 512, the bearings may advantageously serve to minimize axial stresses on one or more portions of the drive train of the spinal adjustment implant 500, including, but not limited to one or more of the radially-poled permanent magnet 516, the housings 518, 520, the lead screw(s) (to be discussed in additional detail, below), the connection(s) between the magnet and the lead screw (i.e., the pin-based connection). Additionally, the bearings generally allow the system to minimize frictional resistance, thereby reducing the amount of torque required to operate the system, or increasing the possible resultant amount of torque/force that can be generated.

Figure 3B:
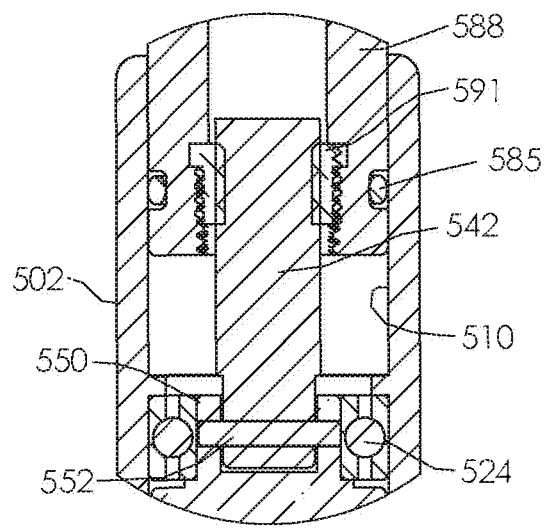
FIGS. 3B and 3C are enlarged views of the spinal adjustment implant of FIG. 3A taken from circles 3 B and 3 C, respectively.
Figure 3C:
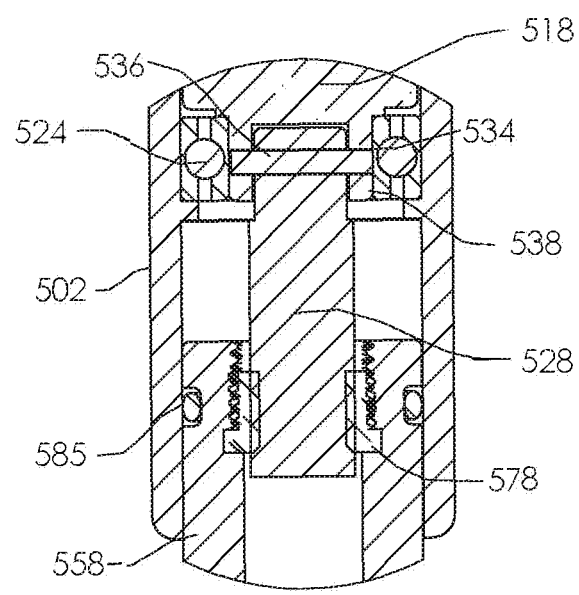

Referring to FIGS. 3A-3C, a first threaded driver 528 (e.g., a lead screw, a screw, a threaded rod, a rotating driver) is connected to the first magnet housing 518 and, therefore, also, the cylindrical, radially-poled permanent magnet 516. In some embodiments the first threaded driver 528 is connected to the first magnet housing 518 using a connection that allows some axial movement, play, or slop between the two (e.g., leaving the two not axially over-constrained). For example, the first threaded driver, 528 may have a hole 532 (e.g., aperture, port, opening) extending substantially horizontally through the first end 530 of the first threaded driver, 528. In much the same way, the first magnet housing 518 may have one or more holes 534 (e.g., aperture, port, opening) extending substantially horizontally therethrough, for example, through an annular projection 538. The hole 532 in the first end 530 may be configured so that it may align with the one or more holes 534 in the annular projection 538. A holder, such as a pin 536 or other fixer, can extend though the one or more holes 534 in the annular projection 538 and the hole 532 in the first end 530 of the first threaded driver, 528, thus creating an interface 540 which rotationally couples the driving member 514 to the first threaded driver 528. In some embodiments, the annular projection 538 and the first end 530 are otherwise rotationally coupled.

In much the same way, a second threaded driver 542 (e.g., a lead screw, a screw, a threaded rod, a rotating driver) is connected to the second magnet housing 520 and, therefore, also, the cylindrical, radially-poled permanent magnet 516. In some embodiments the second threaded driver 542 is connected to the second magnet housing 520 using a connection that allows some axial movement, play, or slop between the two (e.g., leaving the two not axially over-constrained). For example, the second threaded driver 542 may have a hole 546 (e.g., aperture, port, opening) extending substantially horizontally through the first end 544 of the second threaded driver 542. Similarly, the second magnet housing 520 may have one or more holes 548 (e.g., aperture, port, opening) extending substantially horizontally therethrough, for example, through an annular projection 550. The hole 546 in the second end 544 may be configured so that it may align with the one or more holes 548 in the annular projection 550. A holder, such as a pin 552 or other fixer, can extend though the one or more holes 548 in the annular projection 550 and the hole 546 in the first end 544 of the second threaded driver 542, thus creating an interface 554 which rotationally couples the driving member 514 to the second threaded driver 542. In some embodiments, the annular projection 550 and the first end 544 are otherwise rotationally coupled.

In some embodiments, the driving member 514 is directly, mechanically coupled to one or both of the first threaded driver 528 and the second threaded driver 542, such as was described above with respect to the cup and pin structure of the pin and annular flange. However, in other embodiments, the driving member 514 is indirectly coupled to one or both of the first threaded driver 528 and the second threaded driver 542, such as through a gearing system or another type of step down. Gearing systems may advantageously decrease the torque required to generate a given force. In embodiments in which the driving member 514 is directly, mechanically coupled to one or both of the first threaded driver 528 and the second threaded driver 542, rotation of the driving member 514 in first rotational direction 556 causes the rotation of both the first threaded driver 528 and the rotation of the second threaded driver 542 in the same direction, i.e., the first rotational direction 556. In the same way, rotation of the driving member 514 in second rotational direction 559 causes the rotation of both the first threaded driver 528 and the rotation of the second threaded driver 542 in the same direction, i.e., the second rotational direction 559. Though the first and second threaded drivers 528, 542 are illustrated in this embodiment as being screws with male threads, in other embodiments, they may also be hollow rods having internal (female) threads along at least a portion of their length (e.g., all or less than all).

With continued reference to FIGS. 1-3A, the first threaded driver 528 and the second threaded driver 542 may have opposite thread handedness. The first threaded driver 528 may have a right-handed male thread 560. A first rod 558 (e.g., extendible or retractable portion) has a first end 562 telescopically disposed within the cavity 508 of the housing 502, and a second end 564 configured to be coupled to a portion a patient, such as, for example, a portion of the skeletal system. In some embodiments, as illustrated in FIGS. 1-3A, the second end 564 of the first rod 558 is configured to be coupled to a first portion of the skeletal system, such as, but not limited to a first portion of the spinal system (e.g., a first vertebra), via a first extension member 566. The first portion of the spinal system may be a first vertebra. Alternatively, the second end 564 of the first rod 558 may be coupled to a first vertebra directly, via one or more of: a pedicle screw; hook; wire; or other attachment system(s). As shown in FIGS. 1-3A, the first extension member 566 may comprise a rod portion 568 and a base portion 570. The base portion 570 may be secured to the second end 564 of the first rod 558 using a set screw 572 (e.g., by tightening the set screw 572) or other fastener/fastening device. A flat portion 573 may be located on a portion of the first rod 558, in order to provide a surface for interfacing with an end of the set screw 572, for example, to improve resistance to loosening of the set screw 572 with respect to the first rod 558. The rod portion 568 of the first extension member 566 may be coupled to a first vertebra directly, via one or more of: a pedicle screw; hook; wire; or other attachment system(s). As may be seen in FIG. 6A, the first extension member 566 a may extend generally transversely with respect to the housing 502 and/or first rod 558a.

Referring again to FIGS. 1-3A, the first end 562 of the first rod 558 may include a cavity 574 having a first threaded portion 576 incorporating a right-handed female thread 580 configured to mate with the right-handed male thread 560 of the first threaded driver 528. In some embodiments, one of which is shown in FIG. 3C, the cavity 574 comprises a nut 578 bonded or otherwise secured therein. The right-handed male thread 560 of the first threaded driver 528 and the right-handed female thread 580 of the first rod 558 threadingly engage each other such that rotation of the driving member 514 in the first rotational direction 556 causes the first threaded driver 528 to turn in the same first rotational direction 556, thereby causing the first rod 558 to move into the cavity 508 of the housing 502 along a first longitudinal axis 582 (FIG. 1), in a first longitudinal direction 584.

The second threaded driver 542 may comprise a left-handed male thread 586. A second rod 588 (e.g., extendible or retractable portion) has a first end 590 telescopically disposed within the cavity 508 of the housing 502, and a second end 592 configured to be coupled a portion a patient, such as, for example, a portion of the skeletal system. In some embodiments, as illustrated in FIGS. 1-3A, the second end 592 of the second rod 588 is configured to be coupled to a second portion of the spinal system via a second extension member 594. The second portion of the spinal system may be a second vertebra. Alternatively, the second end 592 of the second rod 588 may be coupled to a second vertebra directly, via one or more of: a pedicle screw; hook; wire; or other attachment system. As shown in FIGS. 1-3A, the second extension member 594 may comprise a rod portion 596 and a base portion 598. The base portion 598 may be secured to the second end 592 of the second rod 588 using a set screw 599 (e.g., by tightening the set screw 599).

The rod portion 596 of the second extension member 594 may be coupled to a second vertebra directly, via one of more of: a pedicle screw; hook; wire; or other attachment system. As may be seen in FIG. 6A, the second extension member 594 a may extend in a generally transversely with respect to the housing 502 a and/or second rod 588 a. Referring again to FIGS. 1-3A, the first end 590 of the second rod 588 may include a cavity 597 having a first threaded portion 595 incorporating a left-handed female thread 593. In some embodiments, one of which is shown in FIG. 3B, the cavity 597 comprises a nut 591 bonded or otherwise secured therein. The left-handed male thread 586 of the second threaded driver 542 and the left-handed female thread 593 of the second rod 588 threadingly engage each other such that rotation of the driving member 514 in the first rotational direction 556 causes the second threaded driver 542 to turn in the same first rotational direction 556, thereby causing the second rod 588 to move into the cavity 508 of the housing 502 along a second longitudinal axis 589 (FIG. 1), in a second longitudinal direction 587.

The driving member 514 in combination with the first threaded driver 528 and the second threaded driver 542 may therefore comprise a turnbuckle, such that their rotation in the first rotational direction 556 causes both the first rod 558 and second rod 588 to move into the cavity 508 of the housing 502, thus causing the longitudinal distance L between points A and B to decrease. This motion is capable of generating a force on the spine at the points of attachment and increasing the compressive force(s) between vertebrae. Rotation of the driving member 514, first threaded driver 528 and second threaded driver 542 in a second rotational direction 559, opposite the first rotational direction 556, causes both the first rod 558 and second rod 588 to move out of the cavity 508 of the housing 502, thus causing the longitudinal distance L between points A and B to increase. This motion is capable of generating a force on the spine at the points of attachment and decreasing the compressive force(s) between vertebrae.

In some embodiments, the first threaded driver 528 and the second threaded driver 542 may have the same thread handedness. Both the first threaded driver 528 and the second threaded driver 542 may have a right-handed male thread. Alternatively, both the first threaded driver 528 and the second threaded driver 542 may have a left-handed male thread. As described above, when the first threaded driver 528 and the second threaded driver 542 have opposite thread handedness, rotation of the two in the same direction (such as by rotation of the cylindrical, radially-poled, permanent magnet) will cause the first threaded driver 528 and the second threaded driver 542 to move in opposite directions—depending on the right or left thread handedness, rotation in a first direction will cause both threaded drivers to retract into the housing while rotation in the second, opposite direction will cause both threaded drivers to distract from or extend out of the housing. By contrast, when both the first threaded driver 528 and the second threaded driver 542 have an identical thread handedness (i.e., both right or both left) rotation of the cylindrical, radially-poled, permanent magnet will cause the first and second threaded drivers to move in opposite directions with respect to the housing—depending on the right or left thread handedness, rotation in a first direction will cause the first threaded driver 528 to retract into the housing while causing the second threaded driver 542 to distract from or extend out of the housing (assuming the other or the right or left thread handedness, rotation in the opposite, second direction will cause the first threaded driver 528 to distract from or extend out of the housing while causing the second threaded driver 542 to retract into the housing). As will be discussed in more detail below, a third extension member 581 having a rod portion 579 and a base portion 577 may be reversibly or fixedly coupled to the housing 502. For example, the base portion 577 may be secured to the housing 502 by tightening a set screw 575.

The driving member 514 in combination with the first threaded driver 528 and the second threaded driver 542 may therefore selectively generate a force between two vertebrae (e.g., the vertebrae to which the first extension member 566 and the third extension member 581 are attached) while decreasing the force between the two adjacent vertebrae (e.g., the vertebrae to which the third extension member 581 and the second extension member 594 are attached). In effect, such a system can move a top (or bottom) vertebra closer to a middle vertebra, while moving a bottom (or top) vertebra away from the middle vertebra. Rather than causing motion, this system (as well as any of the other systems disclosed herein) may generate force without causing motion. Though, it is likely that at least some motion will accompany the generation of force, whether it be a distraction force or a compressive force.

To seal the interior contents of the cavity 508 of the housing 502, seals 585, for example, dynamic seals, (shown in FIGS. 3B-3C) may be disposed between each of the first and second rods 558, 588 and the housing 502. The dynamic seals 585 may comprise o-rings, and may be contained within a circumferential groove on either the exterior of the rods 558, 588 or the interior of the housing 502. Of course, many other sealing systems are contemplated, such as but not limited to expandable hydrogel-based systems, bellows or flexible sheaths covering the overlap of the housing and the rod(s), etc.

In some embodiments, one or more of the housing and the rods has an anti-rotation member or a key to prevent rotation of the housing with respect to the rods (and therefore the third extension member 581 with respect to one or both of the first and second extension members 566, 594). For example, in some embodiments, the housing 502 has a protrusion (not shown) configured to engage longitudinal grooves 583 on the rods 558, 588. The protrusion maintains rotational alignment of each of the rods 558, 588 with respect to the housing 502 and allows the rods 558, 588 to move (e.g., extend and extend, retract and retract, extend and retract, or retract and extend) longitudinally with respect to each other while preventing significant rotation with respect to one another. In some embodiments, the anti-rotation member or element prevents substantially all rotational movement of the housing with respect to the rods (or vice versa). In other embodiments, the anti-rotation member or element prevents all rotational movement of the housing with respect to the rods (or vice versa). In still other embodiments, the anti-rotation member or element prevents less than about 10 degrees, less than about 8 degrees, less than about 6 degrees less than about 4 degrees, or less than about 2 degrees of rotational motion of the housing with respect to the rods (or vice versa). Thus, when the spinal adjustment implant 500 is secured to a fusion patient's spine, instrumented portions of the spine can be held static to one another, and substantial movement may only occur when the spinal adjustment implant 500 is adjusted. In some embodiments, substantial fixation of the rotational alignment between each of the rods 558, 588 and the housing 502 is achieved by a member attached at the end of the housing. In other embodiments, substantial fixation of the rotational alignment between each of the rods 558, 588 and the housing 502 is achieved by the rods having non-circular cross-sections (e.g., ovoid, hexagonal, square, a geometric shape, etc.) which are "keyed" to a similarly non-circular cavity (e.g., a mating cavity) within the housing.

The second ends 564, 592 of the first and second rods 558, 588 and the rod portions 568, 596 of the first and second extension members 566, 594 may be sized similar to standard spinal rods. In this way, the second ends 564, 592 of the first and second rods 558, 588 and the rod portions 568, 596 of the first and second extension members 566, 594 may be fixed to the skeletal system or coupled to fixation devices using standard, off-the-shelf orthopedic hardware, such as pedicle screws or otherwise. In some embodiments, the second ends 564, 592 of the first and second rods 558, 588 and the rod portions 568, 596 of the first and second extension members 566, 594 have transverse dimensions, or diameters, in the range of about 3-7 mm, in the range of about 3.5-6.35 mm, greater than about 3.5 mm, greater than about 4.5 mm, or greater than about 5.5 mm. The housing 502 may be coupled to a third portion of the spinal system, for example, a third vertebra via a third extension member 581 having a rod portion 579 and a base portion 577. The base portion 577 may be secured to the housing 502 by tightening a set screw 575. Of course, it will be understood that, while adjustability can be advantageous in some applications, in other applications, any one or more of the first, second, and third extension member may be permanently fixed to the housing and/or the rods (for example, by welding, monolithic formation, or otherwise).

Figure 4:
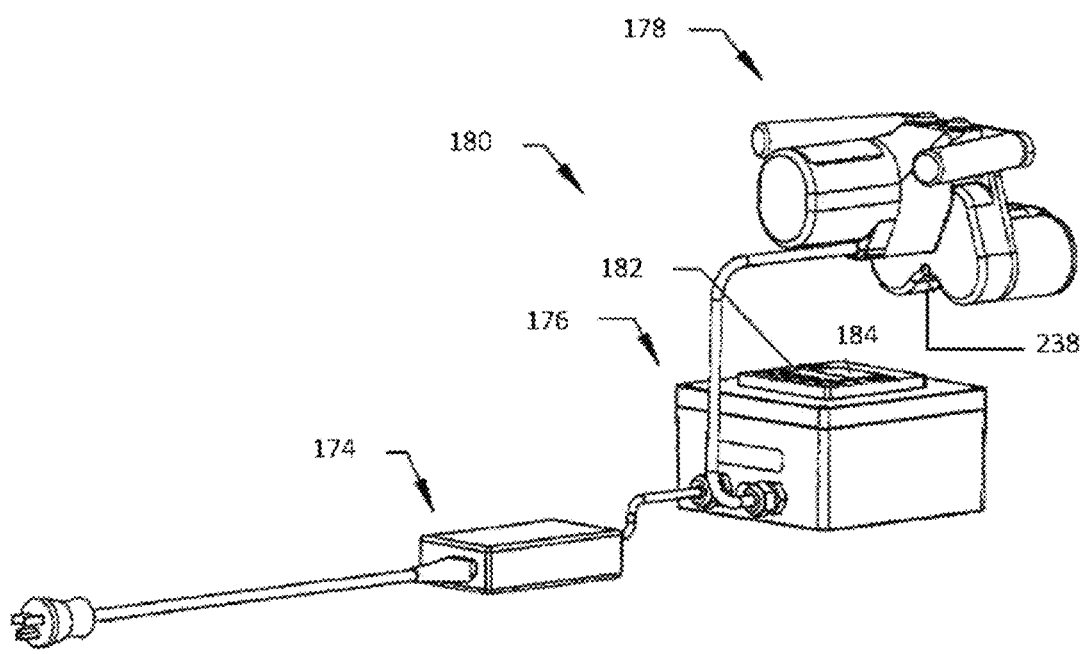
FIG. 4 is an embodiment of an external remote controller for use with an implantable device.

A system incorporating the spinal adjustment implant 500 according to various embodiments of the present invention, may use an External Remote Controller (ERC). FIG. 4 illustrates an example of an External Remote Controller (ERC) 180 which may be used to non-invasively control the spinal adjustment implant 500 by means of a magnetic coupling of torque. ERC 180 comprises a magnetic handpiece 178, a control box 176 (containing a processor) which may be integrated with the handpiece 178 and a power supply 174 such as a battery or external plug for connection to a standard power outlet. The control box 176 includes a control panel 182 having one or more controls (buttons, switches or tactile, motion, audio or light sensors) and a display 184. The display 184 may be visual, auditory, tactile, the like, or some combination of the aforementioned features, or any other display/UI described in this disclosure. The control box 176 may further contain a transceiver for communication with a transceiver in the implant and/or other external devices.

Figure 5:
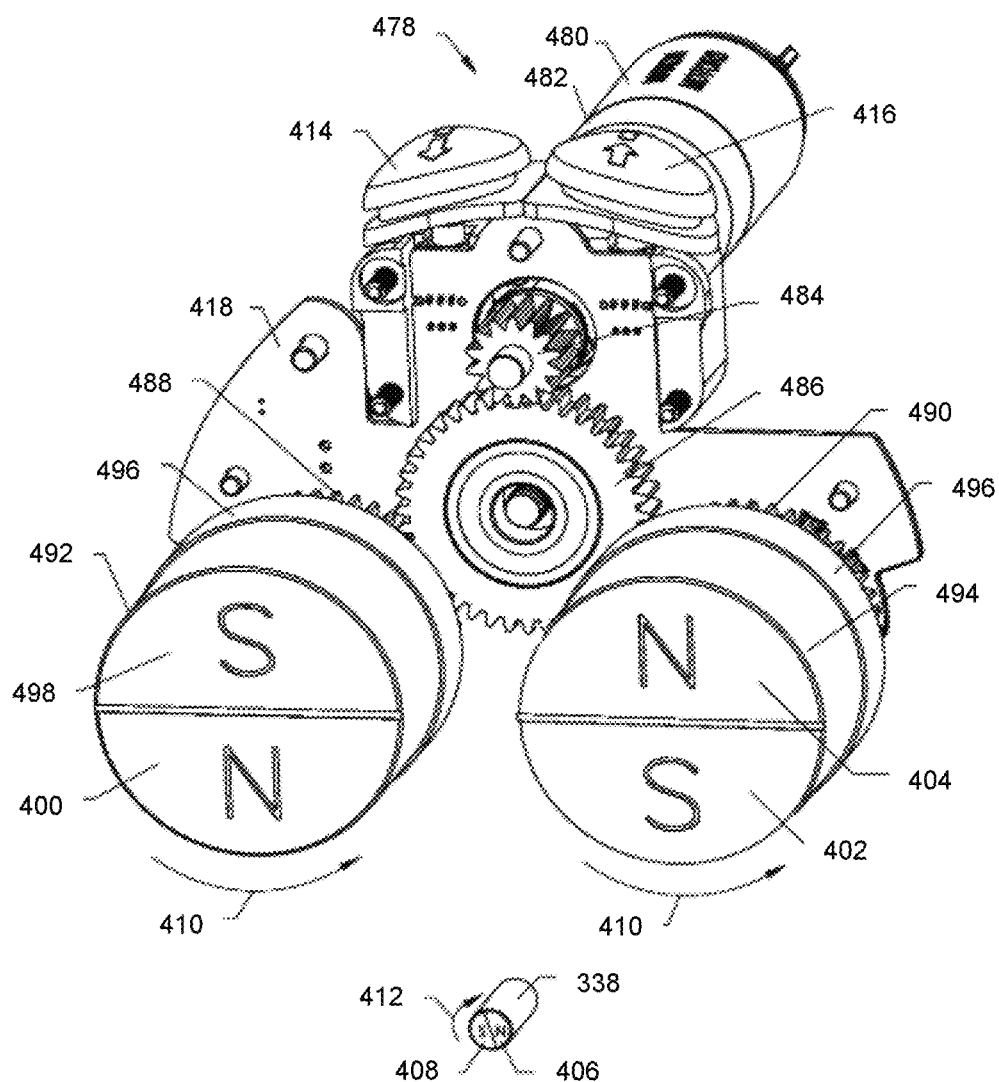
FIG. 5 shows the internal components of a handpiece of the external remote controller of FIG. 4.

FIG. 5 illustrates an internal assembly 478 of the magnetic handpiece 178 configured for applying a moving magnetic field to allow for non-invasive adjustment of the spinal adjustment implant 500 by turning the cylindrical, radially-poled permanent magnet 516 within the spinal adjustment implant 500. The cylindrical, radially-poled permanent magnet 516 of the spinal adjustment implant 500 includes a north pole 406 and a south pole 408. A motor 480 with a gear box 482 outputs to a motor gear 484. The motor gear 484 engages and turns a central (idler) gear 486, which has the appropriate number of teeth to turn first and second magnet gears 488, 490 at identical rotational speeds. First and second magnets 492, 494 turn in unison with the first and second magnet gears 488, 490, respectively. Each magnet 492, 494 is held within a respective magnet cup 496 (shown partially). An exemplary rotational speed is 60 RPM or less. This speed range may be desired in order to limit the amount of current density included in the body tissue and fluids, to meet international guidelines or standards. As seen in FIG. 5, the south pole 498 of the first magnet 492 is oriented the same as the north pole 404 of the second magnet 494, and likewise, the first magnet 492 has its north pole 400 oriented the same and the south pole 402 of the second magnet 494. As these two magnets 492, 494 turn synchronously together, they apply a complementary and additive moving magnetic field to the cylindrical, radially-poled permanent magnet 516. Magnets having multiple north poles (e.g., two or more) and multiple south poles (e.g., two or more) are also contemplated in each of the devices. Alternatively, a single magnet (e.g., a magnet with a larger diameter) may be used in place of the two magnets. As the two magnets 492, 494 turn in a first rotational direction 410 (e.g., counter-clockwise), the magnetic coupling causes the cylindrical, radially-poled permanent magnet 516 to turn in a second, opposite rotational direction 412 (i.e., clockwise). The rotational direction of the motor 480 is controlled by buttons 414, 416. One or more circuit boards 418 contain control circuitry for both sensing rotation of the magnets 492, 494 and controlling the rotation of the magnets 492, 494. Alternatively, one or more electromagnets may be used in place of or in conjunction with the magnets 492, 494.

Figure 6A:
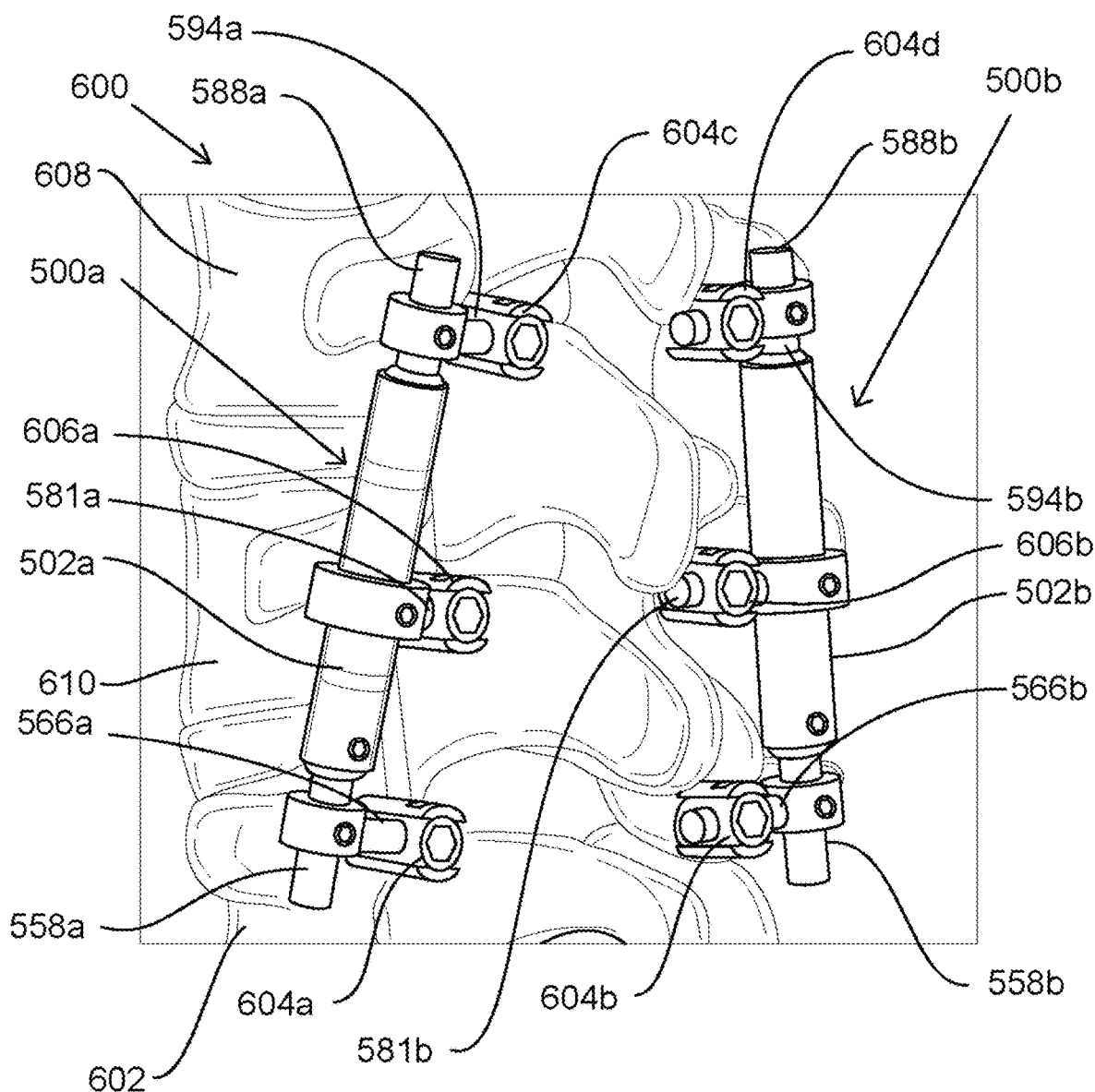
FIGS. 6A-6D show embodiments of spinal adjustment implants, some being coupled to lumbar vertebrae.

Two spinal adjustment implants 500a, 500b coupled bilaterally to three lumbar vertebrae are shown in FIG. 6A. The first spinal adjustment implant 500 and second spinal adjustment implant 500 b may be secured to the spinal system 600 as is described below. The first rod 558 as of the first spinal adjustment implant 500a is secured to the L5 lumbar vertebra 602 by a pedicle screw 604a, while the first rod 558b of the second spinal adjustment implant 500b is secured to the L5 lumbar vertebra 602 by a pedicle screw 604b. The second rod 588a of the first spinal adjustment implant 500a is secured to the L3 lumbar vertebra 608 by a pedicle screw 604c, while the second rod 588b of the second spinal adjustment implant 500b is secured to the L3 lumbar vertebra 608 by a pedicle screw 604d. The first rods 558a, 558b and second rods 588a, 588b may be coupled to the pedicle screws 604a, 604b, 604c, 604d via first and second extension members 566a, 566b, 594a, 594b. The housings 502a, 502b may be secured by pedicle screws 606a, 606b, via third extension members 581a, 581b, to the L4 lumbar vertebra 610. Such securement of the housings 502a, 502 to an intermediary vertebra (L4, 610) between the two vertebrae to be adjusted (L5 and L3, 602, 608) helps assure that the implants 500a, 500b maintain set locations on the spinal system 600 and can serve as reference points to the adjustment of the first rods 558a, 558b and second rods 588a, 588b. Adjusting the spinal adjustment implants 500a, 500b by rotating driving member 514 in the first direction 556 (FIG. 3A) increases compression on and between the L5 lumbar vertebra 602 and L3 lumbar vertebra 608. Increasing compression on implants such as those shown in FIG. 6 may advantageously increase lordosis in the sagittal plane. The spinal adjustment implants 500a, 500b may be secured to the dorsal (posterior) side of the vertebrae 602, 608, 610. In such an implantation configuration, when the implants 500a, 500b decrease in length (causing compression), the dorsal sides of the vertebrae 602, 608, 610 (the locations of pedicle screw insertion) may be brought closer together than the anterior (ventral) sides of the vertebrae 602, 608, 610 (opposite the side of pedicle screw insertion). That differential displacement increases the angle of lordosis.

Figure 6B:
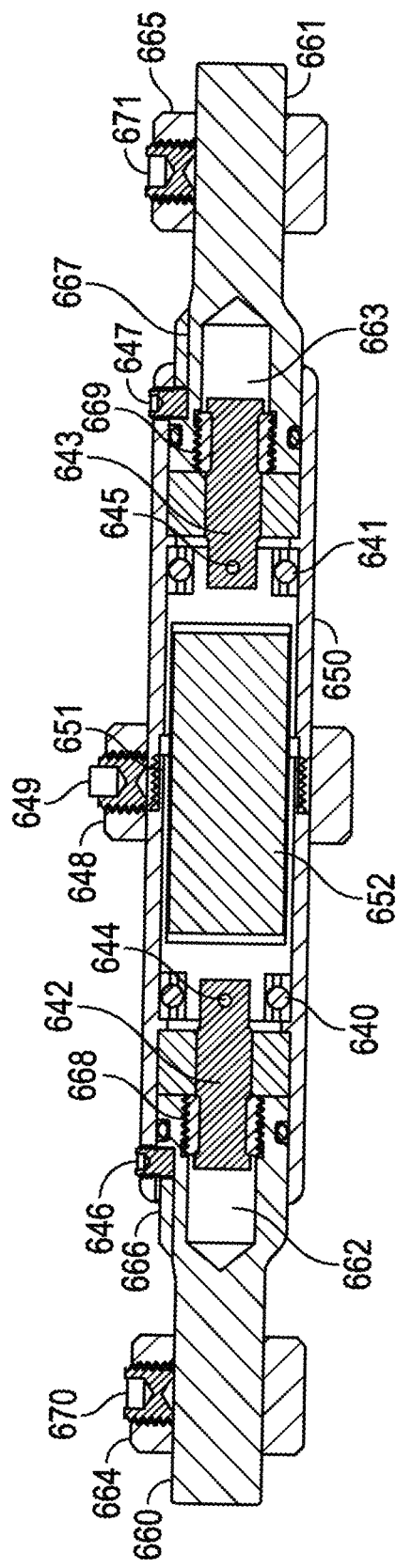

FIG. 6B illustrates an embodiment of an adjustment implant. The implant includes a housing 650. In some embodiments, the housing is formed monolithically. However, in other embodiments, the housing is formed from two halves joined at a joint (e.g., a threaded or welded joint) 651. Using a housing formed from two halves may advantageously ease the manufacturing and assembly process, particularly for parts, such as the thrust bearings, which are held by features of the inner wall of the housing (such as abutments). The implant also includes a first rod 660 and a second rod 661.

The first rod 660 has a proximal end that is at least partially contained within the housing and has a first rod hollow or cavity 662. The proximal portion of the first rod 660 contained within the housing may have a slot, groove, or other linear feature 666 on at least part of its surface. As will be explained below, the slot 666 may serve as a portion of an anti-rotation system. The first rod 660 also has a distal end that extends away from the housing and is used to attach the device to the skeletal system of a patient/subject. In some embodiments, the rod 660 is straight prior to implantation. In other embodiments, the rod 660 is curved prior to implantation. In yet other embodiments, the rod 660 is bendable prior to or during surgery, for example, by an implanting surgeon, so that the rod may best conform to the individual patient into which it is being implanted. The rod may be fixed directly to the patient's skeletal system, for example, using standard pedicle screws. Alternatively, the rod 660 may be attached to the patient's skeletal system using a keyhole extender system that holds the rod 660 some distance away from the skeletal system. The keyhole extender system may include a ring 664 off of which a shaft or bar extends. The ring 664 may be slid up and down the rod 660, thereby improving adjustability. Once the desired position of the ring 664 is identified, it may be reversibly fixed to the rod 660 using a set screw 670.

The proximal end of the first rod 660 has an outer diameter that is just smaller than an inner diameter of the housing 650. In that way, a seal may be formed by using conventional methods, such as o-rings. FIG. 6B shows an annular groove containing an o-ring on an outer surface of the proximal end of the first rod 660. However, it should be understood that a groove for containing an o-ring may be included on the inner surface of the housing.

The housing 650 may be hollow across its entire length. However, while the housing 650 may be hollow, the inner diameter may change across its length. For example, the housing 650 may include one or more corners, steps or abutments to hold one or more internal features of the device, such as portion(s) of the drive train, for example one or more bearing (e.g., thrust bearings and/or radial bearings). As shown in FIG. 6B, the housing 650 includes a step or abutment that holds a radial bearing, which, in turn, holds axially a spindle of the rotating magnet 652 (e.g., a spindle of a housing holding the magnet 652, or a spindle that extends through and is axially fixed with respect to the magnet 652). The housing 650 is also shown as having a set screw, key, or protrusion 646 that mates with the slot to prevent rotation of the rod 660 with respect to the housing 650. In some embodiments, the rod 660 may have a plurality of slots 666 while the housing has a single protrusion 646. In that way, the rotational orientation of the rod 660 with respect to the housing 650 may be changed by merely withdrawing the protrusion 646, rotating the rod 660 until the rod 660 is at the slot 666 closest to the desired rotational orientation, and reinserting the protrusion 646.

As discussed above, the housing 650 holds the rotating magnet 652. In the embodiment illustrated in FIG. 6B, the rotating magnet 652 is coupled to the drive shaft 642 in a one to one manner, such that one rotation of the rotating magnet 652 causes one rotation of the drive shaft 642. Of course, any number of gearing systems, such as or similar to those described elsewhere herein, may be interposed between the rotating magnet 652 and the drive shaft 642. In that way, more turns of the rotating magnet 652 may be required to effectuate a full turn of the drive shaft 642, thereby increasing the torque of the drive shaft 642 by comparison to the rotating magnet 652.

In at least some embodiments, the device shown in FIG. 6B is substantially bilaterally symmetrical from proximal to distal end. Therefore, the opposite elements, such as the second rod 661 and the second drive shaft 643, may be the same as has already been discussed.

Figure 6C:
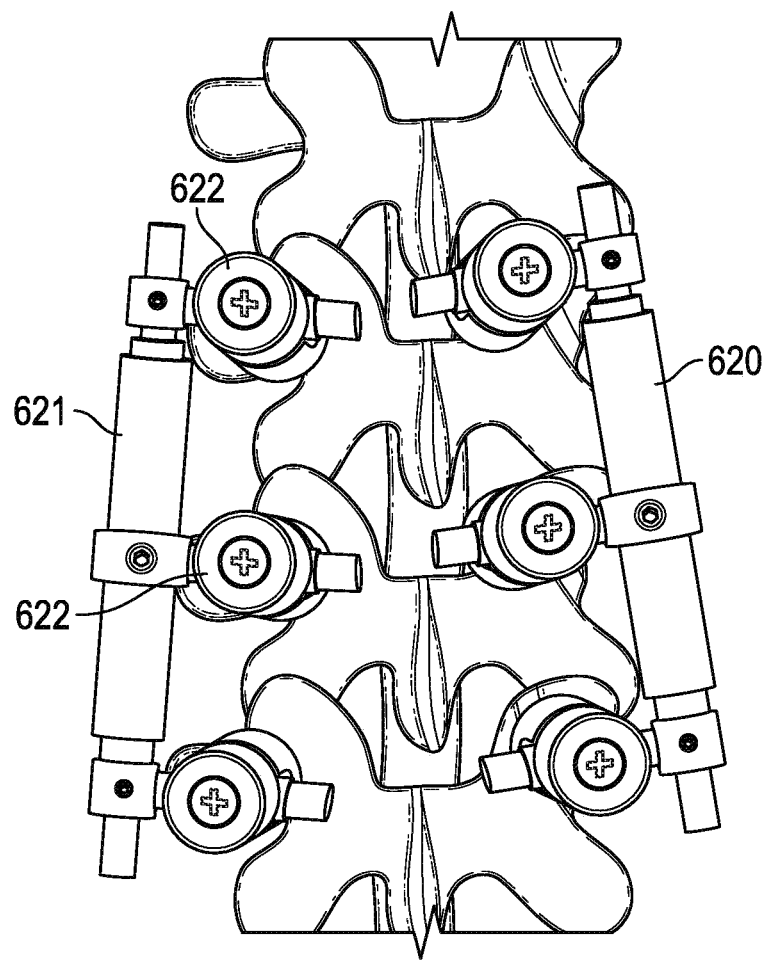

FIG. 6C illustrates two spinal adjustment implants 620 and 621, similar to the two spinal adjustment implants 500a, 500b coupled bilaterally to three lumbar vertebrae shown in FIG. 6. The two spinal adjustment implants 620 and 621 share many of the same features as is described with respect to other embodiments disclosed herein. However, rather than being attached to the three lumbar vertebrae using standard pedicle screws, as is shown in FIG. 6A, the two spinal adjustment implants 620 and 621 are coupled to the three lumbar vertebrae using a different type of specialized screw having a different head 622. As can be seen, the heads of the specialized screws 622 are facing to the rear (the same as the pedicle screws shown in FIG. 6A) of the spine. It should be appreciated that any type of screw and head fixture may be used so long as it adequately anchors the extension rods (and therefore the spinal adjustment implants) with respect to the spine. Depending on the length of the extension rods being used to fix the spinal adjustment implants 620 and 621 to the spine, care may need to be taken not to allow excess rod length to impinge on nervous or other critical tissues. In some embodiments, the excess length of the extension rods, on the side of the pedicle screw opposite the spinal implant, may be trimmed so that the extension rod terminates in a surface substantially flush with the outer surface of the pedicle screw housing.

Figure 6D:
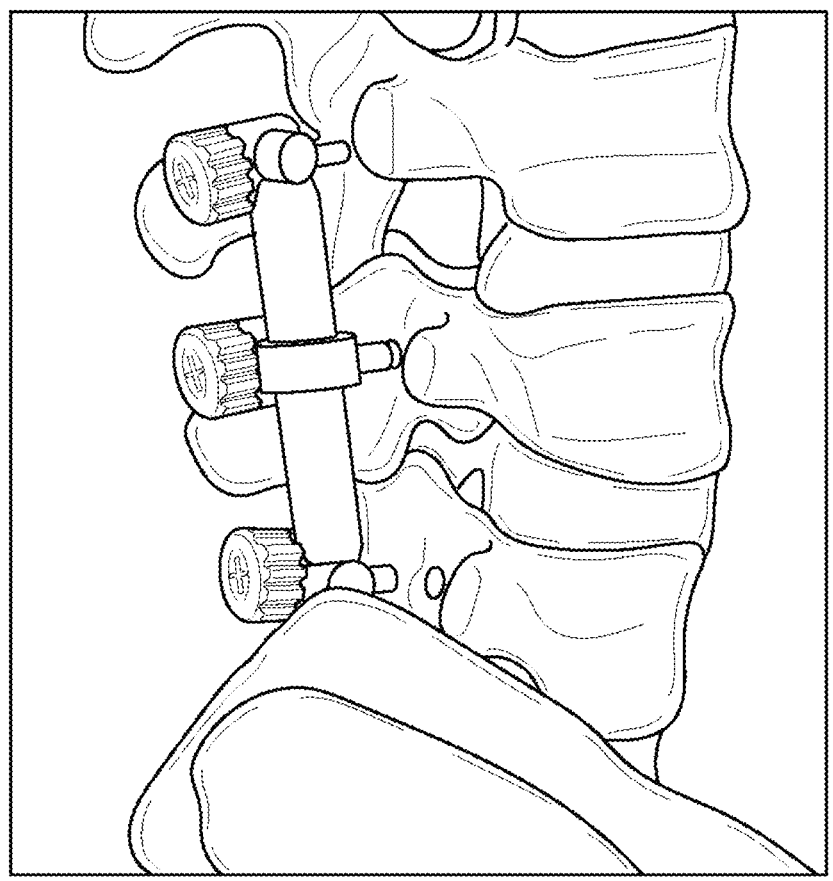

While FIGS. 6A and 6C illustrate two spinal adjustment implants bilaterally implanted next to the spine and attached to the spine using three extension members, each, which are, in turn, fixed to three adjacent vertebrae using pedicle screws and housings. In those figures, the three extension members extend transversely or laterally, and the pedicle screw housings face to the rear of the patient. Stated in another way, the pedicle screws in FIGS. 6A and 6C are inserted into their respective vertebrae substantially in a posterior-anterior direction. FIG. 6D illustrates the right-lateral spinal adjustment implant from a more frontal viewpoint. While FIGS. 6A, 6C, and 6D illustrate the spinal adjustment devices predominantly to the lateral sides of the lumbar spine, it should be understood that the spinal adjustment devices may be placed closer or further away from the spinal midline laterally, or closer or further away from the spinal midline anterior-posteriorly. This may be accomplished through selective placement, including angling, of the pedicle screw as well as inserting the extension member into one side or the other of the pedicle screw housing.

Figure 7:
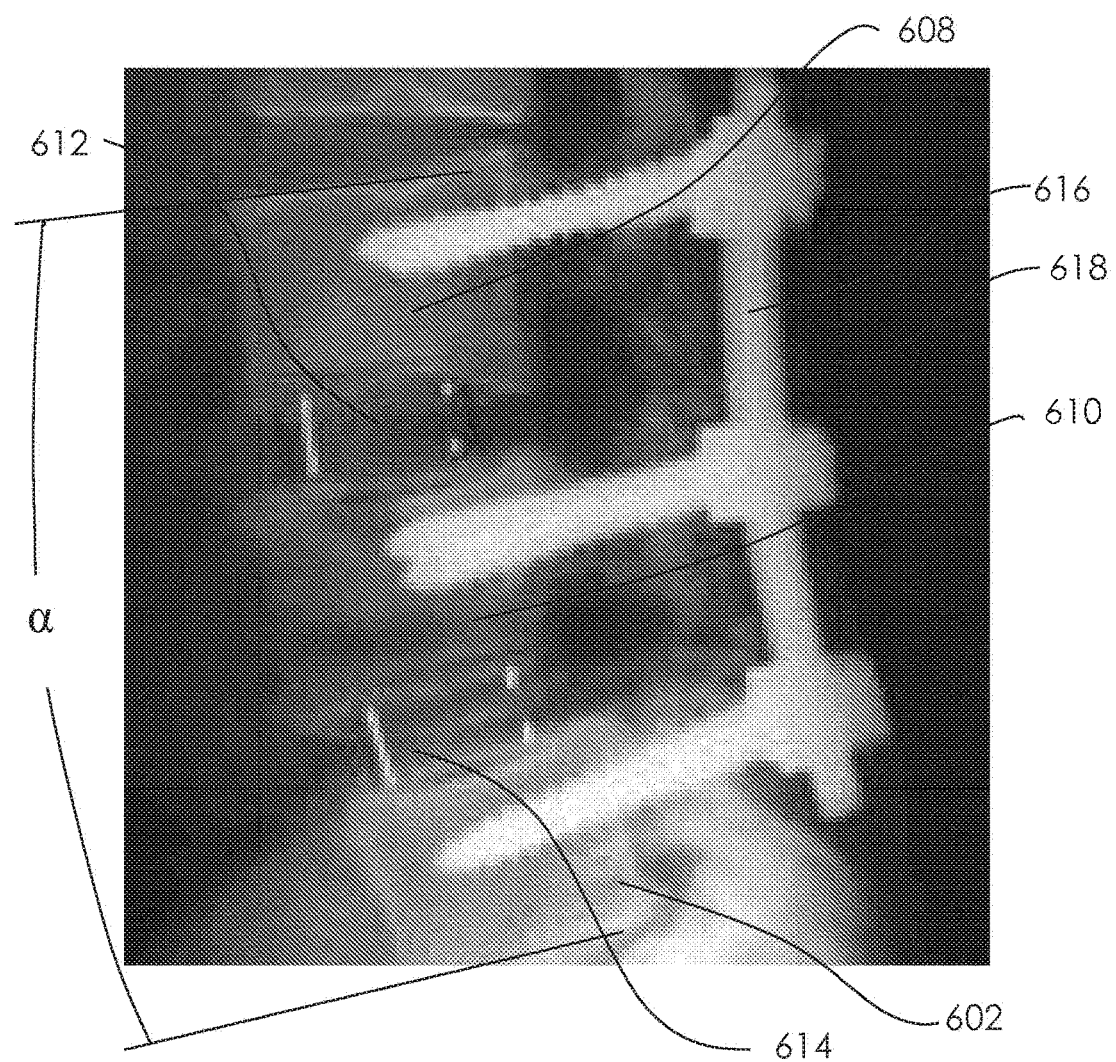
FIG. 7 is a radiographic image of a spinal fusion segment.

Flexion of the first and/or second rods 558a, 558b, 588a, 588b may increase the amount of angle increase that can occur during compressive adjustment. In some embodiments, smaller diameter rods are used to increase the possible flexion. In some embodiments, rods having a diameter of less than about 6.5 mm, less than about 5.5 mm less than about 4.5 mm, less than about 3.5 or less than about 2.5 mm are used. In some embodiments, rods comprise PEEK (polyether ether ketone) to increase flexion. In some embodiments, flexible rods comprise a laser-cut structure and/or a Nitinol structure. In FIG. 7, the lordotic Cobb angle (angle of Lordosis) a between the L3 608 and L5 602 lumbar vertebrae is shown in a radiographic image of an L3-L5 fusion having first and second interbody spacers 612, 614 placed between the vertebral bodies of the L3, L4, and L5 lumbar vertebrae 608, 610, 602. Some flexion of the rods 616, 618 is shown. It will be understood that because the image is taken laterally, rods 616 and 618 are overlaid and thus appear to be only one rod. But, two rods are actually present. The lordotic Cobb angle may be increased (or decreased) by about 0.5-15°, about 1-13°, about 1.5-11°, about 2-9°, about 2.5-7°, or about 3-5° per level through use of the spinal adjustment implants such as those described above (e.g., 500*a*, 500*b*) either unilaterally or bilaterally placed in the L3-L5 segments, for a total L3 to L5 angle increase of about 1-30°.

In some embodiments, one or more gear modules are placed between the driving member 514 and one or both of the first and second threaded drivers 528, 542, in order to increase the amount of compressive force that may be applied during adjustment. In some embodiments, the gear modules comprise planetary gearing, including possibly one or more of sun gears, ring gears and planet gears.

In some embodiments, at least one planetary gear stage (e.g., two, three, four, five, six, or even more planetary gear stages) is included between (operatively coupled to both of and/or between) the permanent magnet and the drive shaft (e.g., drive member, lead screw). Each planetary gear stage can comprise a sun gear and a plurality of planetary gears (e.g., three, four, five, six, or even more planetary gears), which are rotatably held within a frame, e.g., by pins. The sun gear is either a part of the magnet housing (e.g., the sun gear may be directly connected to the magnet/magnet housing), or a part of the gear frame. The rotation of the sun gear causes the planetary gears to rotate and track along inner teeth of a ring gear insert (e.g., a ring gear insert). Each gear stage has a gear reduction ratio (e.g., of 3:1, 4:1, 5:1, 6:1, 7:1, 8:1, or even more), which results in a total gear reduction (e.g., a total gear reduction of 64:1—provided by three planetary gear stages each having a reduction ratio of 4:1). The total reduction ratio is merely the individual reduction radios multiplied. Therefore, a planetary gear system having 4 stages, each with a ratio of 3:1 would have a total reduction ratio of (3×3×3×3):(1×1×1×1), or 81:1. It should be understood that other gear reductions, and numbers of stages may be used.

In some embodiments, a slip clutch is placed between the driving member 514 and one or both of the first and second threaded drivers 528, 542, in order to set a maximum compressive force that can be applied between the two drivers. In some embodiments, a differential is placed between the driving member 514 and the first and second threaded drivers 528, 542 to allow one of the first and second rods 558, 588 to continue adjusting after the other rod is no longer able to adjust due to having reached a threshold resistive force. In some embodiments, the differential incorporates differential gears. The differential gears may include, for example, bevel gears, spur gears, worm gears, and/or a Torsen-type differential—such differential gears will be discussed in more detail, below. In some embodiments, one or more thrust bearings is incorporated in order to protect one or more of the driving member 514, slip clutch(s), gear module(s), and/or differential from excessive stresses. Such thrust bearings may be held substantially fixed with respect to and by the walls of the housing 502, for example, by ledges, abutments, rings, or other structures incorporated into or extending from the housing 502 (e.g., an inner wall of the housing).

FIG. 8 illustrates a spinal adjustment implant 500 *a* implanted in an L3-L5 fusion having first and second interbody spacers 612, 614 placed between the L3 and L4, and L4 and L5 lumbar vertebrae 608, 610, 602, respectively. All of the connections between the rods, extension members and pedicle screws are shown in FIG. 8 as being fixed. Non-invasive actuation and rotation of the driving member 514 (depending on the thread handedness, in the first rotational direction 556 or the second rotational direction 559 (FIG. 3A)) increases compression, e.g., along line C. In combination with flexion of the first and/or second rods, the compressive forces can decrease dorsal distance Dd more than anterior distance Da thereby advantageously increasing the lordotic Cobb angle.

FIG. 9 illustrates an embodiment of a spinal adjustment implant 700. The spinal adjustment implant 700 is similar to the implant 500 of FIGS. 1-3C and 500*a* of FIG. 8, but additionally includes a first pivotable interface 729 between the first rod 758 and pedicle screw 725 and a second pivotable interface 727 between the second rod 788 and pedicle screw 723. Examples of such pivotable interfaces will be discussed in additional detail below, for example with respect to FIGS. 45A-48. Such pivotable interfaces allow the pedicle screws and the vertebrae to which they are attached to change angle more easily; consequently, to decrease Dorsal distance Dd more than Anterior distance Da the spinal adjustment implant need not rely on only potential or minor flexion in the extension rods and/or pedicle screws. The first and second pivotable interfaces 729, 727 may allow a potentially greater increase in the lordotic Cobb angle during compression than that permitted by the spinal adjustment implant 500 *a* of FIG. 8 (which lacks pivotable interfaces 729, 727).

When the magnitude of compression force C is increased by the spinal adjustment implant 700, the L5 lumbar vertebra 602 is able to rotate according to or along arc R1 with respect to an axis of rotation 719 of the first pivotable interface 729. Likewise, the L3 lumbar vertebra 608 is able to rotate according to or along arc R2 with respect to an axis of rotation 721 of the second pivotable interface 727. In some embodiments, the first and second pivotable interfaces 729, 727 are lockable and unlockable to allow free rotation about the axes of rotation 721, 719 during adjustment and to inhibit rotation about the axes of rotation 721, 719 after adjustment is complete. In some embodiments, the first and second pivotable interfaces 729, 727 are non-invasively lockable and unlockable (such as by using a magnetic field to lock and unlock or by using an electromagnetic signal, such as RF, Bluetooth, etc.). In some embodiments the first and second pivotable interfaces 729, 727 are configured to be non-invasively lockable and unlockable as part of the non-invasive adjustment. In some embodiments the first and second pivotable interfaces 729, 727 are configured to be non-invasively lockable and unlockable in conjunction with the rotation of the driving member 514. In some embodiments, the pivotable interfaces 729, 727 are configured to be intermittently locked and unlocked during an adjustment procedure.

Figure 48:
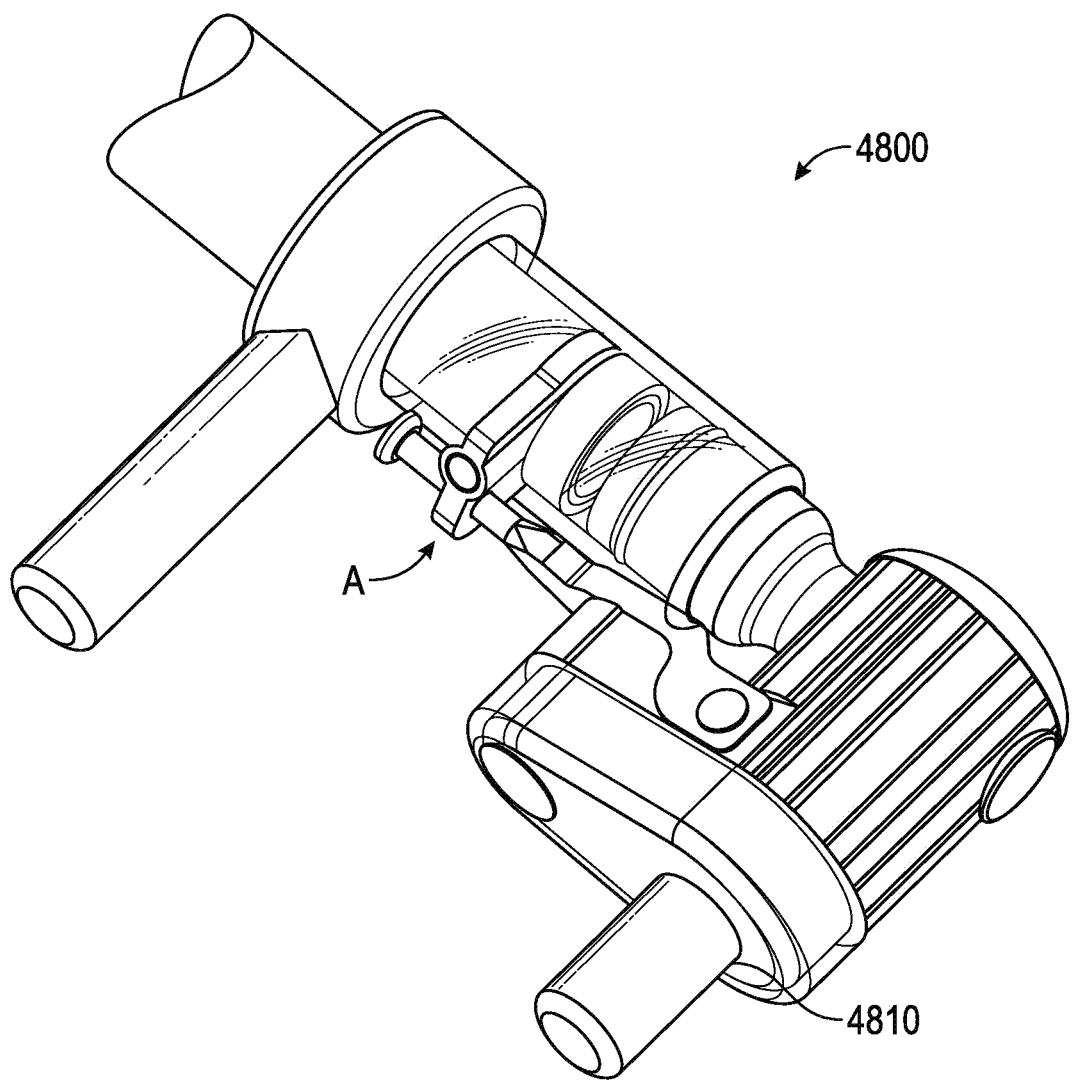
FIG. 48 illustrates an embodiment of a torque-limiting brake is configured to lock and unlock a pivot.

In some embodiments, one or more of the pivotable interfaces is configured to rotate freely in either direction (e.g., clockwise and/or counterclockwise). In some embodiments, one or more of the pivotable interfaces is partially constrained to have free rotation in one direction but no rotation in the other direction—this may be accomplished using a free wheel or other one-way clutching. Examples of devices that may be used to allow unidirectional rotational movement are provided below—in some embodiments, a clutch system, ratchet system, or other motion inhibiting device may be used. In some embodiments, the pivotable interfaces include two-way locking so that they may lock and unlock automatically by the operation of the spinal adjustment implant. For example, the External Remote Controller (ERC) may be used to lock and unlock a magnetic lock which is capable of reversibly removing the rotational freedom of the pivotable interface(s). An example of one such device is shown in FIG. 48. In some embodiments which may be either freely rotating or lockable, there may additionally by constrained rotation or motion, wherein there are limits, extents, or detents that limit the total amount of travel of a particular rotation or motion. In some embodiments, structural motion limiters may be set prior to implantation. For example, the implanting surgeon might evaluate the patient's spine and determine that a maximum correction of 10 degrees per pivotable interface (for a total correction of 20 degrees) is all that is needed and/or permissible. In that case, the surgeon may set each physical motion limiter to "10 degrees" (for example, the pivotable interface may have markings or holes identifying the maximum angle of rotation to which the surgeon may move the physical motion limiter). While 10 degrees was used as an example, it should be understood, that any degree may be use—however, physically, the range of correction will generally be less than about 30, less than about 25, less than about 20, less than about 15, less than about 10, or even less than about 5 degrees per pivotable interface.

Figure 10:
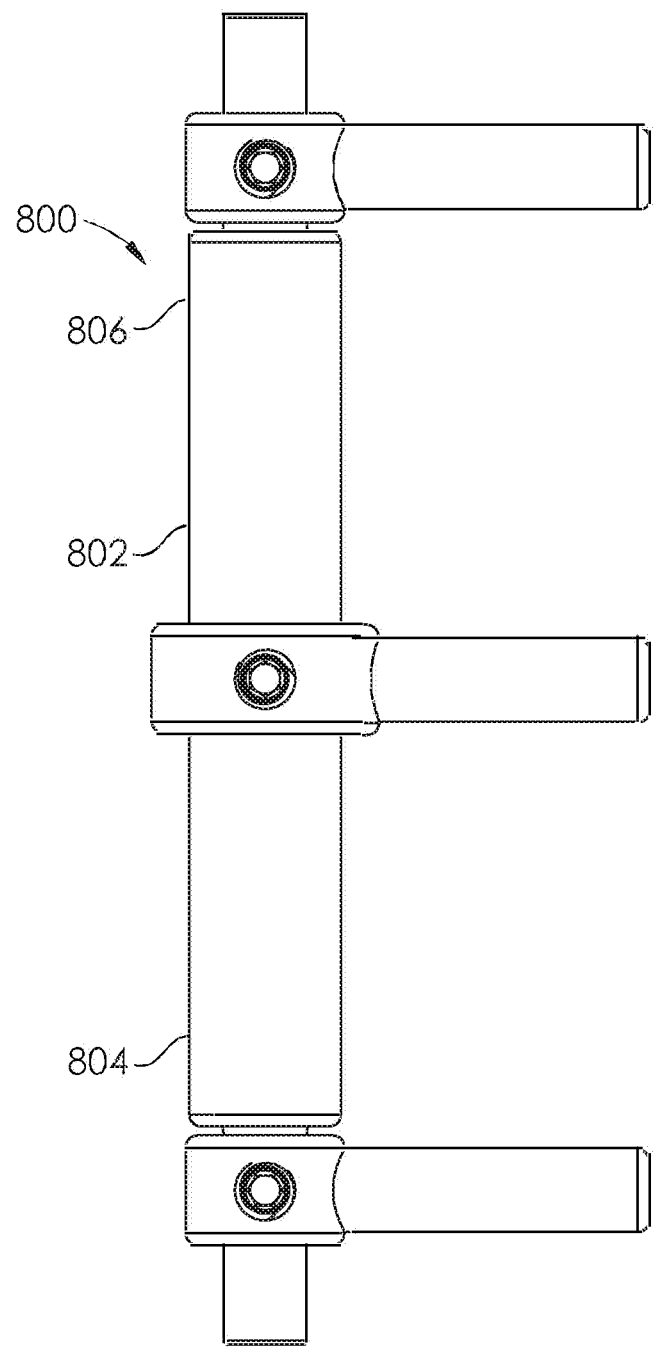
FIG. 10 shows another embodiment of a spinal adjustment implant.

FIGS. 10-12 illustrate a spinal adjustment implant 800 for implantation along the spine of a subject. The spinal adjustment implant 800 comprises a housing 802 having a first end 804 and a second end 806. The housing 802 includes a cavity 808, which extends between the first end 804 of the housing 802 and the second end 806 of the housing 802. The cavity 808 may have a variable inner diameter along its length or may have a generally constant inner diameter. The inner wall 810 of the housing 802 may have circumferential grooves or abutments 812, in order to axially maintain certain elements of the assembly. A driving member 814 is rotatably disposed within the cavity 808. The driving member 814 may comprise any non-invasively rotatable element, such as those described with respect to FIGS. 13-16. The embodiment of the driving member 814 illustrated in FIG. 12 comprises a cylindrical, radially-poled permanent magnet 816 secured within a first magnet housing 818 and a second magnet housing 820.

In the embodiment of FIGS. 10-12, the driving member 814 is positioned longitudinally between two abutments 812 by two radial bearings 824, which facilitate free rotation of the driving member 814 about a driving member axis 826. A first threaded driver 828 has a first end 830 having a shaft 832, and the first magnet housing 818 has a cylindrical cavity 838. A first clutch 836 engages the inside of the cylindrical cavity 838, and inner cavity of the first clutch 836 engages the shaft 832 of the first threaded driver 828. The first clutch 836 is configured to couple rotational motion between the first magnet housing 818 and the first threaded driver 828 in a first rotational direction 856 when the first magnet housing 818 is turned by the radially-poled permanent magnet 816 in a first rotational direction 856. But, the first clutch 836 is configured to cause slippage between the first magnet housing 818 and the first threaded driver 828 when the first magnet housing 818 is turned by the radially-poled permanent magnet 816 in a second rotational direction 859 (e.g., opposite the first rotational direction 856).

A second clutch 842 engages the inside of the cylindrical cavity 844 of the second magnet housing 820, and inner cavity of the second clutch 842 engages the shaft 846 of the second threaded driver 850. The second clutch 842 is configured to couple rotational motion between the second magnet housing 820 and the second threaded driver 850 in the second rotational direction 859 when the second magnet housing 820 is turned by the radially-poled permanent magnet 816 in the second rotational direction 859. But, the second clutch 842 is configured to cause slippage between the second magnet housing 820 and the second threaded driver 850 when the second magnet housing 820 is turned by the radially-poled permanent magnet 816 in the first rotational direction 856.

Incorporation of one-way clutches (e.g., one way clutches 836, 842) may allow the driving member 814 to be capable of independently driving either the first threaded driver 828 or the second threaded driver 850 depending on which direction (e.g., first rotational direction 856 or second rotational direction 859) the driving member 814 is caused to turn. In some embodiments, the first and second clutches 836, 842 comprises a number of different types of one-way clutching, including but not limited to a needle clutch, a free wheel, a sprag clutch, a spring clutch, a face gear, or a ratchet. In some embodiments, the radial bearings or thrust bearings are themselves be configured as one-way clutches (e.g., as a hybrid component). Indeed, any of a number of different clutch mechanisms may be used as the one-way clutches 836, 842. Additional examples are discussed in greater detail, below, with respect to at least FIGS. 40A-40C.

The first and second threaded drivers 828, 850 have second ends 858, 860 having male threads 862, 864, which engage female threads 866, 868 of first and second rods 870, 872. In some embodiments, the spinal adjustment implant 800 is configured for compression (i.e., the threads of both of the first and second threaded drivers 828, 850 and the female threads 866, 868 are right-handed). In other embodiments, the spinal adjustment implant 800 is configured for tension/distraction (i.e., the threads of both of the first and second threaded drivers 828, 850 and the female threads 866, 868 are left-handed).

Extension members 874, 876, 878 may be configured to couple to the first rod 870, second rod 872 and housing 802, respectively. The extension members 874, 876, 878 may be coupled to pedicle screws (not shown). These extension members may be the same as the many other extension members discussed in detail above.

While some illustrated embodiments provide instrumentation to two lumbar levels (L3-L4 and L4-L5), one level only of instrumentation, or greater than two levels of instrumentation are also within the scope of embodiments of the present invention. Indeed, embodiments of the systems for spinal adjustment (including spinal adjustment implants) disclosed herein may have one driving system (e.g., lead screws and permanent magnet, etc.), or more than one driving system. The systems for spinal adjustment disclosed herein may be attached to two vertebrae, to three vertebrae, to four vertebrae, to five vertebrae, to six vertebrae or even more vertebrae, as needed. Regardless, of the number of vertebrae to which the system for spinal adjustment is attached, the device may be a single device, attached to the vertebrae at various points (e.g., the systems shown in FIGS. 1-3 and/or 10-12)—of course, the device may have one or more than one complete drive system. Alternatively, the system for spinal adjustment may be modular, so that multiple (e.g., more than one), smaller devices may be connected to the desired vertebrae (e.g., the system shown in FIG. 20)—these devices will generally, but not always, have their own, unique drive systems (e.g., one drive system per modular portion). As will be readily apparent, because the extension member's attachment rings (having the set screw) may be moved up and down the rods and or the housing, the vertebrae to which the extension members are attached may be adjacent, separated by one or more vertebrae, or a combination of the two.

Besides degenerative disc disease, degenerative deformity patients (adult scoliosis, complex spine) may also be treated with spinal adjustment implants as disclosed herein. Embodiments of the spinal adjustment implants disclosed herein may be used for initial fusion surgery, or in revision surgeries. Embodiments of the spinal adjustment implants disclosed herein may be used to instrument only particular levels of the lumbar vertebrae or vertebrae of other sections of the spine. Embodiments of the spinal adjustment implants disclosed herein may be implanted using minimally invasive surgery (MIS) techniques, for example, using medial placement through a mid-line incision or by placement through small incisions using endoscopes or even operating microscopes.

Figure 13:
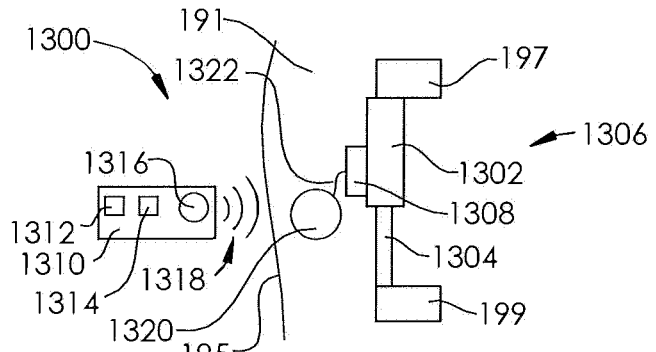
FIGS. 13-16 schematically illustrate various embodiments of a driving element of a non-invasively adjustable spinal implant.

FIGS. 13-16 illustrate embodiments of alternate sources to the cylindrical, radially-poled permanent magnet 516 as the driving member 514 of a spinal adjustment implant 500, 700, 800. FIG. 13 illustrates a non-invasively adjustable system 1300 comprising an implant 1306 having a first implant portion 1302 and a second implant portion 1304, the second implant portion 1304 non-invasively displaceable with relation to the first implant portion 1302. The first implant portion 1302 is secured to a first bone portion 197 and the second implant portion 1304 is secured to a second bone portion 199 within a patient 191. A motor 1308 is operable to cause the first implant portion 1302 and the second implant portion 1304 to displace relative to one another. An external remote controller (ERC) 1310 has a control panel 1312 for input by an operator, a display 1314 and a transmitter 1316. The transmitter 1316 sends a control signal 1318 through the skin 195 of the patient 191 to an implanted receiver 1320. Implanted receiver 1320 communicates with the motor 1308 via a conductor 1322. The motor 1308 may be powered by an implantable battery, or may be powered or charged by inductive coupling.

Figure 14:
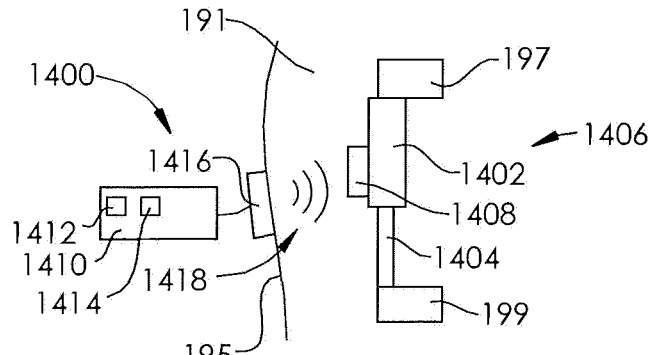

FIG. 14 illustrates a non-invasively adjustable system 1400 comprising an implant 1406 having a first implant portion 1402 and a second implant portion 1404, the second implant portion 1404 non-invasively displaceable with relation to the first implant portion 1402. The first implant portion 1402 is secured to a first bone portion 197 and the second implant portion 1404 is secured to a second bone portion 199 within a patient 191. An ultrasonic motor 1408 is operable to cause the first implant portion 1402 and the second implant portion 1404 to displace relative to one another. An external remote controller (ERC) 1410 has a control panel 1412 for input by an operator, a display 1414 and an ultrasonic transducer 1416, which is coupled to the skin 195 of the patient 191. The ultrasonic transducer 1416 produces ultrasonic waves 1418 which pass through the skin 195 of the patient 191 and operate the ultrasonic motor 1408.

Figure 15:
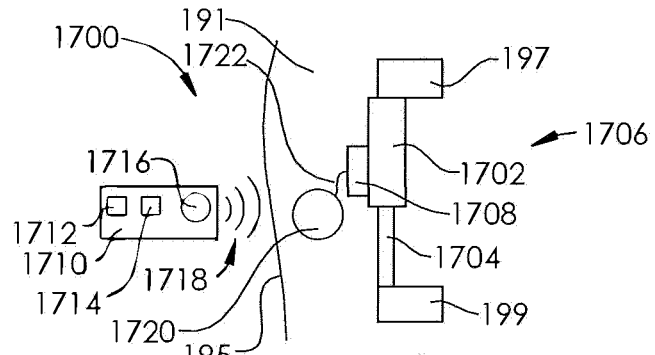

FIG. 15 illustrates a non-invasively adjustable system 1700 comprising an implant 1706 having a first implant portion 1702 and a second implant portion 1704, the second implant portion 1704 non-invasively displaceable with relation to the first implant portion 1702. The first implant portion 1702 is secured to a first bone portion 197 and the second implant portion 1704 is secured to a second bone portion 199 within a patient 191. A shape memory actuator 1708 is operable to cause the first implant portion 1702 and the second implant portion 1704 to displace relative to one another. An external remote controller (ERC) 1710 has a control panel 1712 for input by an operator, a display 1714 and a transmitter 1716. The transmitter 1716 sends a control signal 1718 through the skin 195 of the patient 191 to an implanted receiver 1720. Implanted receiver 1720 communicates with the shape memory actuator 1708 via a conductor 1722. The shape memory actuator 1708 may be powered by an implantable battery, or may be powered or charged by inductive coupling.

Figure 16:
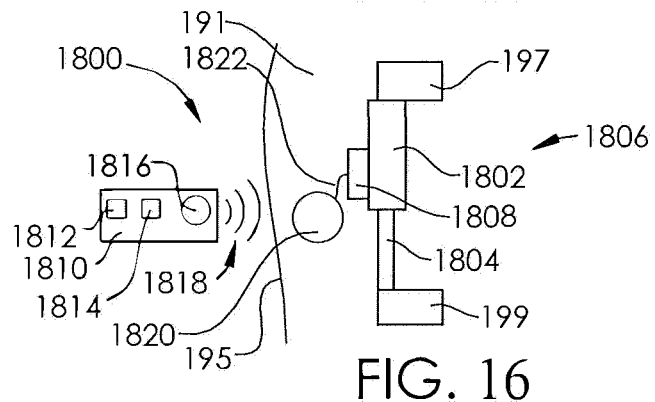

FIG. 16 illustrates a non-invasively adjustable system 1800 comprising an implant 1806 having a first implant portion 1802 and a second implant portion 1804, the second implant portion 1804 non-invasively displaceable with relation to the first implant portion 1802. The first implant portion 1802 is secured to a first bone portion 197 and the second implant portion 1804 is secured to a second bone portion 199 within a patient 191. A hydraulic pump 1808 is operable to cause the first implant portion 1802 and the second implant portion 1804 to displace relative to one another. An external remote controller (ERC) 1810 has a control panel 1812 for input by an operator, a display 1814 and a transmitter 1816. The transmitter 1816 sends a control signal 1818 through the skin 195 of the patient 191 to an implanted receiver 1820. Implanted receiver 1820 communicates with the hydraulic pump 1808 via a conductor 1822. The hydraulic pump 1808 may be powered by an implantable battery, or may be powered or charged by inductive coupling. The hydraulic pump 1808 may alternatively be replaced by a pneumatic pump.

Though not illustrated, another driving element 242 may include a magneto restrictive element. A number of materials may be used to produce the components like the housing, first distraction rod, second distraction rod, first lead screw, and second lead screw, including but not limited to titanium, titanium alloys, titanium 6-4, cobalt-chromium alloys, and stainless steel. The threads on the lead screw in some embodiments may comprise Acme threads, square threads or buttress threads. A number of other possible driving systems are discussed in some detail below.

FIGS. 17-18 illustrate an implant system 1000 comprising a spinal adjustment implant 1002, first pedicle screw 1004 and second pedicle screw 1006. The spinal adjustment implant 1002 includes a housing 1008, which may comprise a first housing portion 1010 and a second housing portion 1012, joined together at a joint 1014 (e.g., similar to the joint described with respect to FIG. 6B). The joint may be a weld joint, adhesive joint, threaded joint, or other type of joint. Alternatively, the housing 1008 may be constructed of a single, monolithic structure, as described in U.S. Pat. No. 9,179,938, which is incorporated by reference herein in its entirety. In certain embodiments, the housing 1008 is coupled at a first end 1016 to a base 1018 having a rod 1020. In some embodiments, housing 1008 is fixedly coupled to the base 1018. In other embodiments, as will be discussed below, the housing 1008 is movably couple to the base 1018, so as to, for example, allow pivoting movement or to allow further distraction/retraction capability (through the addition of another drive system, or the incorporation of another drive member into the currently present drive system). While certain features of the rod 1020 are described below, it should be understood that any modification of this general structure is contemplated by this disclosure.

The rod 1020 may extend in a generally parallel direction to the housing 1008, and be offset from the housing by a distance D. Alternatively, the rod 1020 may extend directly along the longitudinal axis of the housing. The rod 1020 is shown as extending alongside the housing on the same side as the rod 1040. In some embodiments, the rod 1020 and the rod 1040 are not aligned with each other. In some embodiments, the rod 1020 and the rod 1040 are offset by an angle in the range of about 1-180 degrees, about 5-160 degrees, about 10-140 degrees, about 15-120 degrees, about 20-100 degrees, about 25-80 degrees, and about 30-60 degrees or any other degree of offset that may be advantageous—it will be understood that such an offset may be advantageous for applications related to the spine, or applications related to other portions of the skeletal system. The rod 1020 is configured for securement to the second pedicle screw 1006, having a threaded shank 1022 a head 1024 and a tightening nut 1026. While a pedicle screw is described, one of ordinary skill in the art will readily understand that any of a number of systems may be used to fix the rod 1020 to the body of a patient, for example the skeletal system (e.g., a ring and extension member-based system, such as disclosed elsewhere herein).

A rod 1028 (which may share one or more characteristics with rod 1020, just described) is configured to be telescopically moveably into and out of (e.g., moveable/translatable relative/with respect to) an interior 1030 of the housing 1008 at a second end 1036 thereof. The rod 1028 may include one or more longitudinal grooves 1032 which may be engaged by an insert 1034 within the housing 1008, thus allowing longitudinal displacement between the housing 1008 and the rod 1028, but stopping any significant rotation between the housing 1008 and the rod 1028 (this anti-rotation member may function substantially the same as was described above with respect to other embodiments). The rod 1028 may be coupled to a base 1038 having a rod 1040, which may extend in a generally parallel direction to the housing 1008 and/or the rod 1028. The base 1038 may be coupled to the rod 1028 by welding, or by a screw 1029. Alternatively, the base 1038 is pivotably coupled to the rod 1028 so that some rotational movement is allowed between the two at the connection of the two (other types of pivotable/moveable joints are contemplated, such as those that allow unidirectional motion, and/or those that allow movement in more than a single plane (i.e., rotational movement only)). In other embodiments, as will be discussed below, the rod 1028 is movably couple to the base 1038, so as to, for example, allow pivoting movement or to allow further distraction/retraction capability (through the addition of another drive system, or the incorporation of another drive member into the currently present drive system).

The rod 1040 may be configured for securement to the first pedicle screw 1004, which may include similar components as the second pedicle screw 1006. In use, the first pedicle screw 1004 is engaged into a first vertebra, and the second pedicle screw is engaged into a second vertebra. While a pedicle screw is described, one of ordinary skill in the art will readily understand that any of a number of systems may be used to fix the rod 1040 to the body of a patient, for example the skeletal system (e.g., a ring and extension member-based system, such as disclosed elsewhere herein). In some cases, the first and second vertebrae may be adjacent each other. In other cases, the first and second vertebrae may have one or more intervening vertebrae.

The spinal adjustment implant 1002 is configured to be non-invasively shortened or lengthened, in order to move a first and second vertebra with respect to each other. A magnet 1042 (for example, a radially poled, cylindrical magnet) may held within a casing 1046 which is rotatably held within the housing 1008 by a radial bearing 1044. A pin 1048 at one end of the casing 1046 may be insertable within (e.g., held by) an inner bore 1050 of the radial bearing 1044. One or more planetary gear modules 1052, 1054 (such as those discussed above), may couple the magnet 1042 and casing 1046 to a lead screw (e.g., drive member, drive shaft, drive element, etc.) 1056. A thrust bearing 1058 may be secured within the housing 1008 to protect the planetary gear modules (or stages) 1052, 1054 and the magnet 1042 from axial compressive (and/or tensile) stresses.

The lead screw 1056 may be coupled to the gear modules 1052, 1054 or the magnet 1042 (of course, it will be understood that gearing increases the possible torque of the system and therefore the possible force that can be generated by the system). In some embodiments, the lead screw is connected to the gear modules or the magnet using a coupler 1057 that allows some amount of axial play (as discussed above), such as by a pin 1060. The rod 1028 may have a hollow interior 1062, which may contain threads. In some embodiments, the hollow inter 1062 itself is threaded. Alternatively, the hollow interior 1062 may contain a nut 1064 having a female thread 1066 (e.g., the nut may be fixedly bonded to the inner surface of the hollow interior 1062). The external threads of the lead screw 1056 engage the female thread 1066 of the nut 1064, thus allowing movement of the rod 1028 and the housing 1008 towards each other or away from each other, depending on the direction that the lead screw 1056 is turned. The pieces of the system 1000 may be sealed in any of a number of ways to keep out bodily fluids and to keep in any fluids contained by the device (e.g., lubricants or other fluids). Any of the seals discussed elsewhere herein may be used here as well. For example, an o-ring 1068 may be held within a circumferentially extending groove 1070 in the rod 1028 to provide a dynamic seal against an inner surface 1072 of the housing 1008 (of course, the groove may be in the inner surface of the housing as opposed to the outer surface of the rod). A moving magnetic field, for example, applied non-invasively by the External Remote Controlled (ERC) 180 of FIGS. 4-5, may be used in a patient (including but not limited to a conscious patient) to change the length of the spinal adjustment implant 1002, thus changing the distance and/or angle between the first vertebrae and the second vertebrae, Implant system 1000 has been described as having an axially asymmetric drive system. That is to say that, by contrast to the device shown in FIG. 6B, the implant system 1000 has a drive shaft on only one side of the spinning magnet. This means that only one end of the implant system 1000 may extend or retract from within the housing. In some embodiments, that is sufficient.

However, in other embodiments, the housing contains a bilaterally symmetrical drive system, including, for example, one magnet, two gear systems, and two drive shafts (as will be easily understood in view of the disclosure presented herein).

Figure 19:
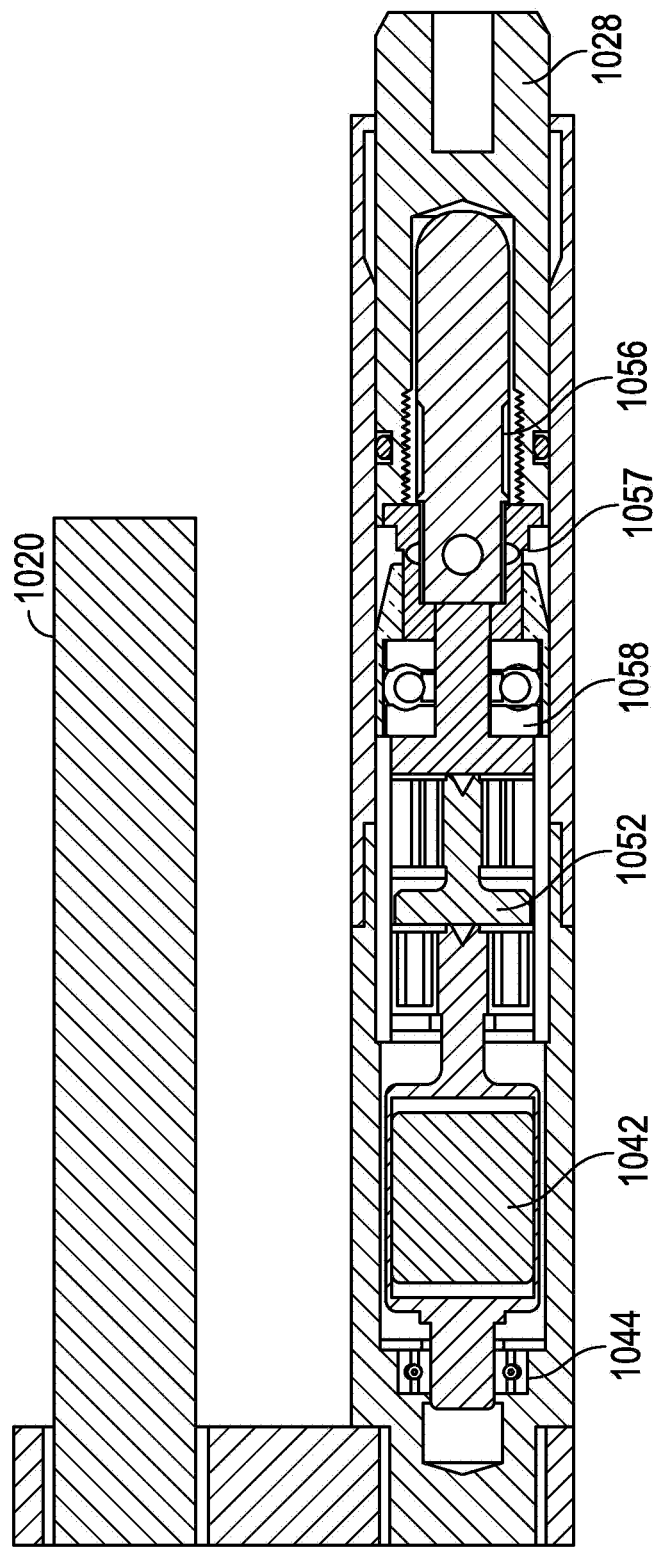
Figure 20:
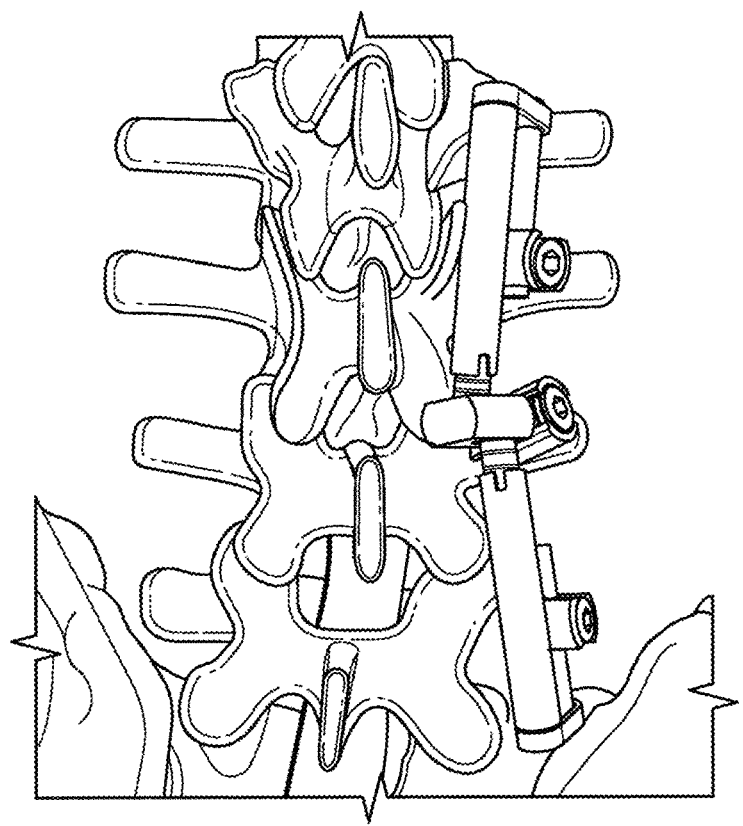
FIG. 20 illustrates two devices of the embodiment shown in FIG. 19 secured to the spinal column in series and having a shared base between them.

FIG. 19 illustrates a cross-sectional view of the system 1000 shown in FIG. 18, but rotated approximately 90 degrees clockwise. FIG. 20 illustrates two systems, such as the system 1000 of FIGS. 18-19 attached to the spinal column in a modular fashion at a joint (which may also be attached to the spinal column). The two devices are secured to the spinal column in series, with a shared base between them. The telescopic rods of each of the implants are secured to the shared base.

FIGS. 21A-21D and FIGS. 22A-22E illustrate an embodiment of the spinal adjustment implant 2100 for implantation along the spinal system of a subject. The spinal adjustment implant 2100 is similar to the implant 700 of FIG. 9 as it provides pivotable interfaces that may allow a potentially greater increase in the lordotic Cobb angle during compression than that permitted by the spinal adjustment implant 500 *a* of FIG. 8. As will be discussed in more detail below, the driving member of the spinal adjustment implant 2100 can be rotated to generate a compression force that allows a first attached vertebra to rotate with respect to a second attached vertebra.

In some embodiments, the spinal adjustment implant 2100 comprises a driving member that is rotatably coupled to a plurality of gears. In some embodiments, the plurality of gears is coupled to a linkage system that can be coupled to a plurality of vertebra. As the driving member is rotated, the plurality of gears translates the rotational motion to cause the linkage system to pivot about center of rotation which can cause one of the attached vertebrae to rotate about the center of rotation.

Figure 21A:
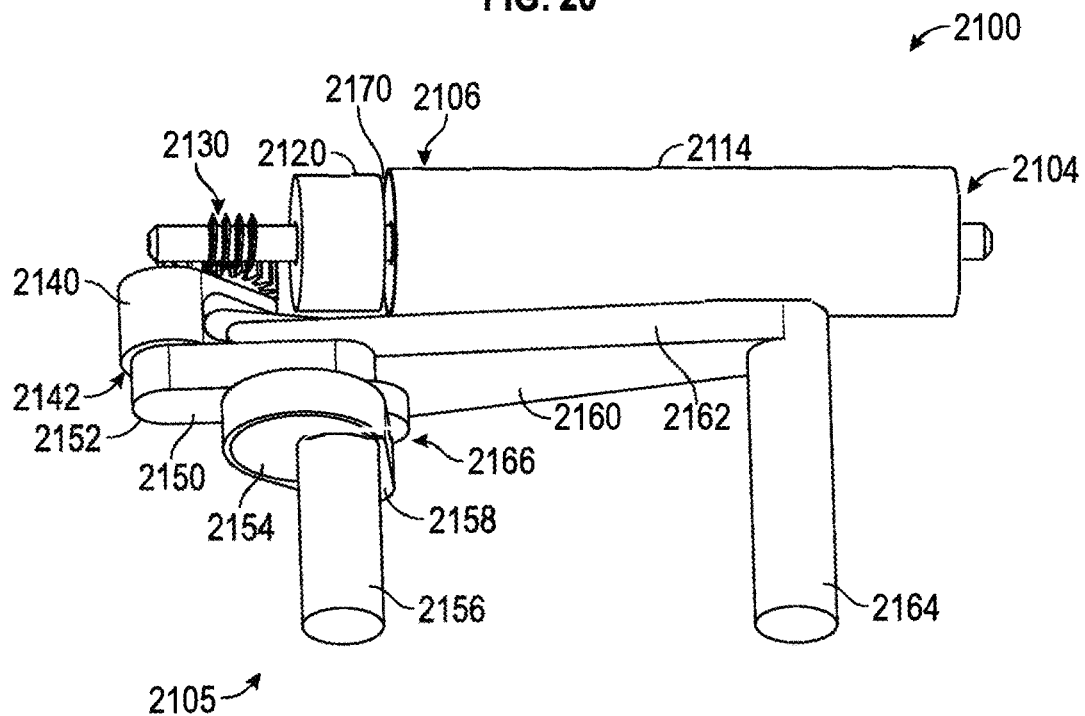
FIGS. 21A-21D illustrate an embodiment of a spinal adjustment implant including a worm gear and a linkage system that are configured to adjust the lordotic angle of a vertebra system.

FIGS. 21A-22E generally illustrate an embodiment which may use a motor or magnet or alternative non-invasively operable drive system to turn a worm (labeled as "worm gear" in provisional) which is engaged to a worm wheel, which moves a link in order to change the distance and/or angle between two rods (red and green) to which pedicle screws may be secured. FIG. 21A illustrates an embodiment of the spinal adjustment implant 2100. In some examples, the spinal adjustment implant 2100 can further include a housing system (not pictured) that can be disposed about the surface of the spinal adjustment implant 2100. The spinal adjustment implant 2100 can include a driving member 2114 having a first end 2106 and a second end 2104. The driving member 2114 may comprise any non-invasively rotatable element, such as a magnet.

In some embodiments, the driving member 2114 can be disposed about a first rod 2170 that extends from the first end 2106 and is rotationally coupled to a gear system 2120. In some embodiments, the gear system 2120 can be a planetary or a harmonic drive. As the driving member 2114 is rotated, the rotation is translated to the gear system 2120. In some embodiments the gear system 2120 can provide a high gear reduction ratio in a limited space. As the driving member 2114 rotates, the rotation causes the gear system 2120 to rotate.

Figure 21B:
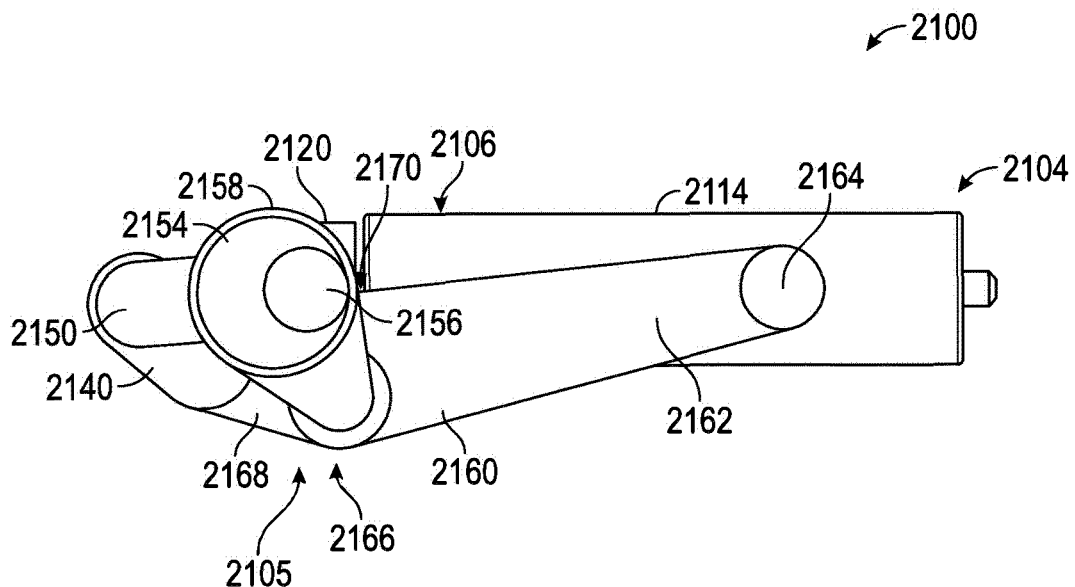
Figure 21C:
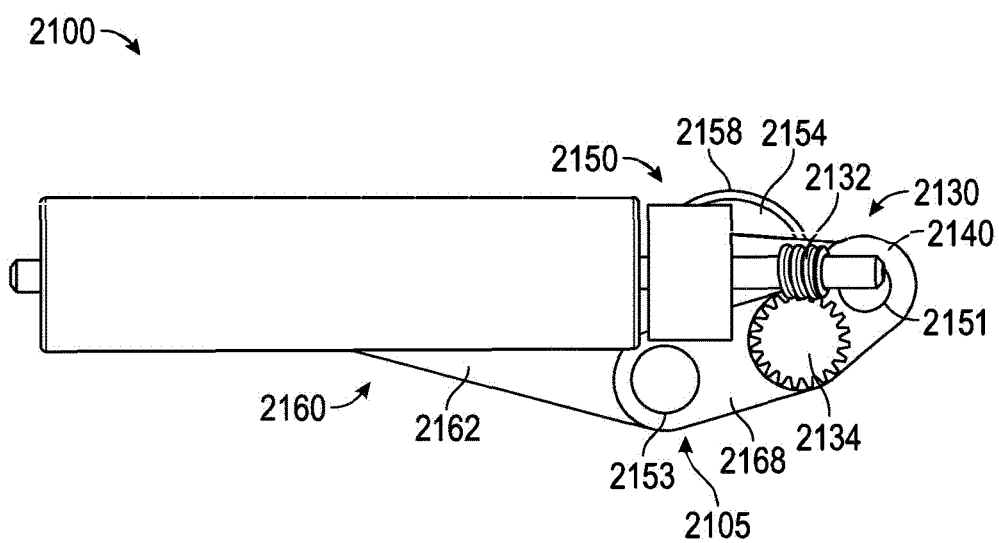

As illustrated in FIG. 21A, the gear system 2120 can be coupled to a second rod 2136 that is coupled to a worm drive 2130. FIG. 21C provides a side view of the worm drive 2130. In some embodiments, the worm drive 2130 includes a worm screw 2132 and a worm wheel 2134. The worm drive 2130 can provide large gear reductions. As well, in some embodiments, the worm drive 2130 can provide a locking feature which can act as a brake to ensure that the worm wheel 2134 does not unintentionally cause the worm screw 2132. As illustrated in FIG. 21C, in some embodiments, the worm screw 2132 is disposed about the second rod 2136 and is threaded to engage with the worm wheel 2134. As discussed above, as the driving member 2114 is rotated, the rotation is translated to the gear system 2120 through the first rod 2170. The gear system 2120 can then cause the rotation of the worm drive 2130 which engages with the worm wheel 2134.

In some embodiments, the worm drive 2130 may engage a linkage system 2105 which can cause the rotation of an attached vertebra. FIGS. 21B-21C illustrate two side views of the spinal adjustment implant 2100 engaged with the linkage system 2105. In some embodiments, the linkage system can include a driven link 2140, a coupler link 2150, and a ground link 2160. In some examples, the worm wheel 2134 of the worm drive 2130 has an extended portion (not illustrated) that engages with a portion of the driven link such that rotation of the worm wheel 2134 can cause rotation of the driven link 2140. As will be discussed below, the driven link 2140 can be movably coupled with the coupler link 2150 to cause a portion of the coupler link 2150 to pivot in a first direction as the driver link 2140 rotates. The coupler link 2150 can be further secured to a ground link 2160 which allows a first attached vertebra to rotate with respect to a second attached vertebra.

In some embodiments, the driven link 2140 can be movably coupled to the coupler link 2150 through the engagement portion 2142 of the driven link 2140. The engagement portion 2142 of the driven link 2140 can be disposed about the protrusion 2151 of the coupler link 2150. A first end of the protrusion 2151 of the coupler link 2150 can be seen in FIG. 21C with the driven link 2140 disposed about it. As will be discussed in more detail below, as the driven link 2140 is rotated, this can cause a portion of the coupler link to pivot.

The coupler link 2150 can comprise a plurality of components. As illustrated in FIG. 21A-21B, in some embodiments, the coupler link 2150 can include a first body 2152, a second body 2143, and a coupler rod 2156. As discussed above, a first end of the first body 2152 of the coupler link 2150 can include a protrusion 2151 that is disposed within an engagement portion of the driven link 2140 and is movably coupled such that rotation of the driven link 2140 can cause the first body 2152 of the coupler link 2150 to pivot. The second end of the first body 2152 of the coupler link 2150 can be movably engaged with the second body 2158 of the coupler link 2150. A coupler rod 2156 can extend from the surface of the second body 2158 to engage with a first vertebra. In some embodiments, as illustrated in FIG. 21A, the coupler rod 2156 can have a base portion 2154 that is movably coupled with the second body 2158. The base portion 2154 can be circular and disposed within an opening in the second body 2158. The second body 2158 of the coupler link 2150 can further include a protrusion 2153 that is movably coupled with the ground link 2160 at the engagement portion 2166. A first end of the protrusion 2153 of the ground link 2160 can be seen in FIG. 21C with the ground link 2160 disposed about it. As will be discussed in more detail below, the movable connection between the ground link 2160 and the second body 2158 of the coupler link 2150 can cause the second body 2158 to rotate about the engagement portion 2166.

The ground link 2160 can anchor the spinal adjustment implant 2100 to a second vertebra to provide for the rotation of the first vertebra attached to the coupler rod 2156 of the coupler link 2150. In some embodiments, the ground link 2160 can include a body 2162, a joint portion 2168, and a ground rod 2164. As illustrated in FIGS. 21A-21B, the body 2162 of the ground link 2160 can include a first end that includes an engagement portion 2166 that is movably engaged with the joint portion 2168, and a portion of the second body 2158 of the coupler link 2150. The body 2162 of the ground link 2160 can further include the ground rod 2164 that extends from a surface of the body 2162 at the second end. In some embodiments, the ground rod 2164 can extend from the surface of the second body 2158 to engage with a second vertebra. In some embodiments, the ground rod 2164 is anchored to the second vertebra to secure the spinal adjustment implant 2100 as the first vertebra is rotated.

Figure 21D:
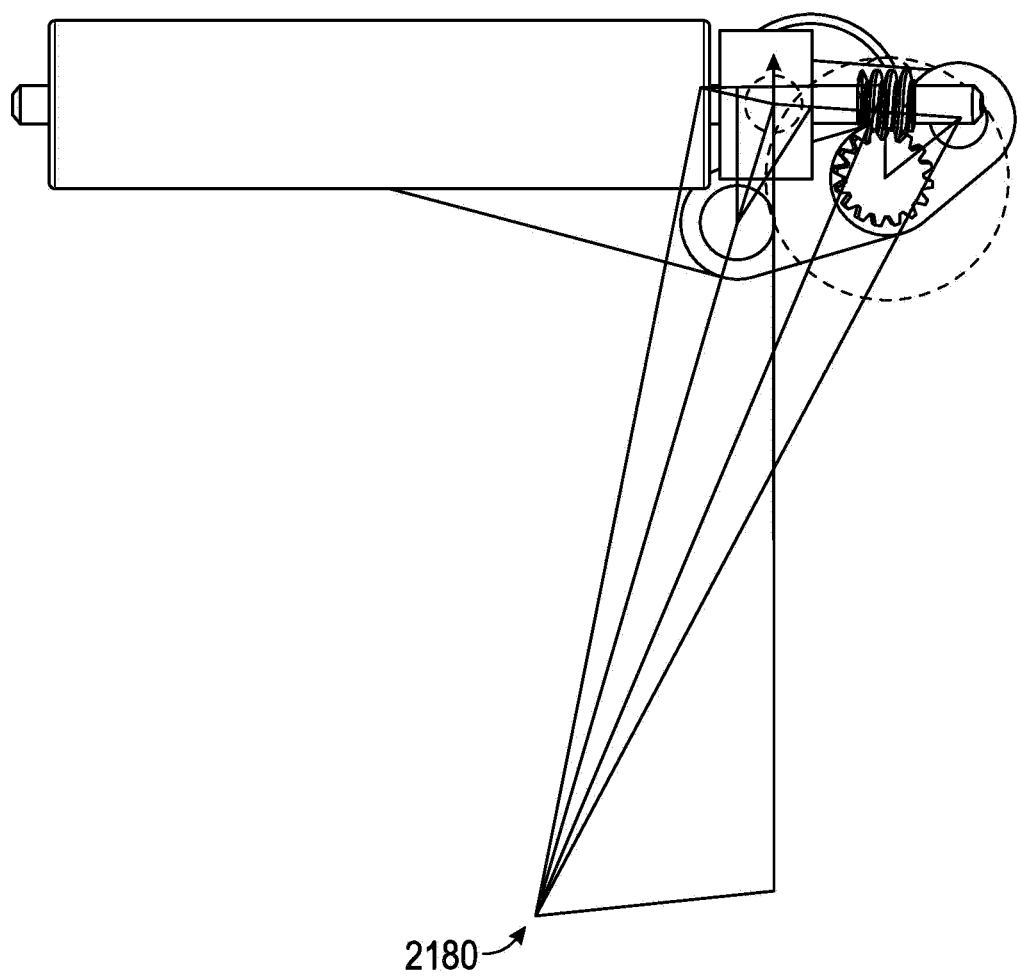

FIG. 21D illustrates the center of rotation 2180 of the spinal adjustment implant 2100. As discussed above, the rotational movement of the driving member 2114 is translated to a rotation of the driven link through the gear system 2120 and the worm drive 2130. As the driven link 2140 is rotated in a first direction, this can cause the first body 2152 of the coupler link 2150 to pivot in a first direction. This pivoting motion is translated to the second body 2158 of the coupler link 2150 and the attached first vertebra attached to the coupler rod 2156. As mentioned above, the body 2162 of the ground link 2160 is secured to a second vertebra. The second body 2158 is movably attached to a first end of the body 2162 of the ground link 2160 such that the second body 2158 can rotate about the engagement portion 2166 of the body 2162, causing the first vertebra to rotate in a first direction relative to the second vertebra.

Figure 22A:
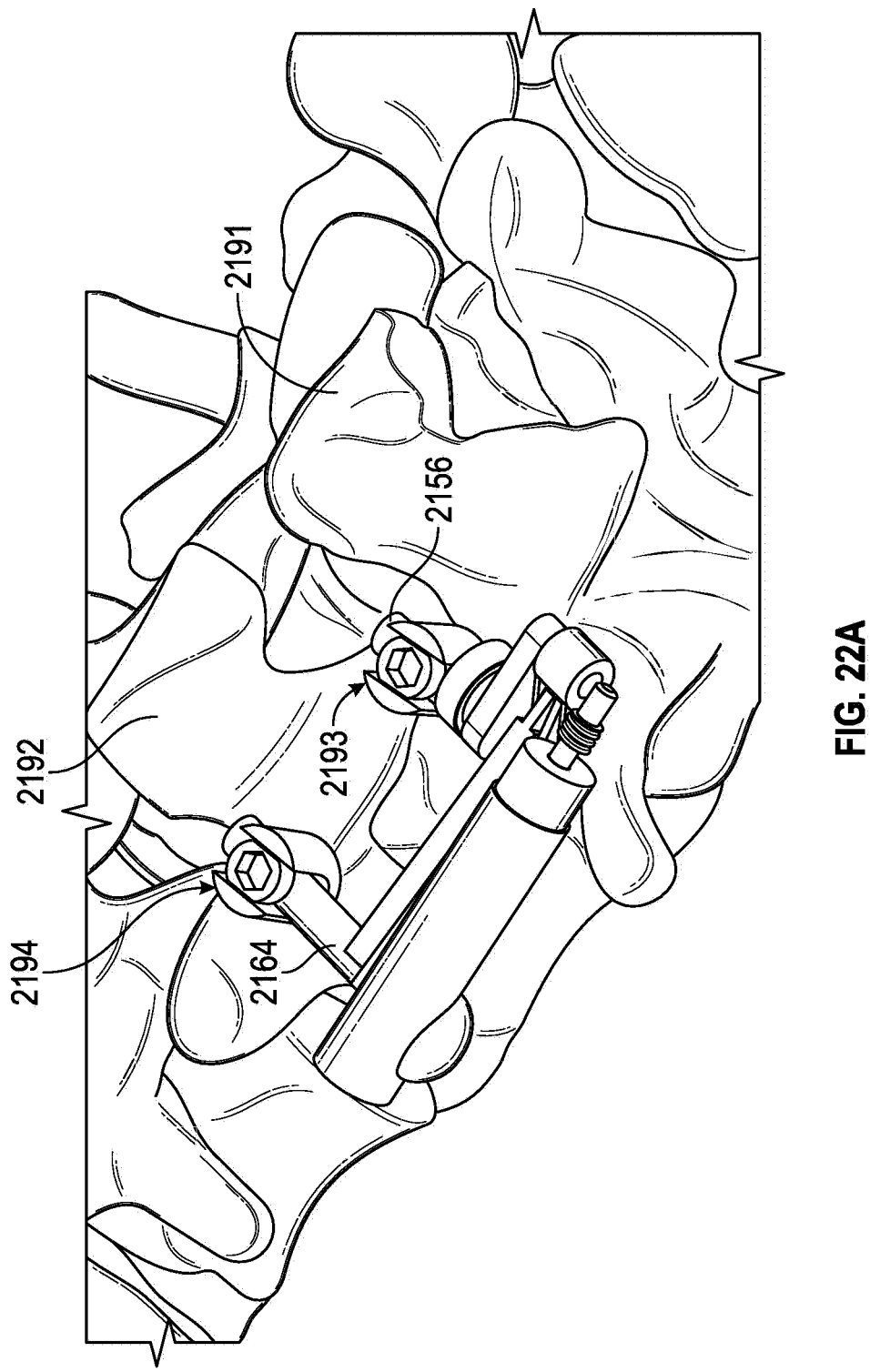
FIG. 22A illustrates the spinal adjustment implant of FIGS. 21A-21D secured to a plurality of vertebra of the spinal system.

FIGS. 22A-22E illustrates an example of the rotation of a first vertebra as a result of the rotation of the driving member 2114. FIG. 22A illustrates the spinal adjustment implant 2100 secured to a first vertebra 2191 and a second vertebra 2192 using a plurality of attachment systems 2193, 2194. In some embodiments, the attachment systems can include one or more of: a pedicle screw, hook, or a wire. As shown in FIG. 22A, the coupler rod 2156 is secured to the first vertebra 2191 using the attachment system 2193 and the ground rod 2164 is secured to the second vertebra 2192 using the attachment system 2194.

Figure 22B:
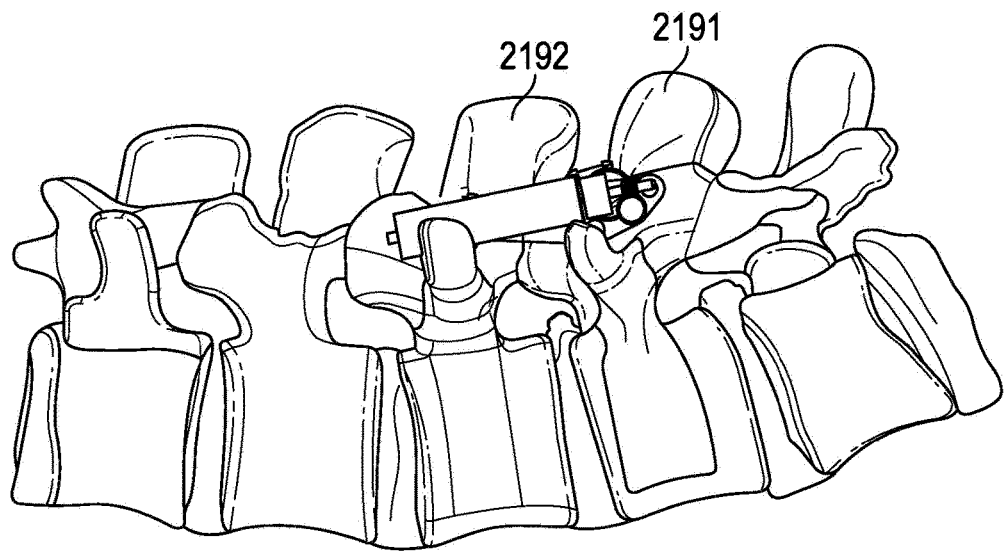
FIGS. 22B-22C illustrate the implanted spinal adjustment implant of FIG. 22A before and after actuation of a drive member that adjusts the lordotic angle of the attached vertebra.
Figure 22C:
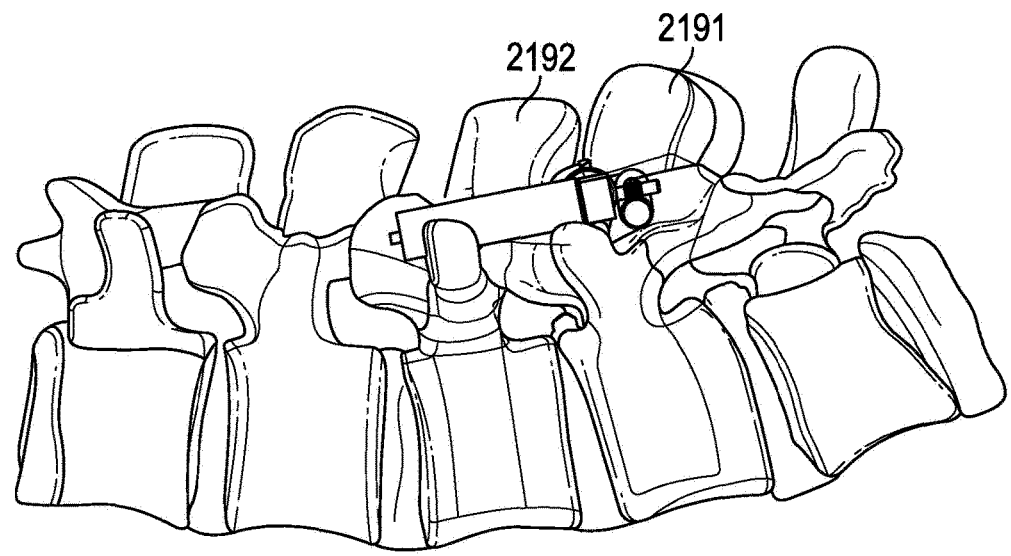
Figure 22D:
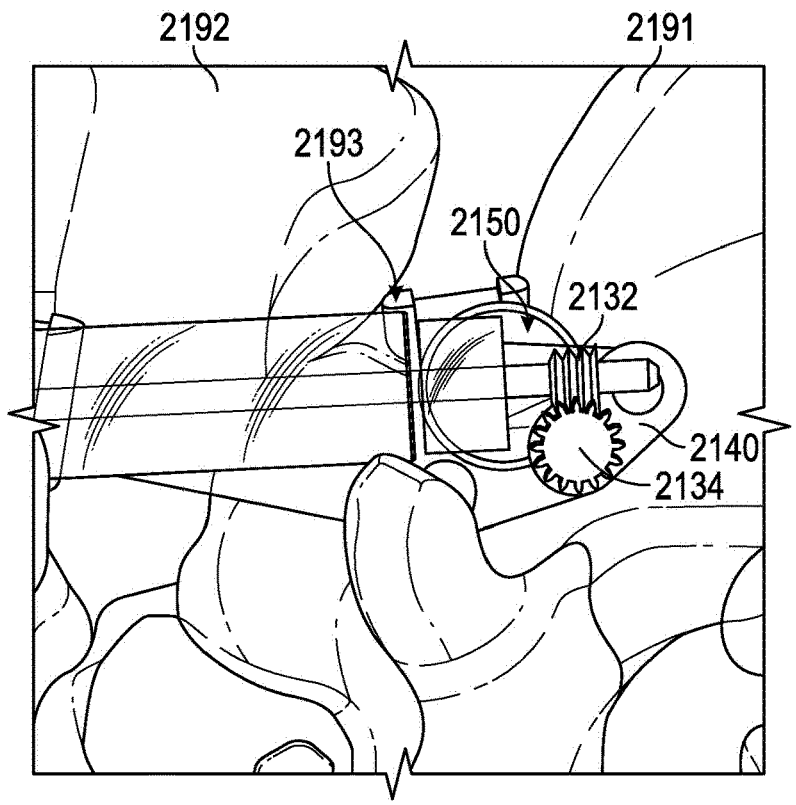
FIGS. 22D-22E illustrate an enlarged view of the implanted spinal adjustment implant of FIG. 22A before and after actuation of a drive member that adjusts the lordotic angle of the attached vertebra.
Figure 22E:
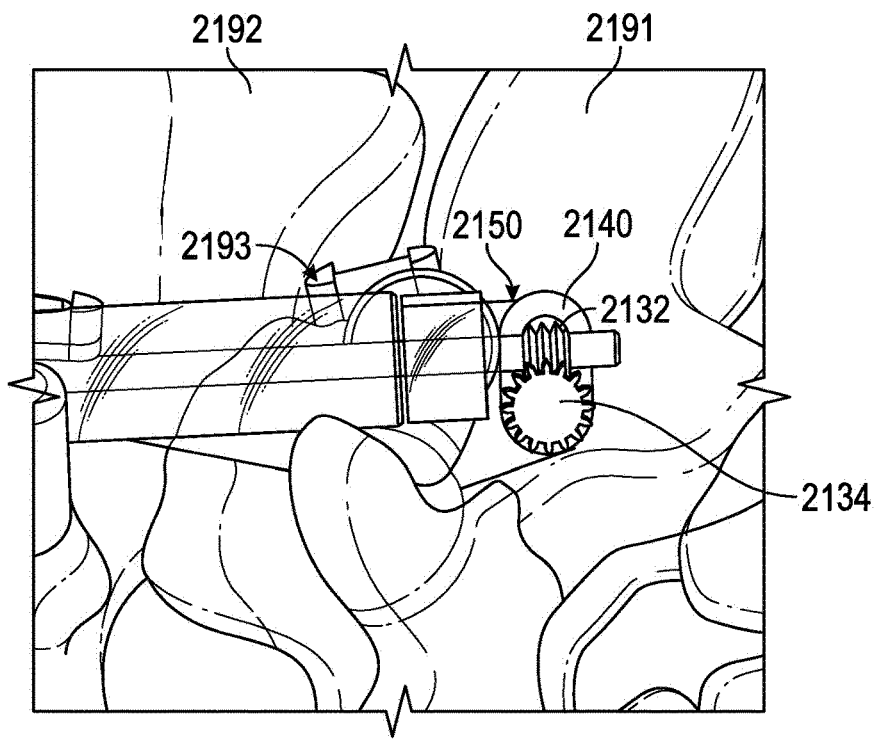

FIGS. 22B-22C illustrate the position of the first vertebra 2191 and second vertebra 2192 as the driving member 2114 is rotated. FIG. 22B illustrates the position of the first vertebra 2191 before the driving member 2114 is rotated. As can be seen, a distance exists between the first vertebra 2191 and the second vertebra 2192. FIG. 22C illustrates the position of the first vertebra 2191 after the driving member 2114 is rotated. As illustrated, the first vertebra 2191 is rotated such that it is in close proximity with the second vertebra. FIGS. 22D-22E illustrate a close up view of the linkage system of the spinal adjustment implant 2100 before and after the driving member 2114 is rotated. As seen in FIG. 22E, the rotation of the driving member 2114 rotates the worm drive 2130 such that the driven link 2140 pivots in a first direction and the coupler link 2150 rotates in a first direction about the center of rotation 2180. The rotation of the coupler link 2150 rotates the attached first vertebra 2191 such that the distance between the first vertebra 2191 and the second vertebra 2192 is reduced.

Figure 23A:
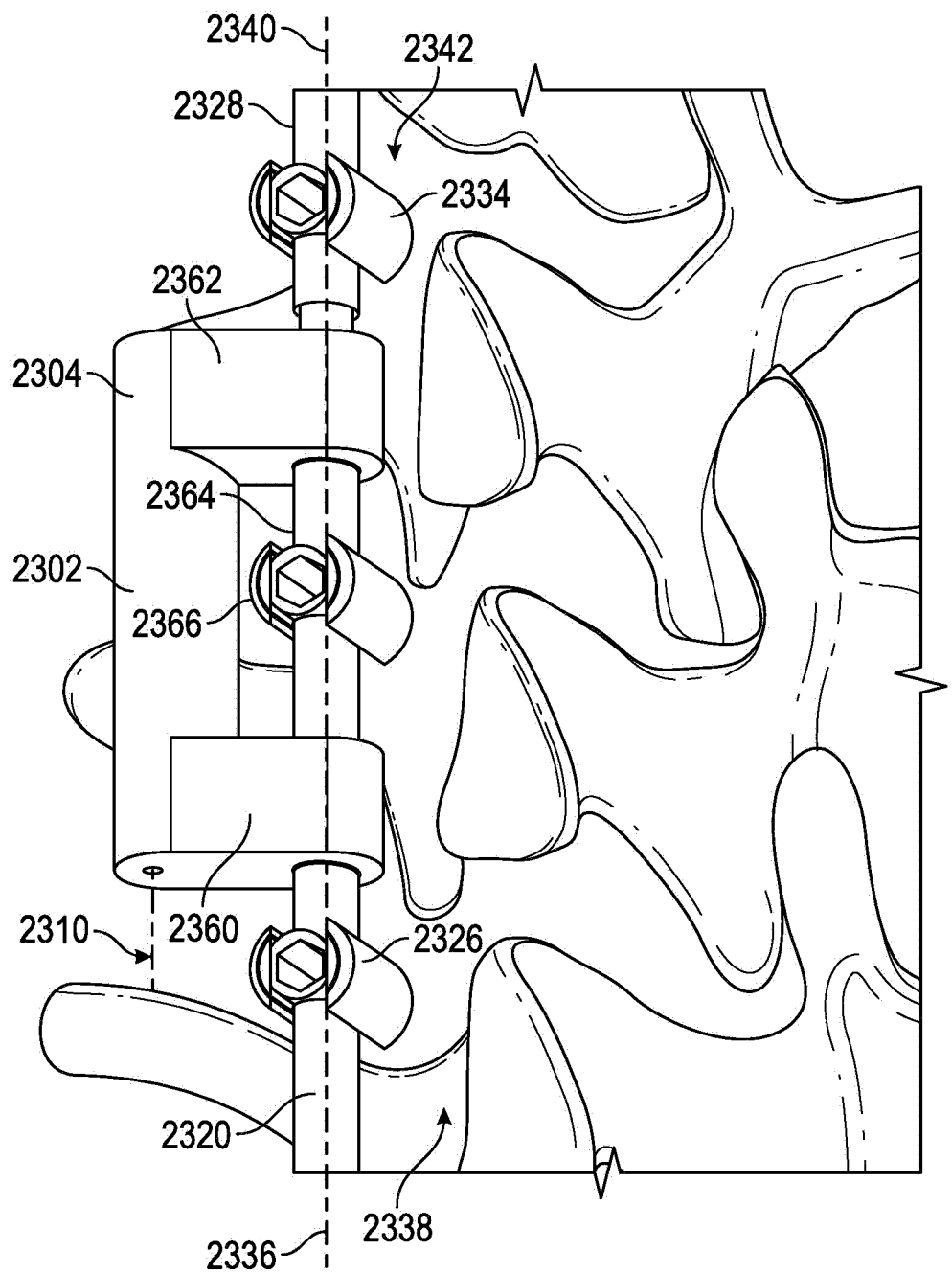
FIG. 23A illustrates an embodiment of a spinal adjustment implant including one or more gear modules.
Figure 23B:
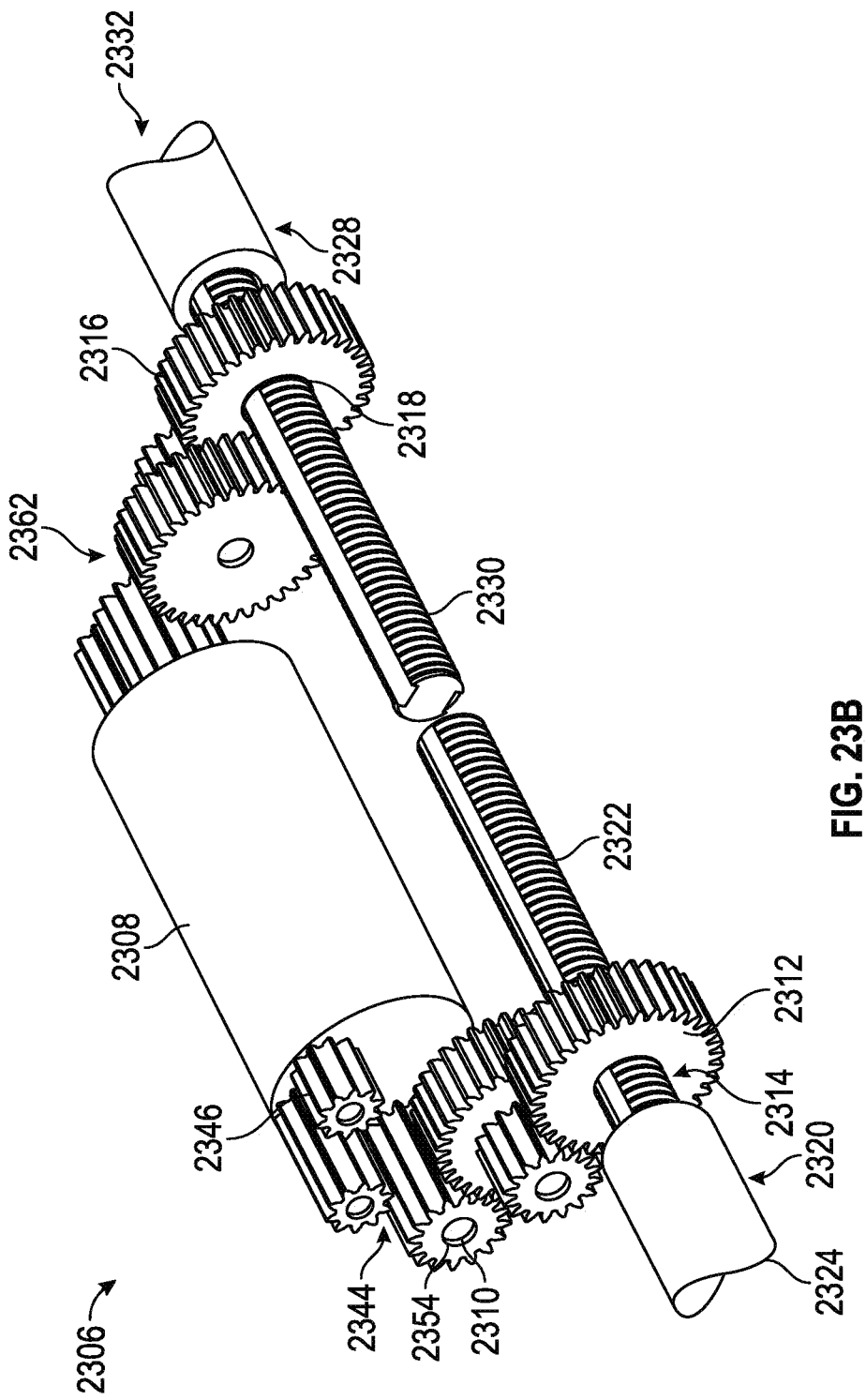
FIG. 23B shows the internal components of the spinal adjustment implant of FIG. 23A.
Figure 23C:
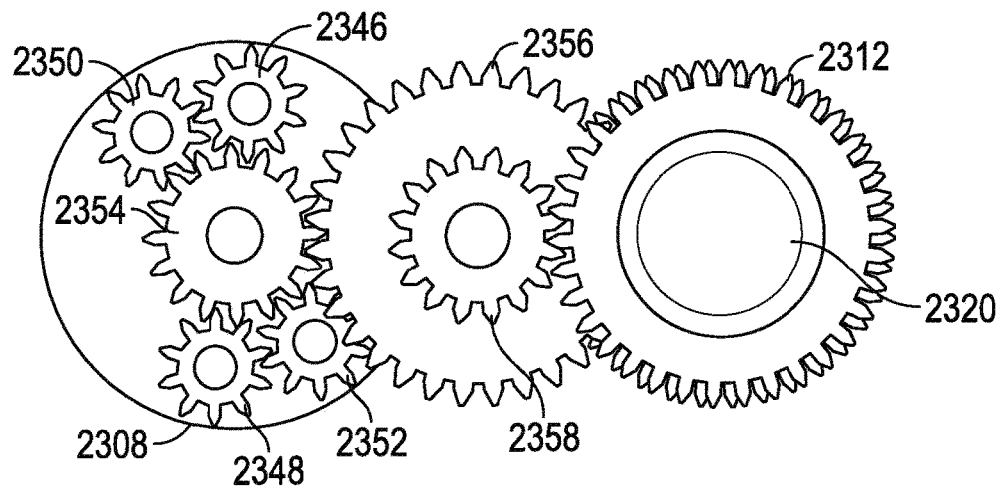
FIG. 23C shows a gear module and other internal components of the spinal adjustment implant of FIGS. 23A and 23B.

FIGS. 23A-23C generally illustrate an embodiment using differential gearing, including one or more sun gears and planetary gears, to increase the amount of force that can be placed on the vertebrae during adjustment (e.g., compression) via relatively high gear ratios. The compact packaging of the gears increases the efficiency of the torque, and thus force, that can be delivered within a small profile implant. FIGS. 23A-C illustrate a spinal adjustment implant 2300 for implantation along the spinal system of a subject. In some cases, the subject may be a patient having degenerative disc disease that necessitates fusion of some or all of the lumbar vertebrae through fusion surgery. The spinal implant 2300 is configured to be used in place of traditional rods, which are used to maintain posterior decompression and stabilize during fusion surgery. Some embodiments of the spinal implant 2300 are compatible with interbody spacers placed between the vertebrae being treated. The spinal adjustment implant 2300 may comprise a housing 2302 which includes a first end and a second end. The housing 2302 includes a cavity 2304 which may be substantially similar to the cavities described in other embodiments disclosed herein. The cavity 2304 may include elements configured to maintain certain elements of the assembly within the housing 2304, for example, protrusions, grooves, or abutments. The housing 2302 may be made from materials which are biocompatible and which may allow for relatively small wall thicknesses while maintaining the structural integrity of the housing 2302 when in use. For example, the housing 2302 may comprise titanium alloys, ceramics and/or biocompatible polymers. Various sizes and shape of the housing 2302 are expressly contemplated, although preferably the housing 2302 is sized to be implanted within the body of a patient. For example, in the embodiments illustrated in FIGS. 23A-C the housing 2302 comprises a cylindrical shape, can have an outer diameter of about 10 mm, and can have a length of about 45 mm. In some embodiments the housing 2302 may be from about 20 mm to about 70 mm long, from about 30 mm to about 60 mm long, or from about 40 mm to about 50 mm long. In some embodiments the housing 2302 may have a diameter from about 5 mm to about 20 mm, from about 7 mm to about 15 mm, or from about 9 mm to about 11 mm.

A driving member 2306 is rotatably disposed within the cavity 2304 of the housing 2302. The driving member 2306 may comprise any non-invasively rotatable element, for example a rotatable element that is substantially similar to rotatable elements described in other embodiments disclosed herein. The particular embodiment of the driving member 2306 illustrated in FIGS. 23A-C comprises a cylindrical, radially-poled permanent magnet 2308 that is secured within the cavity 2304. The magnet 2308 is disposed in the cavity 2304 such that the magnet 2308 is free to rotate about a central axis 2310 within the cavity 2304. The magnet may be secured within the cavity by means substantially similar to those means described in other embodiments disclosed herein. It is contemplated that the magnet 2308 may comprise a variety of shapes and sizes. In the embodiment illustrated in FIGS. 23A-C the magnet comprises a cylindrical shape. The magnet 2308 is sized to fit within the cavity 2304. In some embodiments the magnet 2308 may be about 9.5 mm in diameter and about 21 mm long. In some embodiments the magnet 2308 may have a diameter from about 5 mm to about 20 mm, from about 7 mm to about 15 mm, or from about 9 mm to about 11 mm. In some embodiments the magnet 2308 may be from about 10 mm to 30 mm long, from about 15 mm to about 25 mm long, or from about 17.5 mm to about 22.5 mm long.

The spinal adjustment implant 2300 can include at least a first rotatable driver 2312 which includes a hole that comprises a female threaded portion 2314. In the embodiment illustrated in FIGS. 23A-C the driving member 2306 includes a first driver 2312 and a second driver 2316. The second driver 2316 can be substantially identical to the first driver 2312 and can include a hole that comprises a female threaded portion 2318. In some embodiments the first and second drivers 2312, 2316 can be coupled to the driving member 2306 by means substantially similar to those described in embodiments disclosed herein. In some embodiments a first rod 2320 has a first end comprising a male threaded portion 2322 and a second end 2324 configured to be coupled to a portion of the skeletal system. In some embodiments the second end 2324 of the first rod 2320 is configured to be coupled to a first portion of the spinal system via means substantially similar to those described in embodiments disclosed herein. The first portion of the spinal system may be a first vertebra. For example, the second end 2324 of the first rod 2320 may be coupled to the first vertebra by a first extension member 2326, or directly via one or more of: a pedicle screw; hook; wire; or other attachment system. The first extension member 2326 may be substantially similar to an extension member described in other embodiments disclosed herein. The first extension member 2326 may extend generally transversely in relation to the housing 2302 and/or first rod 2320. The first extension member 2326 may be coupled to a first vertebra directly, via one or more of: a pedicle screw; hook; wire; or other attachment system. In some embodiments, for example the embodiment illustrated in FIGS. 23A-23B, a second rod 2328 may be substantially similar to the first rod 2320. The second rod 2328 may comprise a first end comprising a male threaded portion 2330 and a second end 2332 configured to be coupled to a portion of the skeletal system, for example a second vertebra. The second rod 2328 may be secured to the second vertebra by a second extension member 2334. The second extension member 2334 may be coupled to the second vertebra directly, via one or more of: a pedicle screw; hook; wire; or other attachment system.

Referring to FIG. 23B, the female threaded portion 2314 of the first driver 2312 and the male threaded portion 2322 of the first rod 2320 threadingly engage each other such that rotation of the first driver 2312 causes the first rod 2320 to move along a first longitudinal axis 2336 (FIG. 23A) in a first longitudinal direction 2338. The female threaded portion 2318 of the second driver 2316 and the male threaded portion 2330 of the second rod 2328 threadingly engage each other such that rotation of the second driver 2316 causes the second rod 2328 to move along a second longitudinal axis 2340 (FIG. 23A) in a second longitudinal direction 2342. Although the drivers 2312, 2316 are described as comprising female threaded portions 2314, 2318 which engage with male threaded portions 2322, 2330 of the rods, in some embodiments the drivers 2312, 2316 may comprise male threaded portions and the rods may comprise corresponding female threaded portions.

The spinal adjustment implant 2300 may additionally comprise a gear module or modules which can be placed between the driving member 2306 and one or both of the first and second threaded drivers 2312, 2316. In some embodiments one or both of the threaded drivers 2312, 2316 may comprise a gear including a plurality of teeth positioned around an outer edge of the driver and configured to engage with the gear modules. For example, each of the first and second drivers 2312, 2316 may comprise 32 teeth. In some embodiments the drivers 2312, 2316 may each comprise from 20 to 40 teeth, from 10 to 80 teeth, or more than 80 teeth. As shown in FIGS. 23A-23C, the first driver 2312 comprises 32 teeth which are configured to engage with the first gear module 2344. The gear module 2344 may comprise a gear train which can provide a high gear reduction between the driving member 2306 and the first driver 2312. A high gear reduction, or step-down, allows for a relatively small torque generated by the driving member 2306 to be amplified, thereby allowing the first driver 2312 to apply high force to the first rod 2320. For example, in some embodiments the gear reduction between the driving member 2306 and the drivers 2312, 2316 may be about 4:1. In some embodiments the gear reduction ratio may be greater than 1:1, for example 2:1, 4:1, 8:1, 16:1 or more. The gear module or modules can comprise planetary gearing, including sun gears, ring gears and planet gears. In some embodiments the gear module may comprise differential gears. The differential gears may include, for example, bevel gears, spur gears, worm gears, and/or a Torsen-type differential.

Referring to FIGS. 23B-23C, the first gear module 2344 may comprise a first grouping of gears 2346, 2348 which are positioned at a first end of the rotatable element, for example the magnet 2308 of the driving member 2306. Although the embodiment illustrated in FIGS. 23A-23C includes two gears 2346, 2348 positioned at the first end of the magnet 2308, it is expressly contemplated that the first grouping of gears may comprise more or fewer gears, for example, one gear, three gears, four gears, five gears, or more. The gears 2346, 2348 of the first grouping of gears are radially arranged around the central axis 2310 of the magnet 2308. The gears 2346, 2348 may comprise, for example, ten teeth. In some embodiments the gears 2346, 2358 may comprise more or fewer teeth, for example, from five to thirty, from seven to twenty, or from ten to fifteen teeth. The gears 2346, 2348 engage with a second grouping of gears 2350, 2352, which are positioned at the first end of the magnet 2308, and are radially arranged around the central axis 2310 of the magnet 2308 adjacent to gears 2346, 2348, respectively. The gears 2350, 2352 may have a height greater than the height of the gears 2346, 2348 such that the gears 2350, 2352 extend outwardly past the gears 2346, 2348 along the direction of the central axis 2310. The gears 2350, 2352 of the second grouping may have the same, or about the same number of teeth as the gears 2346, 2348 of the first grouping, for example ten teeth. Likewise, the second grouping may comprise a number of gears corresponding to the number of gears in the first grouping, for example the second grouping may comprise the same number of gears as the first grouping.

The gears 2350, 2352 of the second grouping may act as planetary gears and can engage with a first sun gear 2354 positioned at a first end of the magnet 2308 such that the central axis of the sun gear 2354 is aligned with the central axis 2310 of the rotatable element, for example the magnet 2308, of the driving member 2306. The sun gear 2354 comprises a greater number of teeth than each of the gears 2350, 2352 so as to provide a gear reduction and amplify the torque generated by the rotatable element of the driving member 2306. For example, the sun gear 2354 may comprise sixteen teeth. In some embodiments the sun gear may comprise from fifteen to thirty teeth, from thirty to fifty teeth, from fifty to one hundred teeth, or more than one hundred teeth. The sun gear 2354 additionally engages with a first intermediate gear 2356 that comprises a greater number of teeth than the sun gear 2354 so as so provide a gear reduction and amplify the input torque from the sun gear 2354. The first intermediate gear 2356 may comprise a number of teeth corresponding to the number of teeth of the sun gear 2352, for example twice as many teeth, four times as many teeth, eight times as many teeth, or more. In some embodiments the first intermediate gear may comprise thirty-two teeth.

The first intermediate gear 2354 can be fixedly attached to the second intermediate gear 2356 such that the central axes of the gears 2354, 2356 are substantially aligned. One rotation of the first intermediate gear 2354 will thereby result in one rotation of the second intermediate gear 2356. The second intermediate gear 2356 comprises fewer teeth than the first intermediate gear 2354, for example half as many teeth, one quarter as many teeth, one eighth as many teeth or fewer. In some embodiments the second intermediate gear 2356 may comprise sixteen teeth. The second intermediate gear 2356 engages with the teeth of the first driver 2312 and provides for a gear reduction between the rotation of the rotatable element of the driving member 2306 and the first driver 2312 as described above. As described above, the first gear module 2344 therefore allows the relatively small torque generated by the driving member 2306 to be converted into a relatively high torque at the first driver 2312, the rotation of which thereby causes the first rod 2320 to move along a first longitudinal axis 2336 (FIG. 23A) in a first longitudinal direction 2338.

The spinal adjustment implant 2300 may additionally comprise a second gear module 2358 which is substantially similar to the first gear module 2344 and is positioned at the second end of the rotatable element of the driving member 2306. The second gear module 2358 can be placed between driving member 2306 and the second driver 2316 and may function in a substantially identical manner as the first gear module 2344 as described above. Additionally, in some embodiments the first and second groupings of gears of the second gears module may be attached or engaged with the corresponding gears of the first and second grouping of the first gear module 2344. For example, the corresponding gears of the first and second groupings of the first and second gears modules may share corresponding axles. The sun gears of the first and second gear modules may not be attached or engaged with one another and the sun gear 2354 of the first gear module may rotate independently from the sun gear of the second gear module 2358.

Furthermore, the threaded portions of the first and second rods 2324, 2328 and the threaded portions of the first and second drivers 2312, 2316 are configured such that rotation of the rotatable element of the driving member 2306 causes a corresponding rotation of the first and second drivers 2312, 2316 which thereby causes the first rod 2324 to move in a first axial direction 2328 and the second rod 2328 to move in a second axial direction 2342.

As illustrated in FIG. 23A, the first and second gear modules 2344, 2358 may be positioned within a first gear module housing 2360 and a second gear module housing 2362, respectively. The gear module housings 2360, 2362 can be attached to, and/or integrally formed with the housing 2302 and positioned at the first and second ends thereof. The gear module housings 2360, 2362 may include cavities configured to maintain the gear modules or modules therein. The cavities may include elements configured to maintain certain elements of the assembly within the housings 2360, 2362, for example, protrusions, grooves, or abutments. The housings 2360, 2362 may be made from materials which are biocompatible and which may allow for relatively small wall thicknesses while maintaining the structural integrity of the housings 2360, 2362 when in use. For example, the housings 2360, 2362 may comprise the same or similar materials as the housing 2302.

The spinal adjustment implant 2300 may further comprise a retainer 2364 which is configured to receive the threaded portions 2322, 2330 of the first and second rods 2320, 2328. The retainer can take the form of, for example, a hollow tube, with the threaded portions 2322, 2330 of the rods disposed therein. The retainer 2364 can be secured to a portion of the skeletal system, for example a third vertebra, preferably positioned between the first and second vertebra. The retainer 2364 can be secured to the third vertebra directly, by a third extension member 2366, and/or in a manner similar to the manner in which the first rod 2320 is secured to the first vertebra as described above. The third extension member 2366 may be coupled to the third vertebra directly, via one or more of: a pedicle screw; hook; wire; or other attachment system. The retainer 2364 can be attached to, and/or integrally formed with the gear module housings 2360, 2362 at the respective ends of the retainer 2364. In this manner the retainer 2364, which is secured to a portion of the skeletal system, may provide support for, and secure, the housing 2302 via the gear module housings 2360, 2362, within the body of the patient. A central axis of the retainer 2364 may be substantially parallel to a central axis of the driving member driving member 2306, with an offset therefrom. In some embodiments the offset between the central axis of the retainer 2364 and the central axis of the housing 2302 and/or driving member 2306 may be about 12 mm. In some embodiments the offset may be from about 4 to about 16 mm, greater than 16 mm, or greater than 32 mm or greater.

FIGS. 24A-24D generally illustrate an embodiment wherein a motor or magnet, etc. drives a worm that engages and turns a worm gear which may be rotationally coupled (e.g., in serial) with a pinion that drives a rack. FIGS. 24A-D illustrate another embodiment of the spinal adjustment implant 2400. The spinal adjustment implant 2400 includes a drive member 2402, a first rod 2404, a second rod 2406, a first securement portion 2408, a second securement portion 2410, and a third securement portion 2412.

Figure 24A:
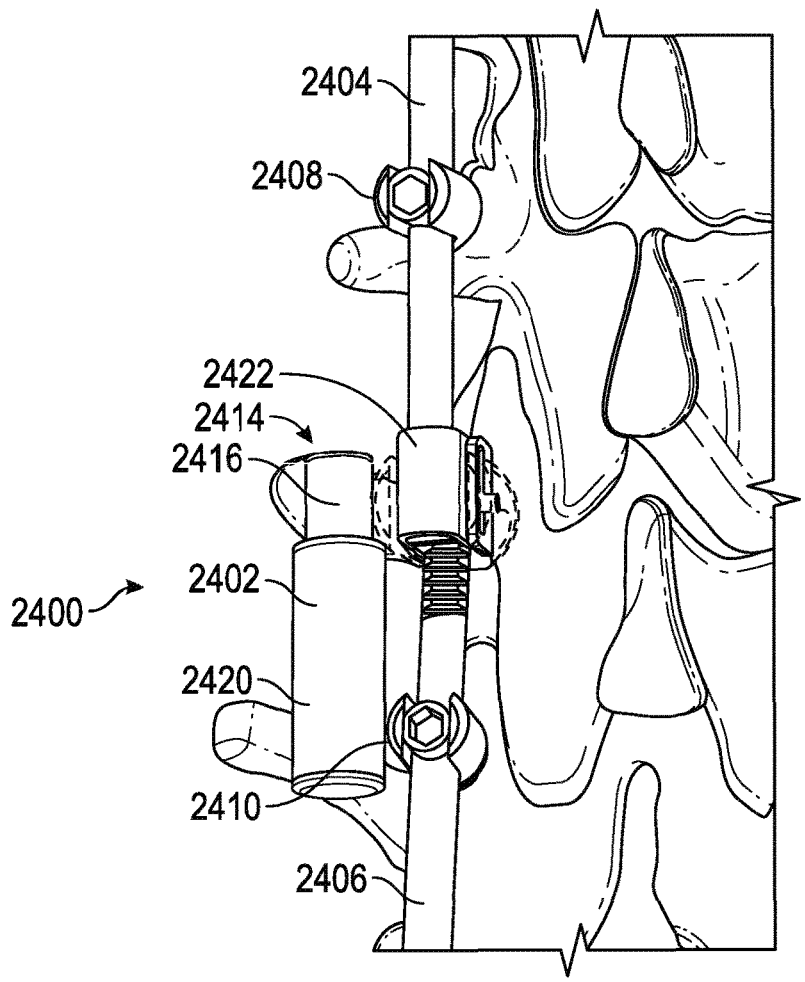
FIGS. 24A-D illustrate another embodiment of the spinal adjustment implant.
Figure 24B:
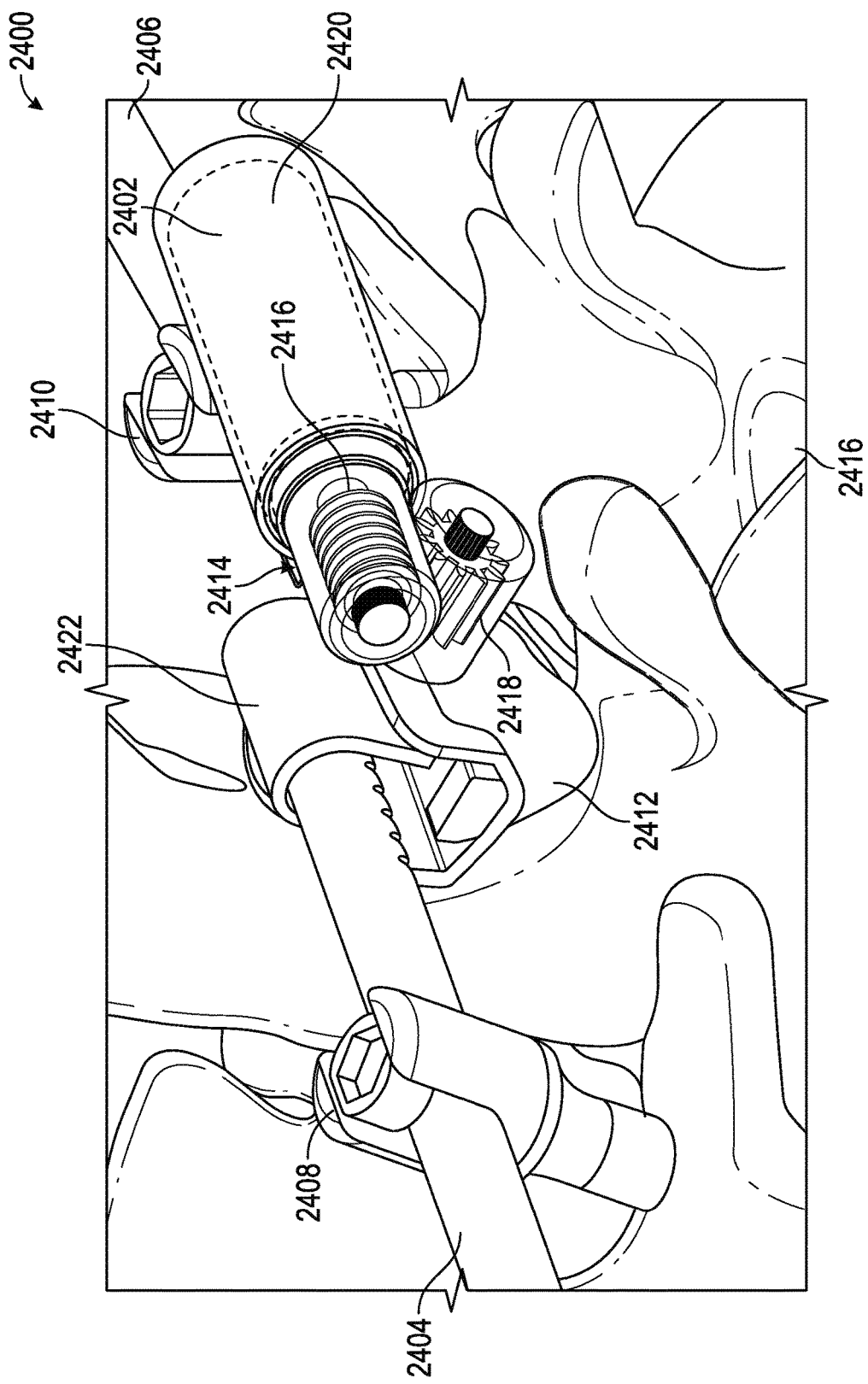

As illustrated in FIG. 24A-24B, the driving member can include a first end that is attached to a worm screw 2416 of a worm drive 2414. As the drive member 2402 rotates, the worm screw 2416 of the worm drive 2414 is rotated. The worm screw 2416 is configured to engage the worm wheel 2418 of the worm drive 2414 and translates the rotational energy of the drive member 2402 and worm screw 2416 in a first direction to a rotation in a second direction. In some embodiments, the driving member can be a magnet. The magnet may be 9 mm in diameter and 25 mm long. The drive member 2402 and the worm drive 2414 can be covered in a flexible membrane or below covering assembly that can be configured to protect the teeth of the worm drive 2414 from body materials. In some embodiments, this housing 2420 can be 10 mm in diameter, 38 mm long, and 10 mm in offset.

Figure 24C:
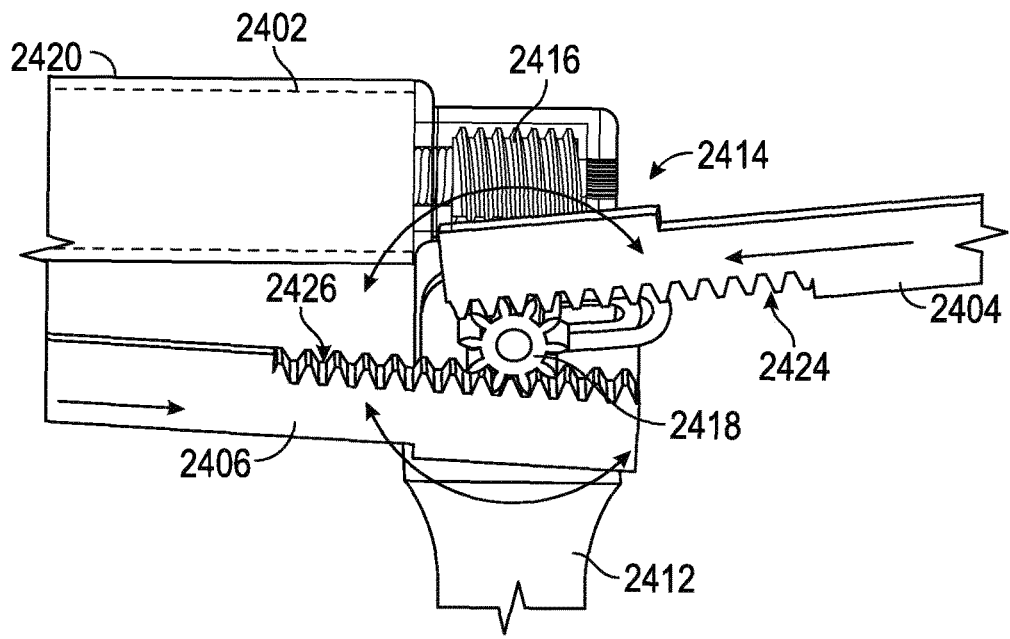

In some embodiments, the first rod 2404 and the second rod 2406 can include a tooth portion that is configured to engage the teeth of the worm wheel 2418. The first rod 2404 and second rod 2406 can include an external housing 2422 that can secure the position of the first rod 2404 and second rod 2406 about the worm wheel 2418. As illustrated in FIG. 24C, one end of the first rod 2404 is located above one end of the second rod 2406. In some embodiments, the first rod 2404 has a first engagement portion 2424 that includes a plurality of teeth that is configured to engage the teeth of the worm wheel 2418 above the second rod 2406. In some embodiments, the second rod 2406 has a second engagement portion 2426 that includes a plurality of teeth that is configured to engage the teeth of the worm wheel 2418 below the first rod 2404.

FIG. 24C illustrates the movement of the first rod 2404 and the second rod 2406 as the worm wheel 2418 of the worm drive 2414 is rotated. As shown by the arrows in FIG. 24C, as the worm wheel 2418 rotates in a first direction, it causes the first engagement portion 2424 of the first rod 2404 and the second engagement portion 2426 of the second rod 2406 to engage with the teeth and to move past each other. As the first rod 2404 and the second rod 2406 move past each other, the first rod 2404 pivots downward near the engagement portion to cause the opposite end of the first rod 2404 to tilt upward. Similarly, as the worm wheel 2418 engages the second engagement portion 2426 of the second rod 2406, the second rod 2406 pivots downward near the engagement portion to cause the opposite end of the second rod 2406 to tilt upward. In some embodiments, this compression near the worm wheel 2418 can occur simultaneously in both the first rod 2404 and the second rod 2406 as shown. The compression does not need to be purely linear as there is a rotational degree of freedom. In some embodiments, the first rod 2404 and the second rod 2406 can be bent past each of the respective engagement portions.

Figure 24D:
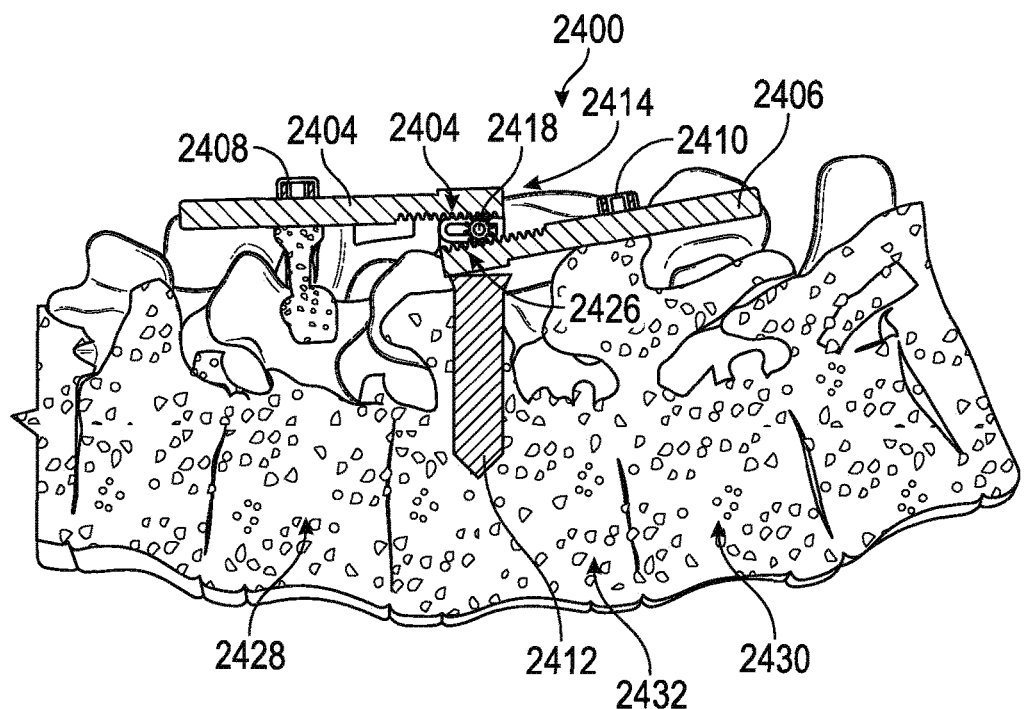

FIG. 24D illustrates a cross sectional view of the spinal adjustment implant 2400 as it is implanted into a plurality of vertebra of the spinal system. The first rod 2404 can be secured to a first vertebra 2428 of the spinal system using a first securement portion 2408. In some embodiments, the first securement portion 2408 can be a screw. In some embodiments, the second rod 2406 can be secured to a second vertebra 2430 of the spinal system using a second securement portion 2410. Similarly, in some embodiments, the second securement portion 2410 can be a screw. In some embodiments, a third securement portion 2412 adjacent to the second engagement portion 2426 of the second rod 2406 can be secured to a middle vertebra 2432 of the spinal system. In some embodiments, the middle vertebra 2432 can be located between the first vertebra 2428 and the second vertebra 2430.

As illustrated in FIG. 24D, the third securement portion 2412 can be the point about which compression of the first vertebra 2428 and second vertebra 2430 occur. As seen, as the worm wheel 2418 rotates, the first engagement portion 2424 of the first rod 2404 can move past the second engagement portion 2426 of the second rod 2406. The ends of the first rod 2404 and second rod 2406 where the respective engagement portions are located bend downward, such that either ends of the first rod 2404 and second rod 2406 bend upwards. This can create a curve in the spinal system about the middle vertebra 2432.

FIGS. 25A-25E generally illustrate an embodiment including a Torsen differential which may allow a single motor or magnet output (rotation) to drive two sides of an implant at the same rate, or at different rates from each other. For example, different displacement rates or different angulation change rates. FIGS. 25A-25E illustrate a spinal adjustment implant 2500 for implantation along the spinal system of a subject. The spinal adjustment implant 2500 is similar to the implant 700 of FIG. 9 as it includes a first pivotable interface and a second pivotable interface that may allow a potentially greater increase in the lordotic Cobb angle during compression than that permitted by spinal adjustment implants such as the spinal adjustment implant 500 of FIGS. 1-3C. As discussed above for related implants, the spinal implant 2500 is configured to be used in place of traditional rods, which are used to main posterior decompression and stabilize during fusion. Some embodiments of the spinal implant 2500 are compatible with interbody spacers placed between the vertebrae being treated.

The spinal implant 2500 comprises a housing 2502 having a first end 2504 and a second end 2506. The housing 2502 can include a plurality of portions that extend between the first end 2504 of the housing 2502 and the second end 2506 of the housing 2502. In some embodiments, the housing 2502 can include a first extendible portion 2508, a planet housing 2512, a second extendible portion 2510, and a magnet housing 2514.

The planet housing 2512 can include openings at both ends and a cavity 2513 there through. As will be discussed in more detail below, the planet housing 2512 can be configured to house a plurality of gears that can translate rotational motion into a longitudinal extension or retraction through the housing 2502.

In some embodiments, the planet housing 2512 is positioned longitudinally between the first extendible portion 2508 and the second extendible portion 2510. The first extendible portion 2508 is located at the first end 2504 of the housing 2502 and the second extendible portion 2510 is located at the second end 2506 of the housing 2502. The first extendible portion 2508 and the second extendible portion 2510 can both include a first cavity 2509 and a second cavity 2511 respectively that can house a screw. In some embodiments, the first extendible portion 2508 and the second extendible portion 2510 can include a projection portion 2516, 2518 that extends perpendicularly from the surface of the first extendible portion 2508 and second extendible portion 2510 respectively. A rod 2517 can be configured to extend from the projection 2516 in a first direction and a rod 2519 can be configured to extend from the projection 2518 in a second direction such that the rod 2517 and rod 2519 extend in opposite directions away from each other. As will be discussed in more detail below, in some embodiments, the first cavity 2509 and the second cavity 2511 can include an inner thread that can each threadingly engage their respective screws such that rotation of each of the screws can cause the first extendible portion 2508 and the second extendible portion 2510 to extend or retract from the planet housing 2512.

The magnet housing 2514 can be located adjacent to the planet housing 2512 such that the magnet housing 2514 and the planet housing 2512 run parallel to one another. The magnet housing 2514 can include a cavity 2514 which extends between the first end 2504 and the second end 2506. The cavity 2514 may have a variable inner diameter along its length or may have a generally constant inner diameter. The inner wall of the magnet housing 2514 may have circumferential grooves or abutments (not illustrated) that axially maintain certain elements of the assembly. A driving member 2520 can be rotatably disposed within the cavity 2515. The driving member 2520 may comprise any non-invasively rotatable element such as those described in relation to FIGS. 20-23. In some embodiments, the driving member 2520 can be a magnet. In some embodiments, the magnet may be 9.5 mm in diameter and 41 mm long. Of course it will be understood that other dimensions may be used. In some embodiments, the planet housing 2512 and the magnet housing 2514 can include a side opening near the second end of the planet housing 2512 and magnet housing 2514 that provides an interior connection between the planet housing 2512 and the magnet housing 2514. As will be discussed in more detail below, the interior connection can house a gear system that translates rotational movement of the driving member 2520 into longitudinal translation (e.g., extension or retraction) of the first extendible portion 2508 and the second extendible portion 2510.

FIG. 2C illustrates an enlarged view of the second end 2506 of the spinal adjustment implant 2500 with the housing 2502 removed. In some embodiments the housing 2502 can include a driving member 2520, a worm drive 2530, a miter gear mesh 2540, a first screw 2524, a second screw 2522, a Torsen differential 2524 that is housed in a planet carrier 2552.

In some embodiments, the driving member 2520 can be disposed about a rod 2531 that extend from the second end 2506 and is rotationally coupled to a worm drive 2530. The worm drive 2530 can include a worm screw 2532 and a worm wheel 2534. In some embodiments, the worm gear reduction may be 20:1. As the driving member 2520 is rotated, the attached rod 2531 rotates the worm drive 2530 which causes the worm wheel 2534 to turn.

In some embodiments, the worm drive 2530 may engage a miter gear mesh 2540 which can translate the rotational energy of the worm drive 2530 into longitudinal movement along the length of the housing 2502. A type of bevel gear, miter gears are useful for transmitting rotational motion at a 90 degree angle. In some embodiments, the miter gear mesh 2540 can translate rotational motion at a 90 degree angle with a 1.3:1 ratio. In some embodiments, the miter gear mesh 2540 can be replaced with any type of gear system that can translate rotational motion at an angle. The miter gear mesh 2540 can include a first gear 2542 and a second gear 2544. In some embodiments, the first gear 2542 is attached to the worm wheel 2534, such that rotation of the worm wheel 2534 causes rotation of the first gear 2542. The first gear 2542 can have a plurality of teeth that can engage with the teeth of the second gear 2544. The second gear 2544 can be disposed about a rod 2523 such that rotation of the second gear 2544 causes rotation of the rod 2523 in the same direction.

In some embodiments, the second gear 2544 of the miter gear mesh 2540 can be attached to a rod 2554 that engages with a Torsen differential 2550 that is located within a planetary carrier 2552. A Torsen differential, and in similar gear systems, serves to provide a mechanical self-locking center differential which regulates the power between the front and rear axles according to demand. A Torsen differential operates on the basis of torque sending and responds to varying rotational forces between the input and output shafts. This can enable variable distribution of the driving torque between the axles. On a Torsen differential, the plurality of output gears are interconnected by worm gears. This can limit high differential rotational speeds, but still balance the speeds when cornering. As will be discussed in more detail below, the Torsen differential 2550 can provide a different rate of rotation of attached members.

Figure 25A:
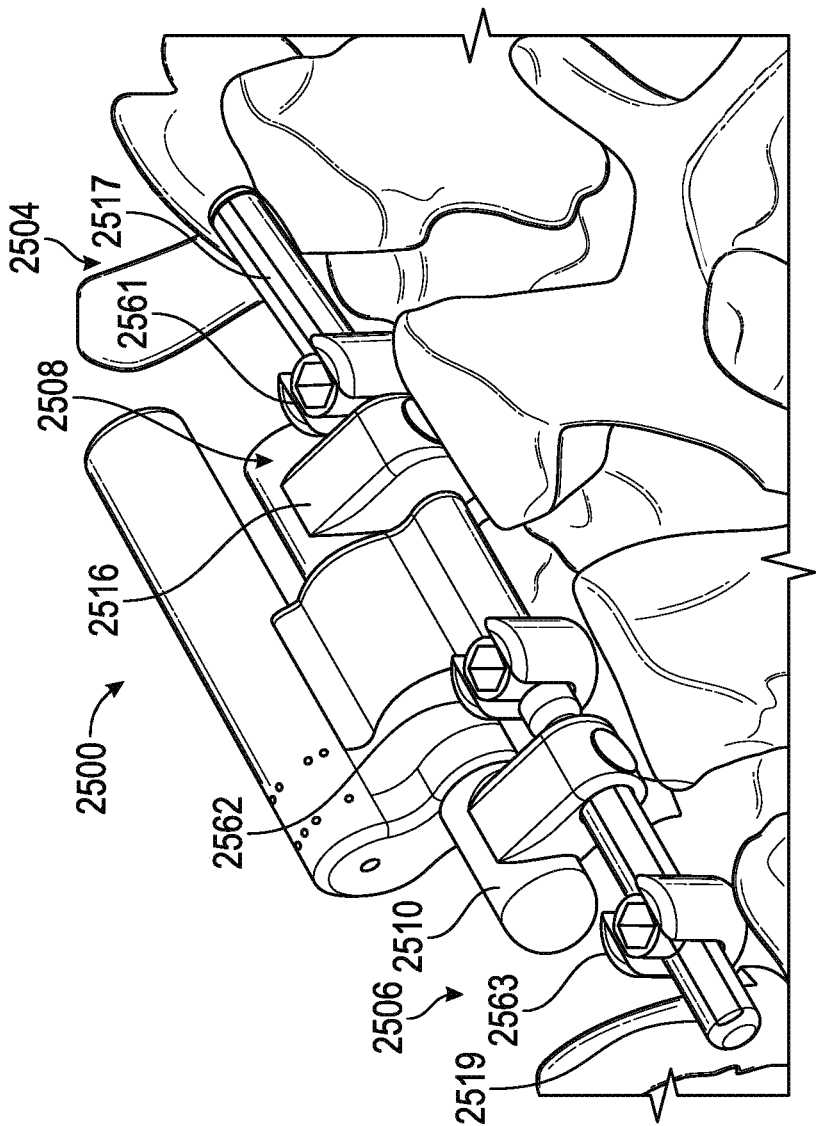
FIG. 25A illustrates an embodiment of a spinal adjustment implant including a Torsen differential that is configured to adjust the lordotic angle of a vertebra system. The Torsen differential allows a drive member to drive the two ends of the spinal adjustment implant at the same or different rate to provide for the same or different displacement rate or angulation rate of change.
Figure 25B:
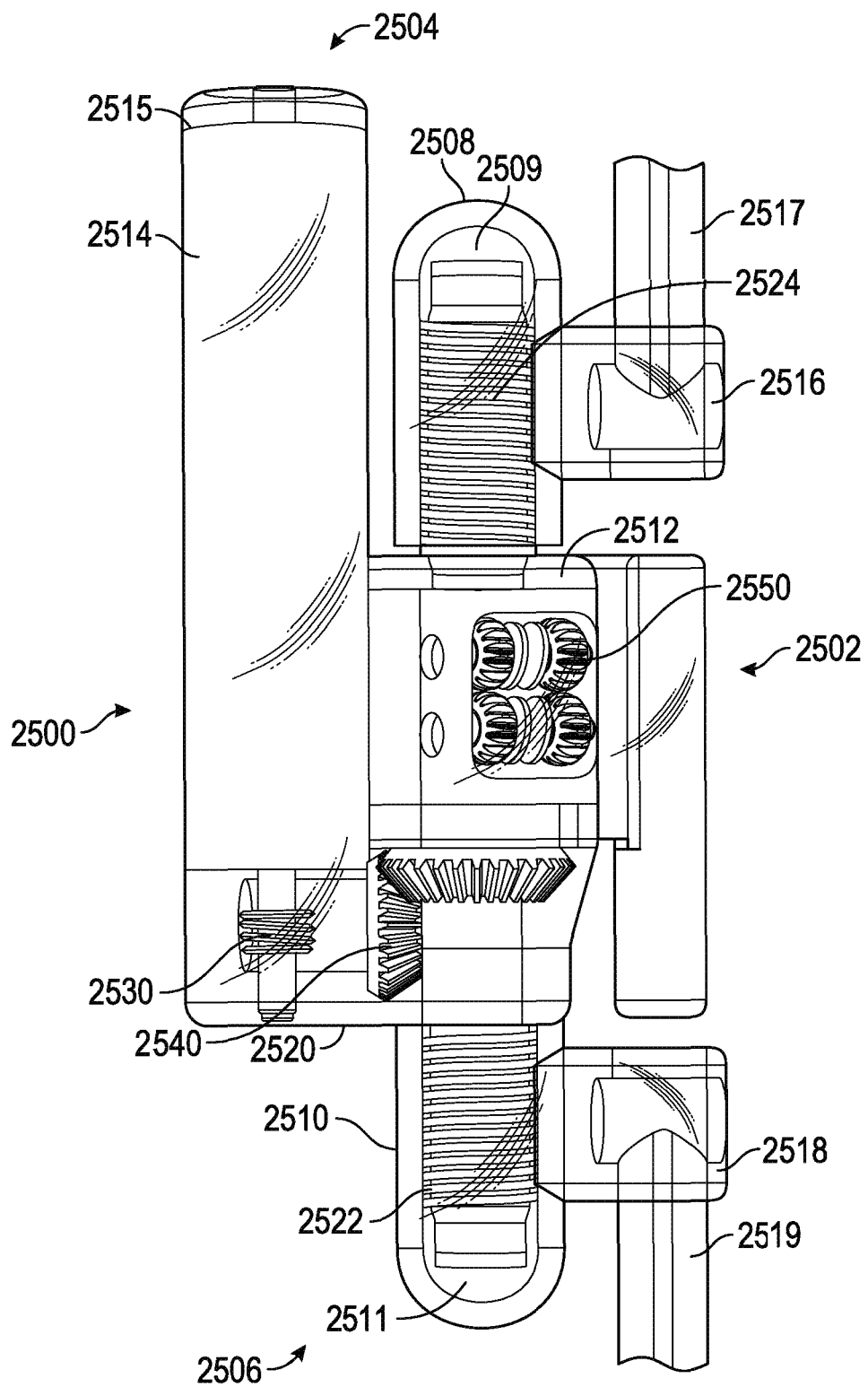
FIG. 25B illustrates a top view of the spinal adjustment implant of FIG. 25A where the internal gears and drive systems of the spinal adjustment implant are visible.
Figure 25C:
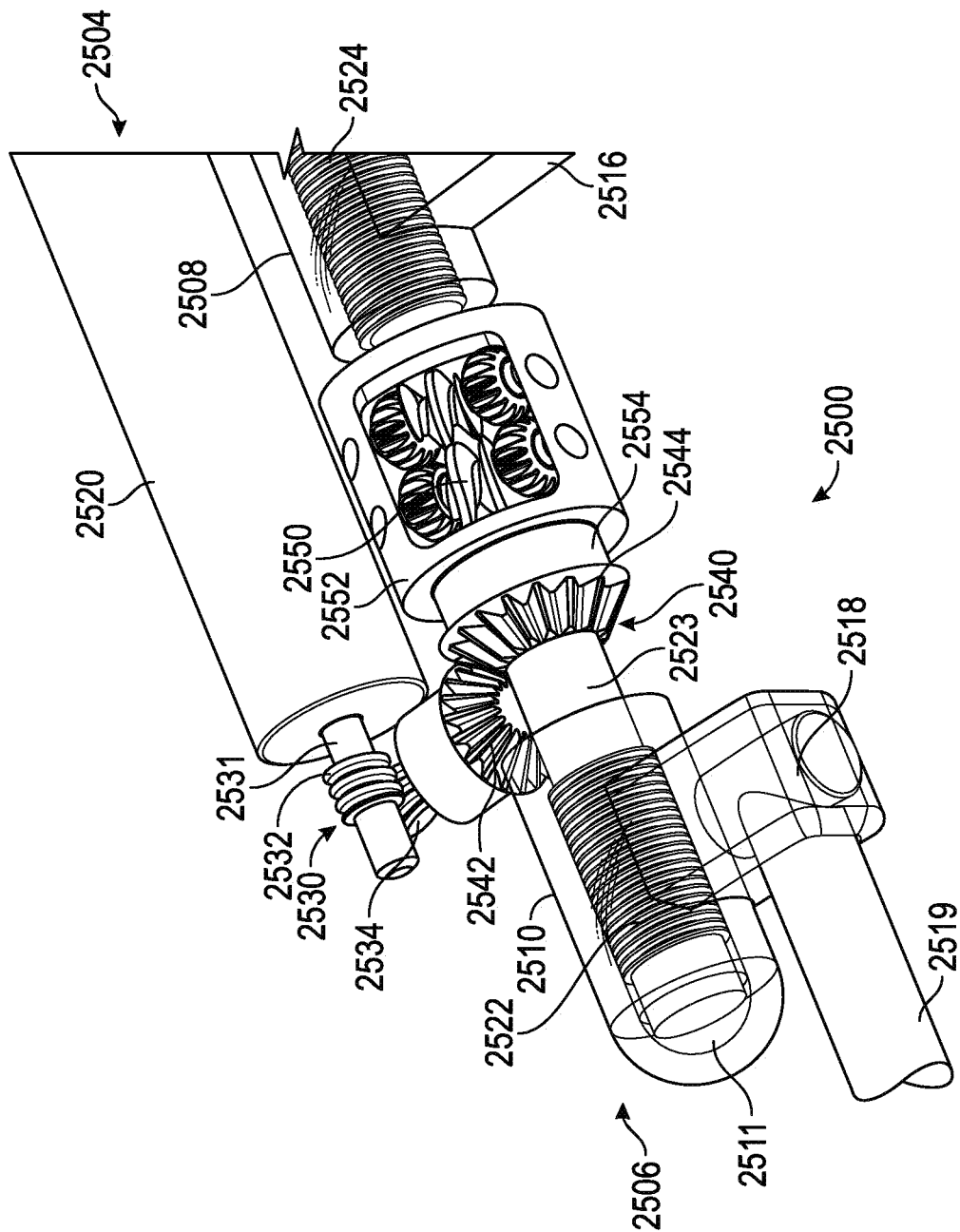
FIG. 25C illustrates a perspective view of the spinal adjustment implant of FIG. 25A with the housing removed.
Figure 25D:
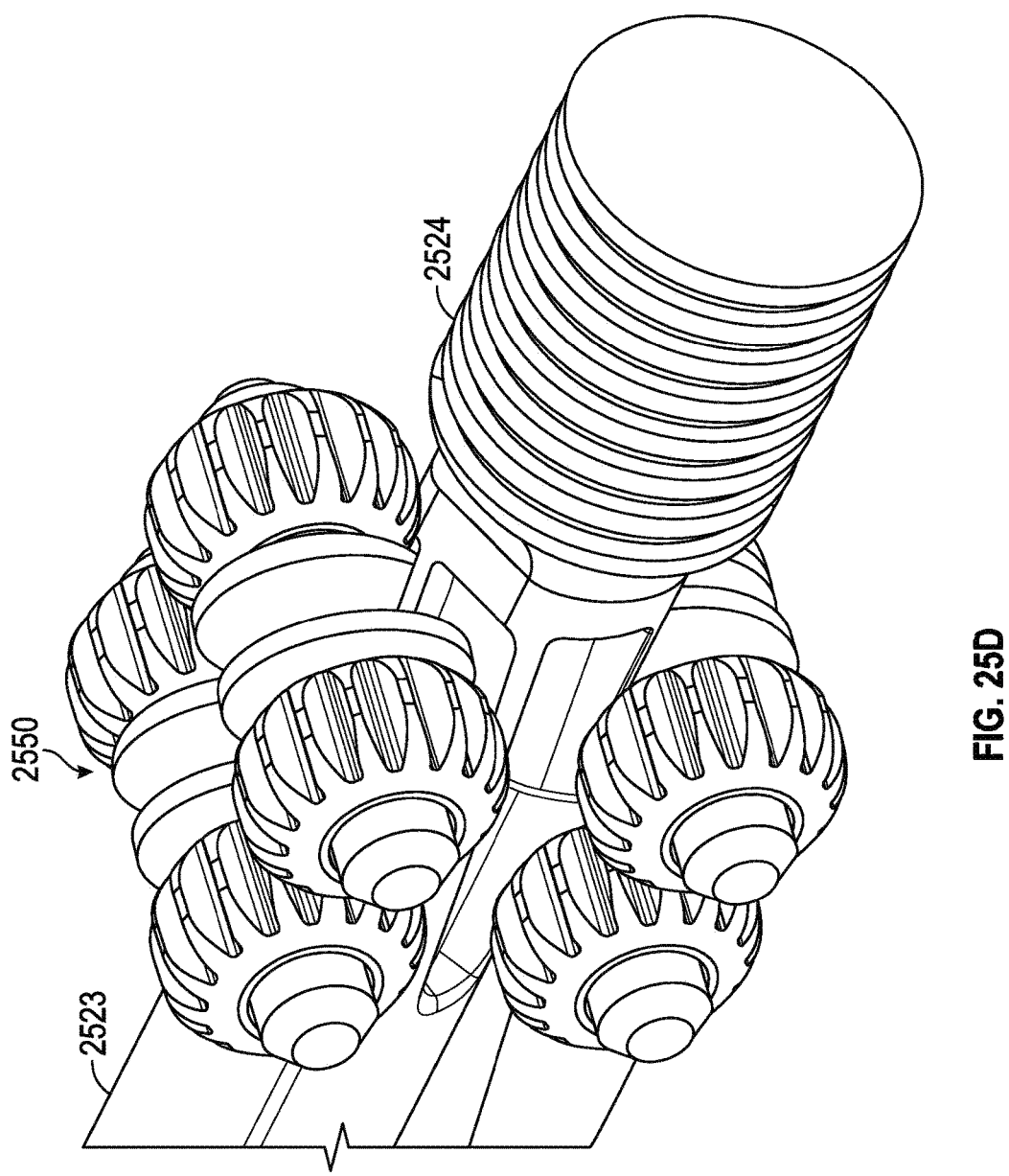
FIG. 25D illustrates an enlarged view of the Torsen differential of the spinal adjustment implant of the FIG. 25A.

FIG. 25D illustrates an enlarged view of the Torsen differential 2550 without the planetary carrier 2552. As can be seen, the Torsen differential 2550 can engage with the rod 2554 at a second end 2506 and a portion of the first screw 2524 at a first end 2504. In some embodiments, as illustrated in FIG. 25B-25D, rotation of the rod 2554 by miter gear mesh 2540 can cause the Torsen differential 2550 to translate the rotational energy to the first screw 2524.

As discussed above, the spinal adjustment implant 2500 can be sued to non-invasively maintaining or changing the magnitude of compression between two vertebrae following fusion surgery (post-operatively) and/or non-invasively changing the magnitude of lordosis. As well, because the spinal adjustment implant 2500 includes a plurality of pivotal interfaces, the spinal adjustment implant 2500 can provide for a potentially greater increase in the lordotic Cobb angle during compression. This can be done by first rotating the driving member 2520 which causes rotation of the worm screw 2532 of the worm drive 2530. The worm screw 2532 engages with the worm wheel 2534 of the worm drive 2530 and rotates the attached first gear 2542 of the miter gear mesh 2540. As discussed above, the first gear 2542 of the miter gear mesh 2540 engages with the second gear 2544 of the miter gear mesh 2540 to translate the rotational energy at an angle. The rotation of the second gear 2544 rotates the attached rod 2523 and engages the Torsen differential 2550. As discussed above, the Torsen differential 2550 can engage with a portion of the first screw 2524 to rotate the first screw 2524. As well, the rod 2523 is attached to the second screw 2522 and rotates the screw. In some embodiments, the Torsen differential 2550 can provide the same or a different rate of rotation of the first screw 2524 and the second screw 2522. In some embodiments, this can provide for different displacement rates between the first screw 2524 and the second screw 2522. In some embodiments, this can produce the same or different angulation change rate between vertebrae that are attached to the spinal adjustment implant 2500.

As discussed above, in some embodiments, the first extendible portion 2508 and the second extendible portion 2510 further include a first cavity 2509 and second cavity 2511 respectively. Each of the first cavity 2509 and second cavity 2511 can further include a threaded interior that can be configured to movably engage the first screw 2524 and second screw 2522 respectively. In some embodiments, the rotation in a first rotational direction of the driving member 2520 causes both the first screw 2524 and the second screw 2544 to move into the first cavity 2509 and second cavity 2511 respectively. This can cause the rod 2517 attached to the first extendible portion 2508 and the rod 2519 of the second extendible portion 2510 to move towards each other and reduce the reach of the rod 2517 and rod 2519. This motion is capable of generating a force on the spine at the points of attachment of the spinal adjustment implant 2500 and increasing the compressive force(s) between the vertebrae.

Similarly, in some embodiments, the rotation in a second rotational direction of the driving member 2520 causes both the first screw 2524 and the second screw 2544 to extend out of the first cavity 2509 and second cavity 2511 respectively. The rotation in a second rotational direction can cause the first extendible portion 2508 and the second extendible portion 2510 to move in opposite directions along the same axis. This can cause the rod 2517 attached to the first extendible portion 2508 and the rod 2519 of the second extendible portion 2510 to move away from each other and increase the reach of the rod 2517 and rod 2519. This motion is capable of generating a force on the spine at the points of attachment of the spinal adjustment implant 2500 and decreasing the compressive force(s) between the vertebrae.

In some embodiments, the inner threading of the first cavity 2509 and second cavity 2511 can cause the first screw 2524 and second screw 2544 to rotate to move the attached first extendible portion 2508 and second extendible portion 2510 to move in the same direction along the same axis. For example, the first extendible portion 2508 can move in a first direction along the axis, wherein the first screw 2524 extends out of the first cavity 2509 and the second extendible portion 2510 can move in a first direction as well along the axis, wherein the second screw 2544 retracts into the second cavity 2511. The attached rod 2517 and rod 2519 thereby move in the first direction. In some embodiments, the distance between the rod 2517 and rod 2519 can maintain their distance, reduce their distance, or increase in distance. The aforementioned embodiment could apply in the reverse as well—wherein the first extendible portion 2508 and second extendible portion 2510 move in a second direction along the axis.

Figure 25E:
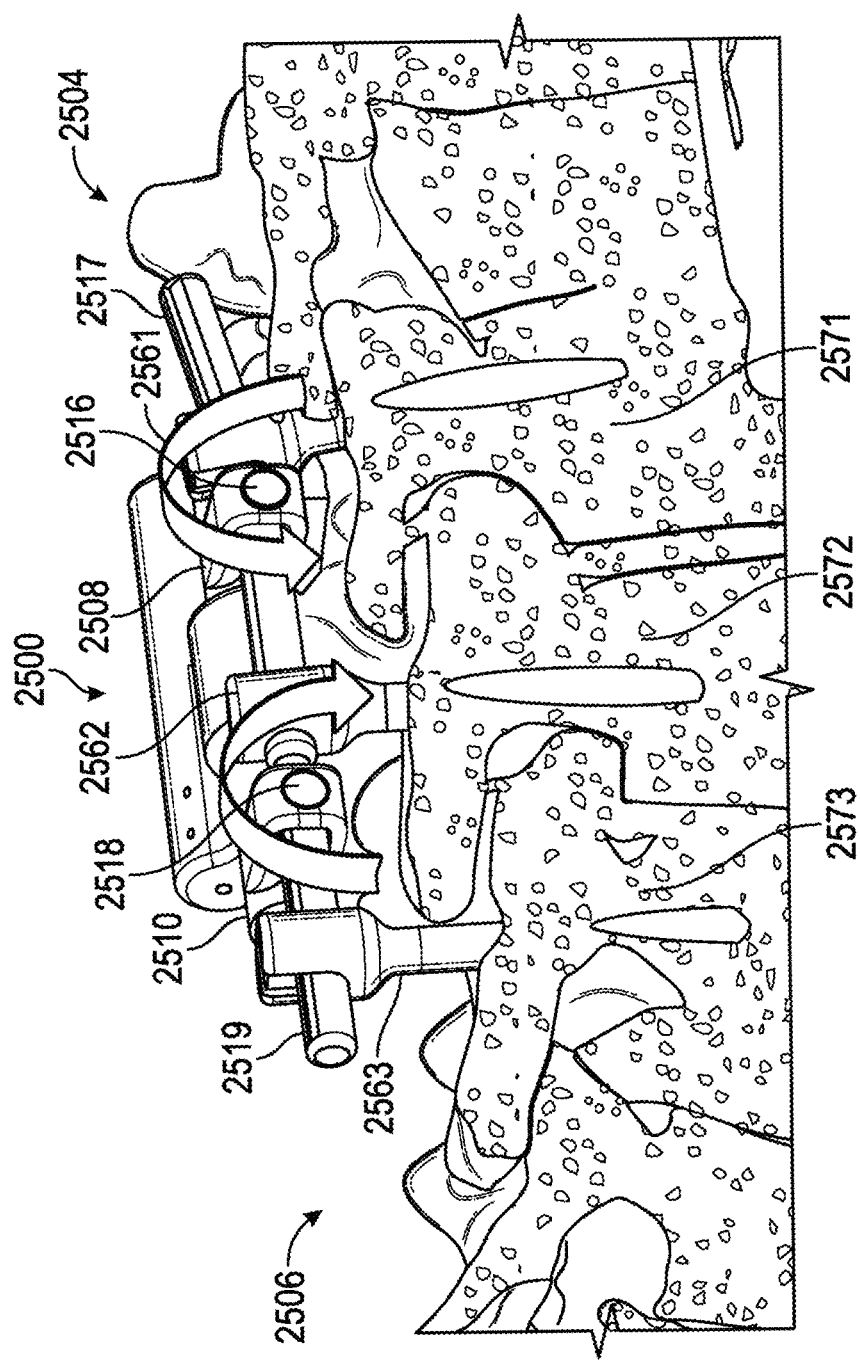
FIG. 25E illustrates a cross-sectional view of the spinal system with the spinal adjustment implant of FIG. 25A attached and indicating the angles of rotation of the spinal adjustment implant.

FIGS. 25A and 25E illustrate the spinal adjustment implant 2500 secured to a plurality of vertebra. The spinal adjustment implant 2500 can be secured to a plurality of vertebrae that are secured using a plurality of rods. As illustrated in FIG. 25E, the spinal adjustment implant 2500 includes a first rod 2561 located near the first end 2504 of the housing 2502. The first rod 2561 can be configured to couple to a first portion of the spinal system. The first portion of the spinal system may be a first vertebra 2571. In some embodiments, the spinal adjustment implant 2500 includes a second rod 2563 located near the second end 2506 of the housing 2502. The second rod 2563 can be configured to couple to a second portion of the spinal system. The second portion of the spinal system may be a second vertebra 2573. In some embodiments, the spinal adjustment implant 2500 includes a middle rod 2562 located between the first end 2504 and the second end 2506 of the housing 2502. The middle rod 2562 can be configured to couple to a third portion of the spinal system. The third portion of the spinal system may be a third vertebra 2572 located between the first vertebra 2571 and the second vertebra 2573. As indicated, a first angle of rotation is in a clockwise direction while a second angle of rotation is in a counter-clockwise direction. As noted in FIG. 25A, the Torsen differential can cause the rotation about the first and second angles of rotation to occur at the same or different rates.

In some embodiments, the first rod 2561 and second rod 2563 can serve as a plurality of pivotable interfaces that can allow a potentially greater increase in the lordotic Cobb angle during compress. As is illustrated in FIG. 25E, the first rod 2561 and second rod 2563 allow the secured first vertebra 2571 and the second vertebra 2573 to pivot about the middle rod 2563 that is secured to the third vertebra 2572. The direction of the rotation of the rods is illustrated by the curved arrows illustrated in FIG. 25E. In some embodiments, the first rod 2561 and second rod 2563 are non-invasively lockable and nonlockable. In some embodiments, the first and second rods 2561, 2563 are configured to be non-invasively lockable and unlockable as part of the non-invasive adjustment. In some embodiments, the first and second rods 2561, 2563 are configured to be non-invasively lockable and unlockable in conjunction with the rotation of the driving member 2520.

In some embodiments, the first and second rods 2561, 2563 are intermittently locked and unlocked during an adjustment procedure.

In some embodiments, one or more of the pivotable interfaces is configured to rotate freely in either direction (e.g., clockwise and/or counterclockwise). In some embodiments, one or more of the pivotable interfaces is partially constrained to have free rotation in one direction but no rotation in the other direction—this may be accomplished using a free wheel or other one-way clutching. In some embodiments, the rods include two-way locking so that they may lock and unlock automatically by the operation of the spinal adjustment implant. For example, the Eternal Remote Controller (ERC) may be used to lock and unlock a magnetic lock which is capable of reversibly removing the rotational freedom of the pivotable interface(s). In some embodiments which may be either freely rotating or lockable, there may additionally be constrained rotation or motion, wherein there are limits, extents, or detents that limit the total amount of travel of a particular rotation or motion.

FIGS. 26A-26H generally illustrate a motor or magnet that by use of a cam is able to intermittently lock or unlock a mechanism, as it is adjusted. In some embodiments, the unlocking may temporarily allow for change in angulation, which is then locked again, after the change occurs. FIGS. 26A-26H illustrate various views of a pivot lock mechanism 2600, according to some embodiments. The pivot lock mechanism 2600 may be used, for example, to lock and unlock the first and second pivotable interfaces 729, 727 of the spinal adjustment implant 700 shown in FIG. 9. The pivot lock mechanism 2600 includes a motor 2602 operably coupled to a drive shaft 2608. In some embodiments, the motor 2602 comprises a magnet that may be magnetically coupled to one or more other magnets. For example, in some embodiments, the motor 2602 may be magnetically coupled to the one or more magnets of the magnetic handpiece 178 shown in FIGS. 4 and 5. In some embodiments, the magnet 2602 comprises a cylindrical, radially-poled permanent magnet, although any suitable size, shape, and polarity is appreciated. The magnet may include a north pole 2618 and a south pole 2620. As shown in FIGS. 26A-26H, the drive shaft 2608 may extend longitudinally from the motor 2602. In some embodiments, the center longitudinal axes of the motor 2602 and the drive shaft 2608 are aligned. The motor 2602 and the drive shaft 2608 may be operably coupled such that the drive shaft 2608 rotates when the motor 2602 rotates. In some embodiments, the drive shaft 2608 and the motor 2602 rotate at the same angular velocity and/or at different angular velocities. For example, in some embodiments, the motor 2602 rotates at one, two, three, or more discreet angular velocities, and/or at any angular velocity between a minimum and maximum value. However, it should be appreciated that the motor 2602 and the drive shaft 2608 may rotate at any suitable angular velocity. In some embodiments, the motor 2602 can rotate in either direction (e.g., clockwise and/or counterclockwise).

The pivot lock mechanism 2600 further includes a rod 2616, a pivot member 2614, and a pin 2615. In some embodiments, a first end of the rod 2616 may be attached to, for example, a pedicle screw, and a second end of the rod 2616 may be attached to the pivot member 2614. In some embodiments, the rod 2616 can be any of the rods disclosed herein, such as the rod shown in FIG. 48. The pin 2615 may couple the pivot member 2614 to a pivot slide 2612. In some embodiments, the pivot slide 2612 includes a slot 2621 configured to accommodate first and second pivot locks 2604 a, 2604 b. The first and second pivot locks 2604 a, 2604 b may be constrained to vertical motion and may be independently spring loaded downward with corresponding first and second elastic members 2606 a, 2606 b, respectively. In some embodiments, the first and second elastic members 2606 a, 2606 b comprise springs, such as, for example, compression springs. As the pivot member 2614 rotates, the pivot slide 2612 is configured to translate horizontally back and forth. For example, in some embodiments, the pivot slide 2612 may be able to cyclically translate in opposing first and second directions. In some embodiments, the horizontal translation of the pivot slide 2612 is perpendicular relative to the vertical motion of the first and second pivot locks 2604 a, 2604 b. Translation of the pivot slide 2612 may cause the rod 2616 to adjust the positioning of one or more pedicle screws and/or the positioning of one or more other rods.

As shown in FIGS. 26D and 26E, the slot 2621 has two ramps 2622, 2624 spaced opposite of each other. The bottom surface of the slot 2621 that extends between the two ramps 2622, 2624 may be flat or any other suitably shaped surface. The first and second pivot locks 2604 a, 2604 b may be configured to settle into ramps 2624, 2622, respectively, regardless of the angle of the rod 2616. In some embodiments, the rod 2616 is unable to force the pivot slide 2612 to move when the first and second pivot locks 2604 a, 2604 b are in place. FIGS. 26D and 26E illustrate two exemplary views showing the first and second pivot locks 2604 a, 2604 b locked in place.

The pivot lock mechanism 2600 also includes a cam 2610 operably coupled to the drive shaft 2608. The cam 2610 alternately unlocks and locks the pivot member 2614 by engaging the first and second pivot locks 2604 a, 2604 b. Rotation of the cam 2610 may alternately unlock and lock the pivot member 2614 as it is rotated. For example, in some embodiments, unlocking the pivot lock mechanism 2600 may temporarily allow for a change in angulation of the rod 2616, after which the pivot member 2614 may be locked.

Figure 26A:
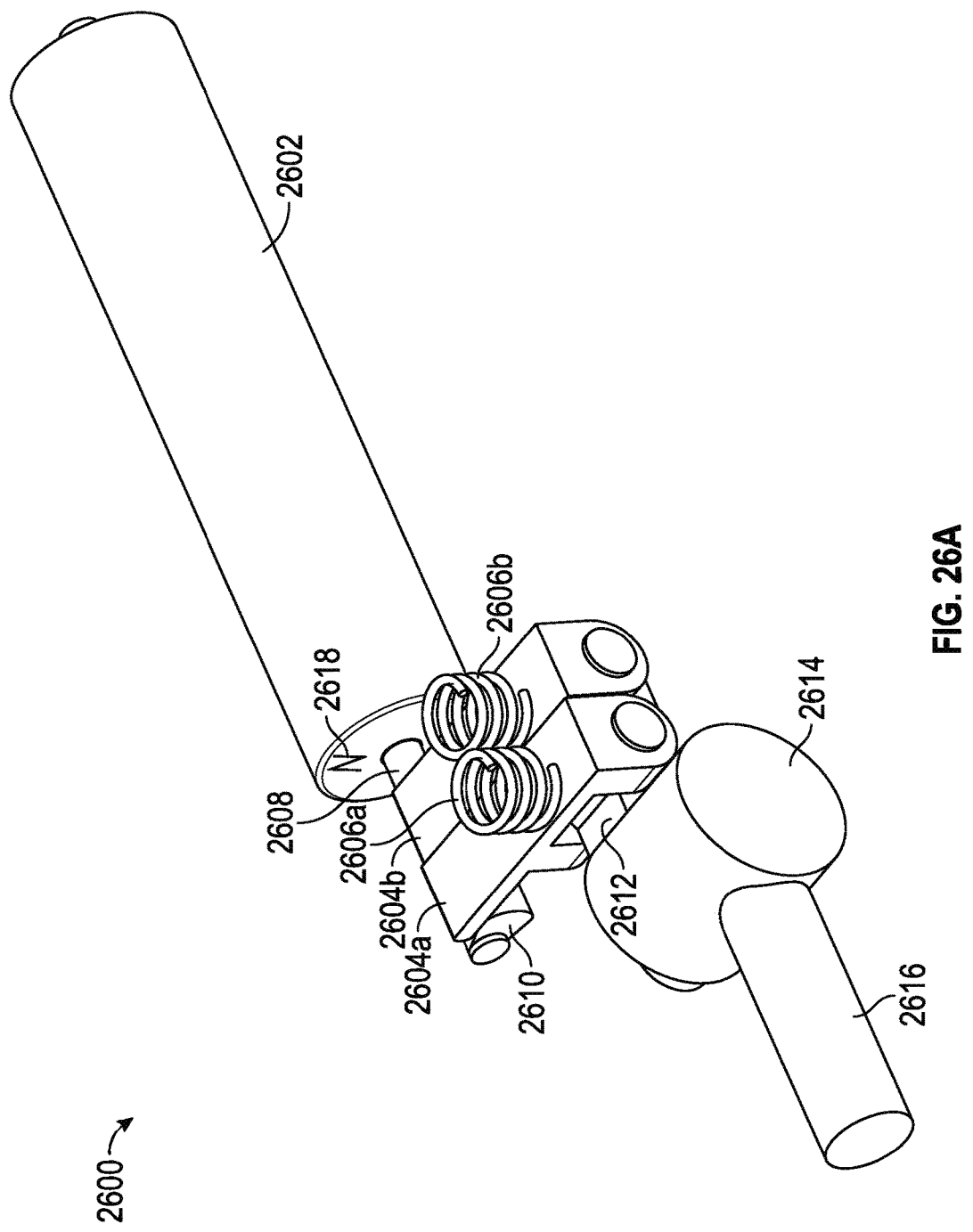
Figure 26F:
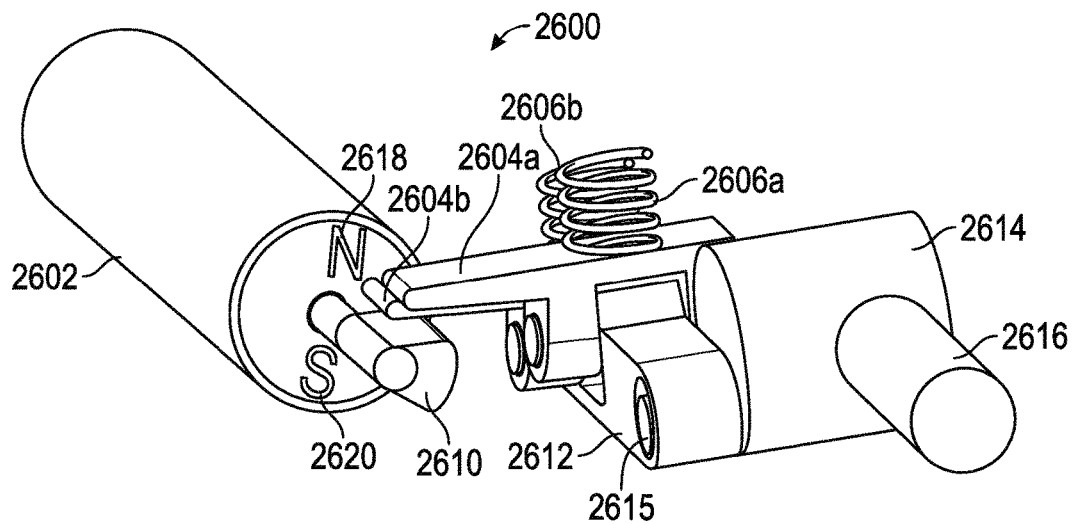
Figure 26G:
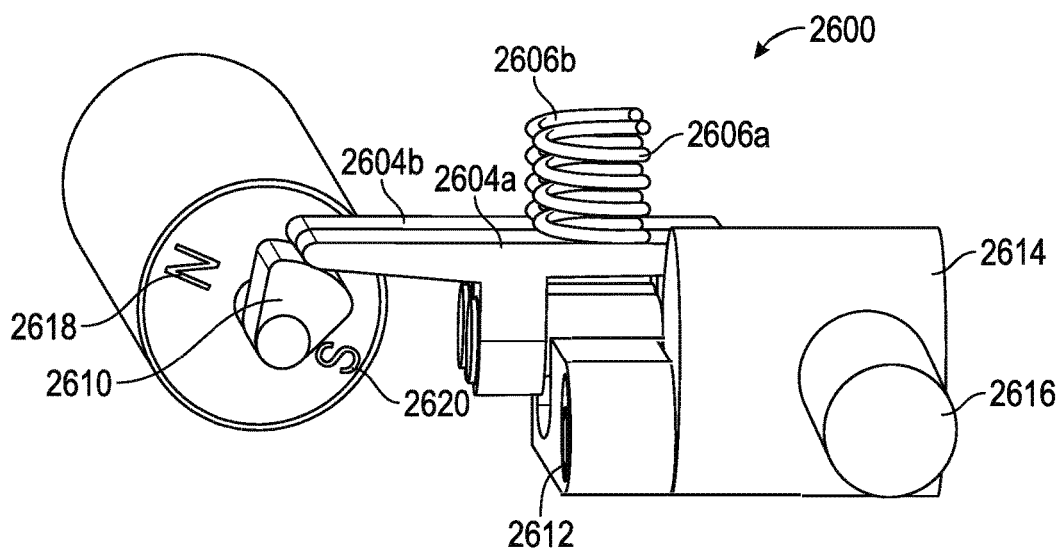
Figure 26H:
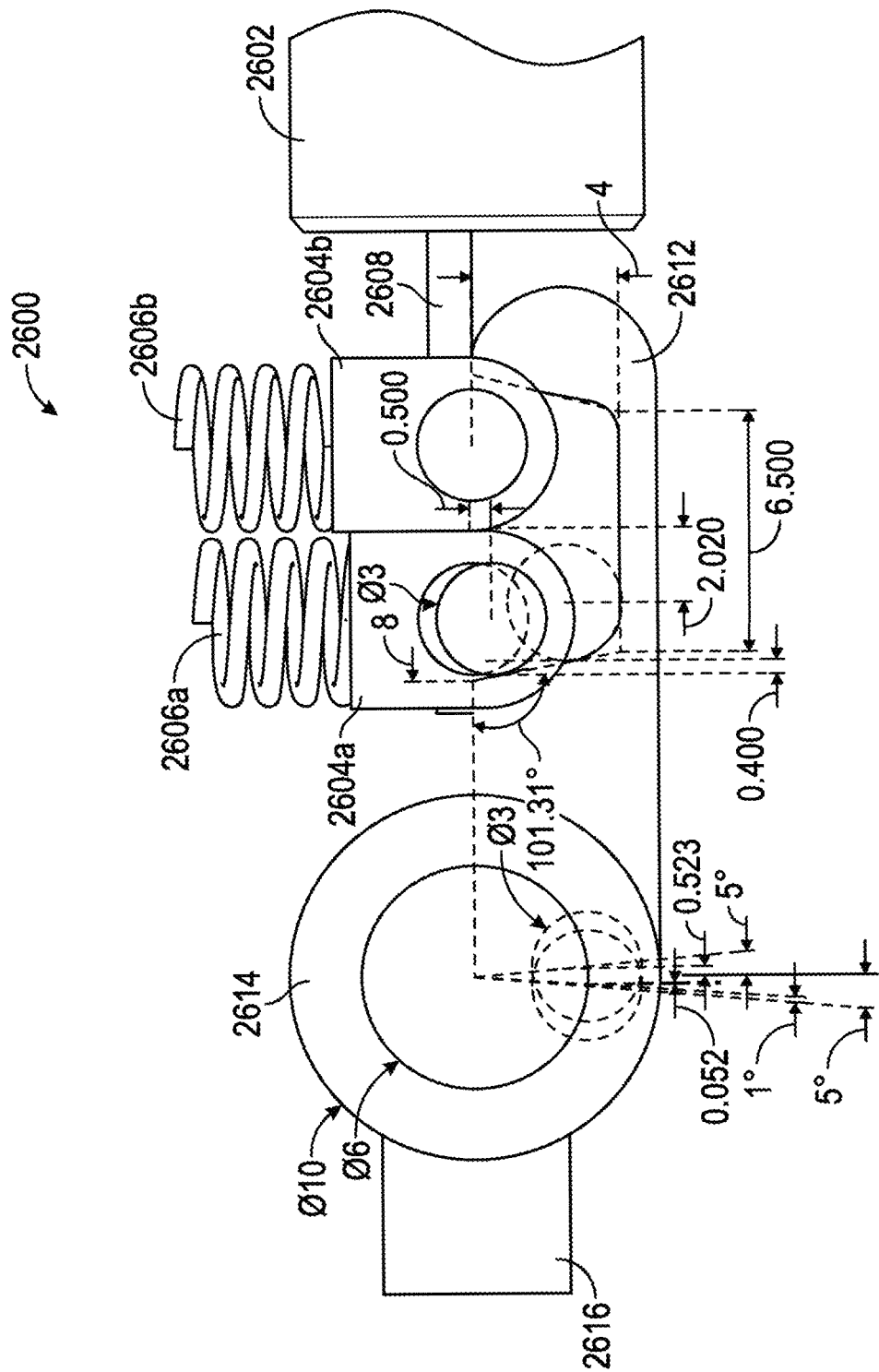

For example, as shown in FIG. 26G, the cam 2610 may intermittently unlock the pivot member 2614 by lifting the first and/or second pivot locks 2604 a, 2604 b upward by overcoming the downward force exerted by the first and/or second elastic members 2606 a, 2606 b, respectively. In some embodiments, when the pivot member 2614 is unlocked, a rotation of the pivot member 2614 in the range of about 1 degree to about 45 degrees may cause a translation of the pivot slide 2612 in the range of about 0.01 mm to about 0.8 mm, although any suitable range for these respective movements are appreciated. For example, in some embodiments, a 10 degree rotation of the pivot member 2614 may cause a 0.5 mm translation in the pivot slide 2612. As shown in FIG. 26F, the cam 2610 may intermittently lock the pivot member 2614 when the first and/or second pivot locks 2604 a, 2604 b settle back into the slot 2621 after the cam 2610 disengages the first and/or second pivot locks 2604 a, 2604 b. In some embodiments, the cam 2610 may lift the first and/or second pivot locks 2604 a, 2604 b for a prescribed duration, the duration of which may be controlled by the cam shape and/or gearing. As a result, as the cam 2610 is rotated by the drive shaft 2608, the first and second pivot locks 2604 a, 2604 b may move in opposing first and second vertical directions. Further, in some embodiments, the cam 2610 may rotate in either direction (e.g., clockwise and/or counterclockwise), and in other embodiments, the cam 2610 may rotate in only one direction (e.g., only clockwise or counterclockwise). With reference to FIG. 26H, various dimensions of the pivot lock mechanism 2600 are shown. However, it should be understood that while certain dimensions are shown in FIG. 26H, other suitable dimensions are also appreciated.

FIGS. 27-30 illustrate various types of spinal implant adjustment structures 2700, according to some embodiments. The adjustment structures 2700 may be used, for example, to adjust one or more rods of the spinal implants shown in FIGS. 1-12. For example, the adjustment structures 2700 may be functionally similar to driving members 514 and 814 shown in FIGS. 3A and 12. Similar to driving members 514 and 814, the adjustment structures 2700 may be configured to engage first and second threaded drivers to cause pistoning of one or more corresponding rods. For example, with reference to implant structures illustrated in FIG. 3A, in some embodiments the adjustment structures 2700 may be used in lieu of driving member 514 to rotate the first and second threaded drives 528, 542 to cause the first and second rods 558, 588 to move into or out of the cavity 508 of the housing 502, thereby causing the longitudinal distance L between points A and B to decrease or increase. Of course, it should be appreciated that any of the adjustment structures 2700 shown in FIGS. 27-30 may be used as a driving member in any of the spinal implant embodiments described herein.

Figure 27:
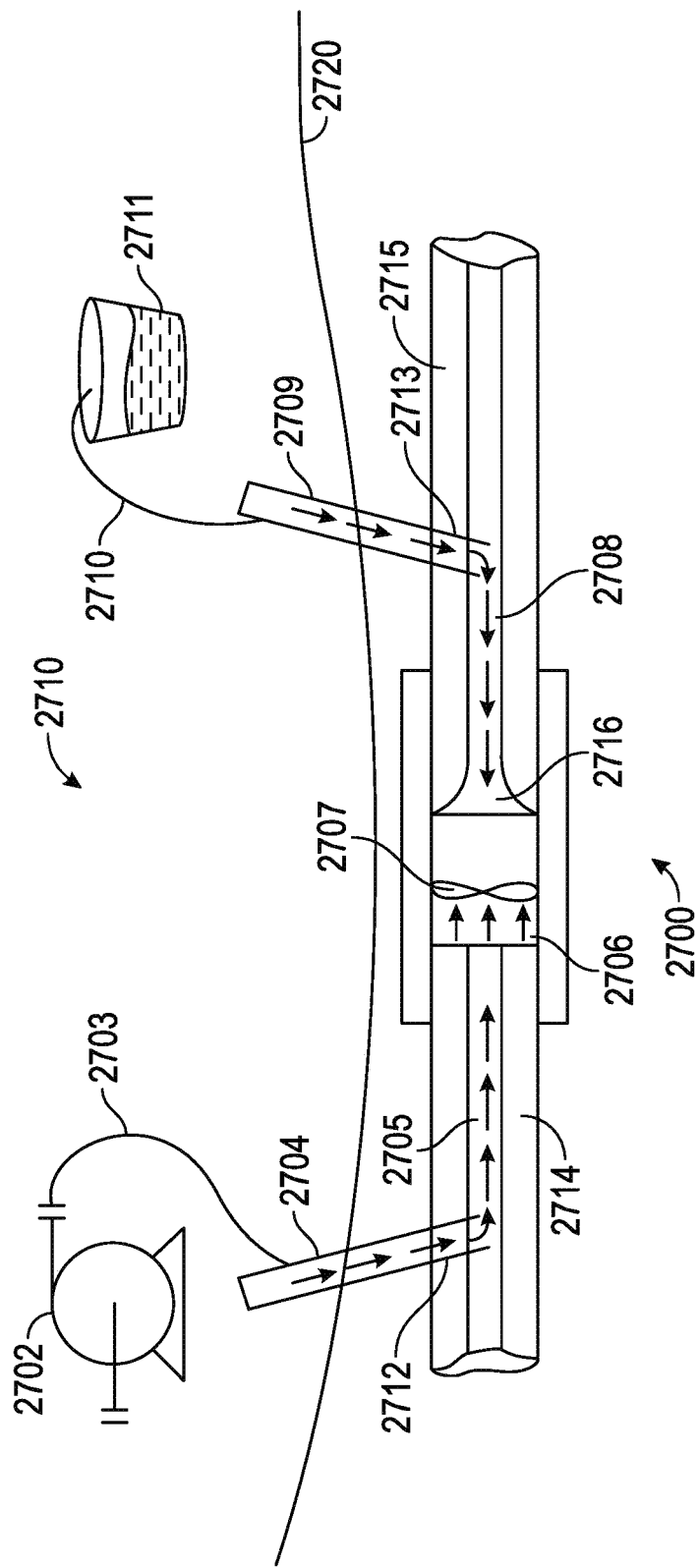
FIG. 27 illustrates a hydraulic activated adjustment structure for use in an adjustable spinal implant.
Figure 28:
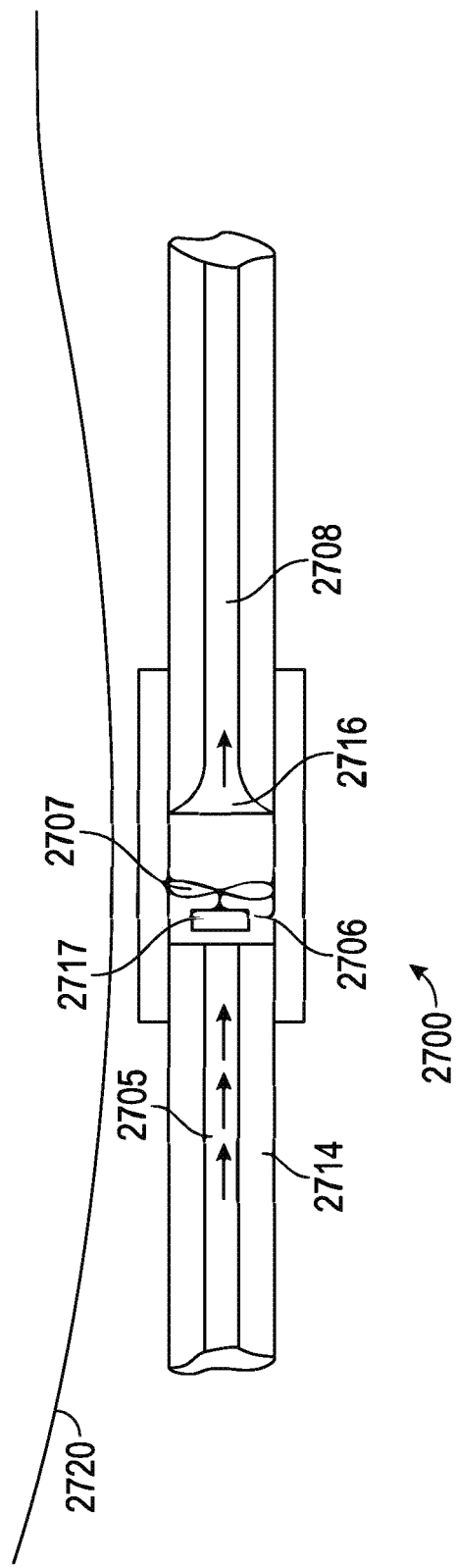
FIG. 28 illustrates a magnetic fluid pump activated adjustment structure for use in an adjustable spinal implant.
Figure 29:
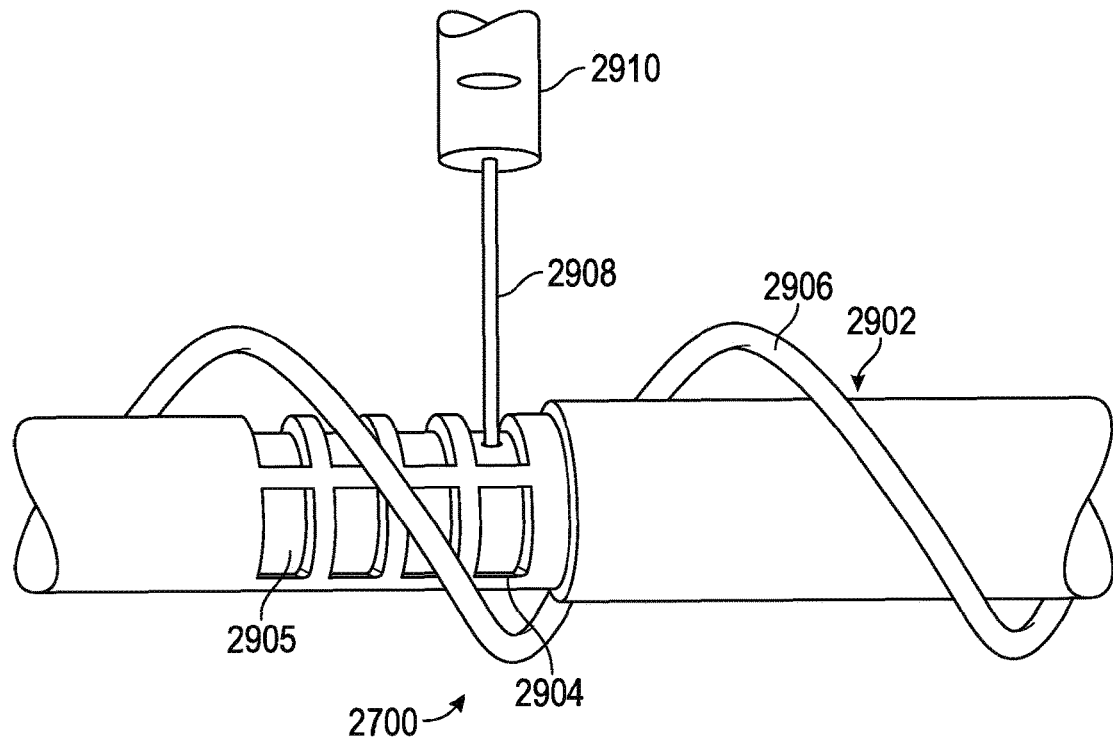
FIG. 29 illustrates a composite fluid coil spring assembly with a skeleton structure.
Figure 30:
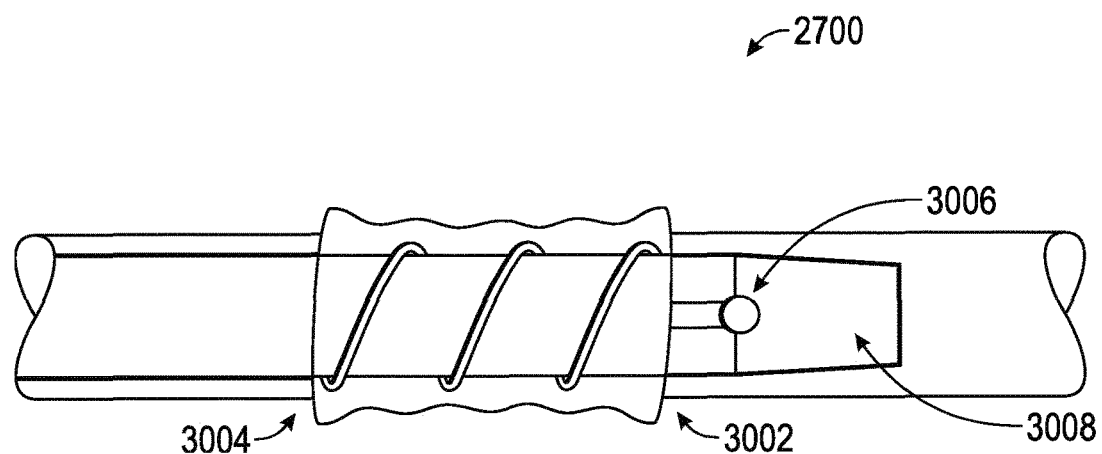
FIG. 30 illustrates a composite fluid coil spring assembly with a compression spring.

Each of the adjustment structures 2700 shown in FIGS. 27-30 may be activated in a different way to rotate one or more threaded drivers and cause pistoning of one or more corresponding implant rods. For example, FIG. 27 illustrates hydraulic activation, FIG. 28 illustrates magnetic fluid pump activation, and FIGS. 29 and 30 illustrate composite fluid coil spring activation. Similar to the driving members described above, the adjustment structures 2700 are configured to rotate one or more threaded drivers by delivering energy to them when activated.

As shown in FIG. 27, the hydraulic activated adjustment structure 2700 may be fluidically connected to a minimally invasive hydraulic system 2710. The hydraulic system 2710 may include a fluid pump 2702, first and second tubing segments 2703, 2710, first and second hypo needles 2704, 2709, and a fluid reservoir 2711. The adjustment structure 2700 may include first and second cannulated rods 2714, 2715 into which the first and second hypo needs 2704, 2709 may be inserted after being inserted through the skin 2720 and subdermal tissue. In some embodiments, the first and second cannulated rods 2714, 2715 have one or more access points (e.g., access points 2712 and 2713) positioned along their length so that the first and second hypo needles 2704, 2709 may access the first and second cannulas 2705, 2708 of the first and second cannulated rods 2714, 2715. Each access points may be, for example, a hole covered by septum such as a rubber stopper which prevents surrounding bodily fluid from entering the adjustment structure 2700.

As shown in FIG. 27, the adjustment structure 2700 may include a chamber 2706 which houses an impeller 2707. As fluid is pumped through the chamber 2706, the impeller rotates. In some embodiments, the rotation of the impeller drives the first and second cannulated rods 2714, 2715, and in some embodiments, the rotation of the impeller drives first and second threaded drivers (not shown), thereby causing pistoning of the first and second cannulated rods 2714, 2715. Further, as shown in FIG. 27, in some embodiments, the chamber 2706 may be tapered into a nozzle at one end to increase the velocity of the fluid flowing past the impeller 2707. In some embodiments, the first and second cannulas 2705, 2708 are the same or different sizes depending on the flow rate to be achieved across the impeller 2707. In some embodiments, fluid is post-operatively delivered to the adjustment structure 2700 via a simple procedure such as an injection. The injected fluid may increase or decrease the length of the implant by turning the impeller 2707 as described above. In some embodiments, the fluid pumped by the hydraulic system may be saline, although any suitable fluid is appreciated. For example, in other embodiments, a biphasic fluid may be used so that its change in characteristics (e.g., volume) can be harnessed. For example, $SF_6$ (Sulfur Hexafluoride) or $C_3F_8$ (Octafluoropropane) may be used. In addition, in some embodiments, a ratchet mechanism may be used in tandem to maintain device length change as the impeller rotates.

FIG. 28 generally illustrates an implant comprising a magnetically-driven impeller to drive fluid pressure and/or flow changes to cause pistoning adjustment of a rod which is dynamically sealed within a cavity of a housing. The adjustment structure 2700 illustrated in FIG. 28 is similar to that shown in FIG. 27 except that the impeller 2707 in FIG. 28 is driven by a magnet rotor 2717 rather than fluid flow alone. In some embodiments, the magnetically-driven impeller 2707 drives fluid pressure and/or flow changes to cause pistoning adjustment of one or more rods (e.g., first and second cannulated rods 2714, 2715). In some embodiments, the one or more rods may be sealed within a cavity of a housing of the spinal implant, and in some embodiments, the one or more rods may be dynamically sealed within a cavity of a housing of the spinal implant. Although not shown, a hydraulic system may be connected to the adjustment structure 2700. In some embodiments, the magnetically-driven impeller 2707 moves fluid from a first reservoir to a second reservoir of the hydraulic system.

FIG. 29 generally illustrates an implant having a support structure (e.g., a skeleton) that has an internal pressurized chamber or series of chambers that cooperatively maintain axial stiffness. By selectively removing fluid from one or more chamber (some or all of the fluid), the pressure may be controllably decreased, thereby lessening the total axial compression, and allowing the controlled shortening of the implant. Each chamber may be configured to be permanently punctured, wherein all of its fluid is removed, or may have a resealable skin, wherein a controlled amount of fluid may be removed, or even replaced. FIG. 29 illustrates an adjustment structure 2700 comprising a composite fluid coil spring assembly 2902. In some embodiments, the assembly 2902 includes a support structure 2904 (also referred to as a skeleton) and an extension spring 2906. In some embodiments, the extension spring 2906 supplies a compressive force (i.e., potential energy) to the support structure 2904. The support structure 2904 may include one or more fluid filled chambers 2905 that maintain the axial stiffness of the extension spring 2906. In some embodiments, the chambers 2905 may be pressurized. By selectively removing fluid from one or more of the chambers 2905 (e.g., some or all of the fluid), the pressure in one or more of the chambers 2905 may be controllably decreased, thus lessening the total axial compression exerted by the extension spring 2906, and thereby allowing the length of the implant to be controllably shortened. In some embodiments, each chamber may be configured to be permanently punctured, wherein all of its fluid is removed, or may have a resealable skin, wherein a controlled amount of fluid may be removed, or even replaced. By selectively replacing fluid into one or more the chambers 2905, the pressure in one or more of the chambers 2905 may be controllably increased, thus increasing the total axial compression exerted by the extension spring 2906, and thereby allowing the length of the implant to be controllably lengthened. The support structure 2904 thereby controls the amount of collapse and/or expansion of the extension spring 2906. The one or more chambers 2905 store compressive energy by resisting the compressive force exerted by the extension spring 2906. By selectively removing fluid from one or more of the chambers 2905 (e.g., some or all of the fluid), the extension spring 2906 becomes activated (i.e., it is allowed to compress). In some embodiments, a needle 2908 and a syringe 2910 may be used to remove fluid from one or more of the chambers 2905, although any suitable fluid removal method and/or apparatus is appreciated. In some embodiments, saline may be used to fill the chambers 2905, although any suitable fluid is appreciated.

FIG. 30 generally illustrates an implant that is similar to the embodiment in FIG. 29, but the "skeleton" is replaced by a compression spring. Fluid may be removed (as described in relation to FIG. 29) or, as shown in FIG. 30, a magnetic release valve may be operated non-invasively (with an external magnetic field), to open an orifice to allow fluid to escape (pressure to decrease). FIG. 30 illustrates a composite fluid coil spring assembly 3002 that is similar to the spring assembly 2902 shown in FIG. 29, but the support structure 2904 of spring assembly 2902 is replaced by a compression spring 3004. Fluid may be removed or replaced as described above in relation to FIG. 29, or, as shown in FIG. 30, a magnetic release valve 3006 may be operated non-invasively (e.g., with an external magnetic field), to open an orifice to allow fluid to escape into a fluid reservoir 3008 and allow the pressure to decrease in the compression spring 3004, thereby allowing the length of the implant to be controllably shortened. In some embodiments, fluid may be replaced in the compression spring 3004, thereby allowing the length of the implant to be controllably lengthened. In some embodiments, the compression spring 3004 is installed in tension. The compression spring 3004 may store fluid in one or more pressurized compartments. In some embodiments, one or more of the compartments may be incrementally drained via the magnetic release valve 3006. By selectively removing fluid from one or more of the chambers 2905 (e.g., some or all of the fluid), the compression spring 3006 becomes activated (i.e., it is allowed to compress).

Figure 31A:
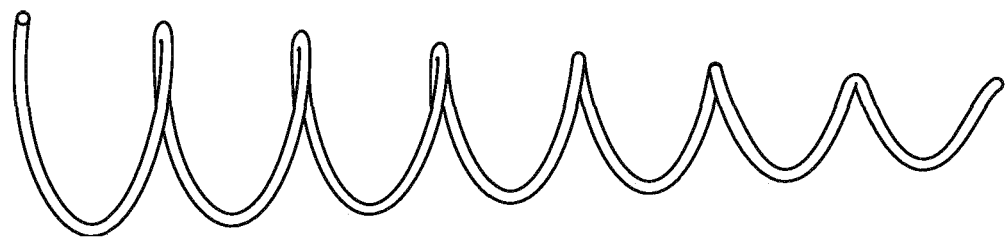
FIGS. 31A-31C illustrate different types of springs that may be incorporated, for example into the embodiment of FIG. 30, to vary the application of force as conditions are varied.
Figure 31B:
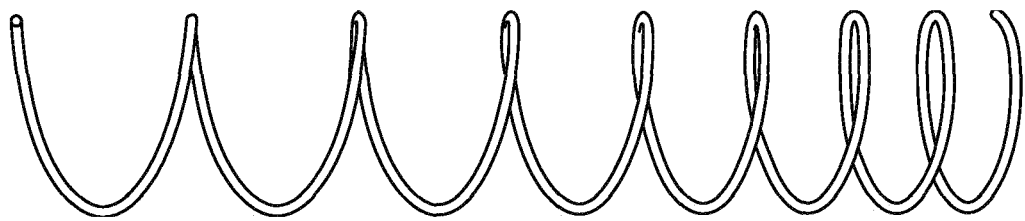
Figure 31C:
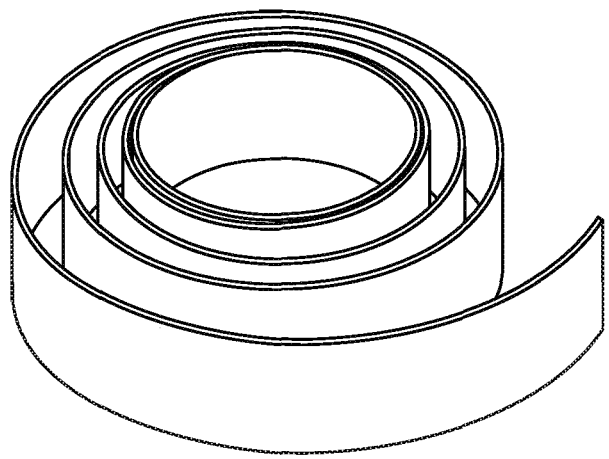

FIGS. 31A-31C illustrate different types of springs 3100 that may be incorporated, for example into the embodiment of FIG. 30, to vary the application of force as conditions are varied.

Figure 32:
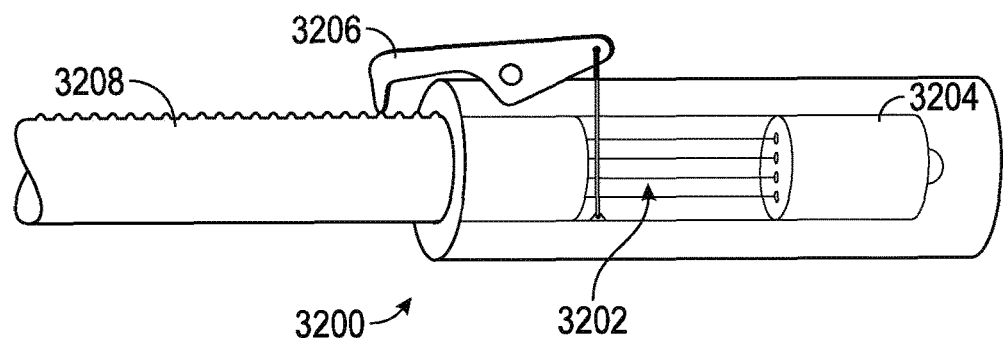
FIG. 32 illustrates an implant having a Nitinol spring.

FIG. 32 illustrates an implant 3200 having one or more shaped memory Nitinol wires 3202 in tension whose length may be made to change upon application of current (for example, non-invasively through inductive coupling, or via a battery 3204). A change in length of the Nitinol wires 3202 may cause a ratchet 3206 to controllably change the length of the implant 3200 by allowing a teethed bar 3208 to freely slide past. The Nitinol wires 3202 may store potential energy which may be activated remotely via electronics that apply current to the wires. In some embodiments, the application of current to the Nitinol wires causes the Nitinol wires to undergo a phase change, such as, for example, changing state and/or shape. For example, in some embodiments, the Nitinol wires 3202 contract when current is run through them, shortening the implant 3200. Further, in certain embodiments, one or more of the Nitinol wires 3202 may be Nitinol springs. In some embodiments, the ratchet 3206 may be disengaged with the teethed rod 3208 when current is running through the wires 3202.

Figure 33:
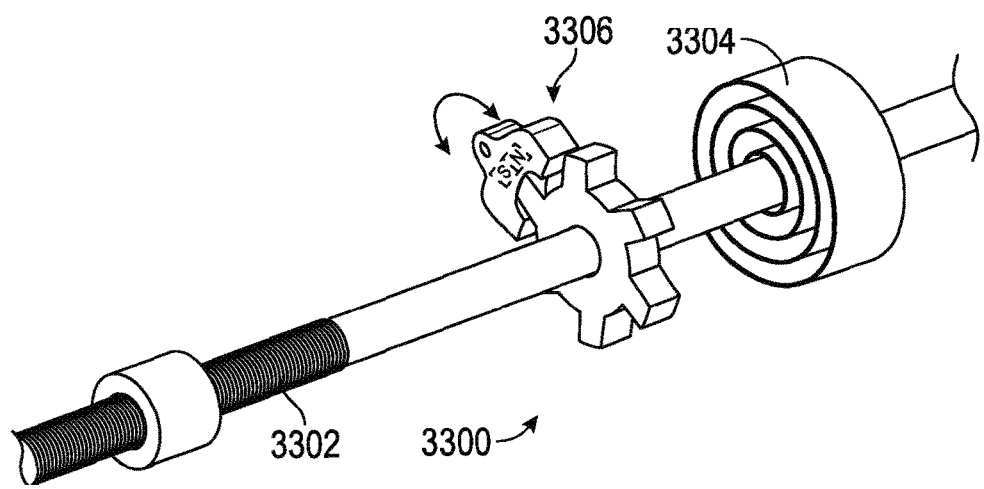
FIG. 33 illustrates an implant having a magnetically operated rotational ratchet.

FIG. 33 illustrates an implant 3300 having a magnetically operated rotational ratchet 3306 that allows the controlled rotation and compression of a lead screw 3302. A torsion spring 3304 supplies the potential energy, such that, when the ratchet is in release mode, the lead screw 3302 is turned until the ratchet locks back down. As shown in FIG. 33, in some embodiments, the torsion spring 3304 may be a pre-wound spiral torsion spring, although any suitable torsion spring is appreciated.

Figure 34A:
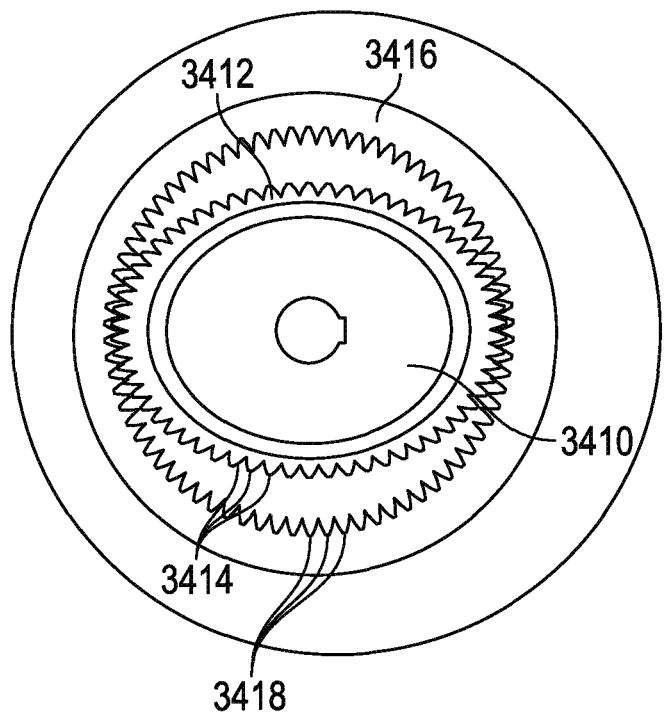
FIGS. 34A and 34B show various embodiments of harmonic drives that may be used together with any of the embodiments described herein.
Figure 34B:
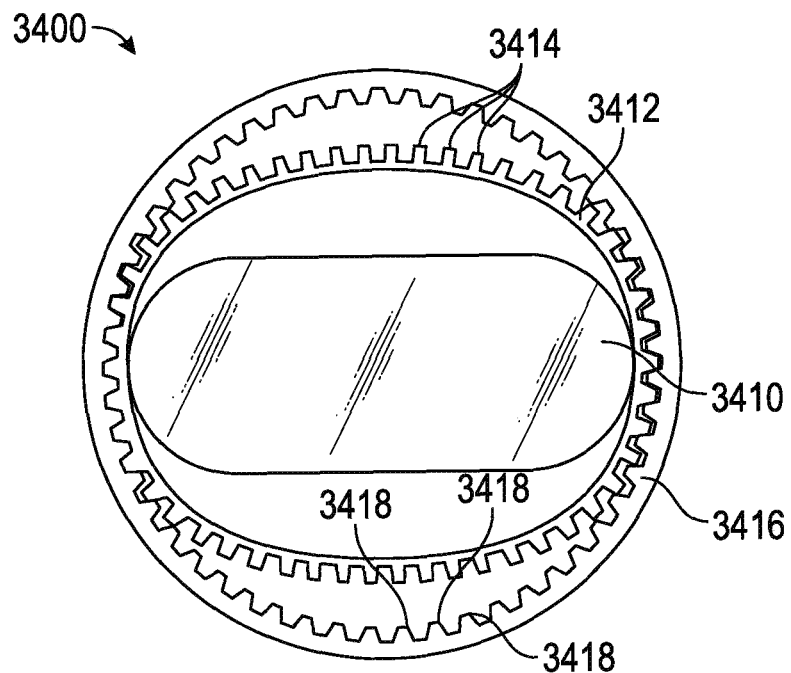

FIGS. 34A-34B generally illustrate a harmonic drive that may be used together with any of the embodiments described herein, to increase efficiency (decrease losses, e.g., frictional losses). In some embodiments, a harmonic drive, also known as a strain wave gear, may be used. A harmonic drive, for example, the embodiments shown in FIGS. 34A and 34B, may be used together with any of the embodiments described herein, to increase efficiency. Using a harmonic drive may decrease losses, such as, for example, frictional losses. Some advantages of using a harmonic drive include, but are not limited to, a possible extremely large gear reduction (150:1), an efficiency between 60-90% depending on the design, and the ability to have the input/output shafts generally along the same axis. In some embodiments, the gear reduction ratio may be 120:1. In some embodiments, the efficiency may be 82%.

FIG. 34B shows a harmonic drive 3400 with a wave generator 3410, flex spline 3412, and circular spline 3416. Some advantages of a strain gear wave include, but are not limited to, lack of backlash, compactness and lightweight, high gear ratios, reconfigurable ratios within a standard housing, good resolution and excellent repeatability (linear representation) when repositioning inertial loads, high torque capability, and coaxial input and output shafts. High gear reduction ratios may be possible in small volume. For example, a harmonic drive may produce a ratio from 30:1 up to 320:1 in the same space in which planetary gears typically only produce a 10:1 ratio.

The wave generator 3410 is attached to an input shaft (not shown). The flex spline 3412 is like a shallow cup, where the sides of the flex spline 3412 are very thin but the bottom is thick and rigid. This results in significant flexibility of the walls at the open end due to the thin wall but rigidity in the closed side, where the closed side may be tightly secured, for example, to a shaft. Teeth 3414 are positioned radially around the outside of the flex spline 3412. The flex spline 3412 fits tightly over the wave generator 3410, so that when the wave generator plug is rotated, the flex spline 3412 deforms to the shape of a rotating ellipse but does not rotate with the wave generator 3410. The flex spline 3412 may attach to an output shaft (not shown). The output shaft may have a maximum rating of 30-70 mNm. The circular spline 3416 is a rigid circular ring with teeth 3418 on the inside. The flex spline 3412 and wave generator 3410 are placed inside the circular spline 3416, meshing the flex spline teeth 3414 and the circular spline teeth 3418. Because the flex spline 3412 has an elliptical shape, its teeth 3414 only actually mesh with the circular spline teeth 3418 in two regions on opposite sides of the flex spline 3412 along the major axis of the ellipse.

In some embodiments, the wave generator 3410 may be the input rotation. As the wave generator plug rotates the flex spline teeth 3414 that are meshed with the circular spline teeth 3418 change. The major axis of the flex spline 3412 actually rotates with the wave generator 3410, so the points where the teeth mesh revolve around the center point at the same rate as the wave generator 3410. In some embodiments, there are fewer flex spline teeth 3414 than there are circular spline teeth 3418, for example, two fewer teeth. This means that for every full rotation of the wave generator 3410, the flex spline 3412 would be required to rotate a small amount, for example, two teeth, backward relative to the circular spline 3416. Thus, the rotation of the wave generator 3410 results in a much slower rotation of the flex spline 3412 in the opposite direction. The gear reduction ratio may be calculated by:

$$\text{reduction ratio} = \frac{(\text{flex spline teeth} - \text{circular spline teeth})}{\text{flex spline teeth}}$$

For example, if there are 200 flex spline teeth and 202 circular spline teeth, the reduction ratio is (200−202)/200=− 0.01. Thus, the flex spline would spin at 1/100 the speed of the wave generator plug and in the opposite direction.

Figure 35A:
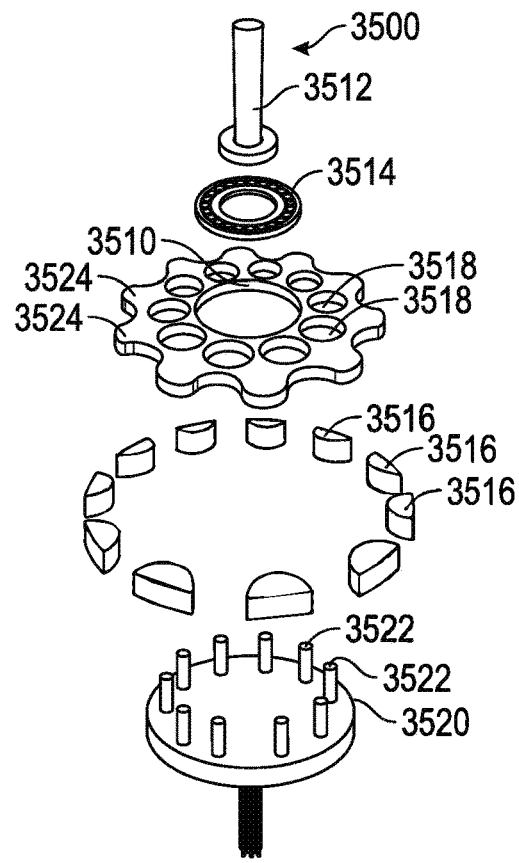
FIG. 35A is an exploded view of a cycloidal drive that may be used together with any of the embodiments described herein.
Figure 35B:
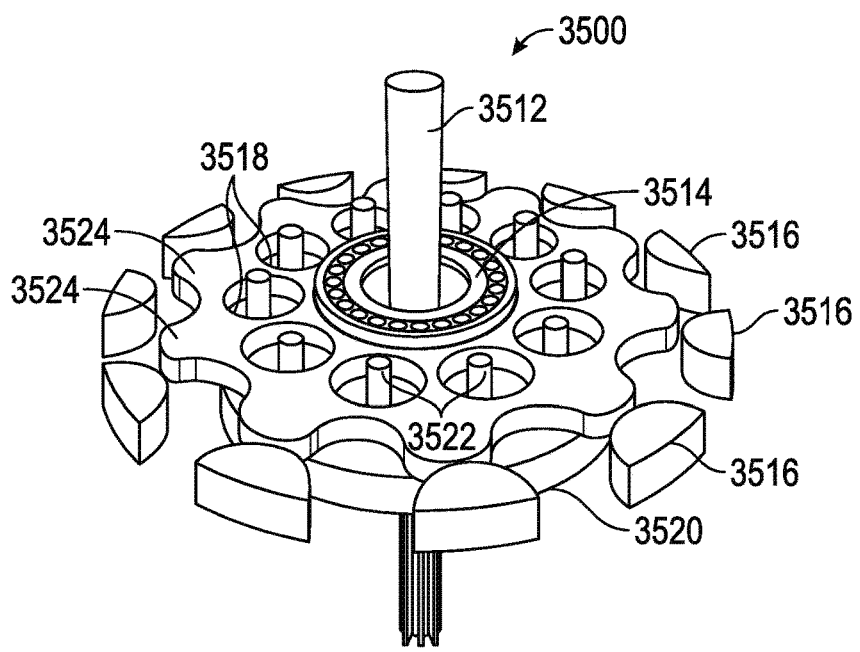
FIG. 35B is an assembled view of the embodiment illustrated in FIG. 35A.

FIG. 35 generally illustrates a cycloidal drive that may be used together with any of the embodiments described herein. The cycloidal drive can allow for high ratios (thus significantly reduced speed, increase precision, increased torque delivery) in a small profile. The cycloidal disc (gold) is driven by an input shaft (green) having an eccentric bearing (green/white), thus turning the cycloidal disc in relation to the circumferentially oriented ring pins (white semi-circles) which are attached to the chassis. (The green shaft may be driven by a magnet or motor). The holes in the cycloidal disc drive the output disc (purple) via the pins (purple). In some embodiments, a cycloidal drive may be used, such as the cycloid drive illustrated in FIGS. 35A and 35B. A cycloidal drive, also known as a cycloidal speed reducer is a mechanism for reducing the speed of an input shaft by a certain ratio. A cycloidal drive allows for high ratios in a small profile; thus, resulting in significantly reduced speed, increased precision, and increased torque delivery. The reduction ratio of the cycloidal drive may be obtained from:

$$\text{reduction ratio} = \frac{(\text{number of ring pins} - \text{number of cycloidal disc lobes})}{\text{number of cycloidal disc lobes}}$$

In some embodiments, the reduction ratio may be up to 119:1 for single stage and up to 7569:1 for double stage. In some embodiments, the efficiency may approach 93% for single stage and approach 86% for double stage.

The cycloidal disc 3510 is driven by an input shaft 3512 mounted eccentrically to a bearing 3514, thus turning the cycloidal disc 3510 in relation to the circumferentially oriented ring pins 3516 that are attached to the chassis. The cycloidal disc 3510 independently rotates around the bearing 3514 as it is pushed against the ring gear. The holes 3518 in the cycloidal disc 3510 drive the output disc 3520 via the pins 3522. In some embodiments, the number of ring pins 3516 is larger than the number of lobes 3524 in the cycloidal disc 3510 causing the cycloidal disc 3510 to rotate around the bearing 3514 faster than the input shaft 3512 is moving it around, giving an overall rotation in the direction opposing the rotation of the input shaft 3512. In some embodiments, the input shaft 3512 may be driven by a magnet or motor.

Figure 36:
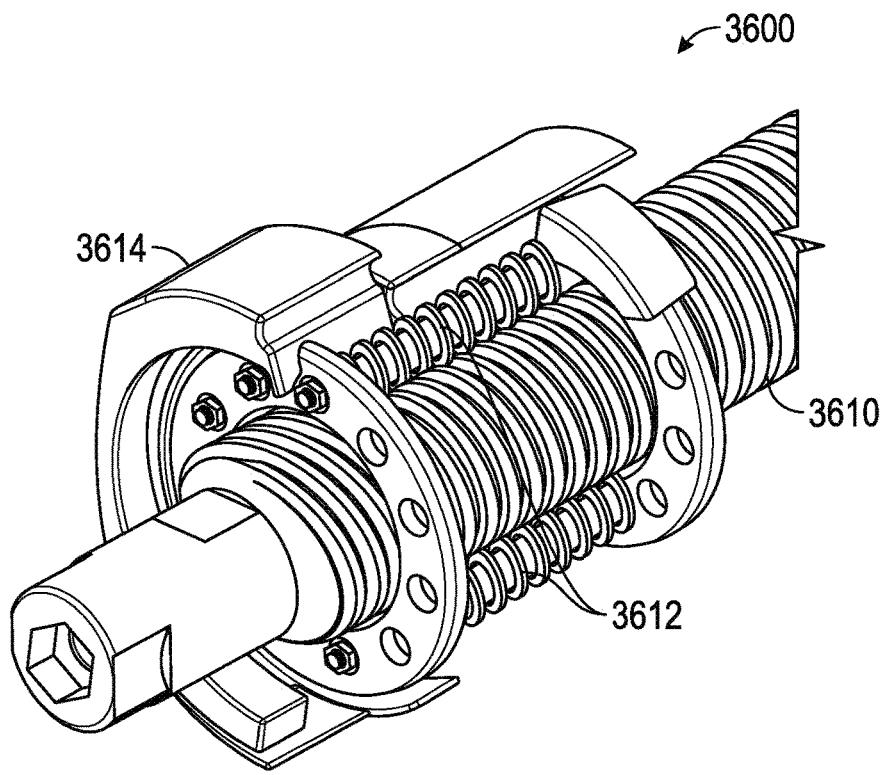
FIG. 36 shows an embodiment of a roller screw drive that may be used together with any of the embodiments described herein.

FIG. 36 generally illustrates a roller screw drive which may be used together with any of the embodiments described herein. The roller screw drive may allow for increased precision and torque magnification. A roller screw drive, such as the embodiment shown in FIG. 36, may be used together with any of the embodiments described herein. The roller screw drive may convert rotational motion to linear motion. The roller screw drive may allow for increased precision and torque magnification. In some embodiments, the roller screw drive has 75-90% efficiency.

The screw shaft 3610 has a multi-start V-shaped thread, which provides a helical raceway for multiple rollers 3612 radially arrayed around the screw shaft 3610 and encapsulated by a threaded nut 3614. In some embodiments, the thread of the screw shaft 3610 is identical to the internal thread of the nut 3614. In some embodiments, the thread of the screw shaft 3610 is opposite to the internal thread of the nut 3614.

Figure 37:
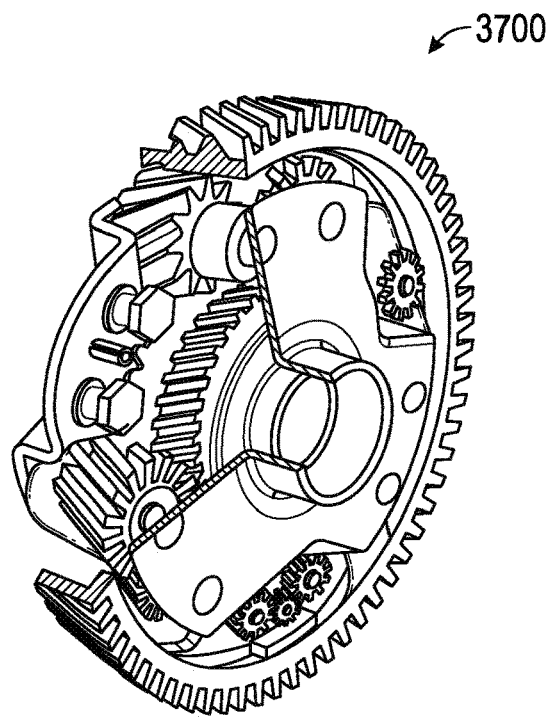
FIG. 37 shows a cut-away view of a spur gear that may be used together with any of the embodiments described herein.

A spur gear, such as the embodiment shown in FIG. 37, may be used together with any of the embodiments described herein. In some embodiments, a spur gear may be used as a differential. The advantages of using a spur gear may include, but are not limited to, allowing one side to keep advancing even if the other side is stalled, increasing efficiency, being less complex and flexible, and being able to be designed to fit around a central screw.

Figure 38:
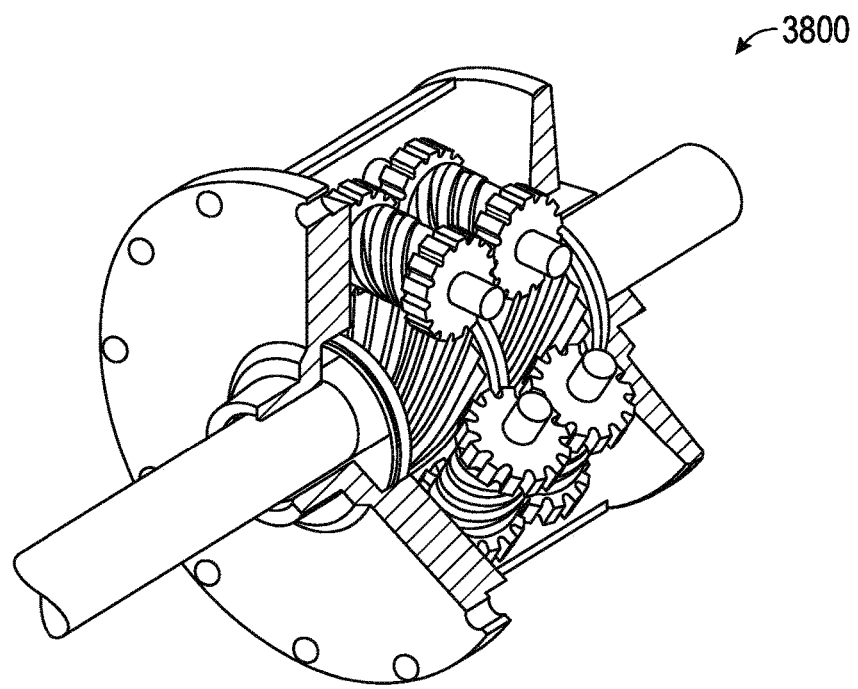
FIG. 38 shows a cut-away view of a Torsen-type differential, or worm gear, that may be used together with any of the embodiments described herein.

A Torsen-type (also commonly known as a worm gear), such as the embodiment shown in FIG. 38, may be used together with any of the embodiments described herein. In some embodiments, a worm gear may be used as a differential. The advantages to using a worm gear differential may include, but are not limited to, allowing one side to keep advancing even if the other side has stalled, limiting or eliminating the ability to back-drive the system.

Figure 39:
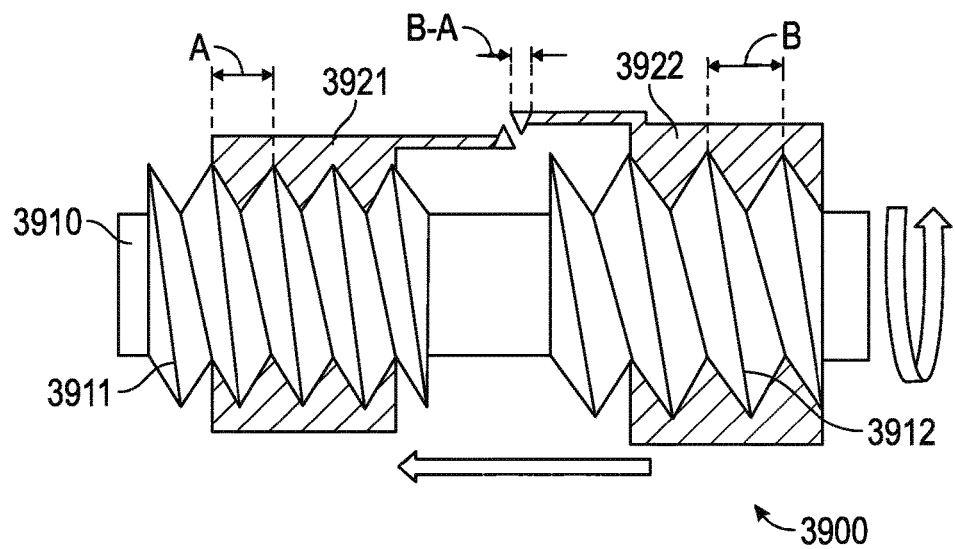
FIG. 39 shows a differential screw that may be used together with any of the embodiments described herein.

A differential screw, such as the embodiment shown in FIG. 39, may be used together with any of the embodiments described herein. A single screw 3910 has a first threaded portion 3911 having a first pitch A and a second threaded portion 3912 having a second pitch B. Both first threaded portion 3911 and second threaded portion 3912 have the threads in the same direction as each other. The screw 3910 may have a driving member (not shown) directly attached to the screw 3910 or attached to the screw 3910 via gearing, etc. The first housing portion 3921 may be attached to a first vertebra (not shown) and the second housing portion 3922 may be attached to a second vertebra (not shown). As the screw 3910 is turned (non-invasively) in a first rotational direction, the first housing portion 3921 moves in a first longitudinal direction in relation to the screw 3910 and the second housing portion 3921 moves in a first longitudinal direction in relation to the screw 3910. However, because the second housing portion 3922 and the second threaded portion 3912 have a larger thread pitch B than the thread pitch A of the first housing portion 3921 and first threaded portion 3911, the second housing portion 3922 begins to "overtake" the first housing portion 3921 and so the two housing portions move relatively closer to each other. The longitudinal distance that housings move relatively towards each other is equal to the difference in pitch (B-A) per turn of the screw.

Figure 40A:
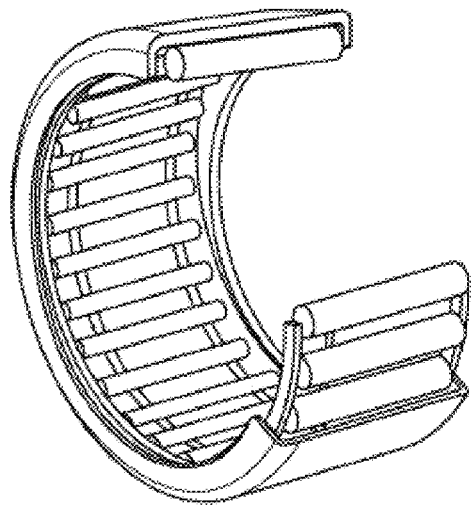
FIGS. 40A-40C illustrate various embodiments of clutches which may be used together with any of the embodiments described herein.
Figure 40B:
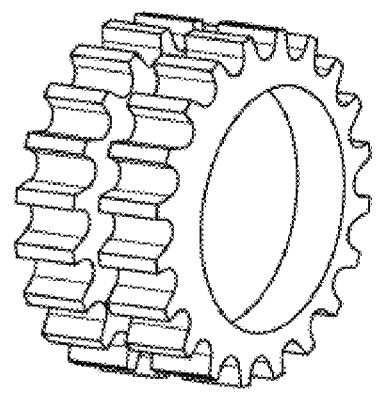
Figure 40C:
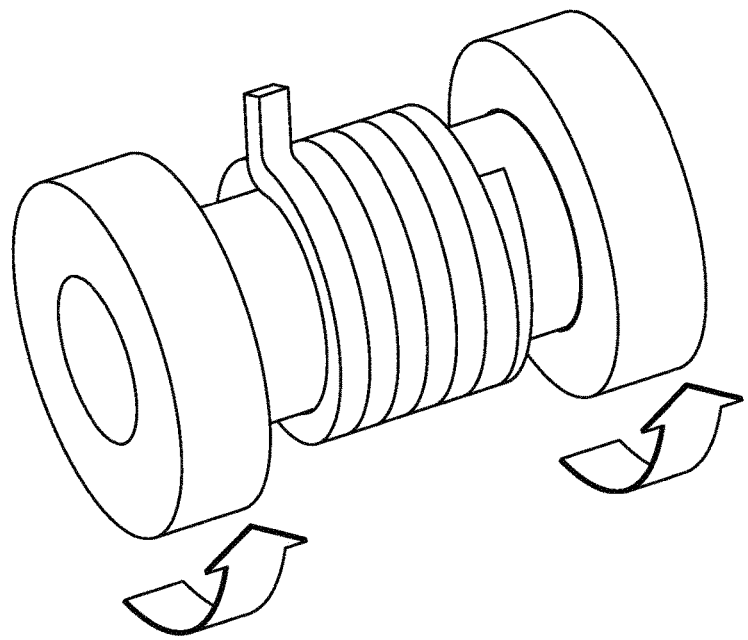

In some embodiments, clutches, such as, for example, those shown in FIGS. 40A-40C, may be required to eliminate the ability for the system to back-drive. Two types of clutches may help: over running or on/off. Over running clutches only run in one direction, may lack controls, and may limit and/or eliminate the ability to drive the system in both directions. Examples of over running type clutches include: ratchet, needle clutch, free wheel, sprag clutch, spring clutch, face gear. On/off clutches may lock in either direction and need to be controlled (unlocked). Examples of on/off type clutches include: spring clutch with tang and face gears.

Figure 41:
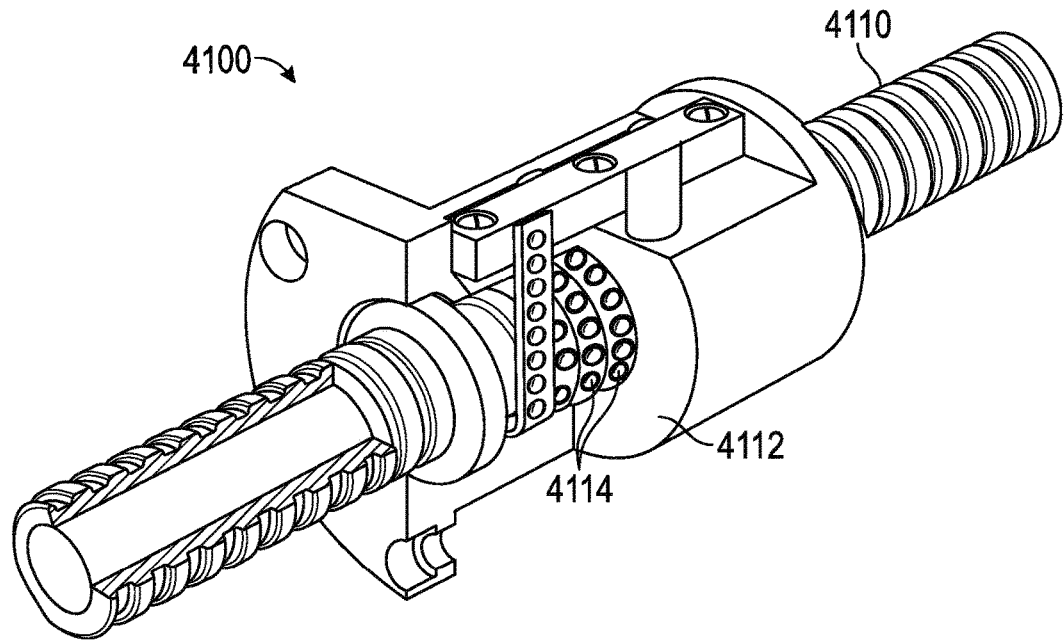
FIG. 41 shows a partial cut-away and partial cross-sectional view of a ball screw mechanism that may be used together with any of the embodiments described herein.

In some embodiments, a ball screw mechanism, such as, for example, the embodiment shown in FIG. 41, may be used together with any of the embodiments described herein, to increase efficiency, and decrease losses (e.g., frictional losses). Using a ball screw mechanism may decrease losses, for example, frictional losses. In some embodiments, a ball screw mechanism may translate rotational to linear motion. The ball bearings 4114 fit between the screw shaft 4110 and the nut 4112. The ball bearings 4114 may reduce friction and input torque and as a result improve efficiency.

Figure 42:
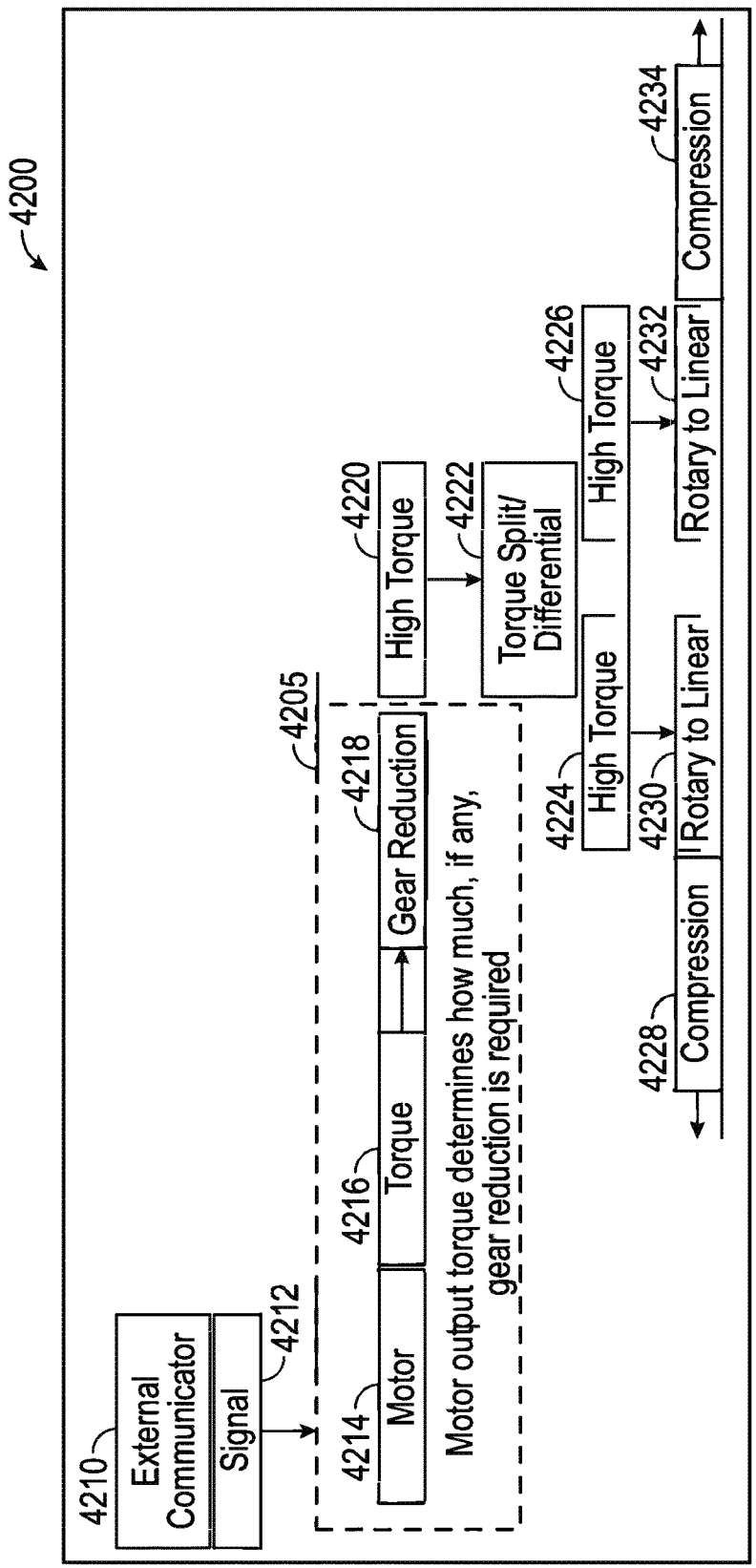
FIGS. 42-44 are flow charts, illustrating embodiments of systems of torque split, differential, and/or gear reduction.
Figure 43:
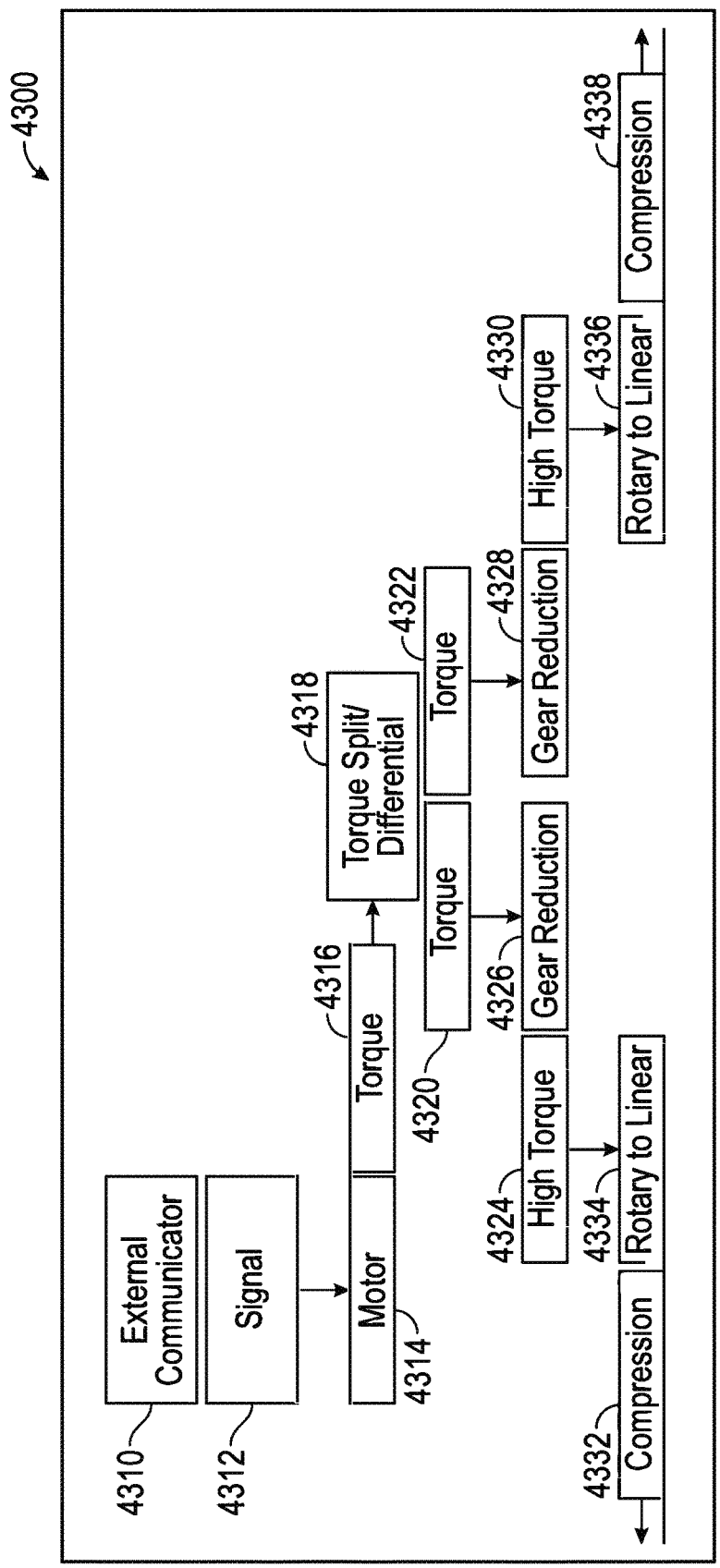
Figure 44:
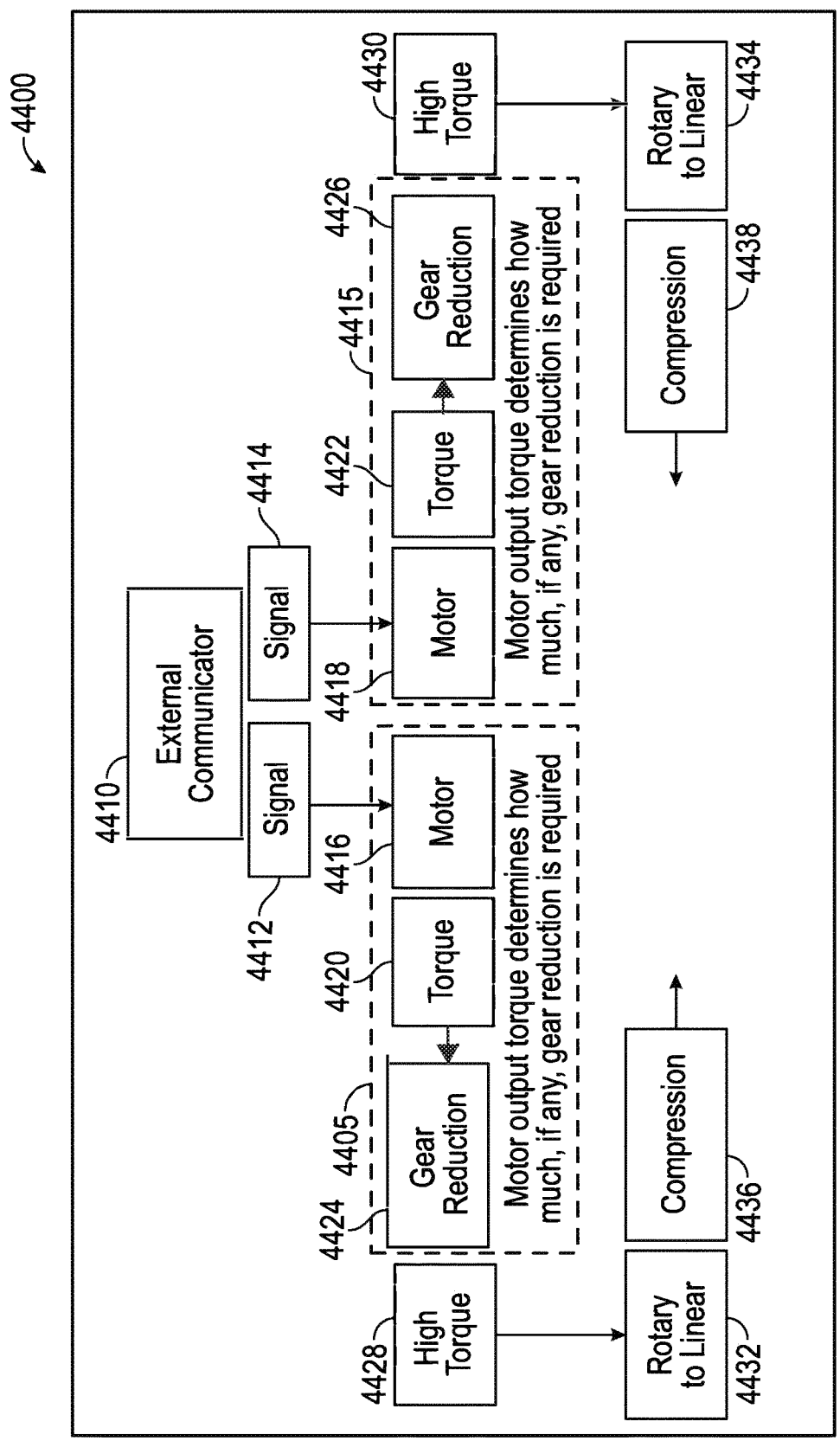

FIGS. 42-44 illustrate three different systems of torque split, differential, and/or gear reduction. The features shown in FIGS. 42-44 may be used in various combinations, not all of which may be shown in the figures. The flow charts show some embodiments of systems, where a signal or signals from an external communicator results in compression. In some embodiments, as illustrated by system 4200 in FIG. 42, an external communicator 4210 may generate and transmit a signal 4212 to a motor 4214 in subsystem 4205. The motor output torque 4216 determines how much, if any, gear reduction 4218 is required. The high torque 4220 is split over a differential 4222. In some embodiments, the torque split ratio can vary from 100/0 to 50/50. In some embodiments, the torque split ratio is 50/50 so that half the high torque is transmitted to a first side 4224 and half the high torque is transmitted to a second side 4226. In some embodiments, the high torque on the first side 4224 may be converted from rotary to linear motion 4230 resulting in compression to the first side 4228. In some embodiments, the high torque on the second side 4226 may be converted from rotary to linear motion 4232 resulting in compression on the second side 4234. In some embodiments, the rotary to linear motion conversion mechanisms on the first and second sides 4230 and 4232 are the same or substantially similar. In some embodiments, the rotary to linear motion conversion mechanisms on the first and second sides 4230 and 4232 are different. In some embodiments, the amounts of compression on the first and second sides 4228 and 4234 are the same or substantially similar. In some embodiments, the amounts of compression on the first and second sides 4230 and 4232 are different.

In some embodiments, as illustrated by system 4300 in FIG. 43, an external communicator 4310 may generate and transmit a signal 4312 to a motor 4314. The motor output torque 4316 is split over a differential 4318. In some embodiments, the torque split ratio can vary from 100/0 to 50/50. In some embodiments, the torque split ratio is 50/50 so that half the torque is transmitted to a first side 4320 and half the torque is transmitted to a second side 4322. In some embodiments, the torque on the first side 4320 is transferred by gear reduction 4326 to increase the amount of torque, resulting in a high torque 4324. In some embodiments, the torque on the second side 4322 is transferred by gear reduction 4328 to increase the amount of torque, resulting in a high torque 4330. In some embodiments, the first side gear reduction 4326 is by the same value as the second side gear reduction 4326. In some embodiments, the first and second sides have different gear reduction values. In some embodiments, the first and second gear reductions may be done by similar reduction drives. In some embodiments, the first and second gear reductions may be done by the different style reduction drives. In some embodiments, gear reduction 4326 or 4328 may not be necessary, depending on the value of the torque 4320 or 4322. In some embodiments, the high torque on the first side 4324 may be converted from rotary to linear motion 4334 resulting in compression to the first side 4332. In some embodiments, the high torque on the second side 4330 may be converted from rotary to linear motion 4336 resulting in compression on the second side 4338. In some embodiments, the rotary to linear motion conversion mechanisms on the first and second sides 4334 and 4336 are the same or substantially similar. In some embodiments, the rotary to linear motion conversion mechanisms on the first and second sides 4334 and 4336 are different. In some embodiments, the amounts of compression on the first and second sides 4332 and 4338 are the same or substantially similar. In some embodiments, the amounts of compression on the first and second sides 4332 and 4238 are different.

In some embodiments, as illustrated by system 4400 in FIG. 44, an external communicator 4410 may generate and transmit a first signal 4412 and a second signal 4414 to a first motor 4416 and a second motor 4418, respectively. In some embodiments, the external communicator may generate and transmit at least one signal, such as, for example, one, two, ten, or one hundred signals. In some embodiments, the first signal 4412 and the second signal 4414 are the same or substantially similar. In some embodiments, the first and second signals 4412 and 4414 are different. The first motor 4416 is part of a subsystem 4405 and the second motor 4418 is part of a subsystem 4415. The motor output torques 4420 and 4422 determine how much, if any, gear reduction 4424 and 4426 is required. In some embodiments, the first motor output torque 4420 and the second motor output torque 4422 are the same or substantially similar values. In some embodiments, the first and second motor output torques 4420 and 4422 are different values. In some embodiments, there may be no gear reduction. In some embodiments, the high torque on the first side 4428 may be converted from rotary to linear motion 4432 resulting in compression to the first side 4336. In some embodiments, the high torque on the second side 4430 may be converted from rotary to linear motion 4434 resulting in compression on the second side 4438. In some embodiments, the rotary to linear motion conversion mechanisms on the first and second sides 4432 and 4434 are the same or substantially similar. In some embodiments, the rotary to linear motion conversion mechanisms on the first and second sides 4432 and 4434 are different. In some embodiments, the amounts of compression on the first and second sides 4436 and 4438 are the same or substantially similar. In some embodiments, the amounts of compression on the first and second sides 4436 and 4438 are different.

Figure 45A:
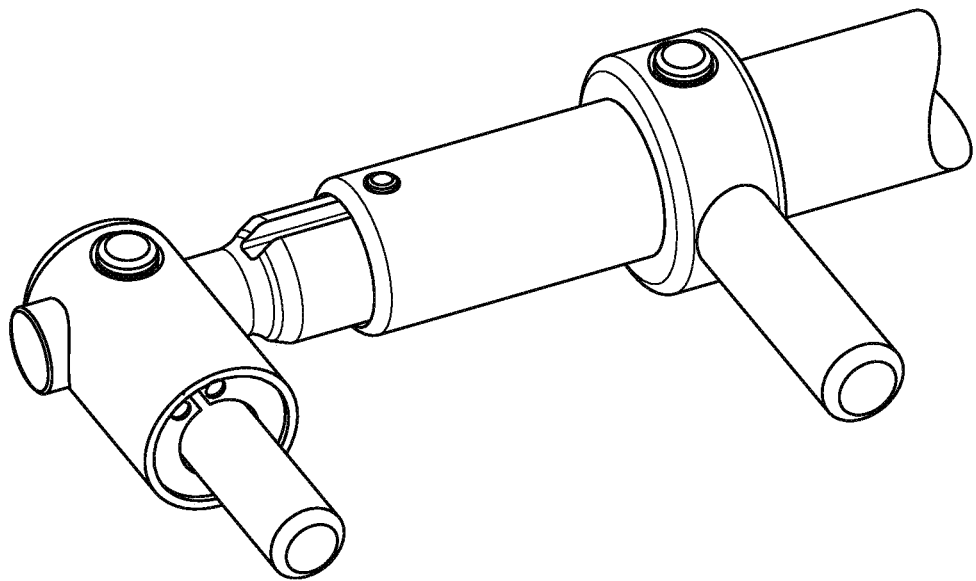
FIGS. 45A-45C show various pivots for coupling rods to pedicle screws.
Figure 45B:
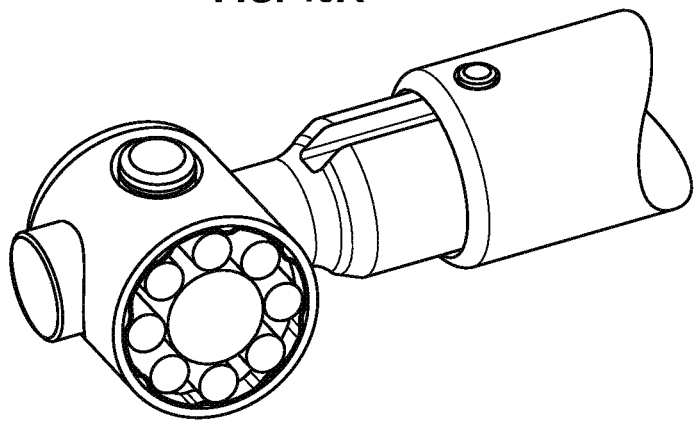
Figure 45C:
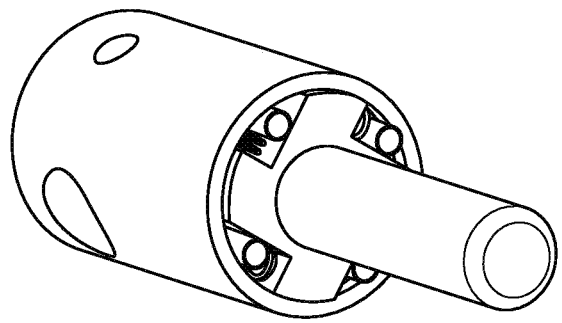
Figure 46A:
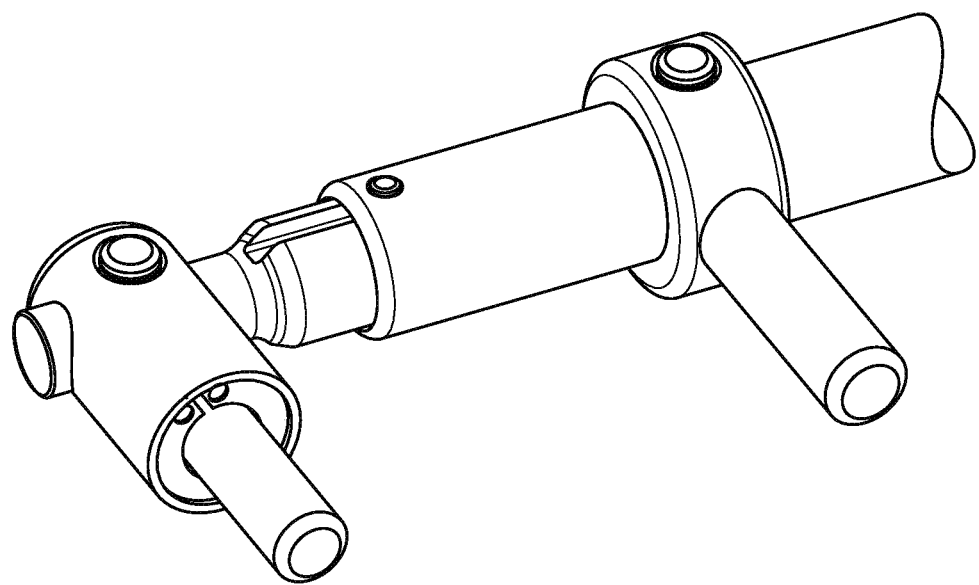
FIGS. 46A and 46B are detailed views of an embodiment of a pivot having a sprag clutch.
Figure 46B:
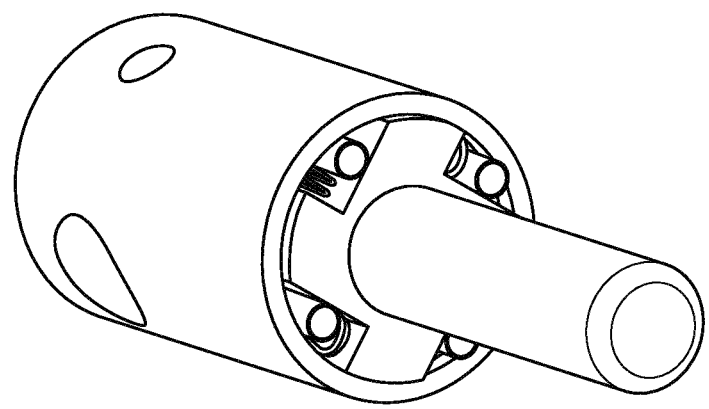

FIGS. 45A-45C generally illustrate various types of a pivot for coupling to pedicle screws, which are able to turn only in a single direction, thus allowing, for example, an increase in lordosis, without a loss. This, the implant will be adjustable only in a first angular direction, and will not allow back adjustment in the opposite angular direction. FIG. 45C illustrates a pivot with a sprag clutch. In some embodiments, a one way locking pivot, such, as for example, the embodiments shown in FIGS. 45A-45C, may be used for coupling to pedicle screws. The pivot may move in one rotational direction but not the other. In some embodiments, for example, the pivot may be configured to be movable in the rotational direction at which lordosis is increased and not be movable in the opposite direction; thus, increasing lordosis without a loss. In some embodiments, the pivot may comprise a freewheel or other one-way clutching concepts presented herein. Alternatively, one way pivoting may be provided by a ratchet or other type of commonly known device allowing rotation in one way but not the other. In some embodiments, the pivot may comprise a sprag clutch, such as for example, the embodiments shown in FIGS. 46A and 46B. Using a pivot may allow an extra degree of freedom for lordotic compression but may limit how much compression.

Figure 47:
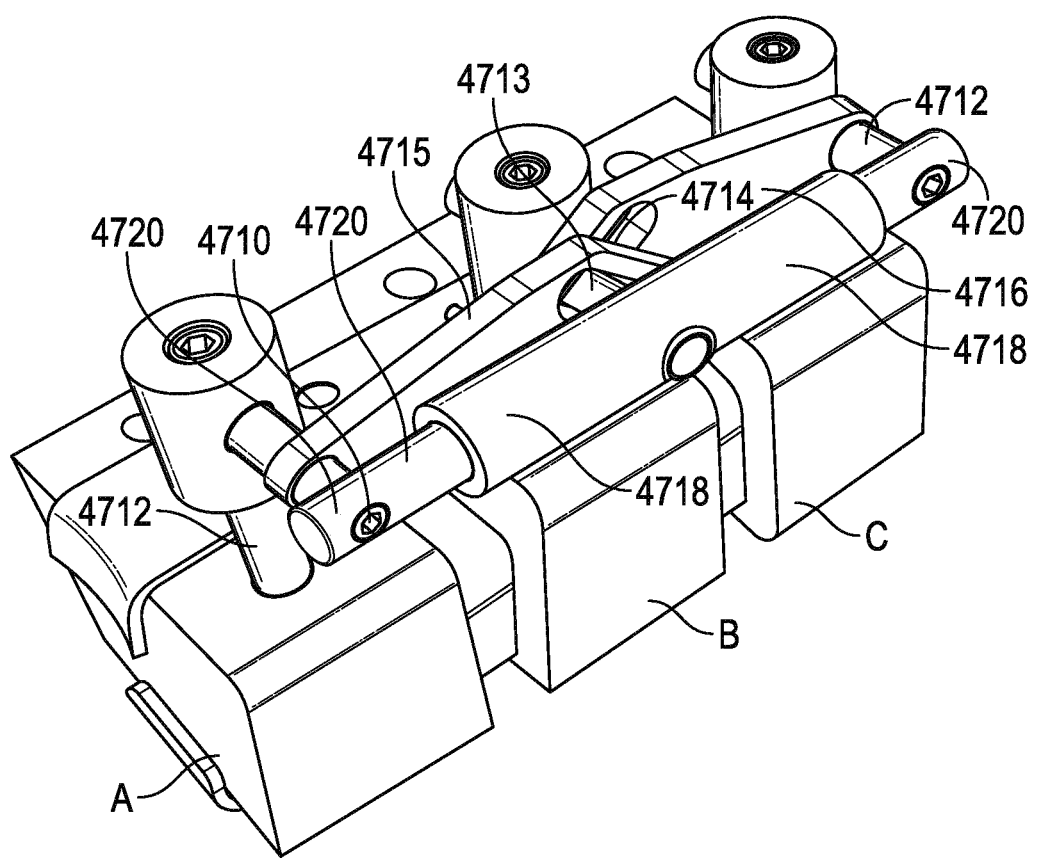
FIG. 47 shows another embodiment of a pivot coupled to pedicle screws and vertebrae.

FIG. 47 shows an embodiment where the pivot's 4710 rotation is controlled by axial movement (e.g., retraction) of an implant. In some embodiments, a pivot may include extension members 4712 that are partially constrained. For example, they may be constrained in a single linear degree of freedom, for example, slidable in a groove or slot 4713 or 4714. A first linkage 4715 and a second linkage 4716 are similar to the boom and stick of a backhoe. The housing 4718 and rod 4720 are similar to the backhoe cylinder. Noninvasive shortening of the length of the implant (via retraction of rod 4720 into housing 4718) allows slots 4713 and 4714 of first linkage 4715 and second linkage 4716, respectively, slide along the housing extension member, which attaches the housing 4722 to the middle pedicle screw that is connected to vertebra B. The two outer extension members 4712 are rigidly secured respectively to the first and second linkages 4715 and 4716, and thus, they cause the two outer pedicle screws to rotate and force an increase of lordosis between vertebra A and vertebra C.

In some embodiments, a torque-limiting brake that is configured to lock and unlock a pivot may be used, such as, for example, the embodiment shown in FIG. 48. The pivot may allow for changes in angulation, such as to change an angle of lordosis. At a threshold torque, slippage occurs at point A, thus unlocking the brake and allowing the pivot 4810 to temporarily unlock.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. In addition, while a number of variations of the invention have been shown and described in detail, other modifications, which are within the scope of this invention, will be readily apparent to those of skill in the art based upon this disclosure. It is also contemplated that various combinations or sub-combinations of the specific features and aspects of the embodiments may be made and still fall within the scope of the invention. Accordingly, it should be understood that various features and aspects of the disclosed embodiments can be combined with or substituted for one another in order to form varying modes of the disclosed invention. Thus, it is intended that the scope of the present invention herein disclosed should not be limited by the particular disclosed embodiments described above, but should be determined only by a fair reading of the claims that follow. Therefore, in addition to the many different types of implantable retraction or distraction devices that are configured to be non-invasively adjusted, implantable non-invasively adjustable non-distraction devices are envisioned, including, for example, adjustable restriction devices for gastrointestinal disorders such as GERD, obesity, or sphincter laxity (such as in fecal incontinence), or other disorders such as sphincter laxity in urinary incontinence. These devices, too, may incorporate magnets to enable the non-invasive adjustment.

Similarly, this method of disclosure, is not to be interpreted as reflecting an intention that any claim require more features than are expressly recited in that claim. Rather, as the following claims reflect, inventive aspects lie in a combination of fewer than all features of any single foregoing disclosed embodiment. Thus, the claims following the Detailed Description are hereby expressly incorporated into this Detailed Description, with each claim standing on its own as a separate embodiment.

What is claimed is:

1. An adjustable implant, comprising:
   a first end configured to affix the adjustable implant to a first location of a subject;
   a second end configured to affix the adjustable implant to a second location of the subject;
   an actuator configured to be activated from an external location; and
   a cycloidal drive comprising:
      an input shaft rotatably coupled to the actuator,
      a cycloidal disc rotatably coupled to the input shaft,
      an output disc rotatably coupled to the cycloidal disc, and
      an output shaft extending from a first surface of the output disc, wherein rotation of the output shaft cause a change in the relative distance between the first end and the second end,
   wherein the cycloidal disc comprises a plurality of lobes circumferentially spaced about a perimeter of the cycloidal disc.

2. The adjustable implant of claim 1, wherein the input shaft is mounted to an eccentric bearing and the cycloidal disc is configured to rotate about the eccentric bearing.

3. The adjustable implant of claim 2, wherein the cycloidal disc comprises a central aperture configured to receive the eccentric bearing therein, and a plurality of holes circumferentially spaced about the central aperture.

4. He adjustable implant of claim 3, wherein the output disc comprises a plurality of pins extending from a second surface of the output disc opposite the first surface, wherein the plurality of pins are configured to engage the plurality of holes in the cycloidal disc.

5. The adjustable implant of claim 1, further comprising a plurality of circumferentially oriented ring pins configured to engage the plurality of lobes.

6. The implant of claim 1, wherein the actuator comprises a rotatable permanent magnet configured to be rotated by a rotating magnetic field.

7. The implant of claim 6, wherein the rotatable permanent magnet is disposed within an internal cavity of a magnet housing rotatably coupled to the input shaft.

8. The implant of claim 1, wherein the actuator comprises a motor coupled to a power source.

9. The adjustable implant of claim 1, wherein the cycloidal drive comprises one gear stage and has a speed reduction ratio of up to about 119:1.

10. The adjustable implant of claim 1, wherein the cycloidal drive comprises two gear stages and has a speed reduction ratio of up to about 7569:1.

11. A system comprising:
the adjustable implant of claim 1; and
an external adjustment device configured to activate the actuator.

12. The system of claim 11, further comprising a plurality of circumferentially oriented ring pins configured to engage the plurality of lobes.

* * * * *